United States Patent
Lee et al.

(10) Patent No.: US 12,127,476 B2
(45) Date of Patent: Oct. 22, 2024

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Yun Suk Lee, Cheonan-si (KR); Nam Geol Lee, Cheonan-si (KR); Jung Hwan Park, Cheonan-si (KR); Bum Sung Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 672 days.

(21) Appl. No.: 17/309,586

(22) PCT Filed: Nov. 19, 2019

(86) PCT No.: PCT/KR2019/015809
§ 371 (c)(1),
(2) Date: Jun. 7, 2021

(87) PCT Pub. No.: WO2020/116822
PCT Pub. Date: Jun. 11, 2020

(65) Prior Publication Data
US 2022/0037594 A1    Feb. 3, 2022

(30) Foreign Application Priority Data
Dec. 7, 2018    (KR) .................. 10-2018-0156638

(51) Int. Cl.
*H10K 85/60* (2023.01)
*H10K 50/11* (2023.01)
(Continued)

(52) U.S. Cl.
CPC ......... *H10K 85/654* (2023.02); *H10K 85/626* (2023.02); *H10K 85/636* (2023.02);
(Continued)

(58) Field of Classification Search
CPC ............... H10K 85/636; H10K 85/654; H10K 85/6572; H10K 85/6574; H10K 85/6576; H10K 2101/90
See application file for complete search history.

(56) References Cited

U.S. PATENT DOCUMENTS

2021/0091314 A1† 3/2021 Shin

FOREIGN PATENT DOCUMENTS

| KR | 10-2012-0104067 A | 9/2012 |
| KR | 10-2016-0110257 A | 9/2016 |

(Continued)

OTHER PUBLICATIONS

Machine-generated English-language translation of KR-1857632-B1.*
(Continued)

*Primary Examiner* — Vu A Nguyen
(74) *Attorney, Agent, or Firm* — Vorys, Sater, Seymour and Pease LLP; Mih Suhn Koh

(57) ABSTRACT

Provided is the compound represented by Formula 1, an organic electric element including a first electrode, a second electrode, and an organic material layer formed between the first electrode and the second electrode, and electronic device thereof, and by including the compound represented by Formula 1 and compound represented by Formula 2 in the organic material layer, the driving voltage of the organic electric element can be lowered, and the luminous efficiency and life time of the organic electric element can be improved.

17 Claims, 1 Drawing Sheet

(51) Int. Cl.
*H10K 101/00* (2023.01)
*H10K 101/10* (2023.01)

(52) U.S. Cl.
CPC ..... *H10K 85/6572* (2023.02); *H10K 85/6574* (2023.02); *H10K 85/6576* (2023.02); *H10K 50/11* (2023.02); *H10K 2101/10* (2023.02); *H10K 2101/90* (2023.02)

(56) References Cited

FOREIGN PATENT DOCUMENTS

| | | | | |
|---|---|---|---|---|
| KR | 10-2017-0112039 | A | 10/2017 | |
| KR | 10-2018-0008286 | A | 1/2018 | |
| KR | 10-2018-0022574 | A | 3/2018 | |
| KR | 10-2018-0023511 | A | 3/2018 | |
| KR | 20180022574 | A * | 3/2018 | ........... C07D 319/14 |
| KR | 20180023511 | A * | 3/2018 | ........... C07D 209/56 |
| KR | 10-2018-0036529 | A | 4/2018 | |
| KR | 20180036529 | A * | 4/2018 | ........... C07D 487/04 |
| KR | 1857632 | B1 * | 5/2018 | ........... C07D 209/82 |
| KR | 101857632 | B1 * | 5/2018 | ........... C07D 409/14 |
| KR | 10-2019-0013353 | A | 2/2019 | |
| KR | 10-2019-0137006 | A | 12/2019 | |

OTHER PUBLICATIONS

Machine-generated English-language translation of KR-20180022574-A.*
Machine-generated English-language translation of KR-20180036529-A.*
The Korean Office Action for corresponding KR 10-2018-0156638, mailed Oct. 27, 2023, 19 pages.

\* cited by examiner
† cited by third party

COMPOUND FOR ORGANIC ELECTRONIC ELEMENT, ORGANIC ELECTRONIC ELEMENT USING THE SAME, AND AN ELECTRONIC DEVICE THEREOF

CROSS-REFERENCE TO RELATED APPLICATION

This patent application claims priority from and the benefit under 35 U.S.C. § 119 to § 121, and § 365 of Korean Patent Application No. 10-2018-0156638, filed on Dec. 7, 2018 which is hereby incorporated by reference for all purposes as if fully set forth herein. Further, this application claims the benefit of priority in countries other than U.S., which is hereby incorporated by reference herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may comprise a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function. Further, the light emitting material may be divided into a high molecular weight type and a low molecular weight type according to its molecular weight, and may also be divided into a fluorescent material derived from excited singlet states of electron and a phosphorescent material derived from excited triplet states of electron according to its light emitting mechanism. Further, the light emitting material may be divided into blue, green, and red light emitting material and yellow and orange light emitting material required for better natural color reproduction according to its light emitting color.

Meanwhile, when only one material is used as a light emitting material, there occur problems of shift of a maximum luminescence wavelength to a longer wavelength due to intermolecular interactions and lowering of the efficiency of a corresponding element due to deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more than more as size of display becomes larger and larger in the portable display market. Therefore, the power consumption is very important factor in the portable display with a limited power source of the battery, and efficiency and life span issues must also be solved.

Efficiency, life span, driving voltage, and the like are correlated with each other. If efficiency is increased, then driving voltage is relatively lowered, and the crystallization of an organic material due to Joule heating generated during operation is reduced as driving voltage is lowered. As a result, life span tends to increase. However, efficiency cannot be maximized only by simply improving the organic material layer. This is because long life span and high efficiency can be simultaneously achieved when an optimal combination of energy levels and $T_1$ values, inherent material properties (mobility, interfacial properties, etc.), and the like among the respective layers included in the organic material layer is given.

Therefore, there is a need to develop a light emitting material that has high thermal stability and can efficiently a charge balance in the light-emitting layer. That is, in order to allow an organic electric element to fully exhibit excellent features, it should be prerequisite to support a material constituting an organic material layer in the element, for example, a hole injection material, a hole transport material, a light emitting material, an electron transport material, an electron injection material, or the like, by a stable and efficient material. However, the stable and efficient material of organic material layer for an organic electronic element has not been fully developed yet, in particular, it is strongly required to develop host material of the light emitting layer.

Object, Technical Solution and Effects of the Invention

The present invention is to provide compound lowering a driving voltage, improving luminous efficiency and lifetime of the element, an organic electric element comprising the same, and an electronic device thereof.

In an aspect of the present invention, the present invention provides the compound represented by the following formula, organic electric elements comprising the same, and electronic devices thereof.

<Formula 1>

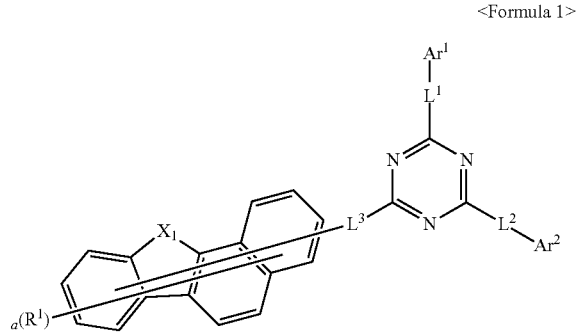

In another aspect of the present invention, the present invention provides an organic electric element comprising compound represented by Formula 1 and compound represented by Formula 2 in a light emitting layer, and an electronic device thereof.

<Formula 2>

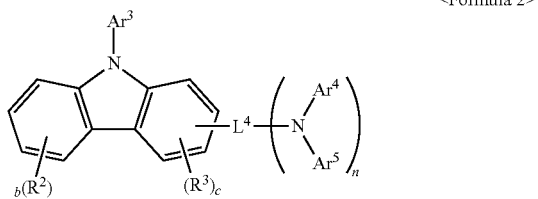

By using the compound according to embodiment of the present invention, a driving voltage of element can be lowered and the luminous efficiency and lifetime of the element can be also significantly improved.

DETAILED DESCRIPTION

Figure 1:
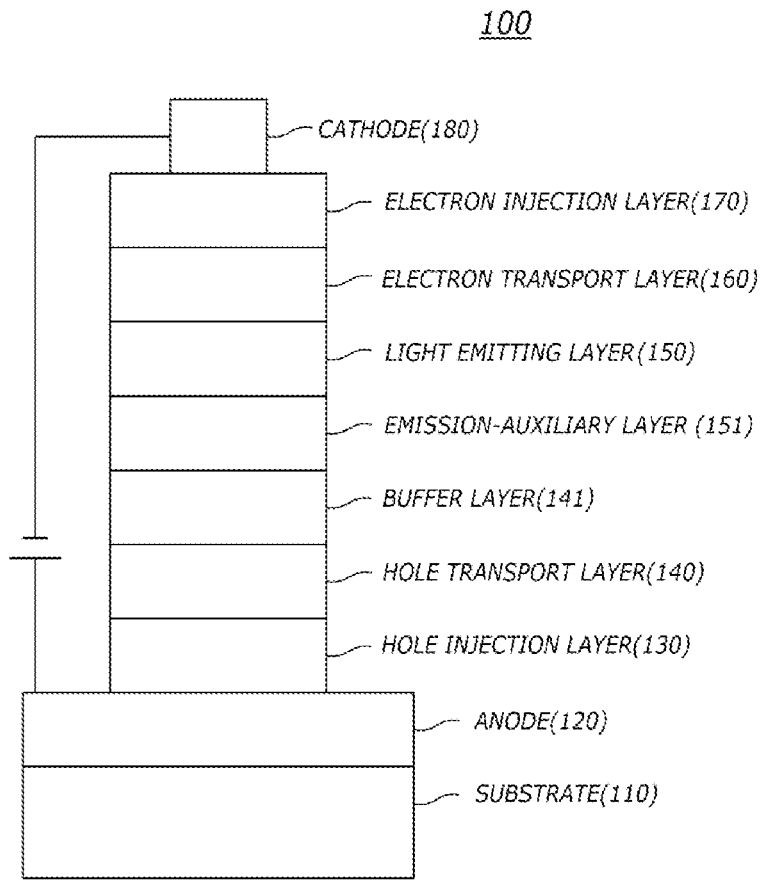
FIG. 1 illustrates an example of an organic electroluminescent element according to the present invention: 100 is an organic electric element, 110 is a substrate, 120 is a first electrode, 130 is a hole injection layer, 140 is a hole transport layer, 141 is a buffer layer, 150 is a light emitting layer, 151 is an emission-auxiliary layer, 160 is an electron transport layer, 170 is an electron injection layer, and 180 is a second electrode.
Figure 2:
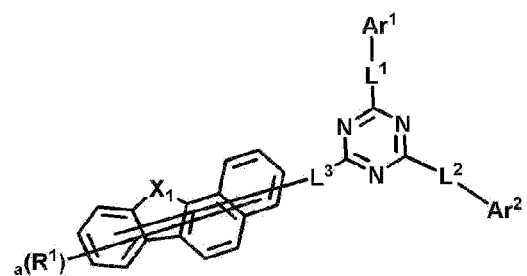
FIG. 2 illustrates Formula according to an aspect of the present invention

Unless otherwise stated, the term "aryl group" or "arylene group" as used herein has, but not limited to, 6 to 60 carbon atoms. The aryl group or arylene group in the present invention may comprise a monocyclic ring, ring assemblies, a fused polycyclic system, spiro-compounds and the like. In addition, unless otherwise stated, a fluorenyl group may be comprised in an aryl group and a fluorenylene group may be comprised in an arylene group.

Unless otherwise stated, the term "fluorenyl group" or "fluorenylene group" as used herein means univalent or bivalent functional group in which R, R' and R" are all hydrogen in the following structure, "substituted fluorenyl group" or "substituted fluorenylene group" means that at least any one of R, R' and R" is a substituent other than hydrogen, and the case where R and R' are bonded to each other to form the spiro compound together with the carbon bonded to them is comprised.

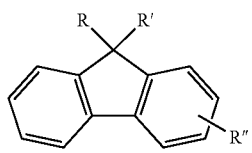

The term "spiro-compound" as used herein has a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

The term "heterocyclic group" used in the specification comprises a non-aromatic ring as well as an aromatic ring like "heteroaryl group" or "heteroarylene group". Unless otherwise stated, the term "heterocyclic group" means, but not limited to, a ring containing one or more heteroatoms and having 2 to 60 carbon atoms. Unless otherwise stated, the term "heteroatom" as used herein refers to N, O, S, P or Si and heterocyclic group means a monocyclic, ring assemblies, a fused polycyclic system or spiro compound containing a heteroatom.

The term "heterocyclic group" used in the specification may comprise compound comprising a heteroatom group such as $SO_2$, $P=O$, etc., as the following compounds, instead of carbon forming a ring.

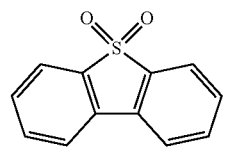 [SMILES: O=S1(=O)c2ccccc2-c2ccccc21]

The term "aliphatic ring group" as used herein refers to a cyclic hydrocarbon except for aromatic hydrocarbons, and comprises a monocyclic ring, ring assemblies, a fused polycyclic system, spiro compounds, and the like, and unless otherwise specified, it means a ring of 3 to 60 carbon atoms, but not limited thereto. For example, a fused ring formed by benzene being an aromatic ring with cyclohexane being a non-aromatic ring corresponds to aliphatic ring group.

In this specification, a 'group name' corresponding to an aryl group, an arylene group, a heterocyclic group, and the like exemplified for each symbol and its substituent may be written in the name of functional group reflecting the valence, and may also be described as the name of a parent compound. For example, in the case of phenanthrene which is a kind of aryl group, it may be described by distinguishing valence such as 'phenanthryl (group)' when it is 'monovalent group', and 'phenanthrylene (group)' when it is 'divalent group', and regardless of its valence, it may also be described as 'phenanthrene' which is a parent compound name. Similarly, in the case of pyrimidine, it may be described as 'pyrimidine' regardless of its valence, and it may also be described as the name of corresponding functional group such as pyrimidinyl (group) when it is 'monovalent group', and 'pyrimidinylene (group)' when it is 'divalent group'.

In addition, in the present specification, the numbers and alphabets indicating a position may be omitted when describing a compound name or a substituent name, For example, pyrido[4,3-d]pyrimidine, benzopuro[2,3-d]pyrimidine and 9,9-dimethyl-9H-fluorene can be described as pyridopyrimidine, benzofurropyrimidine and dimethylfluorene, respectively. Therefore, both benzo[g]quinoxaline and benzo[f] quinoxaline can be described as benzoquinoxaline.

In addition, unless otherwise expressed, where any formula of the present invention is represented by the following formula, the substituent according to the index may be defined as follows.

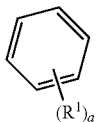

In the above formula, where a is an integer of zero, the substituent $R^1$ is absent, that is, hydrogen atoms are bonded to all the carbon constituting the benzene ring. Here, chemical formulas or compounds may be written described by omitting the indication of hydrogen bonded to carbon. In addition, one substituent $R^1$ is bonded to any carbon of the carbons forming the benzene ring when "a" is an integer of 1. Similarly, where "a" is an integer of 2 or 3, for example, as in the following formulas, substituents $R^1$s may be bonded to the carbon of the benzene ring. Also, where "a" is an integer of 4 to 6, substituents $R^1$s are bonded to the carbon of the benzene ring in a similar manner. Further, where "a" is an integer of 2 or more, $R^1$s may be the same or different from each other.

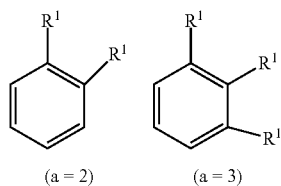

In addition, unless otherwise specified in the present specification, the ring formed by bonding between adjacent groups may be selected from the group consisting of a $C_6$-$C_{60}$ aromatic ring group, a fluorenyl group, a $C_2$-$C_{60}$ heterocyclic group containing at least one heteroatom selected from the group consisting of O, N, S, Si, and P, a $C_3$-$C_{60}$ aliphatic ring, a fused ring of a $C_3$-$C_{60}$ aliphatic ring with a $C_6$-$C_{60}$ aromatic ring group and a combination thereof.

Hereinafter, a laminated structure of the organic electric element comprising the compound of the present invention will be described with reference to FIG. 1.

In the following description of the present invention, a detailed description of known configurations and functions incorporated herein will be omitted when it may make the subject matter of the present invention rather unclear.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

FIG. 1 illustrates an example of an organic electric element according to an embodiment of the present invention.

Referring to the FIG. 1, an organic electric element 100 according to an embodiment of the present invention includes a first electrode 120 formed on a substrate 110, a second electrode 180, and an organic material layer formed between the first electrode 120 and the second electrode 180 and comprising the compound of the present invention. Here, the first electrode 120 may be an anode (positive electrode), and the second electrode 180 may be a cathode (negative electrode). In the case of an inverted organic electroluminescent element, the first electrode may be a cathode, and the second electrode may be an anode.

The organic material layer may include a hole injection layer 130, a hole transport layer 140, a light emitting layer 150, an electron transport layer 160, and an electron injection layer 170 stacked in sequence on the first electrode 120. Here, at least one layer of the organic material layer may be omitted, or a hole blocking layer, an electron blocking layer, an emission-auxiliary layer 151, an electron transport-auxiliary layer, a buffer layer 141, etc. may be further included in the organic material layer, and the electron transport layer 160 or the like may serve as a hole blocking layer.

In addition, although not shown, the organic electric element according to an embodiment of the present invention may further include a protective layer or a layer for improving luminous efficiency. The layer for improving luminous efficiency may be formed on one side of sides of the first electrode or one side of sides of the second electrode, wherein the one side is not facing the organic material layer.

The inventive compound employed in the organic material layer may be used as a material of a hole injection layer 130, a hole transport layer 140, an emission-auxiliary layer 151, an electron transport-auxiliary layer, an electron transport layer 160 or an electron injection layer 170, as host or dopant of a light emitting layer 150, or as a material of a layer for improving luminous efficiency. Preferably, compound of Formula 1 of the present invention or a mixture of compound of Formula 1 and compound of Formula 2 can be used as host of a light emitting layer.

On the other hand, even if the core is same or similar, the band gap, the electrical characteristics, the interface characteristics and the like may be different depending on which substituent is bonded at which position. Therefore, there is a need to study the selection of the core and the combination of the core and the sub-substituent bonded to the core. In particular, long life span and high efficiency can be simultaneously achieved when the optimal combination of energy levels and $T_1$ values, inherent material properties (mobility, interfacial properties, etc.) and the like among the respective layers of an organic material layer is achieved.

Therefore, the energy level and $T_1$ value between the respective layers of the organic material layer, inherent material properties (mobility, interfacial properties, etc.) and the like can be optimized by using compound of Formula 1 or a mixture of compound of Formula 1 and compound of Formula 2 as host of a light emitting layer in the present invention.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or alloy on the substrate to form the anode 120, forming the organic material layer including the hole injection layer 130, the hole transport layer 140, the light emitting layer 150, the electron transport layer 160, and the electron injection layer 170 thereon, and then depositing a material which can be used as the cathode 180, thereon. In addition, an emitting auxiliary layer 151 may be formed between a hole transport layer 140 and a light emitting layer 150, and an electron transport-auxiliary layer may be formed between a light emitting layer 150 and an electron transport layer 160.

In addition, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

In addition, the organic electric element according to the present invention may be selected from group consisting of an organic electroluminescent element, an organic solar cell, an organic photo conductor, an organic transistor, an element for monochromatic illumination and an element quantum dot display.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electric dictionary, a point-to-multipoint (PMP), a remote controller, a navigation unit, a game player, various kinds of TVs, various kinds of computers and so on.

Hereinafter, the compound according to an aspect of the present invention will be described.

Compound according to one aspect of the present invention may be represented by Formula 1.

<Formula 1>

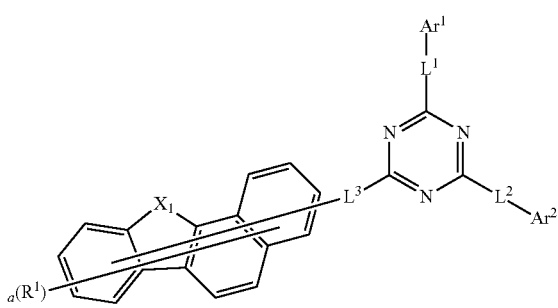

In formula 1, each of symbols may be defined as follows.

$X_1$ is O or S.

$Ar^1$ and $Ar^2$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a fused ring of a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group and a $C_6$-$C_{30}$ aryloxy group.

Where $Ar^1$ and $Ar^2$ are each an aryl group, the aryl group may be preferably a $C_6$-$C_{30}$ aryl group, more preferably a $C_6$-$C_{18}$ aryl group, for example, phenyl, biphenyl, naphthyl, terphenyl, phenanthrene, pyrene, triphenylene, and the like.

Where $Ar^1$ and $Ar^2$ are each a heterocyclic group, the heterocyclic group may be preferably a $C_2$-$C_{30}$ heterocyclic group, more preferably a $C_2$-$C_{18}$ heterocyclic group, for example, pyridine, quinoline, isoquinoline, carbazole, phenylcarbazole, dibenzothiophene, dibenzofuran, dibenzodioxin and the like. Where $Ar^1$ and $Ar^2$ are each a fluorenyl group, the fluorenyl group may be 9,9-diphenylfluorene, 9,9-dimethylfluorene and the like. Where $Ar^1$ and $Ar^2$ are each aliphatic ring, the aliphatic ring may be preferably a $C_3$-$C_{30}$ aliphatic ring, more preferably, a $C_3$-$C_{12}$ aliphatic ring, for example, cyclohexane, cyclohexylcyclohexane, or the like. Where $Ar^1$ and $Ar^2$ are each an alkyl group, the alkyl group may be preferably a $C_2$-$C_{10}$ alkyl group, for example, methyl, t-butyl and the like. Where $Ar^1$ and $Ar^2$ are each an alkenyl group, the alkenyl group may be preferably a $C_2$-$C_{10}$ alkenyl group, for example, ethene, propene and the like.

$L^1$ to $L^3$ are each independently selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, a $C_3$-$C_{60}$ aliphatic ring, and a fused ring of a $C_3$-$C_{60}$ aliphatic ring with a $C_6$-$C_{60}$ aromatic ring.

Where $L^1$ to $L^3$ are each an arylene group, the arylene group may be preferably a $C_6$-$C_{30}$ arylene group, more preferably a $C_6$-$C_{18}$ arylene group, for example, phenyl, biphenyl, naphthyl, terphenyl and the like. Where $L^1$ to $L^3$ are each a heterocyclic group, the heterocyclic group may be preferably a $C_2$-$C_{30}$ heterocyclic group, more preferably a $C_2$-$C_{18}$ heterocyclic group, for example, carbazole, phenylcarbazole, dibenzofuran, dibenzothiophene and the like.

$R^1$ is selected from the group consisting of hydrogen, deuterium, halogen, a cyano group, a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a fused ring of a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and —L'-N($R_a$)($R_b$), and adjacent groups may be bonded to each other to form a ring.

a is an integer of 0-9, and where a is an integer of 2 or more, each of a plurality of $R^1$s are the same as or different from each other.

The ring formed by bonding between neighboring $R^1$s may be a $C_6$-$C_{60}$ aromatic ring group, a fluorenyl group, a $C_2$-$C_{60}$ heterocyclic group containing at least one heteroatom of O, N, S, Si and P, a $C_3$-$C_{60}$ aliphatic ring or a fused ring of a $C_3$-$C_{60}$ aliphatic ring with a $C_6$-$C_{60}$ aromatic ring and the like. Where an aromatic ring is formed by bonding between neighboring $R^1$s, the aromatic ring may be preferably a $C_6$-$C_{30}$ aromatic ring group, more preferably, a $C_6$-$C_{14}$ aromatic ring group, for example, benzene, naphthalene, phenanthrene or the like.

Where $R^1$ is an aryl group, the aryl group may be preferably a $C_6$-$C_{30}$ aryl group, more preferably a $C_6$-$C_{18}$ aryl group, for example, phenyl, naphthyl, biphenyl, terphenyl, phenanthrene, and the like.

L' is selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, a $C_3$-$C_{60}$ aliphatic ring, and a fused ring of a $C_3$-$C_{60}$ aliphatic ring with a $C_6$-$C_{60}$ aromatic ring.

$R_a$ and $R_b$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, and a fused ring of a $C_3$-$C_{60}$ aliphatic ring with a $C_6$-$C_{60}$ aromatic ring.

Preferably, compound derived from Formula 1-1 is excluded from Formula 1.

<Formula 1-1>

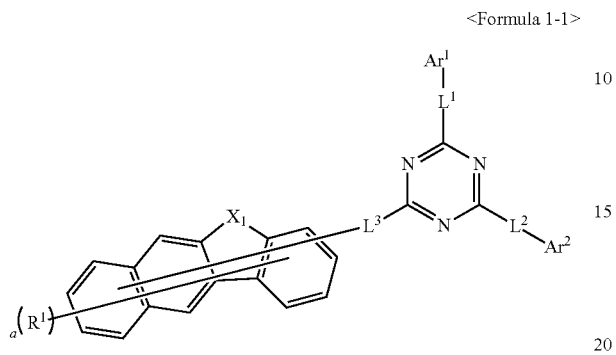

In Formula 1-1, each symbol is as defined for Formula 1. Preferably, $Ar^1$ and $Ar^2$ are each independently selected from the group consisting of a $C_6$-$C_{18}$ aryl group, a fluorenyl group, a $C_2$-$C_{16}$ heterocyclic group comprising at least one heteroatom selected from the group consisting of O, N, S, Si and P, a $C_3$-$C_{60}$ aliphatic ring, a fused ring of a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group and a $C_6$-$C_{30}$ aryloxy group.

Formula 1 may be represented by one of Formula 1-A, 1-A-1 to 1-A-6.

<Formula 1-A>

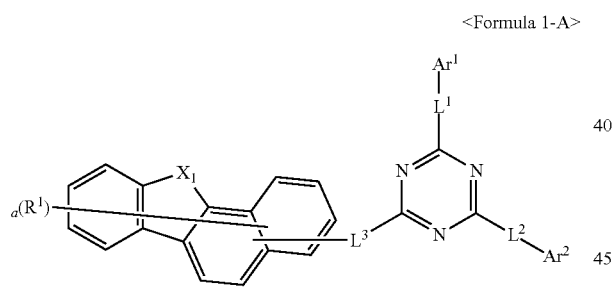

<Formula 1-A-1>

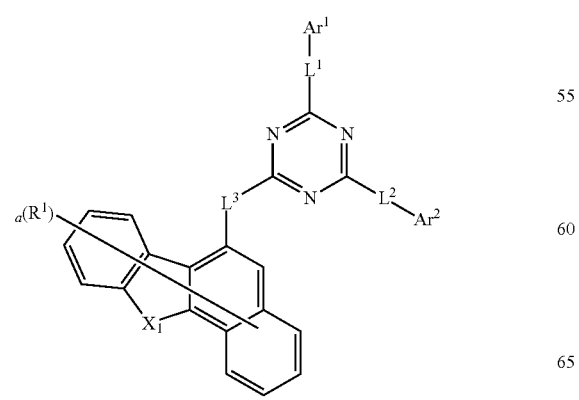

<Formula 1-A-2>

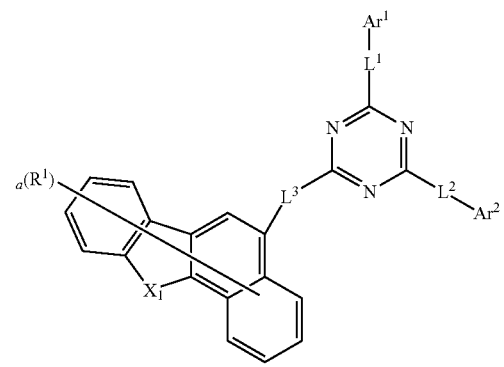

<Formula 1-A-3>

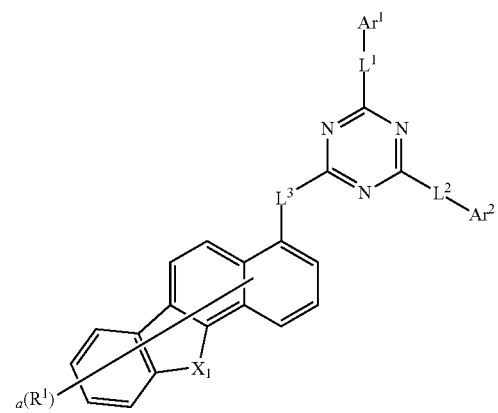

<Formula 1-A-4>

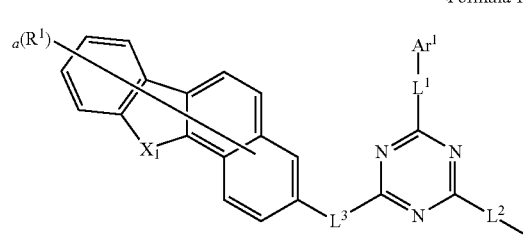

<Formula 1-A-5>

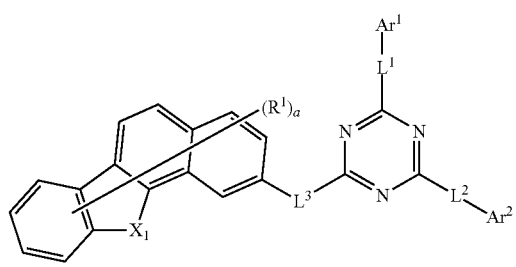

<Formula 1-A-6>

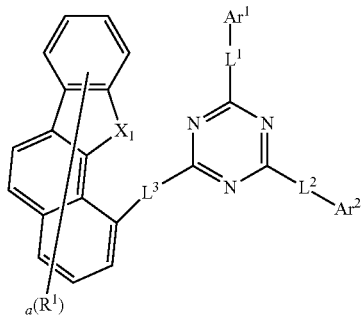

In Formulas 1-A, 1-A-1 to 1-A-6, $Ar^1$, $Ar^2$, $L^1$-$L^3$, $X_1$, $R^1$ and a are the same as defined for Formula 1.

Preferably, when the compound represented by Formula 1-A is used as a single host material, a compound in which both the polycyclic ring including $X_1$ and the triazine moiety are adjacent to the same ring of $L^3$ may be excluded. For example, the following compound may be excluded from Formula 1-A.

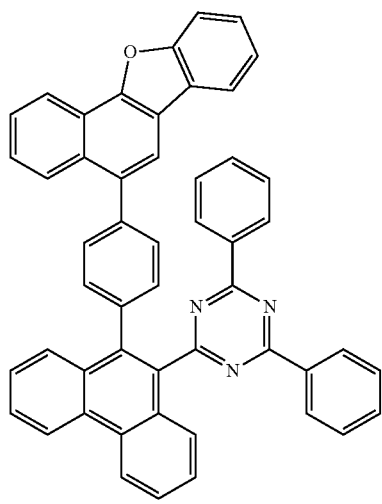 [SMILES: c1ccc(-c2nc(-c3ccccc3)nc(-c3c(-c4ccc(-c5cc6c7ccccc7oc6c6ccccc56)cc4)c4ccccc4c4ccccc34)n2)cc1]

Preferably, Formula 1-A may be Formula 1-A-7.

<Formula 1-A-7>

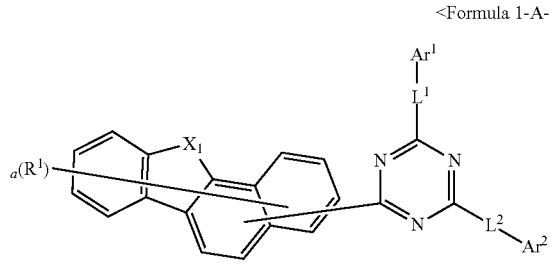

In Formula 1-A-7, $Ar^1$, $Ar^2$, $L^2$, $X_1$, $R^1$ and a are the same as defined for Formula 1.

In addition, preferably, in Formula 1-A, $L^3$ may be a $C_{10}$-$C_{20}$ arylene group; or a $C_7$-$C_{20}$ heterocyclic group containing at least one heteroatom of O, N, S, Si and P, more preferably, the arylene group and the heterocyclic group are a condensed ring condensed with two or more rings.

Also, preferably, in Formula 1-A, $L^1$-$L^3$ may be a single bond or an aryl group (except for a phenyl group).

In addition, Formula 1 may be represented by Formula 1-B or 1-C.

<Formula 1-B>

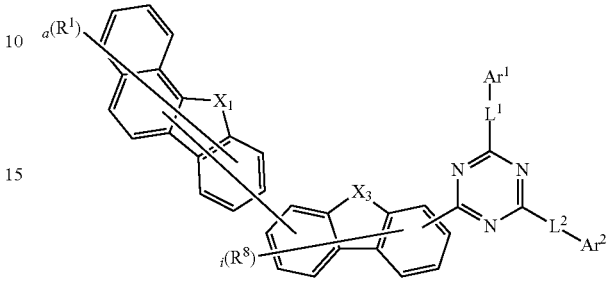

<Formula 1-C>

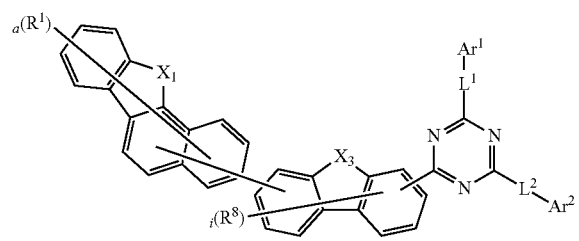

In Formula 1-B or 1-C, each of symbols may be defined as follows.

$Ar^1$, $Ar^2$, $L^1$, $L^2$, $X_1$, $R^1$ and a are the same as defined for Formula 1.

$X_3$ is O or S.

$R^8$ is independently selected from the group consisting of hydrogen, deuterium, halogen, a cyano group, a nitro group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a fused ring of a $C_3$-$C_{20}$ aliphatic ring with a $C_6$-$C_{20}$ aromatic ring, a $C_1$-$C_{20}$ alkyl group, a $C_2$-$C_{20}$ alkenyl group, a $C_2$-$C_{20}$ alkynyl group, a $C_1$-$C_{20}$ alkoxyl group, a $C_6$-$C_{30}$ aryloxy group and -$L^a$-N($R^a$)($R^b$), and adjacent groups may be linked to each other to form a ring.

i is an integer of 0-6, and where i is an integer of 2 or more, each of a plurality of $R^8$s are the same as or different from each other.

$L^a$ is selected from the group consisting of a single bond, a $C_6$-$C_{20}$ arylene group, a fluorenylene group, a $C_2$-$C_{20}$ heterocyclic group comprising at least one heteroatom selected from the group consisting of O, N, S, Si and P, a $C_3$-$C_{20}$ aliphatic ring, and a combination thereof.

$R^a$ and $R_b$ are each independently selected from the group consisting of a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, and a combination thereof.

In addition, Formula 1 may be represented by one of Formula 1-D, 1-D-1 and 1-D-2.

<Formula 1-D>

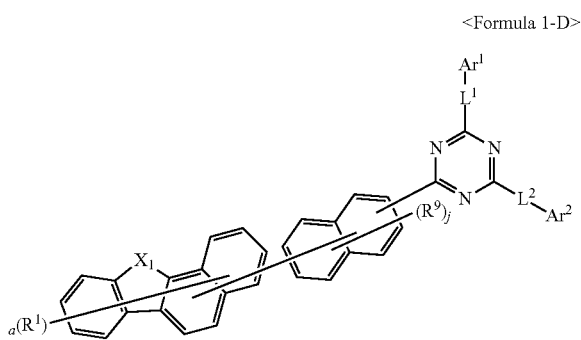

-continued

<Formula 1-D-1>

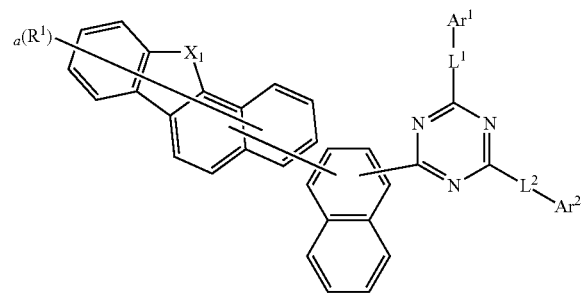

<Formula 1-D-2>

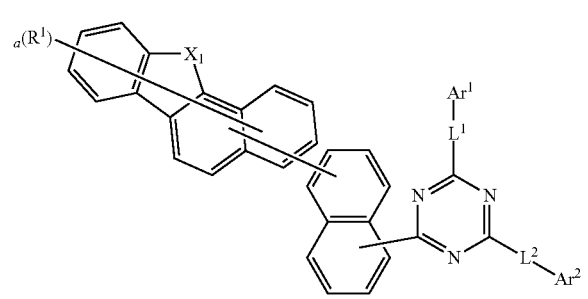

In Formula 1-D, 1-D-1 and 1-D-2, each of symbols may be defined as follows.

$Ar^1$, $Ar^2$, $L^2$, $X_1$, $R^1$ and a are the same as defined for Formula 1.

$R^9$ is independently selected from the group consisting of hydrogen, deuterium, halogen, a cyano group, a nitro group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a fused ring of a $C_3$-$C_{20}$ aliphatic ring with a $C_6$-$C_{20}$ aromatic ring, a $C_1$-$C_{20}$ alkyl group, a $C_2$-$C_{20}$ alkenyl group, a $C_2$-$C_{20}$ alkynyl group, a $C_1$-$C_{20}$ alkoxyl group, a $C_6$-$C_{30}$ aryloxy group and -$L^a$-$N(R^a)(R^b)$, and adjacent groups may be linked to each other to form a ring.

j is an integer of 0-6, and where j is an integer of 2 or more, each of a plurality of $R^9$s are the same as or different from each other.

$L^a$, $R^a$ and $R_b$ are the same as defined for Formula 1-B.

In addition, Formula 1 may be represented by Formula 1-E.

<Formula 1-E>

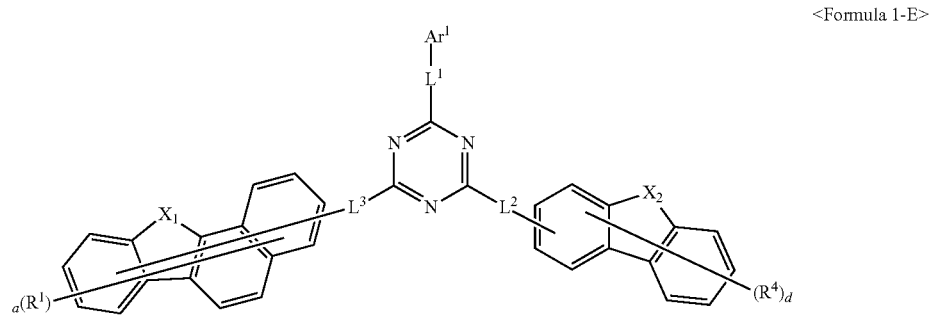

In Formula 1-E, $Ar^1$, $L^1$-$L^3$, $X_1$, $R^1$ and a are the same as defined for Formula 1, and $X_2$ is O or S.

$R^4$ is independently selected from the group consisting of hydrogen, deuterium, halogen, a cyano group, a nitro group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a ring of a $C_3$-$C_{20}$ aliphatic ring with a $C_6$-$C_{20}$ aromatic ring, a $C_1$-$C_{20}$ alkyl group, a $C_2$-$C_{20}$ alkenyl group, a $C_2$-$C_{20}$ alkynyl group, a $C_1$-$C_{20}$ alkoxyl group, a $C_6$-$C_{30}$ aryloxy group and -$L^a$-$N(R^a)(R^b)$, and adjacent groups may be linked to each other to form a ring. Here, $L^a$, $R^a$ and $R_b$ are the same as defined for Formula 1-B.

d is an integer of 0-7, and where d is an integer of 2 or more, each of a plurality of $R^4$s are the same as or different from each other.

Preferably, Formula 1-E may be represented by one of Formulas 1-E-1 to 1-E-7.

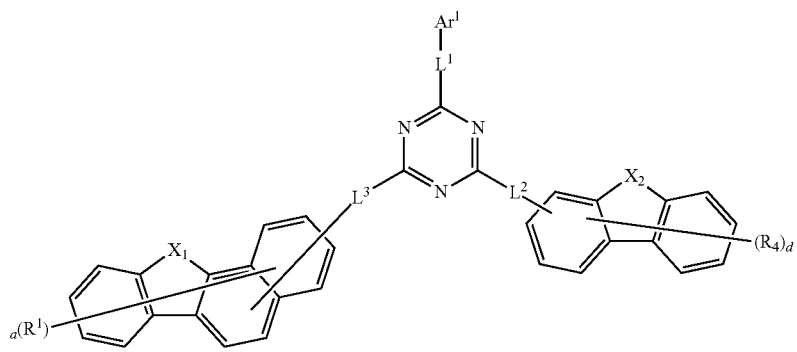
<Formula 1-E-1>
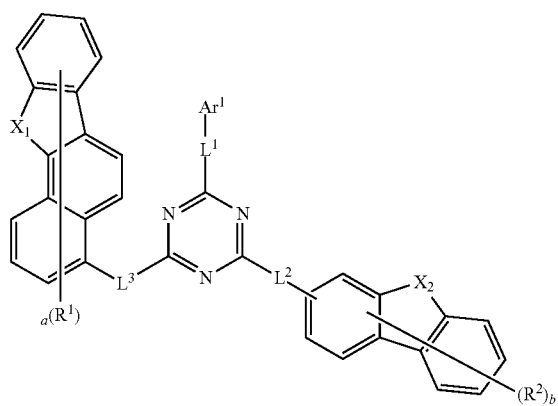
<Formula 1-E-2>
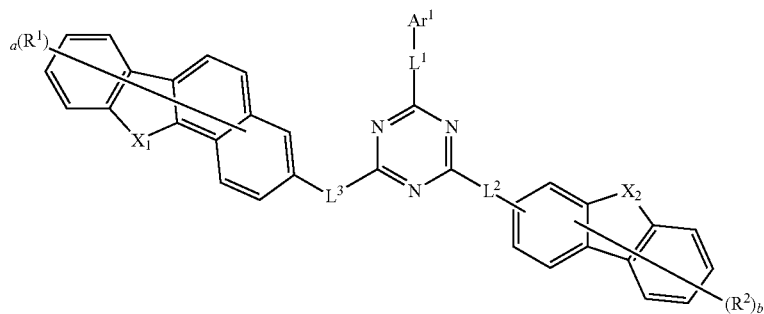
<Formula 1-E-3>
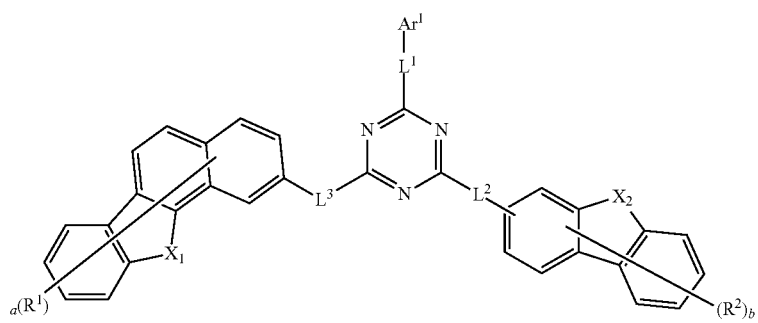
<Formula 1-E-4>

-continued

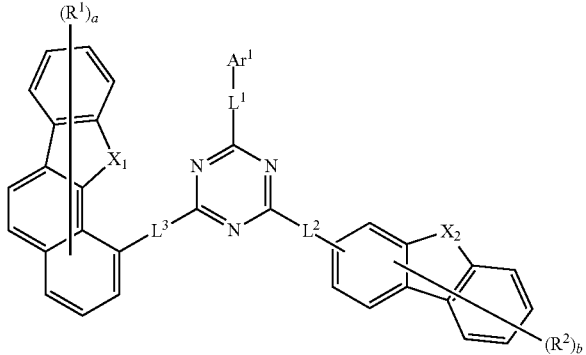

<Formula 1-E-5>

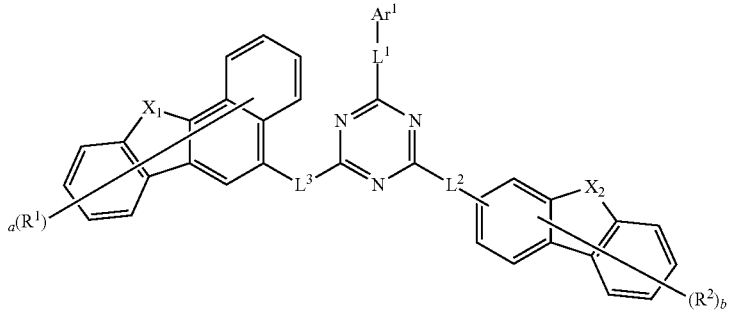

<Formula 1-E-6>

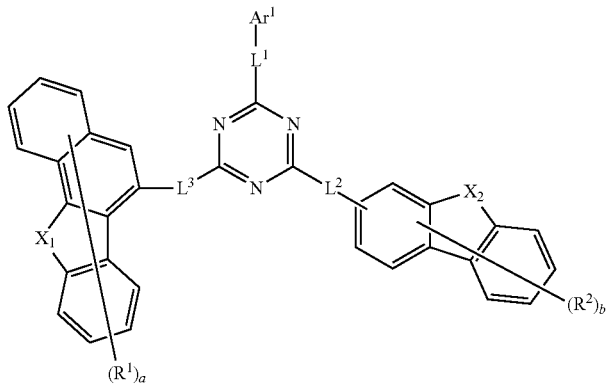

<Formula 1-E-7>

In Formulas 1-E-1 to 1-E-7, each of symbols may be defined as follows.

$Ar^1$, $L^1$-$L^3$, $X_1$, $R^1$ and a are the same as defined for Formula 1, and $X_2$ is O or S.

$R_4$ and $R^2$ may be defined the same as $R^4$ defined in Formula 1-E. Thant is, $R_4$ and $R^2$ are each independently selected from the group consisting of hydrogen, deuterium, halogen, a cyano group, a nitro group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a ring of a $C_3$-$C_{20}$ aliphatic ring with a $C_6$-$C_{20}$ aromatic ring, a $C_6$-$C_{20}$ alkyl group, a $C_2$-$C_{20}$ alkenyl group, a $C_2$-$C_{20}$ alkynyl group, a $C_6$-$C_{20}$ alkoxyl group, a $C_6$-$C_{30}$ aryloxy group and -$L^a$-N($R^a$)($R^b$), and adjacent groups may be linked to each other to form a ring.

b and d are each an integer of 0-7, and where b is an integer of 2 or more, each of a plurality of $R^2$s are the same as or different from each other, where d is an integer of 2 or more, each of a plurality of $R_4$s are the same as or different from each other.

Preferably, in Formulas 1-A, 1-B and 1-C, $Ar^1$ and $Ar^2$ may be different from each other, $Ar^1$ or $Ar^2$ may be a naphthyl group.

In addition, preferably, in Formulas 1-B and 1-C, $Ar^1$ and $Ar^2$ may be each independently an aryl group.

Preferably, the ring formed by bonding between neighboring groups may be a $C_6$-$C_{60}$ aromatic ring group, a fluorenyl group, a $C_2$-$C_{60}$ heterocyclic group containing at least one heteroatom of O, N, S, Si and P, a $C_3$-$C_{60}$ aliphatic ring or a fused ring of a $C_3$-$C_{60}$ aliphatic ring with a $C_6$-$C_{60}$ aromatic ring and the like. Where an aromatic ring is formed by bonding between neighboring groups, the aromatic ring may be preferably a $C_6$-$C_{30}$ aromatic ring group, more preferably, a $C_6$-$C_{14}$ aromatic ring group, for example, benzene, naphthalene, phenanthrene or the like.

Preferably, each symbol in the above Formulas may be further substituted. For example, in Formula 1, Formulas 1-A, 1-B, 1-C, 1-D and 1-E, Formulas 1-A-1 to 1-A-7, Formula 1-D-1, Formula 1-D-2, Formulas 1-E-1 to 1-E-7, $Ar^1$, $Ar^2$, $L^1$-$L^3$, L', $L^a$, $R^1$, $R^2$, $R^4$, $R_4$, $R^8$, $R^9$, $R_a$, $R_b$, $R^a$, $R^b$, and the ring formed by bonding between adjacent groups may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ aliphatic ring group, a $C_7$-$C_{20}$ arylalkyl group and $C_8$-$C_{20}$ arylalkenyl group.

In another aspect of the present invention, the present invention provides an organic electric element comprising a first electrode, a second electrode, and an organic material layer formed between the first electrode and the second electrode, wherein the organic material layer comprises compound represented by Formula 1, preferably, one of Formula 1-A to Formula 1-C, more preferably, compound represented by one of Formula 1-A to Formula 1-C is comprised in a light emitting layer of the organic material layer.

In another aspect of the present invention, the present invention provides an organic electric element comprising a first electrode, a second electrode, and an organic material layer formed between the first electrode and the second electrode, wherein the organic material layer comprises a phosphorescent light emitting layer, and the host of the phosphorescent light emitting layer comprises a first compound represented by Formula 1 and a second compound represented by Formula 2.

<Formula 2>

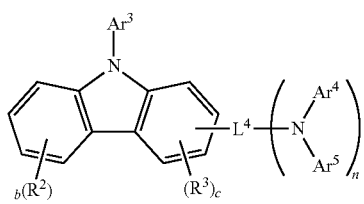

In Formula 2, each of symbols may be defined as follows.

$Ar^3$ to $Ar^5$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a fused ring of a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group and a $C_6$-$C_{30}$ aryloxy group, and $Ar^4$ and $Ar^5$ may be bonded to each other to form a ring. Here, the formed ring is a hetero ring containing one or more N.

n is an integer of 0-3, and where n is an integer of 2 or more, each of a plurality of $Ar^4$s, and each of a plurality of $Ar^5$s are the same as or different from each other.

Where $Ar^3$ to $Ar^5$ are each an aryl group, the aryl group may be preferably a $C_6$-$C_{30}$ aryl group, more preferably a $C_6$-$C_{18}$ aryl group, for example, phenyl, biphenyl, naphthyl, terphenyl, phenanthrene and the like. Where $Ar^3$ to $Ar^5$ are each a heterocyclic group, the heterocyclic group may be preferably a $C_2$-$C_{30}$ heterocyclic group, more preferably a $C_2$-$C_{18}$ heterocyclic group, for example, pyridine, pyrimidine, triazine, carbazole, phenylcarbazole, dibenzothiophene, dibenzofuran and the like. Where $Ar^3$ to $Ar^5$ are each a fluorenyl group, the fluorenyl group may be 9,9-dimethylfluorene, 9,9-diphenylfluorene, 9,9'-spirobifluorene and the like.

$L^4$ is selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, a $C_3$-$C_{60}$ aliphatic ring, and a fused ring of a $C_3$-$C_{60}$ aliphatic ring with a $C_6$-$C_{60}$ aromatic ring.

Where $L^4$ is an arylene group, the arylene group may be preferably a $C_6$-$C_{30}$ arylene group, more preferably a $C_6$-$C_{18}$ arylene group, for example, phenyl, biphenyl, naphthyl, terphenyl and the like. Where $L^4$ is a heterocyclic group, the heterocyclic group may be preferably a $C_2$-$C_{30}$ heterocyclic group, more preferably a $C_2$-$C_{18}$ heterocyclic group, more preferably a $C_2$-$C_{12}$ heterocyclic group, for example, pyridine, triazine, dibenzothiophene, dibenzofuran and the like. Where $L^4$ is a fluorenyl group, the fluorenyl group may be 9,9-dimethylfluorene, 9,9-diphenylfluorene, 9,9'-spirobifluorene and the like.

$R^2$ and $R^3$ are each independently selected from the group consisting of hydrogen, deuterium, halogen, a cyano group, a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a fused ring of a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R^a$)($R^b$), and adjacent groups may be bonded to each other to form a ring. Here, the ring formed by bonding between neighboring groups may be a $C_6$-$C_{60}$ aromatic ring group, a fluorenyl group, a $C_2$-$C_{60}$ heterocyclic group containing at least one heteroatom of O, N, S, Si and P, a $C_3$-$C_{60}$ aliphatic ring or a fused ring of a $C_3$-$C_{60}$ aliphatic ring with a $C_6$-$C_{60}$ aromatic ring and the like.

Where an aromatic ring is formed by bonding between neighboring $R^2$s or neighboring $R^3$s, the aromatic ring may be preferably a $C_6$-$C_{30}$ aromatic ring group, more preferably, a $C_6$-$C_{14}$ aromatic ring group, for example, benzene, naphthalene, phenanthrene or the like.

Where an aromatic ring is formed by bonding between neighboring $R^2$s or neighboring $R^3$s, the aromatic ring may be preferably a $C_6$-$C_{30}$ aromatic ring group, more preferably, a $C_6$-$C_{14}$ aromatic ring group, for example, benzene, naphthalene, phenanthrene or the like.

b is an integer of 0-4, c is an integer of 0-3, and where each of these is an integer of 2 or more, each of a plurality of $R^2$s, and each of a plurality of $R^3$s are the same as or different from each other, L' is selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, a $C_3$-$C_{60}$ aliphatic ring, and a fused ring of a $C_3$-$C_{60}$ aliphatic ring with a $C_6$-$C_{60}$ aromatic ring.

$R_a$ and $R_b$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, and a fused ring of a $C_3$-$C_{60}$ aliphatic ring with a $C_6$-$C_{60}$ aromatic ring.

Formula 2 may be represented by Formula 2-A or Formula 2-B.

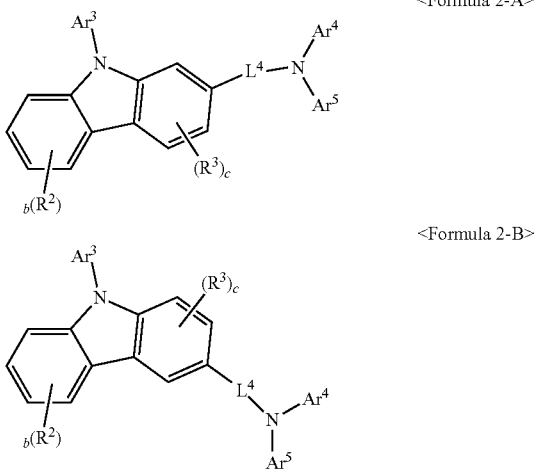

<Formula 2-A>

<Formula 2-B>

In Formulas 2-A and 2-B, wherein, $L^4$, $Ar^3$ to $Ar^5$, $R^2$, $R^3$, b and c are the same as defined for Formula 2.

In addition, Formula 2 may be represented by one of Formula 2-C to Formula 2-F.

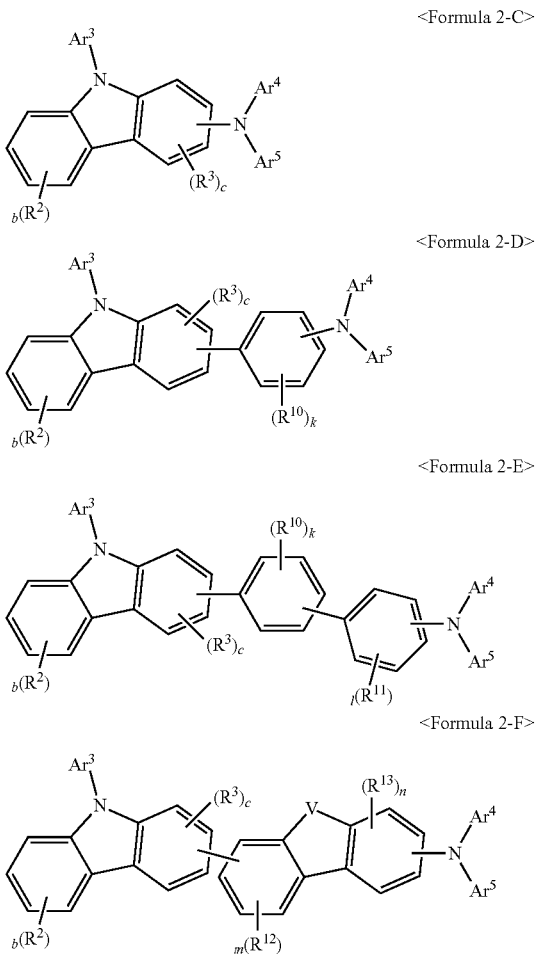

<Formula 2-C>

<Formula 2-D>

<Formula 2-E>

<Formula 2-F>

In Formulas 2-C to Formula 2-F, each symbol can be defined as follows.

$Ar^3$ to $Ar^5$, $R^2$, $R^3$, b and c are the same as defined for Formula 2.

$R^{10}$ to $R^{13}$ are each independently selected from the group consisting of hydrogen, deuterium, halogen, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_6$-$C_{20}$ alkyl group, a $C_2$-$C_{20}$ alkenyl group, a $C_2$-$C_{20}$ alkynyl group, a $C_6$-$C_{20}$ alkoxyl group, a $C_6$-$C_{20}$ aryloxy group, -$L^a$-N($R^a$)($R^b$) and a combination thereof, and adjacent groups may be linked to each other to form a ring.

The ring formed by bonding between neighboring groups may be a $C_6$-$C_{60}$ aromatic ring group, a fluorenyl group, a $C_2$-$C_{60}$ heterocyclic group containing at least one heteroatom of O, N, S, Si and P, a $C_3$-$C_{60}$ aliphatic ring or a fused ring of a $C_3$-$C_{60}$ aliphatic ring with a $C_6$-$C_{60}$ aromatic ring and the like.

Where an aromatic ring is formed by bonding between neighboring $R^{10}$s, $R^{11}$s, $R^{12}$s or neighboring $R^{13}$s, the aromatic ring may be preferably a $C_6$-$C_{30}$ aromatic ring group, more preferably, a $C_6$-$C_{14}$ aromatic ring group, for example, benzene, naphthalene, phenanthrene or the like.

k and l are each an integer of 0-4, n and m are each an integer of 0-3, and where each of these is an integer of 2 or more, each of a plurality of $R^{10}$, each of a plurality of $R^{11}$, each of a plurality of $R^{12}$, and each of a plurality of $R^{13}$ are the same as or different from each other.

V is N-($L^a$-$Ar^a$), O, S or C(R')(R").

R' and R" are each independently selected from the group consisting of hydrogen, deuterium, halogen, a cyano group, a nitro group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a fused ring of a $C_3$-$C_{20}$ aliphatic ring with a $C_6$-$C_{20}$ aromatic ring, a $C_1$-$C_{20}$ alkyl group, a $C_2$-$C_{20}$ alkenyl group, a $C_2$-$C_{20}$ alkynyl group, a $C_1$-$C_{20}$ alkoxyl group, a $C_6$-$C_{20}$ aryloxy group and -$L^a$-N($R^a$)($R^b$), and R' and R" may be linked to each other to form a ring.

$Ar^a$ is selected from the group consisting of a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, and a combination thereof.

$L^a$ is selected from the group consisting of a single bond, a $C_6$-$C_{20}$ arylene group, a fluorenylene group, a $C_2$-$C_{20}$ heterocyclic group comprising at least one heteroatom selected from the group consisting of O, N, S, Si and P, a $C_3$-$C_{20}$ aliphatic ring, and a combination thereof.

$R^a$ and $R_b$ are each independently selected from the group consisting of a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, and a combination thereof.

Formula 2 may be represented by one of the following Formula 2-G to Formula 2-T.

<Formula 2-G>

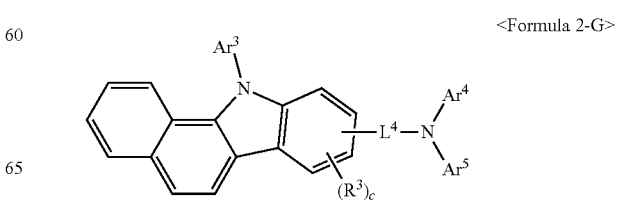

-continued
<Formula 2-H>
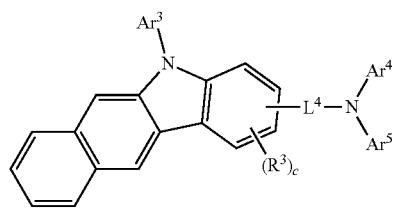
<Formula 2-I>
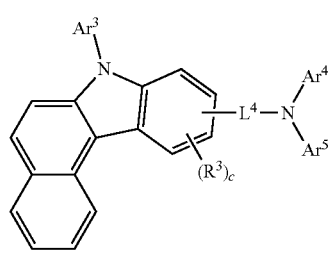
<Formula 2-J>
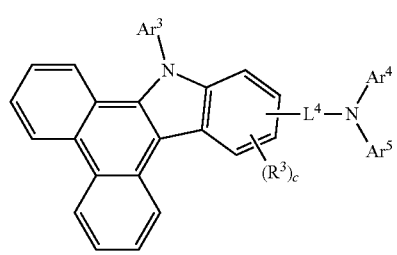
<Formula 2-K>
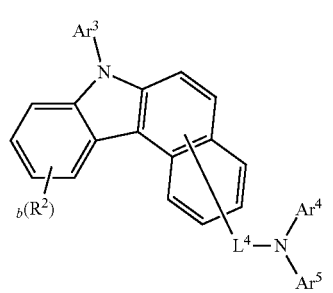
<Formula 2-L>
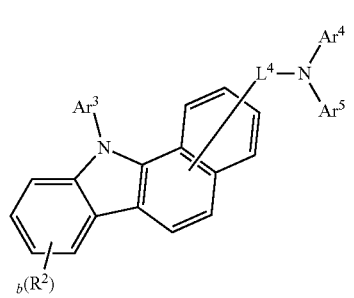
<Formula 2-M>
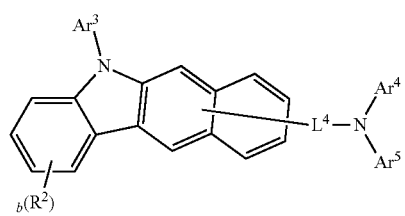
-continued
<Formula 2-N>
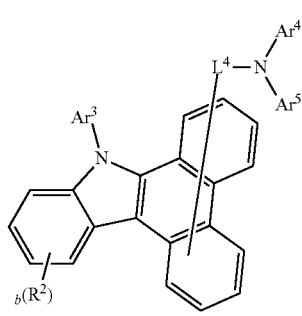
<Formula 2-O>
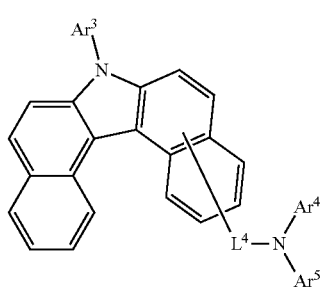
<Formula 2-P>
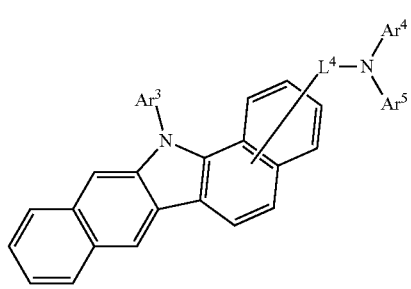
<Formula 2-Q>
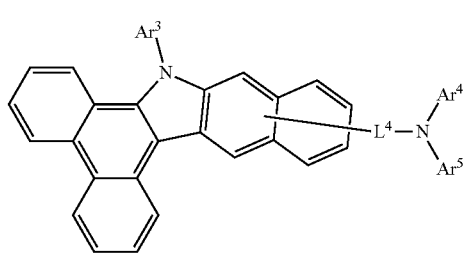
<Formula 2-R>
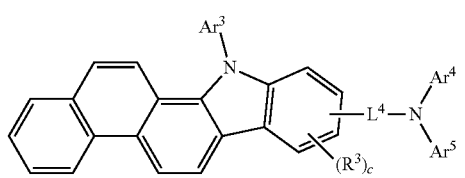
<Formula 2-S>
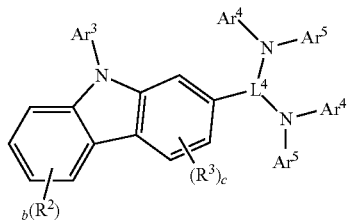

-continued

<Formula 2-T>

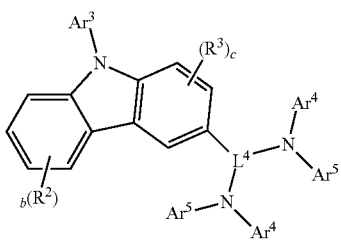

Ar

In Formulas 2-G to 2-T, $Ar^3$ to $Ar^5$, $L^4$, $R^2$, $R^3$, b and c are the same as defined for Formula 2.

Formula 2 may be represented by Formula 2-U.

<Formula 2-U>

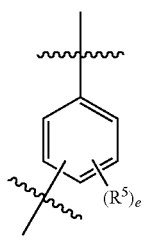

In Formula 2-U, each of symbols may be defined as follows.

$Ar^3$, $Ar^5$, $L^4$, $R^2$, $R^3$, b, c and n are the same as defined for Formula 2.

U is $N-(L^a-Ar^a)$, O, S or C(R')(R'').

$R^{14}$ and $R^{15}$ are each independently selected from the group consisting of hydrogen, deuterium, halogen, a cyano group, a nitro group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a fused ring of a $C_3$-$C_{20}$ aliphatic ring with a $C_6$-$C_{20}$ aromatic ring, a $C_6$-$C_{20}$ alkyl group, a $C_2$-$C_{20}$ alkenyl group, a $C_2$-$C_{20}$ alkynyl group, a $C_6$-$C_{20}$ alkoxyl group, a $C_6$-$C_{20}$ aryloxy group and $-L^a-N(R^a)(R^b)$, and adjacent groups may be linked to each other to form a ring. The ring formed by bonding between neighboring groups may be a $C_6$-$C_{60}$ aromatic ring group, a fluorenyl group, a $C_2$-$C_{60}$ heterocyclic group containing at least one heteroatom of O, N, S, Si and P, a $C_3$-$C_{60}$ aliphatic ring or a fused ring of a $C_3$-$C_{60}$ aliphatic ring with a $C_6$-$C_{60}$ aromatic ring and the like.

Where an aromatic ring is formed by bonding between neighboring $R^{14}$s or neighboring $R^{15}$s, the aromatic ring may be preferably a $C_6$-$C_{30}$ aromatic ring group, more preferably, a $C_6$-$C_{14}$ aromatic ring group, for example, benzene, naphthalene, phenanthrene or the like.

o is an integer of 0-3, p is an integer of 0-4, and where each of these is an integer of 2 or more, each of a plurality of $R^{14}$, and each of a plurality of $R^{15}$ are the same as or different from each other.

R' and R'' are each independently selected from the group consisting of hydrogen, deuterium, halogen, a cyano group, a nitro group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a fused ring of a $C_3$-$C_{20}$ aliphatic ring with a $C_6$-$C_{20}$ aromatic ring, a $C_6$-$C_{20}$ alkyl group, a $C_2$-$C_{20}$ alkenyl group, a $C_2$-$C_{20}$ alkynyl group, a $C_6$-$C_{20}$ alkoxyl group, a $C_6$-$C_{30}$ aryloxy group, and $-L^a-N(R^a)(R^b)$, and R' and R'' may be linked to each other to form a ring.

$Ar^a$ is selected from the group consisting of a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, and a combination thereof.

$L^a$ is selected from the group consisting of a single bond, a $C_6$-$C_{20}$ arylene group, a fluorenylene group, a $C_2$-$C_{20}$ heterocyclic group comprising at least one heteroatom selected from the group consisting of O, N, S, Si and P, a $C_3$-$C_{20}$ aliphatic ring, and a combination thereof.

$R^a$ and $R_b$ are each independently selected from the group consisting of a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, and a combination thereof.

Each symbol in Formula 2 and Formulas 2-A to 2-U may be further substituted. For example, $Ar^3$-$Ar^5$, $R^2$, $R^3$, $R^{10}$ to $R^{15}$, $L^4$, L', $L^a$, $Ar^a$, $R_a$, $R_b$, R', R'', $R^a$, $R^b$ and the ring formed by bonding between adjacent groups may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ aliphatic ring group, a $C_7$-$C_{20}$ arylalkyl group and $C_8$-$C_{20}$ arylalkenyl group.

Preferably, in Formulas 1 and 2, L' to $L^4$ may be each independently one of the following Formulas b-1 to b-13.

<Formula b-1>

<Formula b-2>

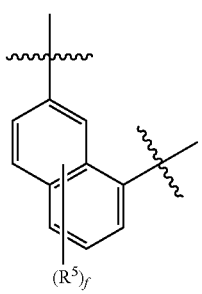

<Formula b-3>
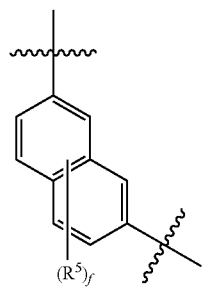

<Formula b-4>
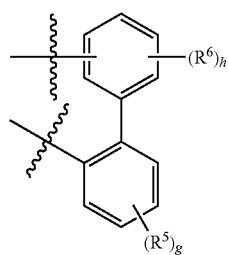

<Formula b-5>
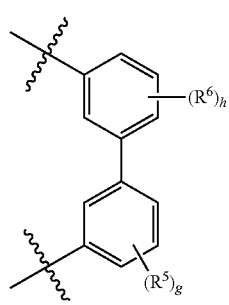

<Formula b-6>
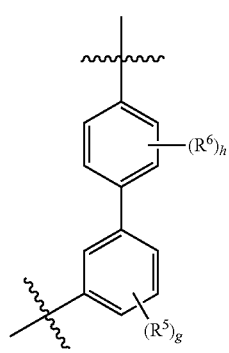

<Formula b-7>
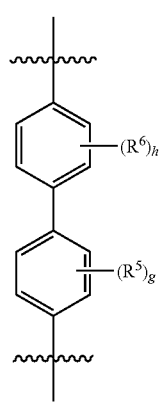

<Formula b-8>
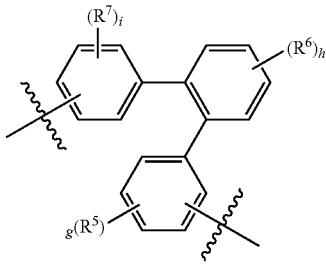

<Formula b-9>
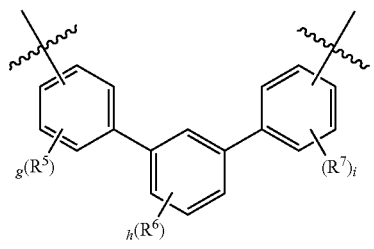

<Formula b-10>
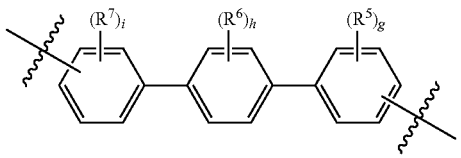

<Formula b-11>
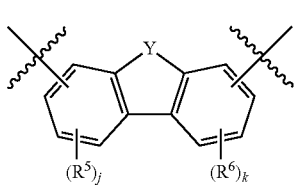

<Formula b-12>
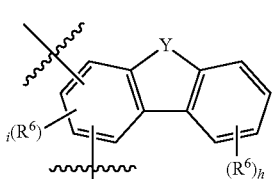

<Formula b-13>
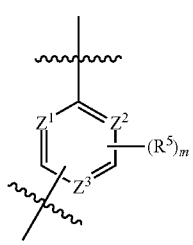

In Formulas b-1 to b-13, each of symbols may be defined as follows.

$R^5$ to $R^7$ are each independently selected from the group consisting of hydrogen, deuterium, halogen, a cyano group, a nitro group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a fused ring of a $C_3$-$C_{20}$ aliphatic ring with a $C_6$-$C_{20}$ aromatic ring, a $C_1$-$C_{20}$ alkyl group, a $C_2$-$C_{20}$ alkenyl group, a $C_2$-$C_{20}$ alkynyl group, a $C_1$-$C_{20}$ alkoxyl group, a $C_6$-$C_{30}$ aryloxy group and -$L^a$-N($R^a$)($R^b$), and adjacent groups may be bonded to each other to form a ring. The ring formed by bonding between neighboring groups may be a $C_6$-$C_{60}$ aromatic ring group, a fluorenyl group, a $C_2$-$C_{60}$ heterocyclic group containing at least one heteroatom of O, N, S, Si and P, a $C_3$-$C_{60}$ aliphatic ring or a fused ring of a $C_3$-$C_{60}$ aliphatic ring with a $C_6$-$C_{60}$ aromatic ring and the like.

Where an aromatic ring is formed by bonding between neighboring $R^5$s, neighboring $R^6$s or neighboring $R^7$s, the aromatic ring may be preferably a $C_6$-$C_{30}$ aromatic ring group, more preferably, a $C_6$-$C_{14}$ aromatic ring group, for example, benzene, naphthalene, phenanthrene or the like.

Y is N-($L^a$-$Ar^a$), O, S or C(R')(R").

$Z^1$ to $Z^3$ are each independently C, C(R') or N, and at least one of $Z^1$ to $Z^3$ is N.

f is an integer of 0-6, e, g, h and i are each an integer of 0-4, j and k are each an integer of 0-3, I is an integer of 0-2, m is an integer of 0-3, and where each of these is an integer of 2 or more, each of a plurality of $R^5$, each of a plurality of $R^6$, and each of a plurality of $R^7$ are the same as or different from each other.

R' and R" are each independently selected from the group consisting of hydrogen, deuterium, halogen, a cyano group, a nitro group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a fused ring of a $C_3$-$C_{20}$ aliphatic ring with a $C_6$-$C_{20}$ aromatic ring, a $C_6$-$C_{20}$ alkyl group, a $C_2$-$C_{20}$ alkenyl group, a $C_2$-$C_{20}$ alkynyl group, a $C_6$-$C_{20}$ alkoxyl group, a $C_6$-$C_{30}$ aryloxy group, and -$L^a$-N($R^a$)($R^b$).

R' and R" in C(R')(R") may be linked to each other to form a ring, and adjacent R's in C(R') may be linked to each other to form a ring.

$Ar^a$ is selected from the group consisting of a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, and a combination thereof.

$L^a$ is selected from the group consisting of a single bond, a $C_6$-$C_{20}$ arylene group, a fluorenylene group, a $C_2$-$C_{20}$ heterocyclic group comprising at least one heteroatom selected from the group consisting of O, N, S, Si and P, a $C_3$-$C_{20}$ aliphatic ring, and a combination thereof.

$R^a$ and $R_b$ are each independently selected from the group consisting of a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, and a combination thereof.

$R^5$ to $R^7$, $L^a$, $Ar^a$, R', R", $R^a$, $R^b$ and the ring formed by bonding between adjacent groups may be each optionally substituted with one or more substituents selected from the group consisting of deuterium, halogen, a silane group unsubstituted or substituted with a $C_6$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_6$-$C_{20}$ aryloxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ aliphatic ring group, a $C_7$-$C_{20}$ arylalkyl group and $C_8$-$C_{20}$ arylalkenyl group.

Specifically, the compound represented by formula 1 may be one of the following compounds, but there is no limitation thereto.

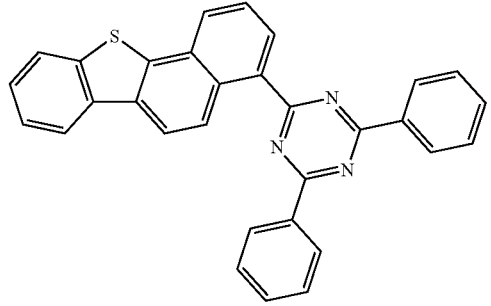

1-1

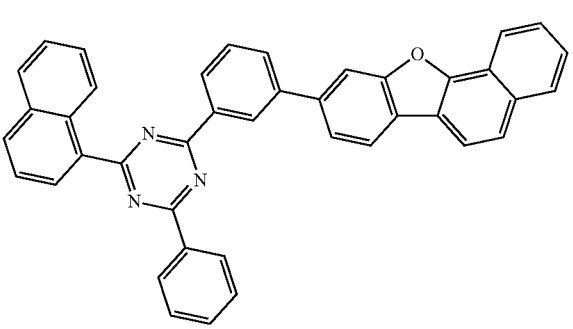

1-2

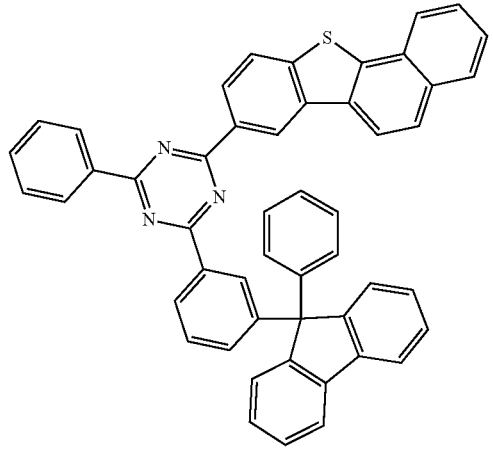

1-3

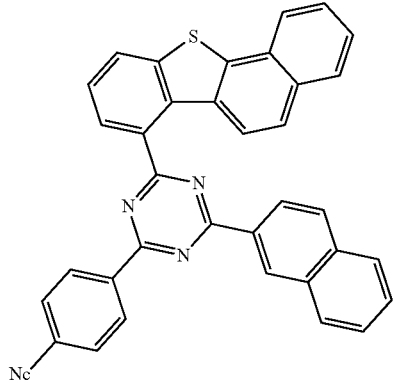

1-4

1-5
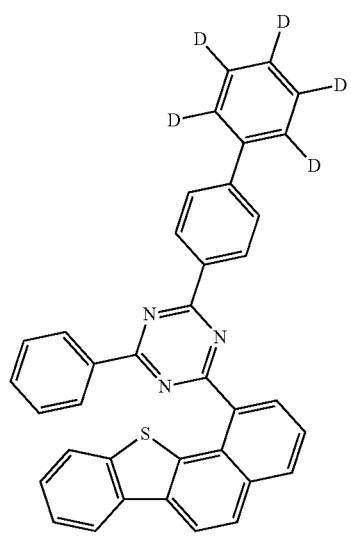
1-6
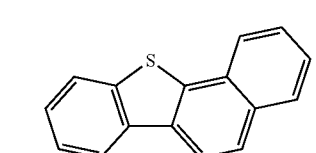
1-7
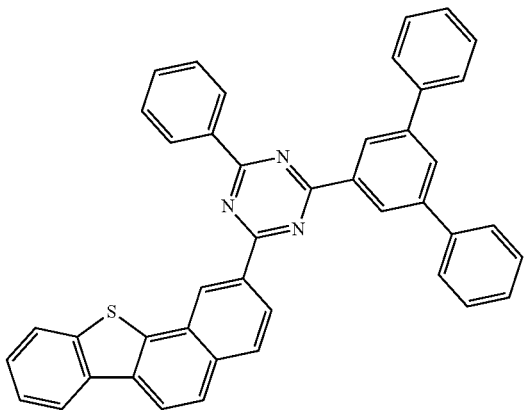
1-8
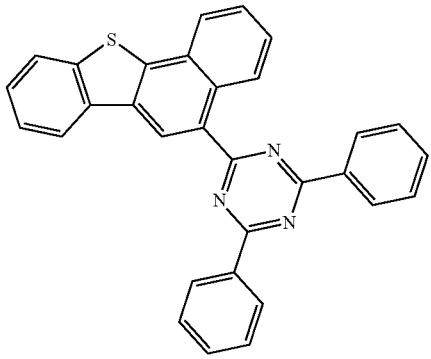
1-9
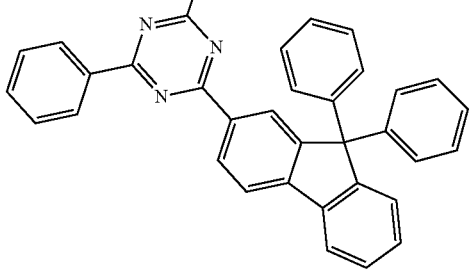
1-10
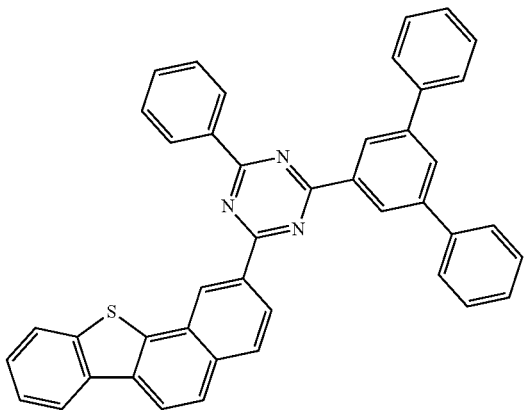

1-11
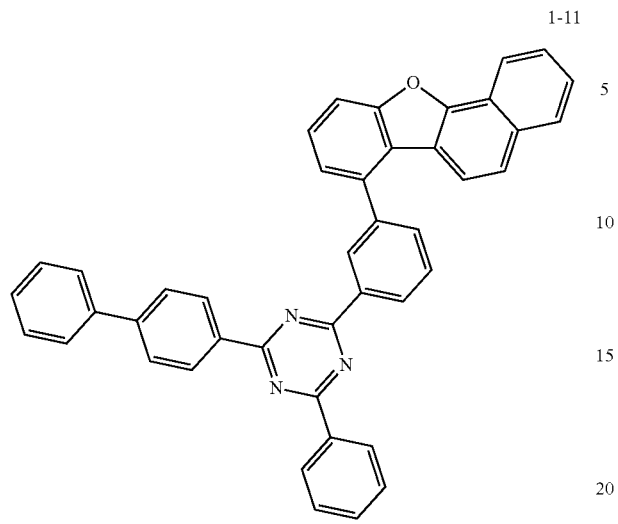
1-14
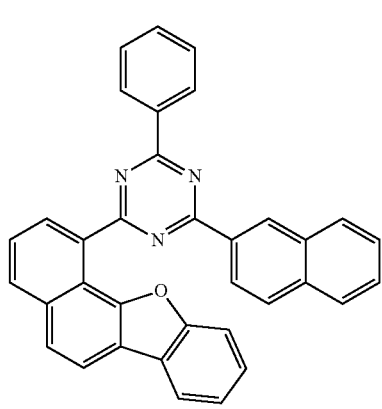
1-12
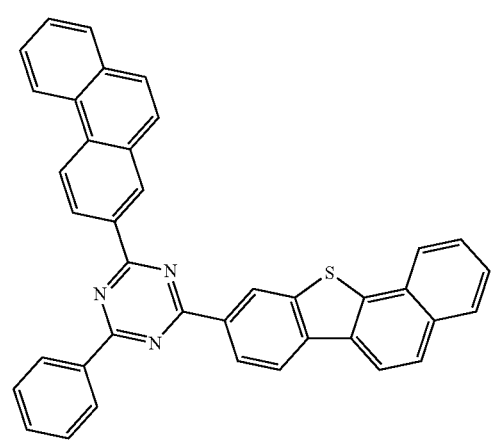
1-15
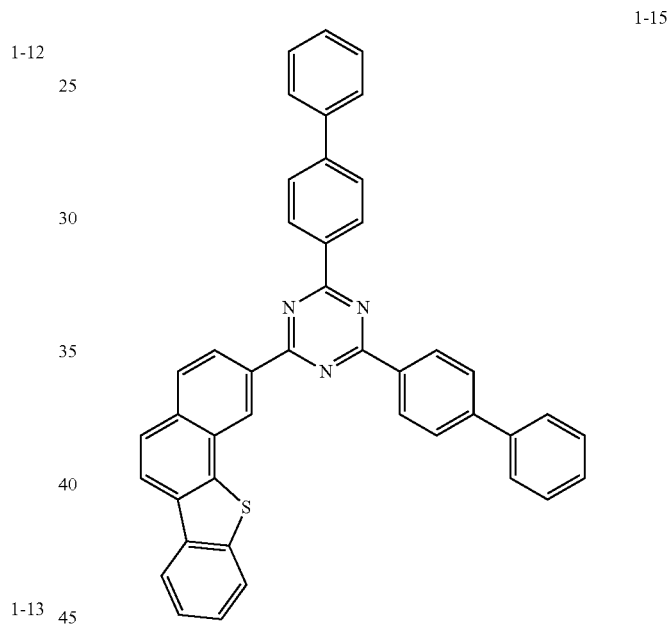
1-13
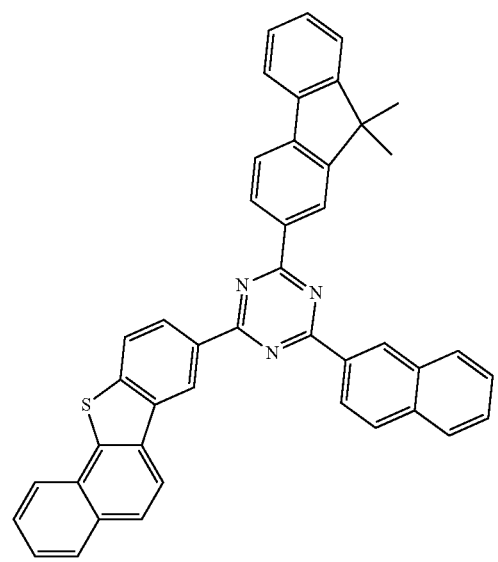
1-16
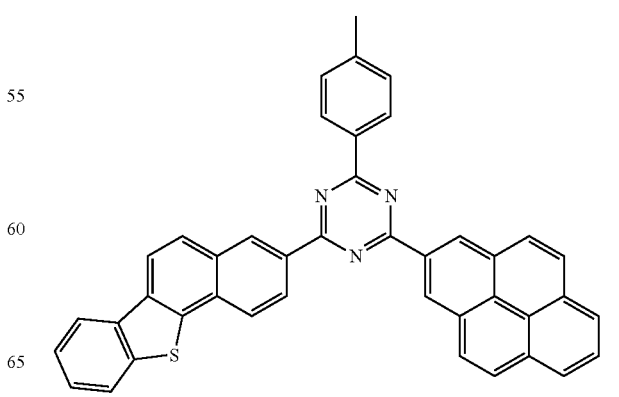

1-17
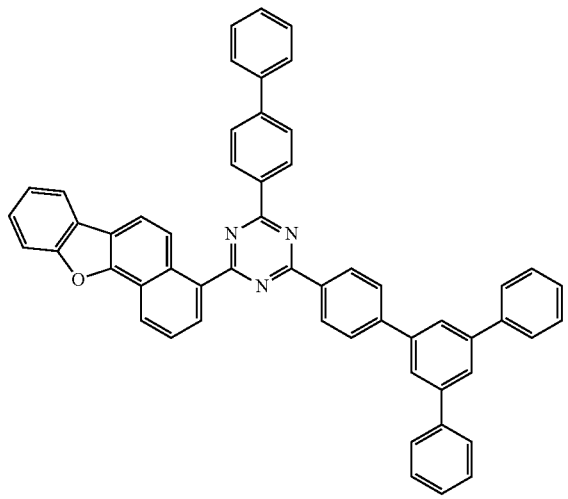
1-18
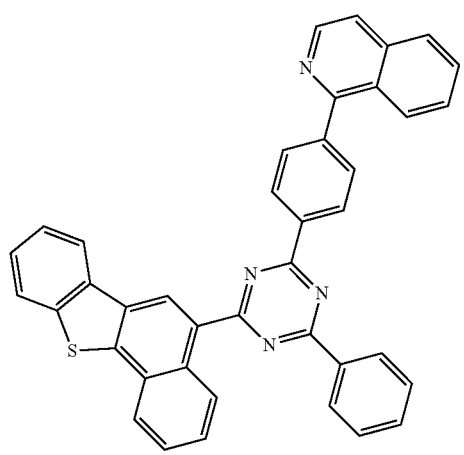
1-19
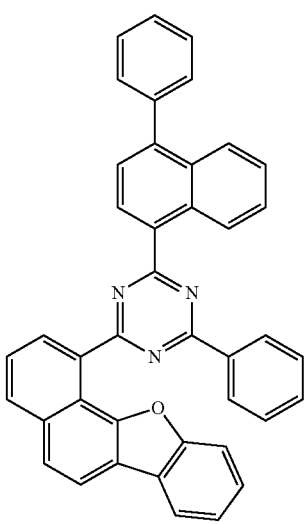
1-20
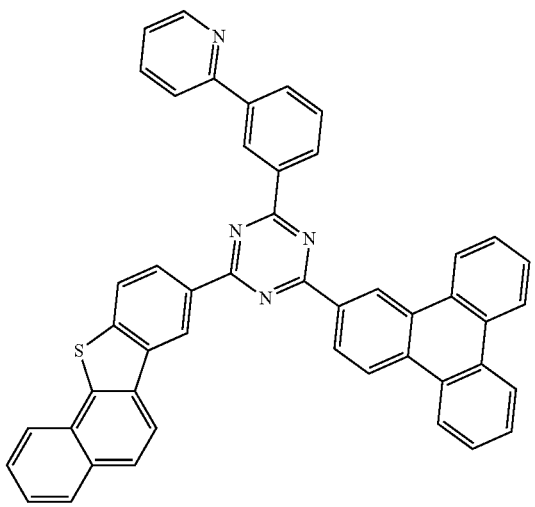
1-21
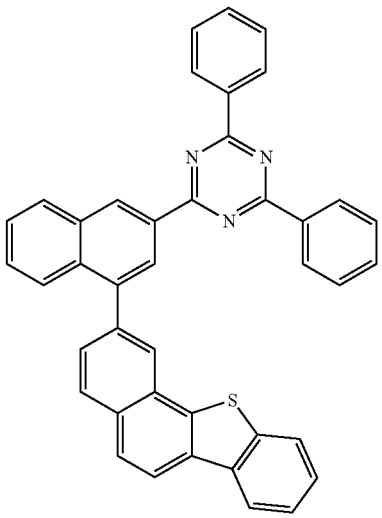
1-22

1-23
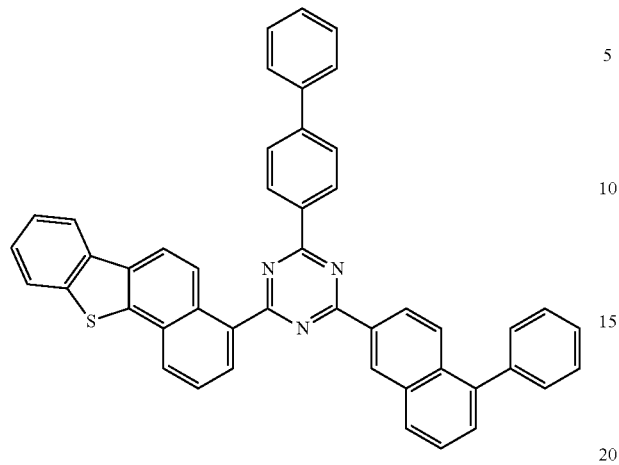
1-24
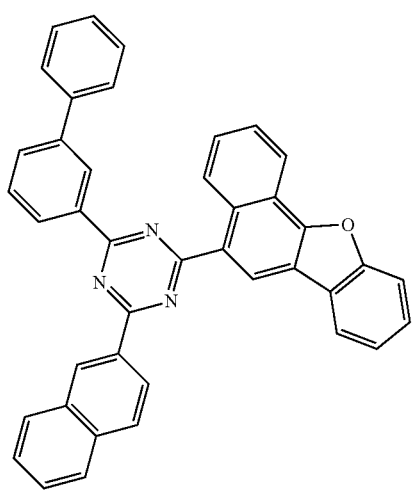
1-25
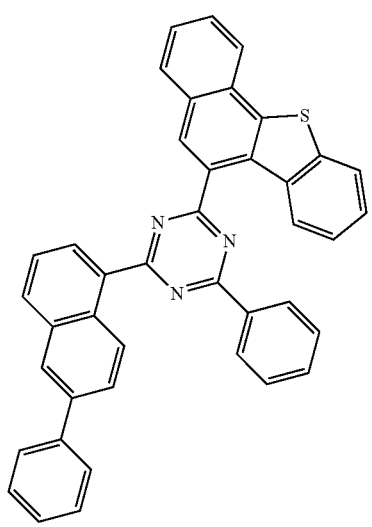
1-26
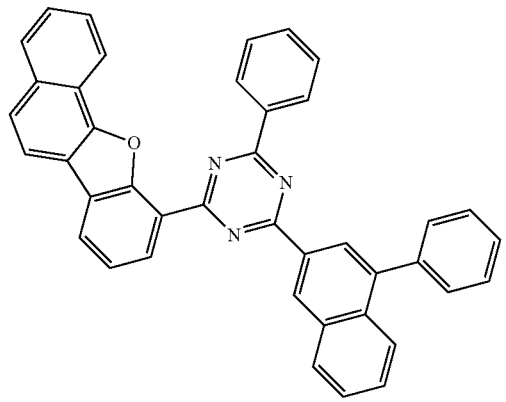
1-27
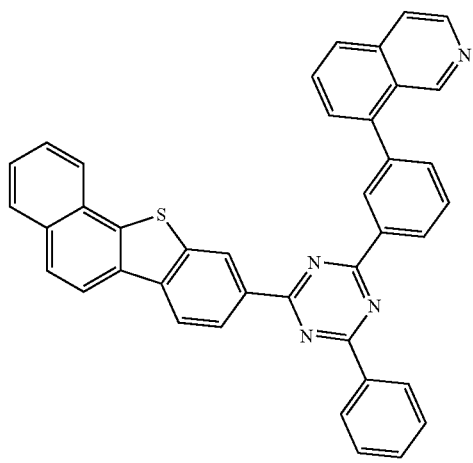
1-28
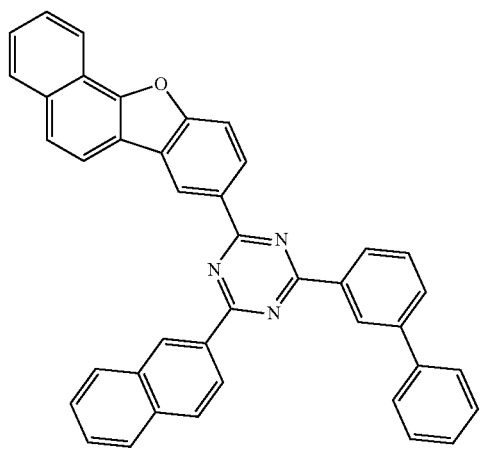

-continued
1-29
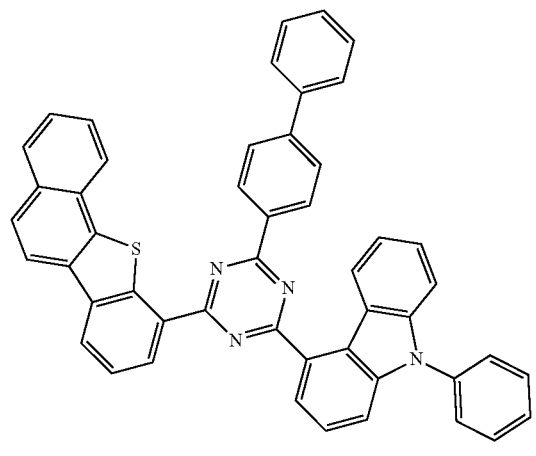
1-30
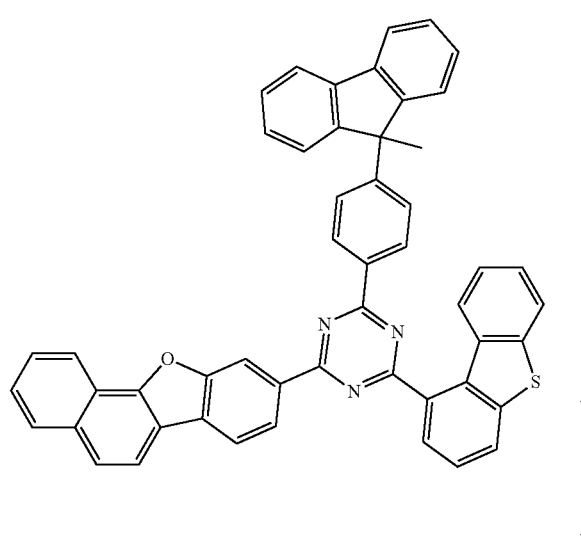
1-31
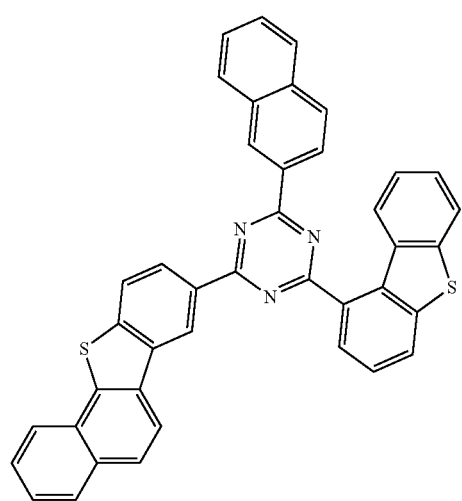
-continued
1-32
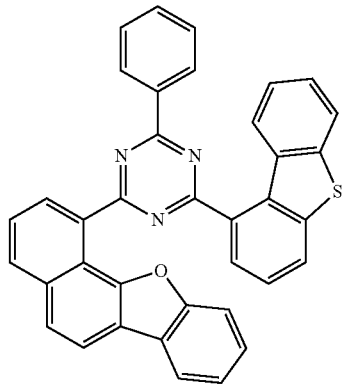
1-33
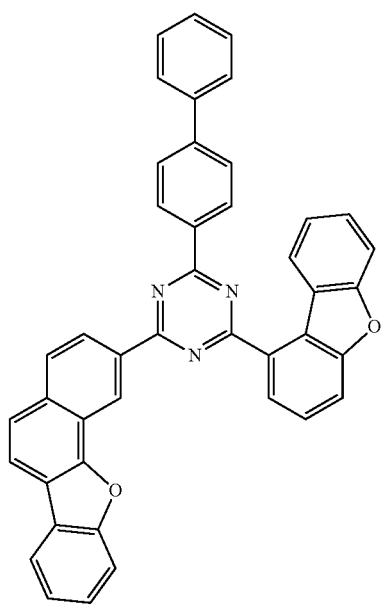
1-34
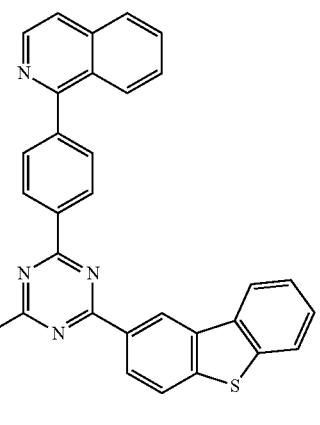

1-35
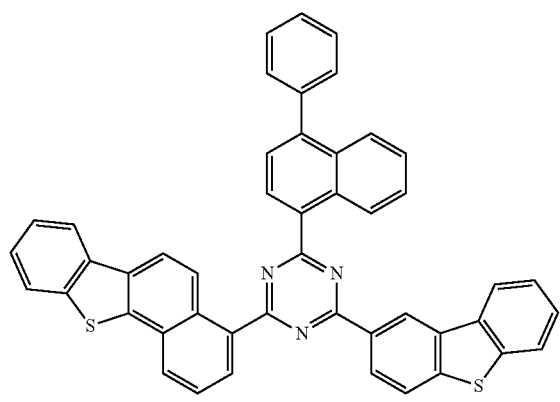
1-36
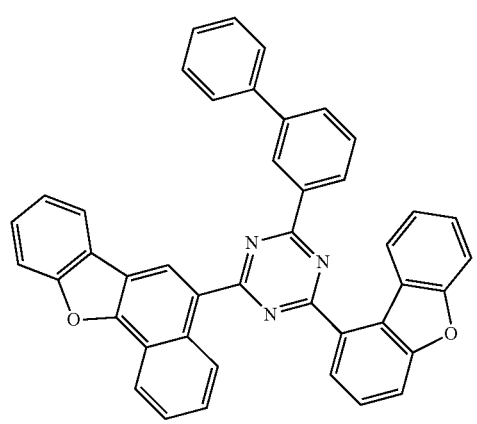
1-37
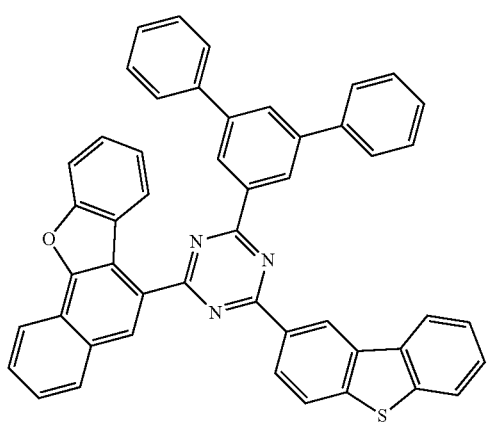
1-38
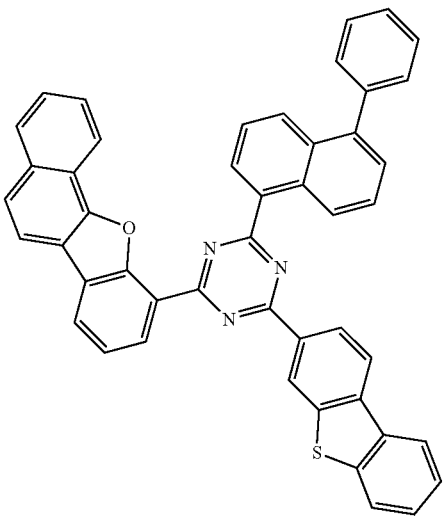
1-39
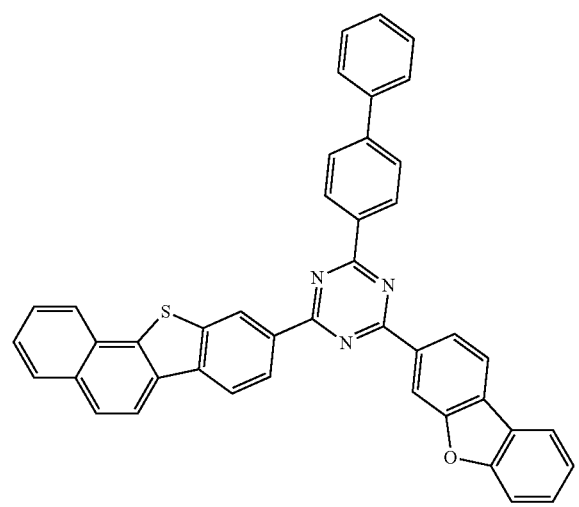
1-40
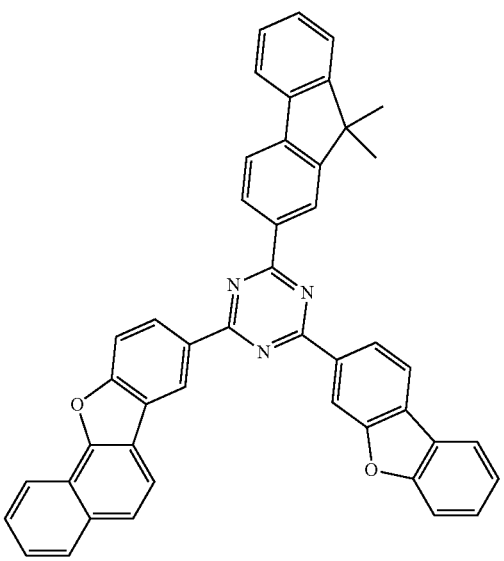

1-41
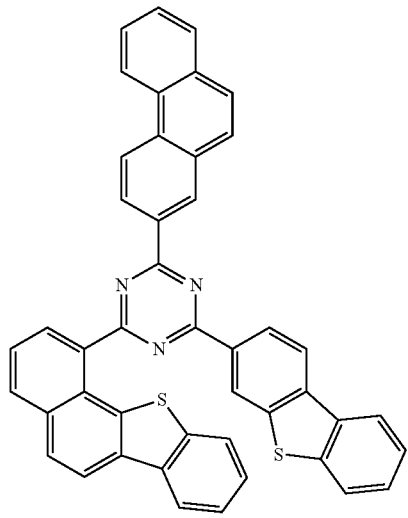
1-44
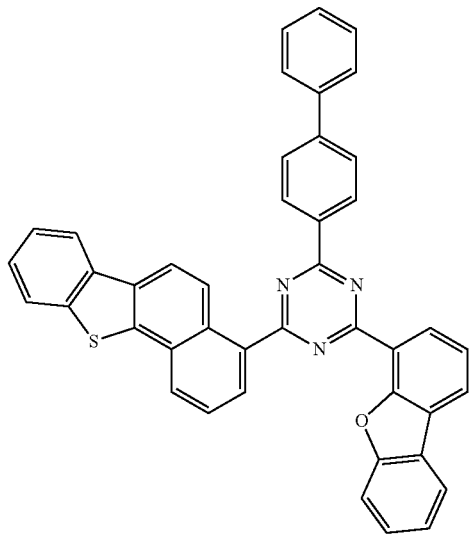
1-42
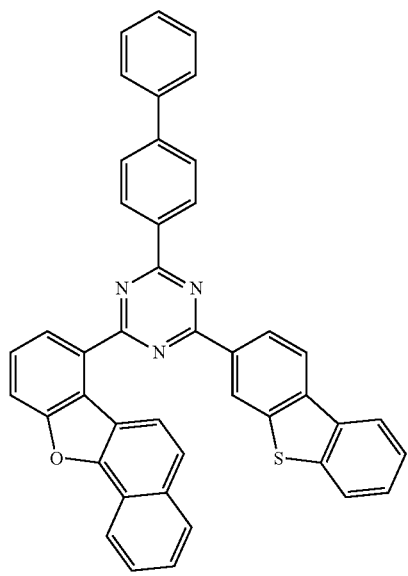
1-45
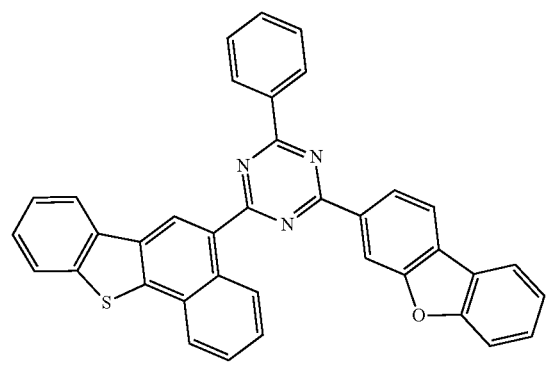
1-43
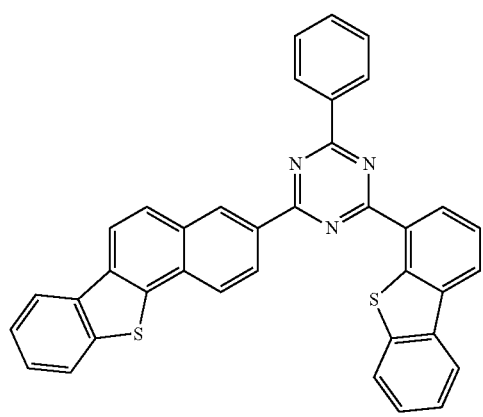
1-46
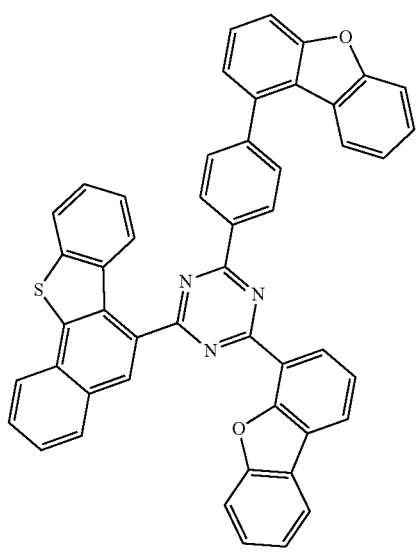

1-47
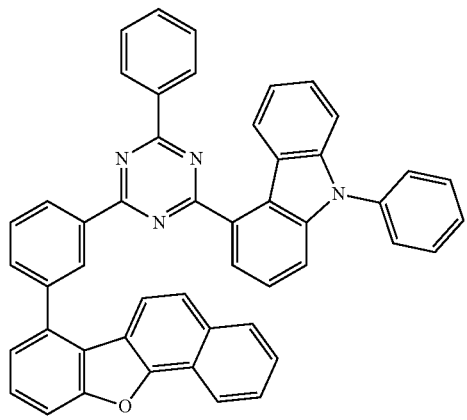
1-48
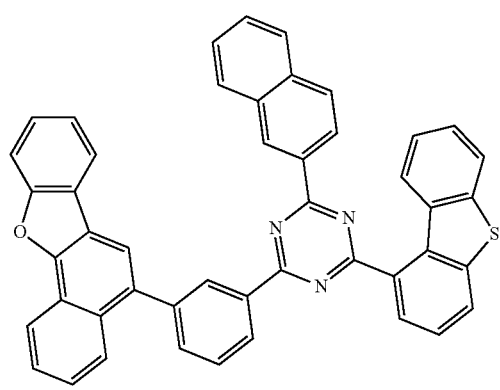
1-49
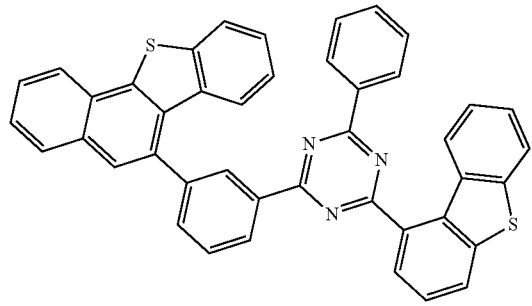
1-50
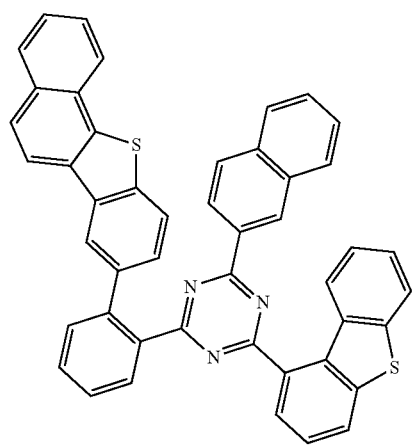
1-51
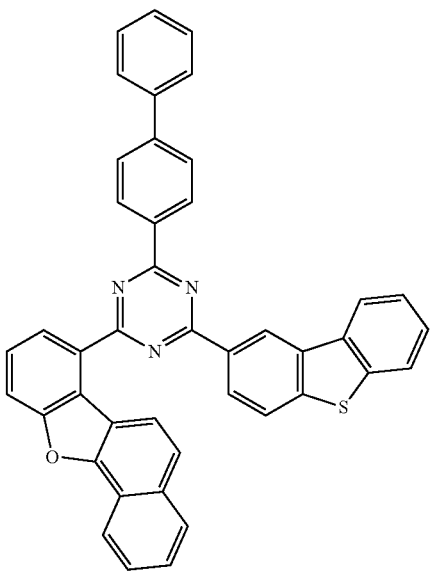
1-52
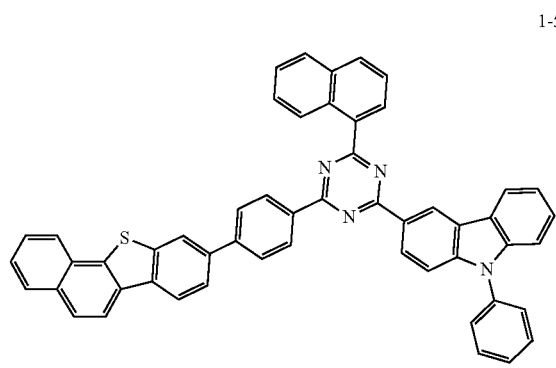
1-53
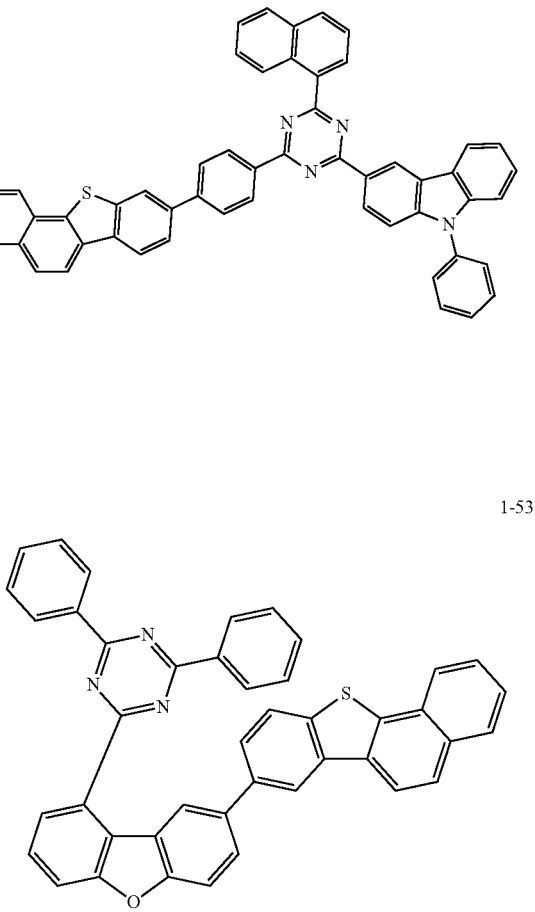

1-54
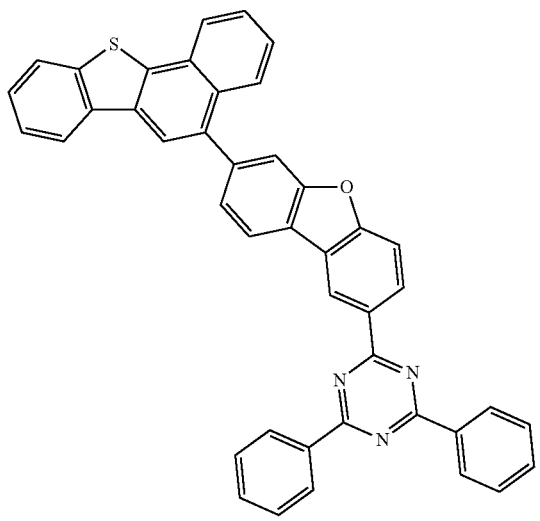
1-55
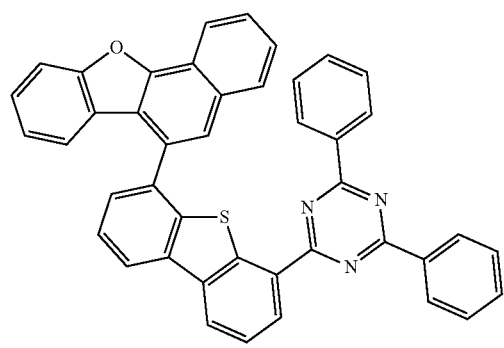
1-56
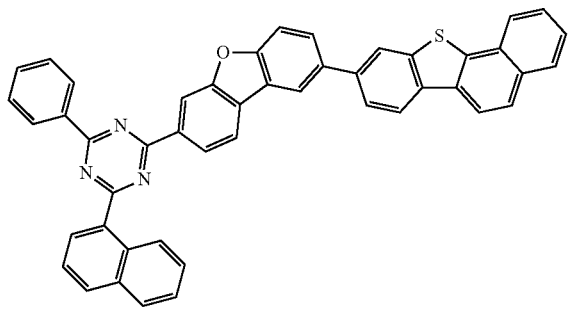
1-57
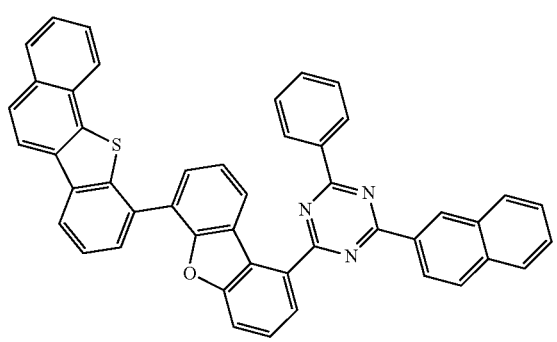
1-58
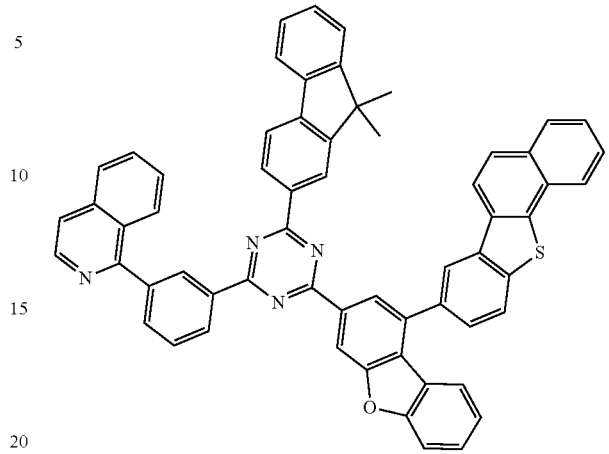
1-59
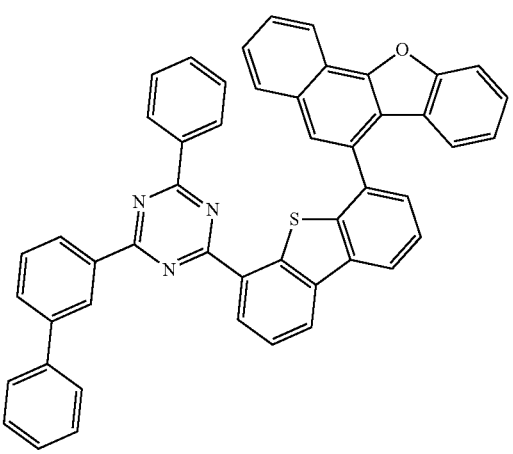
1-60
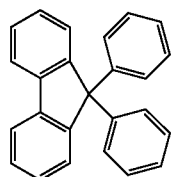

1-61
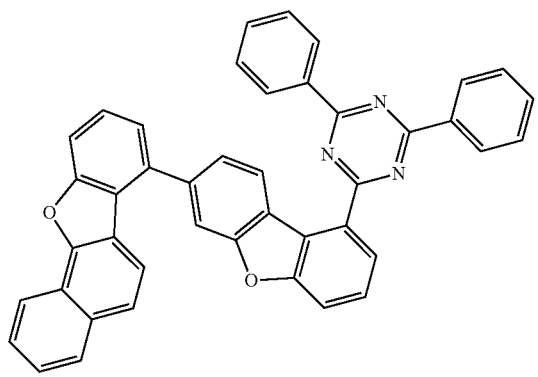
1-62
1-63
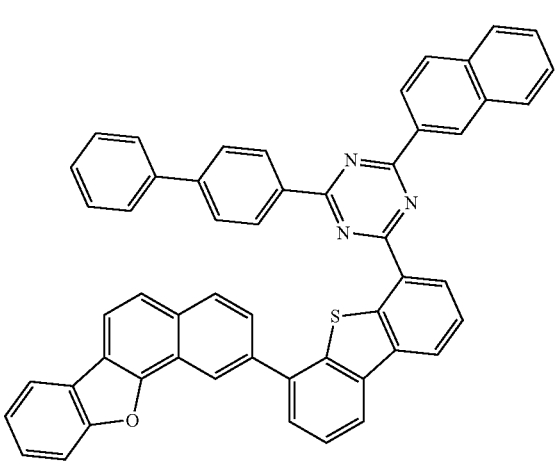
1-64
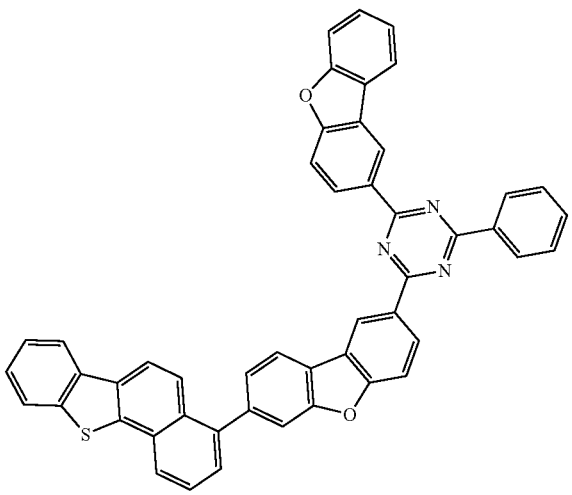
1-65
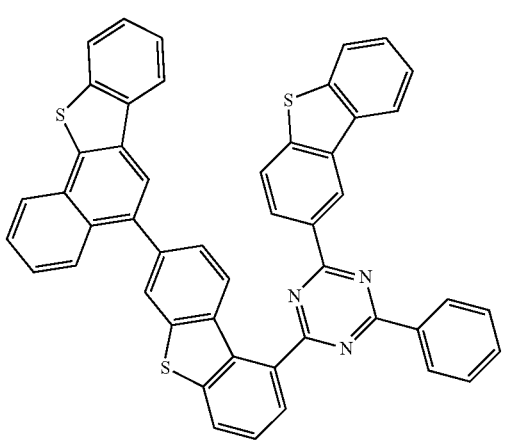
1-66
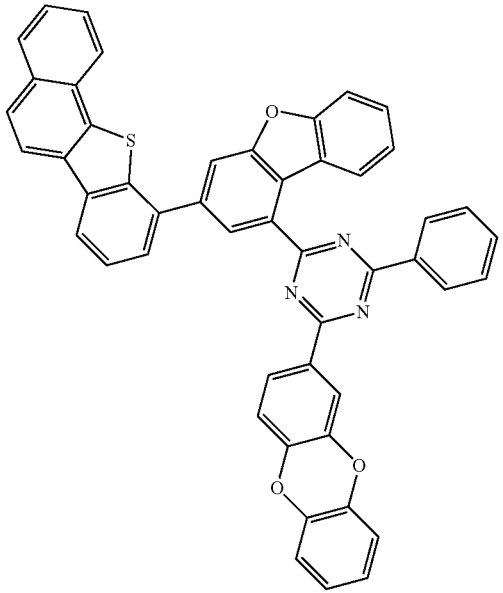

1-67
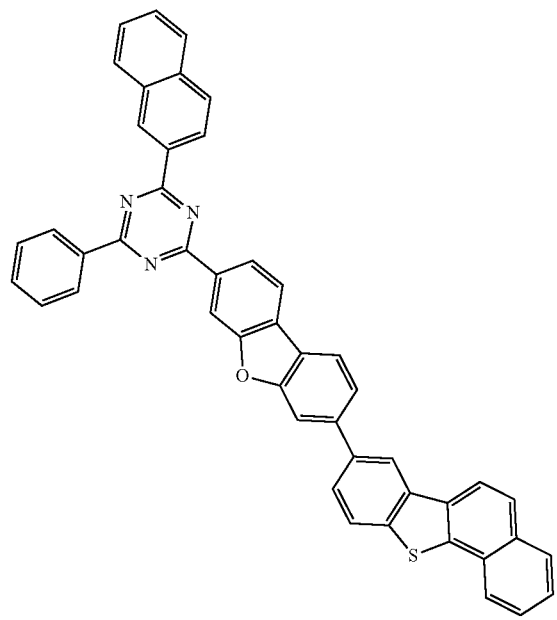
1-68
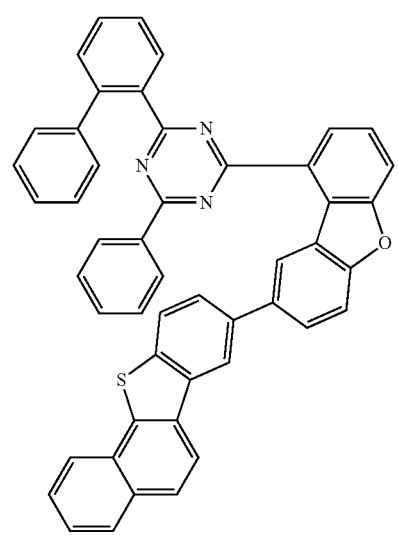
1-69
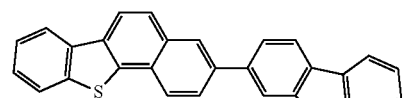
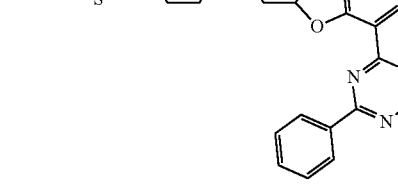
1-70
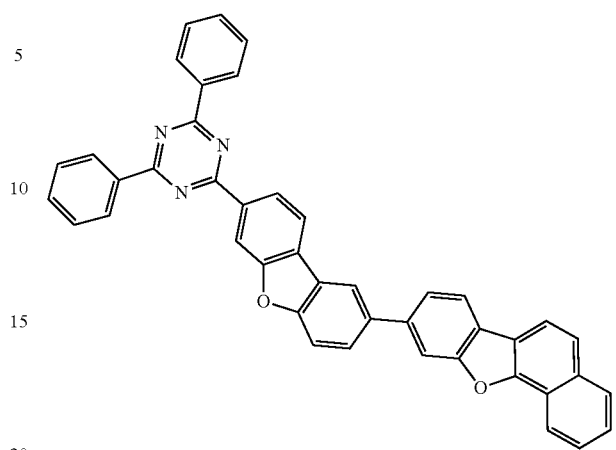
1-71
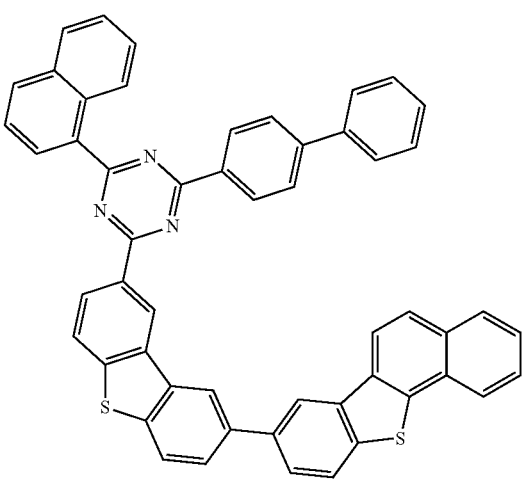
1-72
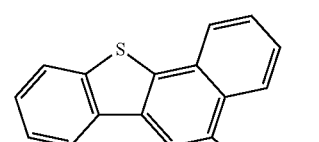
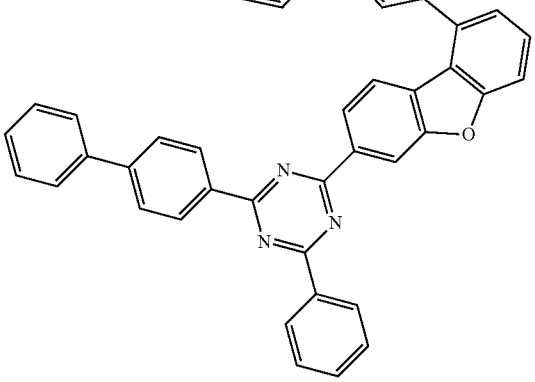

1-73
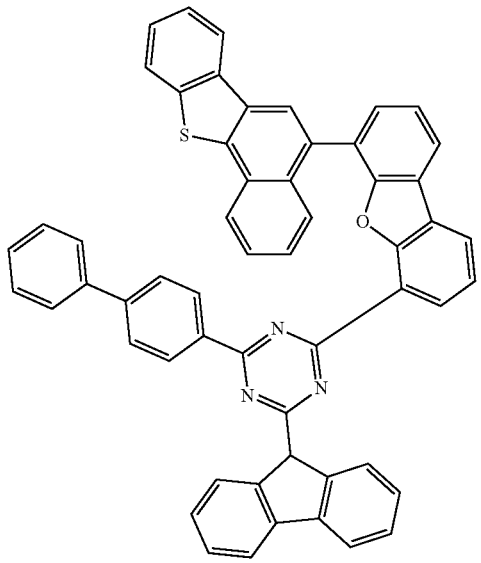
1-74
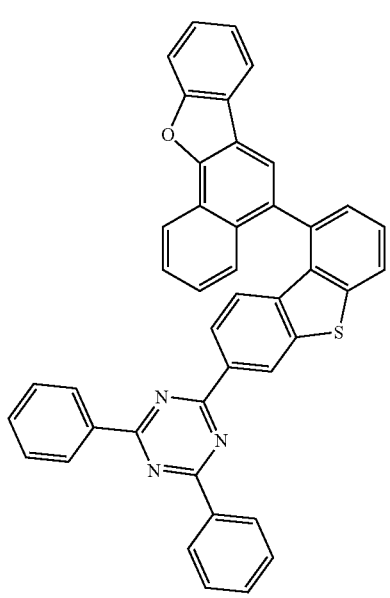
1-75
1-76
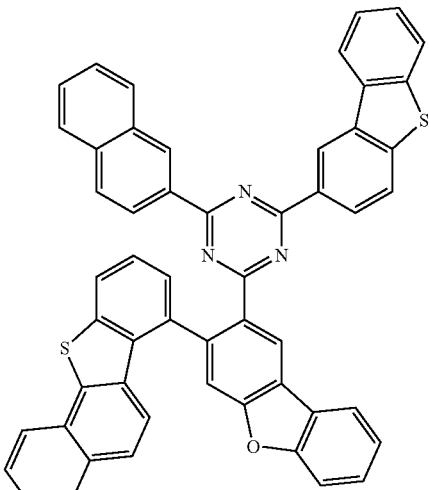
1-77
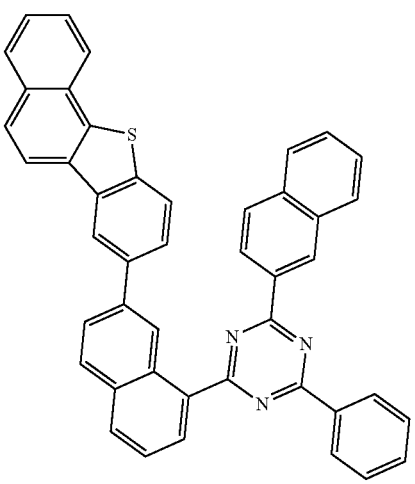
1-78
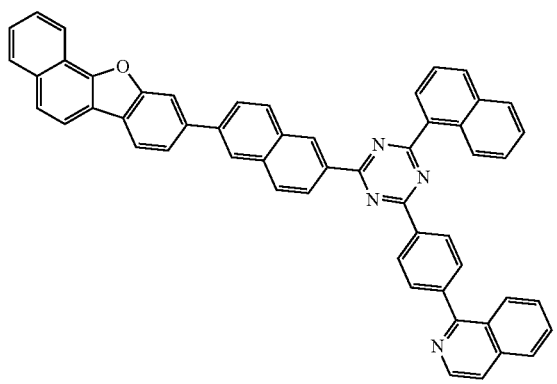

1-79
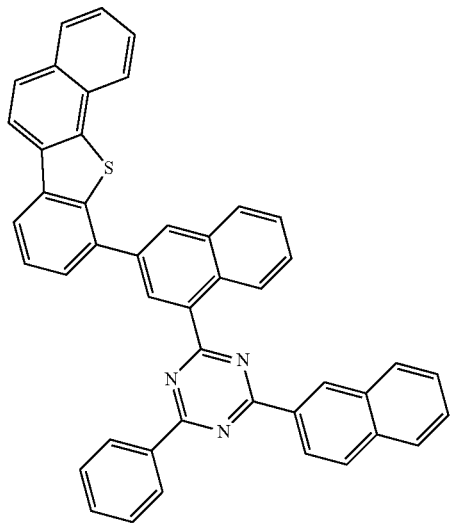
1-80
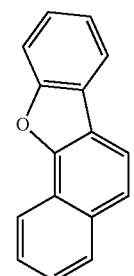
1-81
1-82
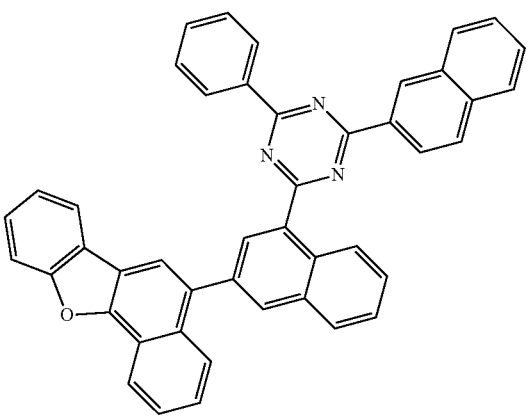
1-83
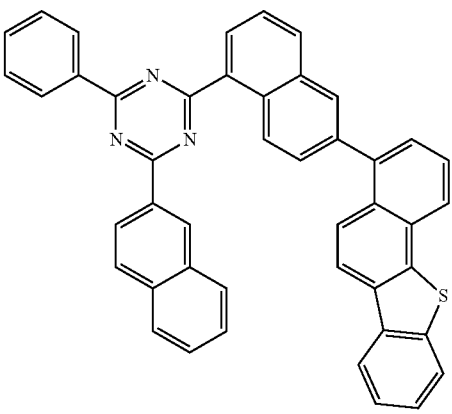
1-84
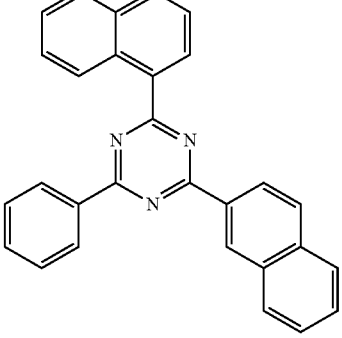

1-85
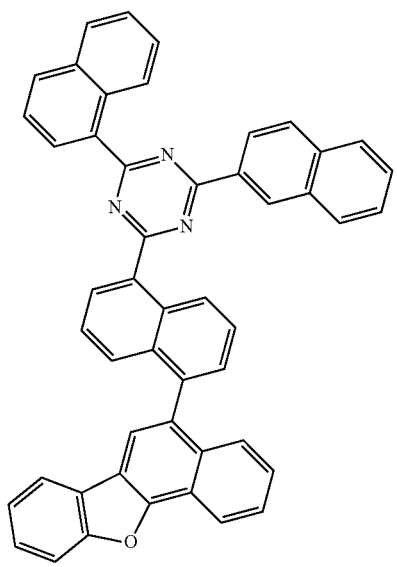
1-89
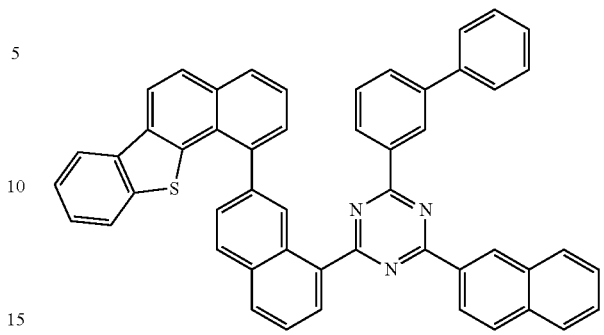
1-86
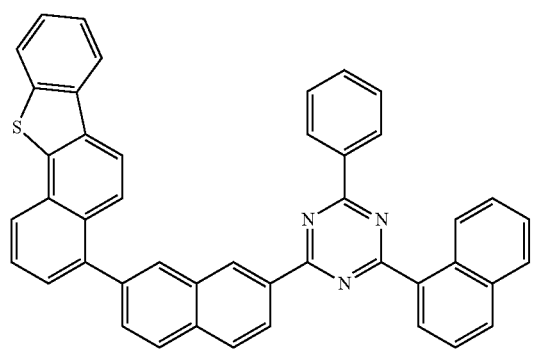
1-90
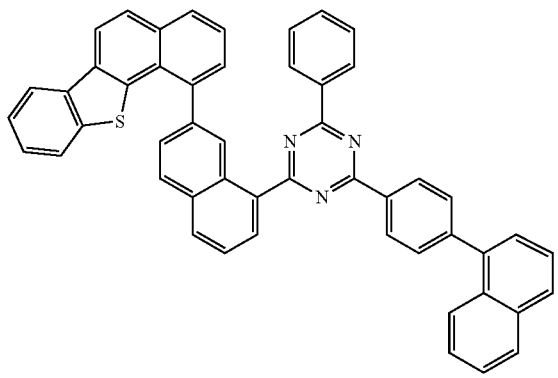
1-87
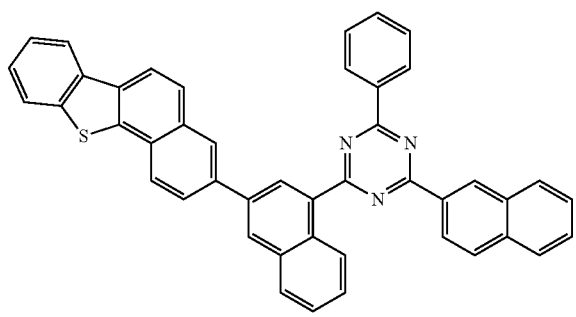
1-91
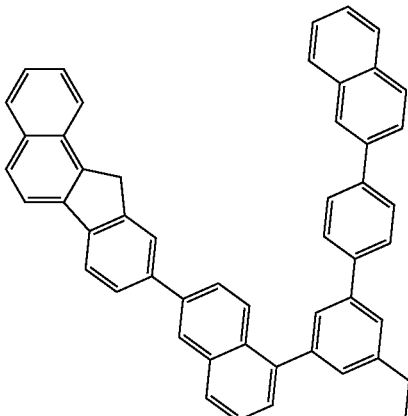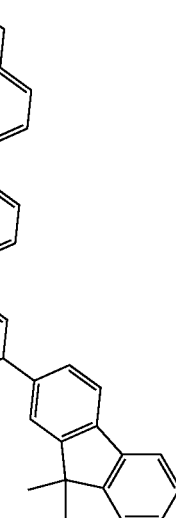
1-88
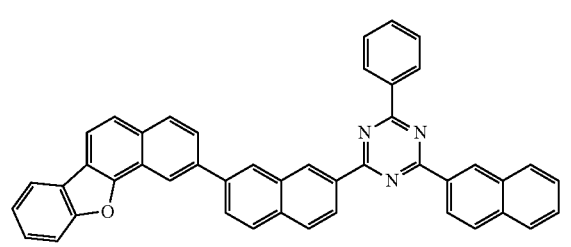

1-92
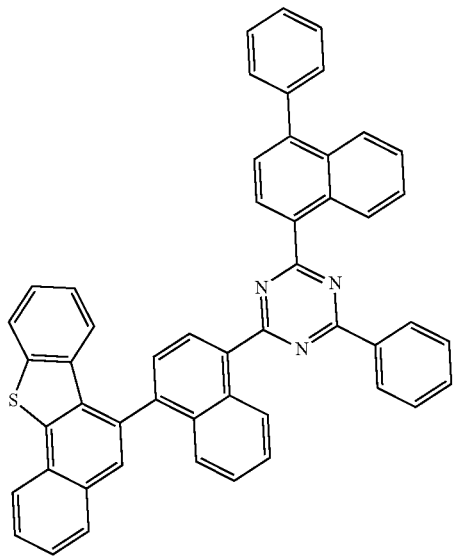
1-93
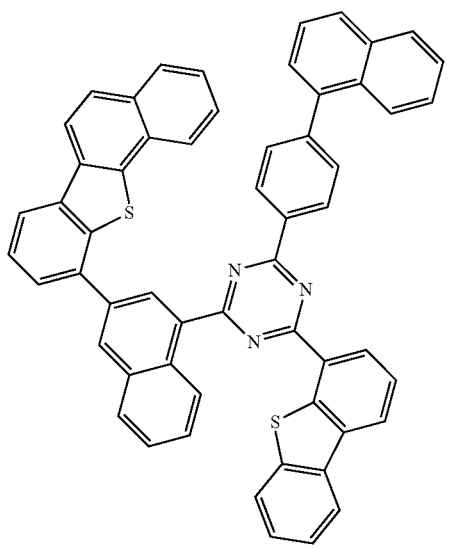
1-94
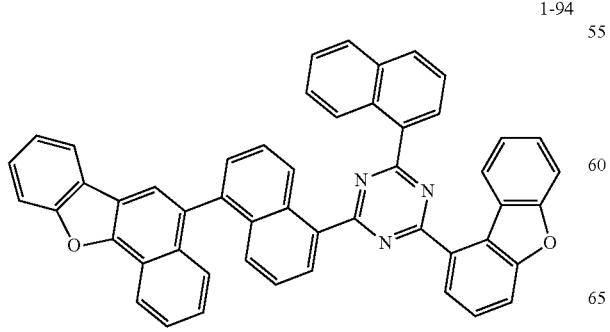
1-95
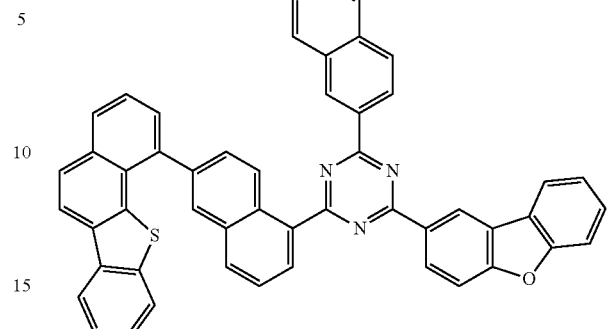
1-96
1-97
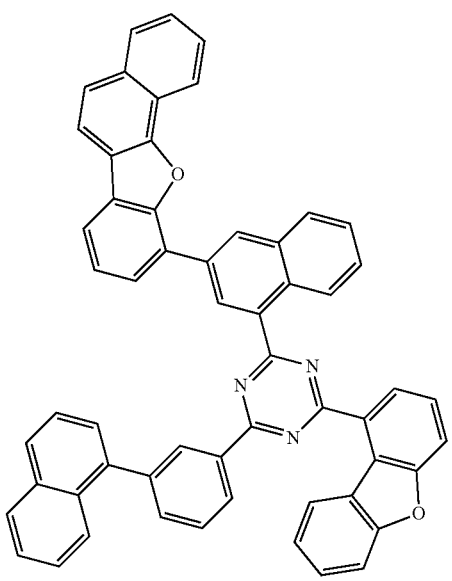

1-98
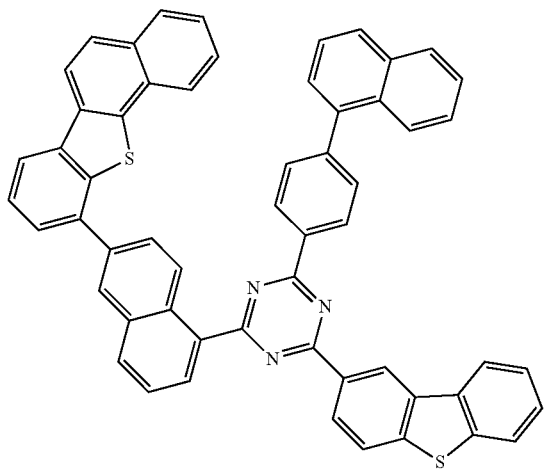
1-99
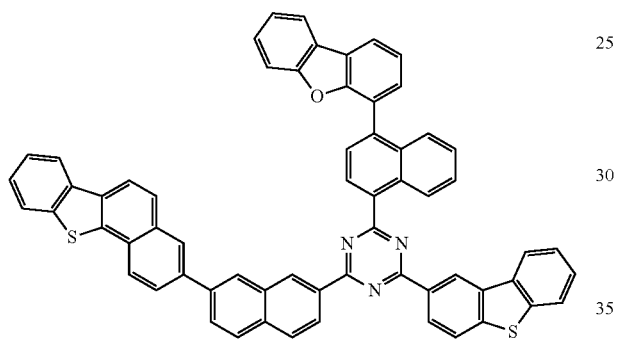
1-100
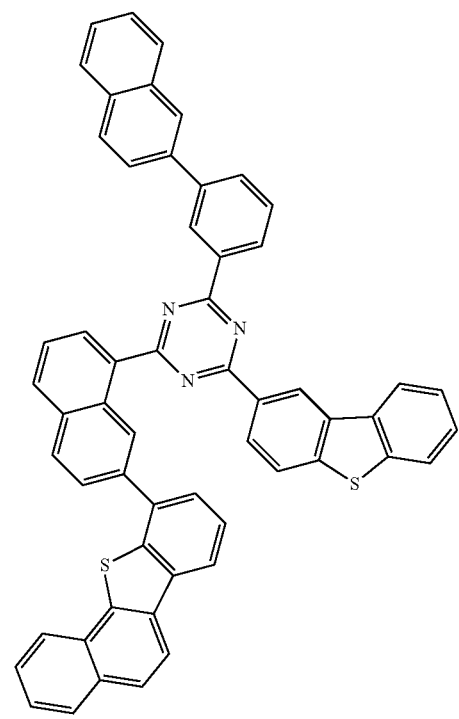
1-101
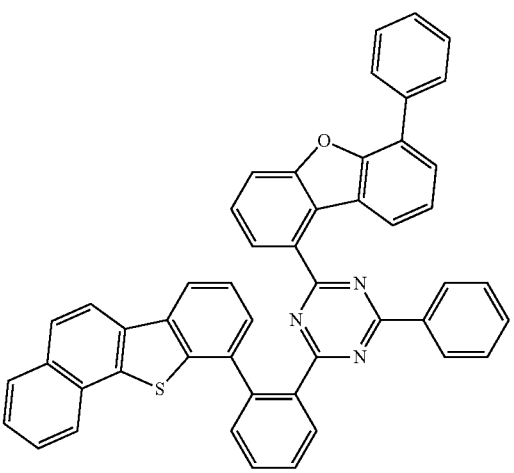
1-102
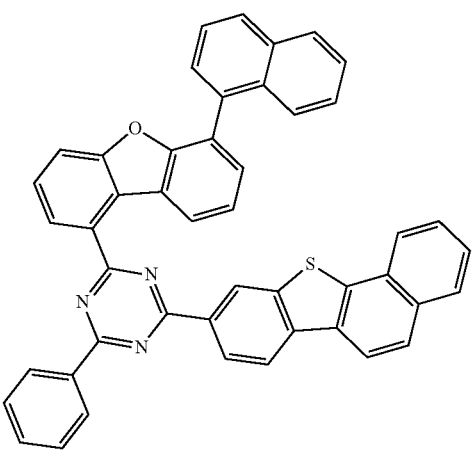
1-103
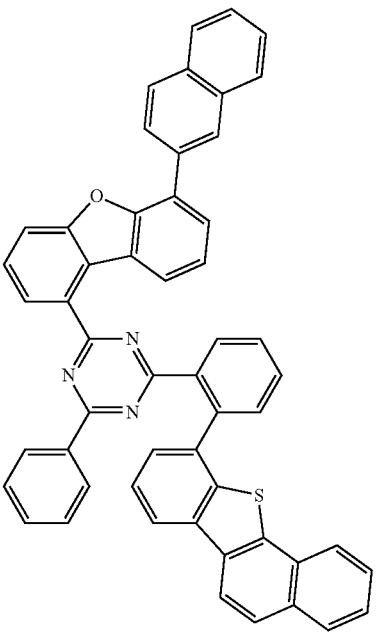

-continued
1-104
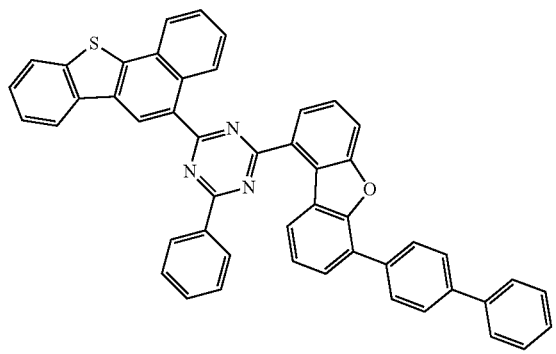
1-105
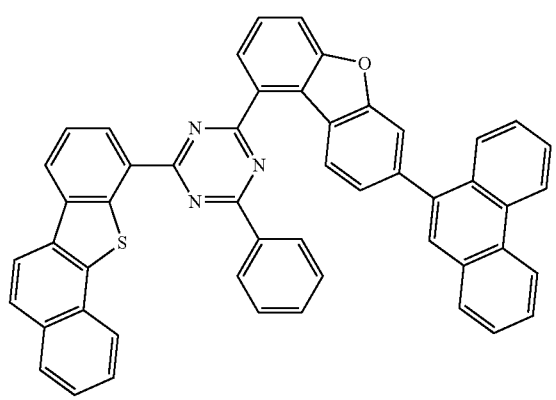
1-106
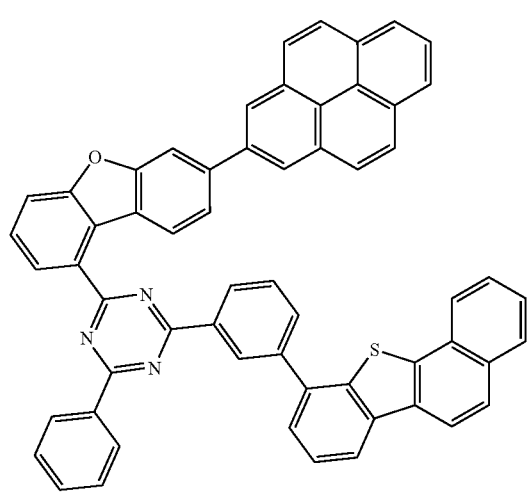
-continued
1-107
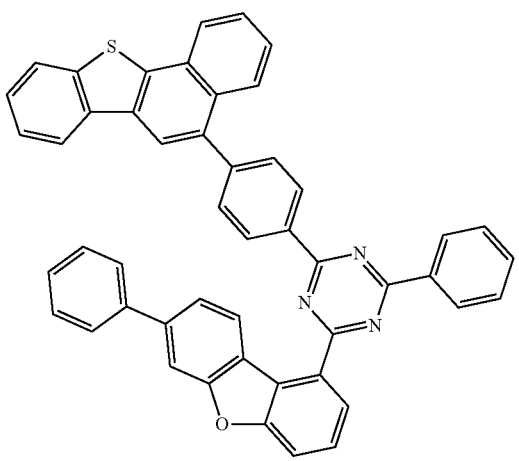
1-108
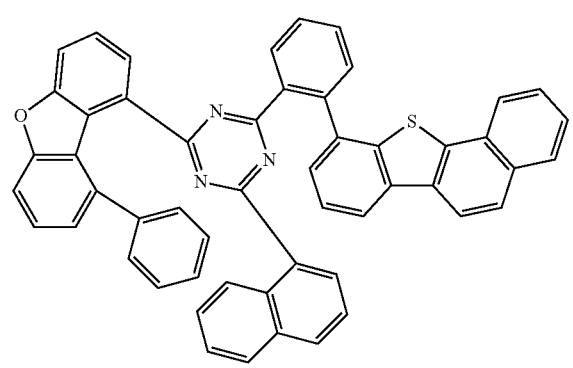
1-109
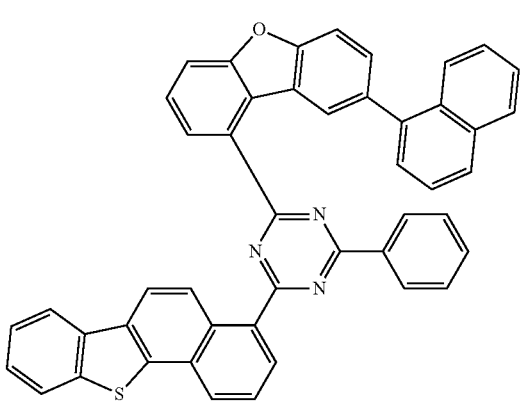

1-110
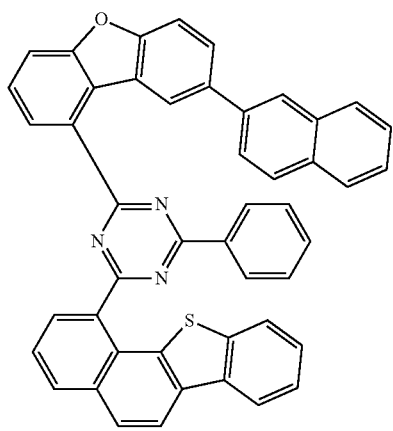
1-111
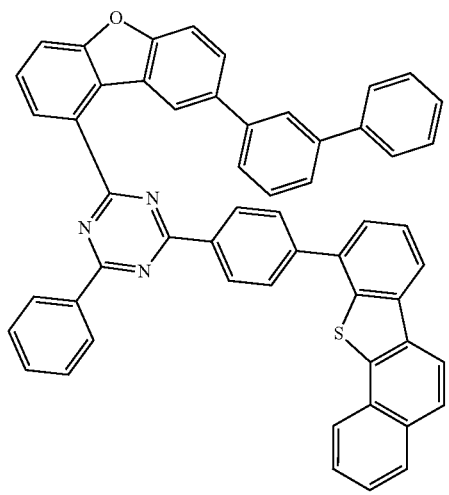
1-112
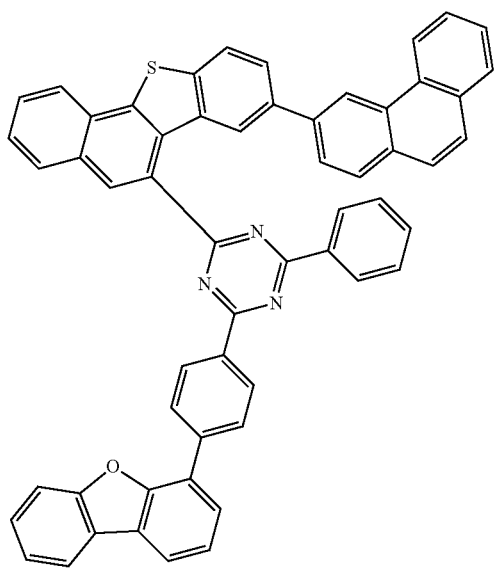
1-113
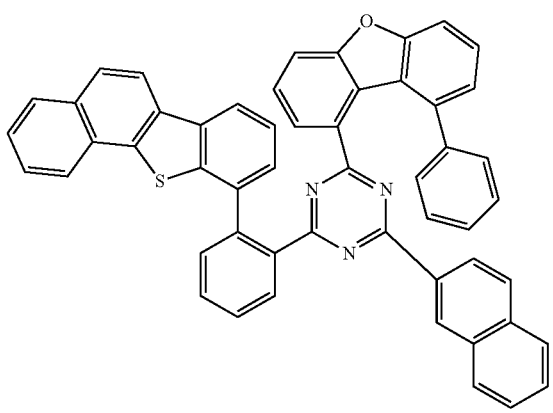
1-114
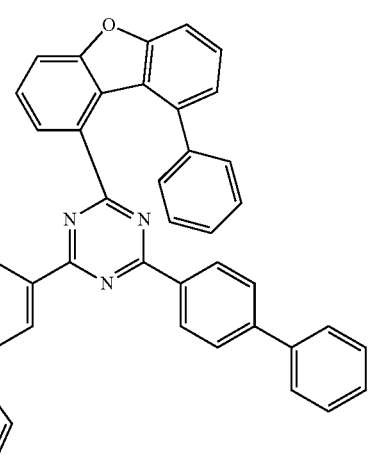
1-115
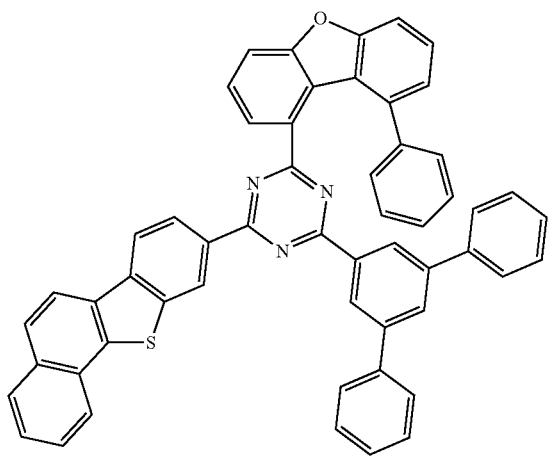

1-116
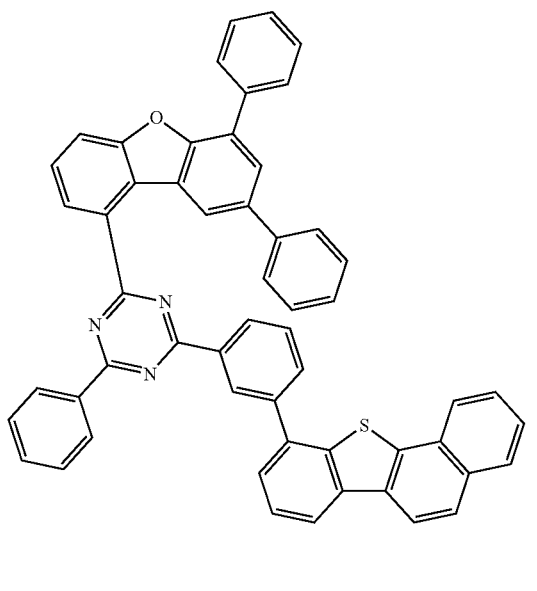
1-117
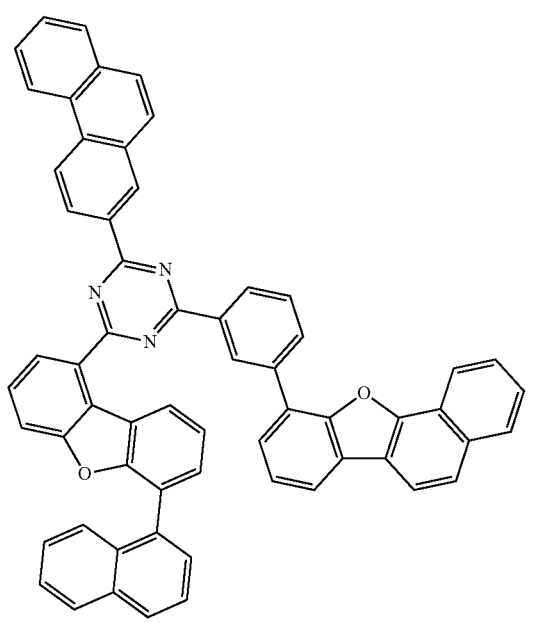
1-119
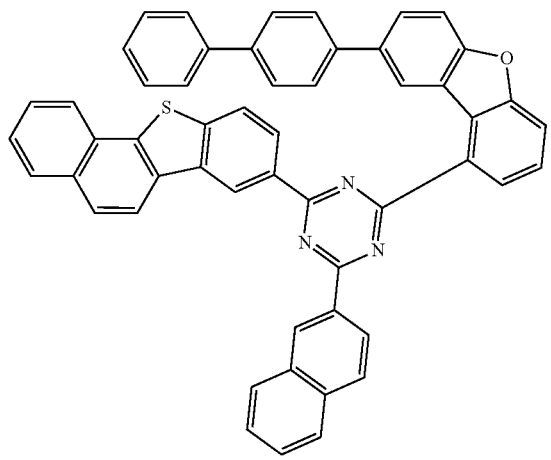
1-120
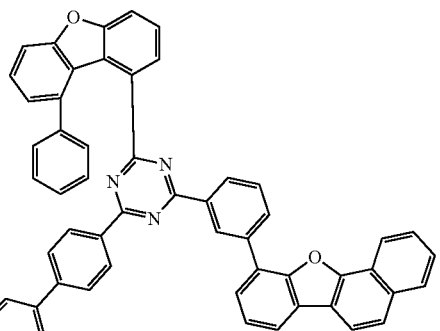
1-121
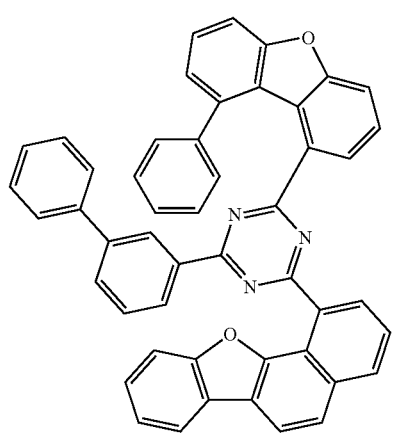
1-118

Specifically, the compound represented by formula 2 may be one of the following compounds, but there is no limitation thereto.
1-122
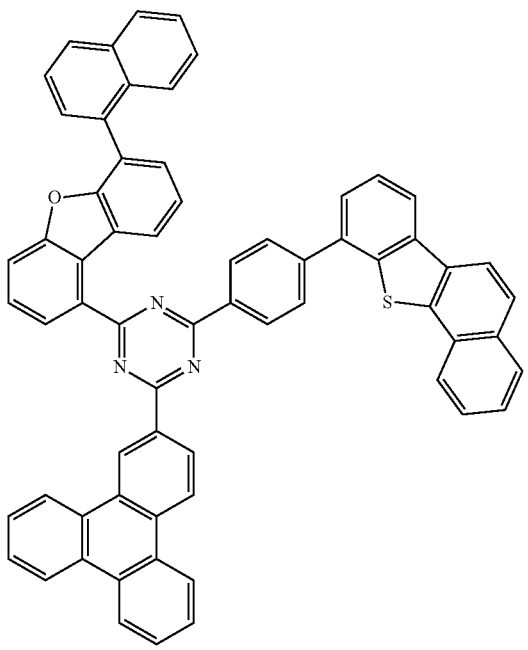
2-1
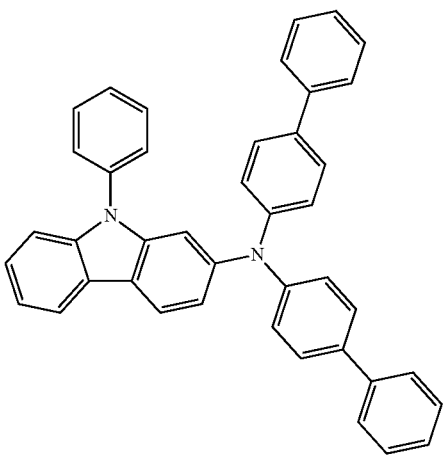
1-123
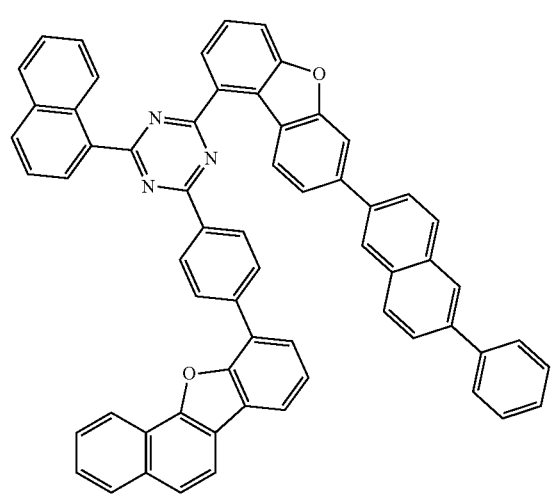
2-2
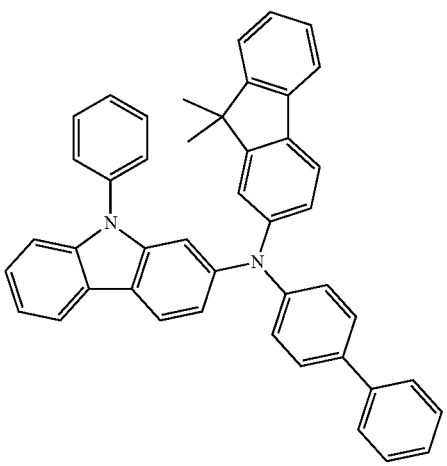
1-124
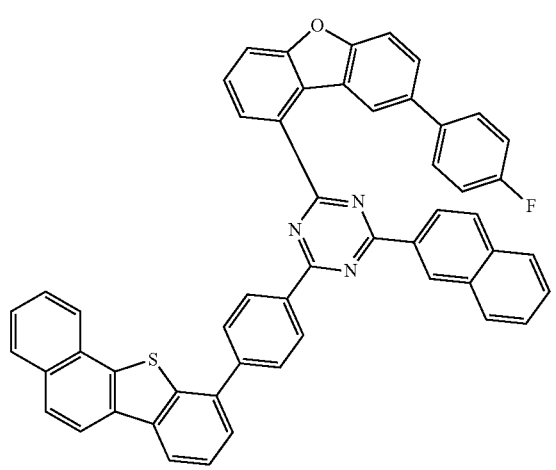
2-3
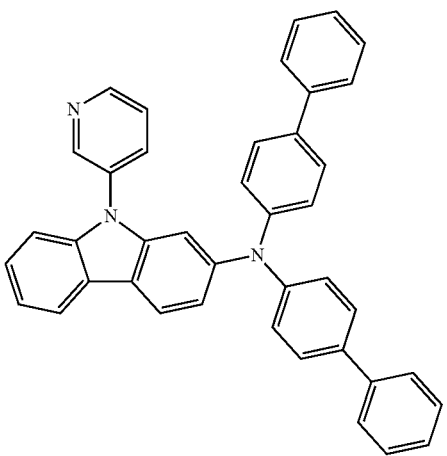

2-4
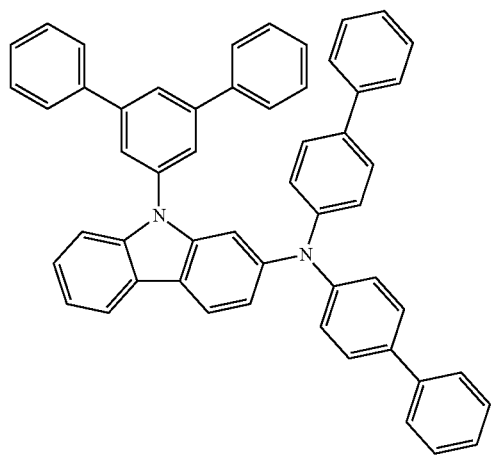
2-5
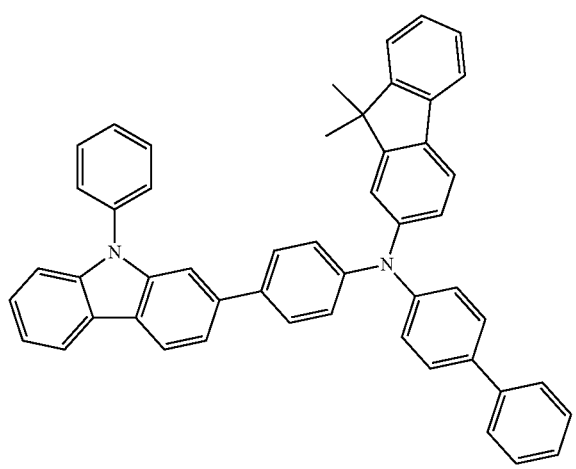
2-6
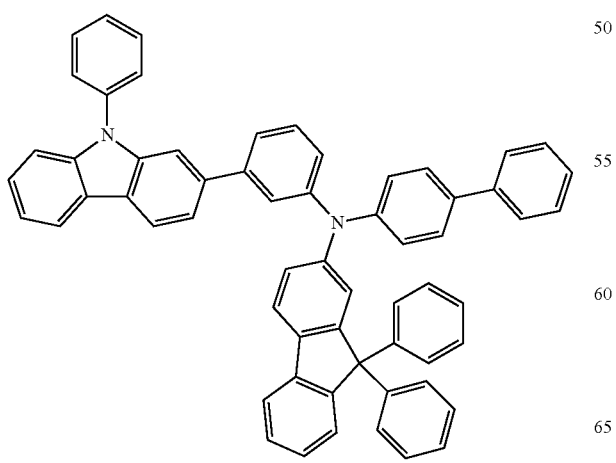
2-7
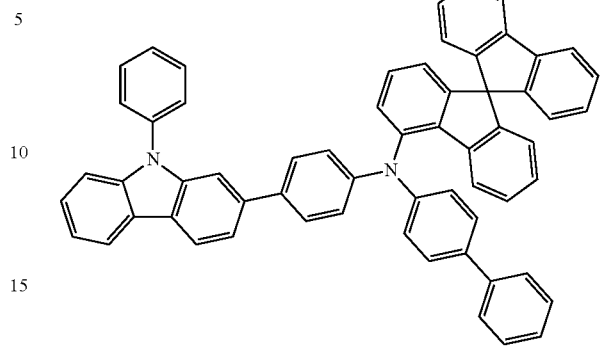
2-8
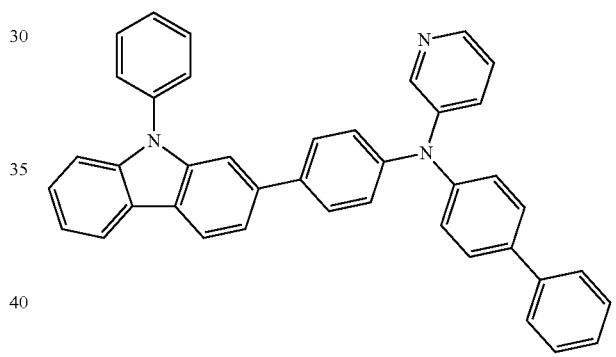
2-9
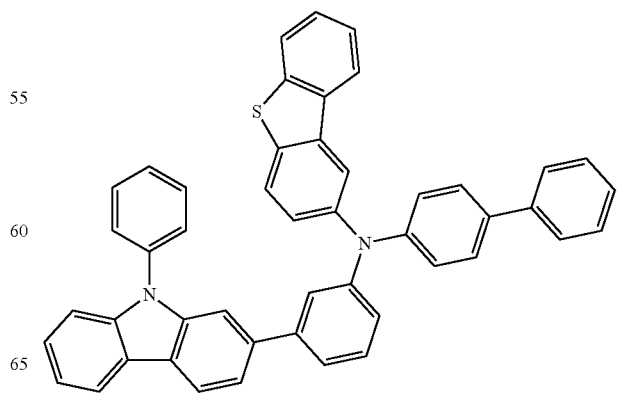

2-10
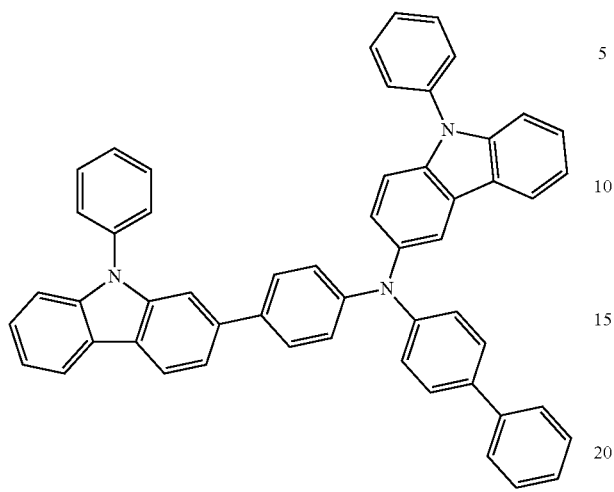
2-11
2-12
2-13
2-14
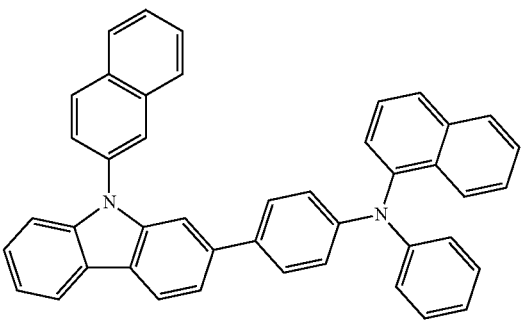
2-15
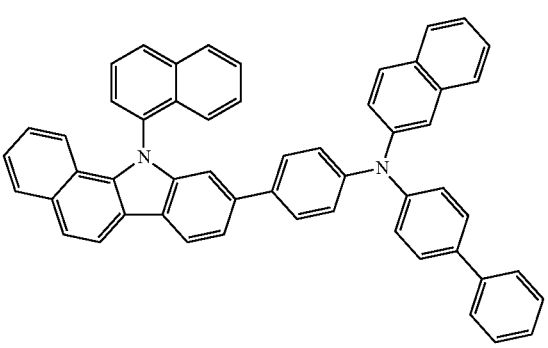
2-16
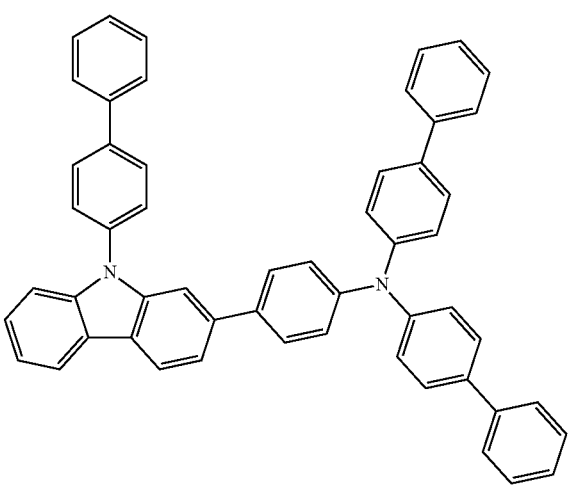
2-17
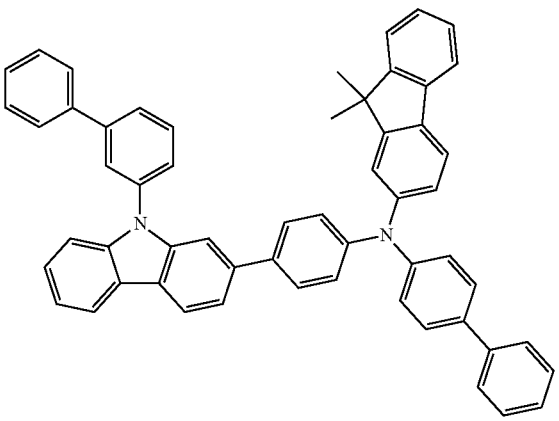

2-18
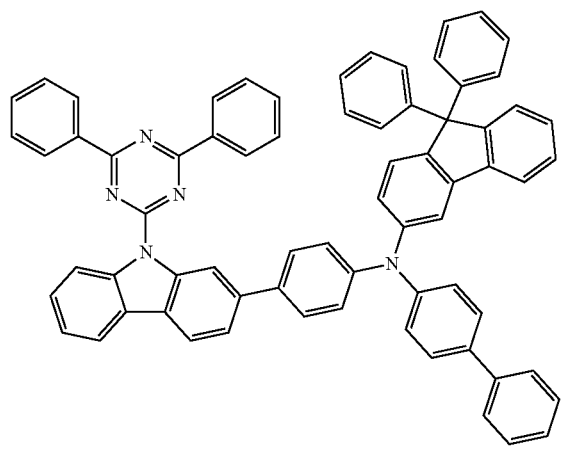
2-19
2-20
2-21
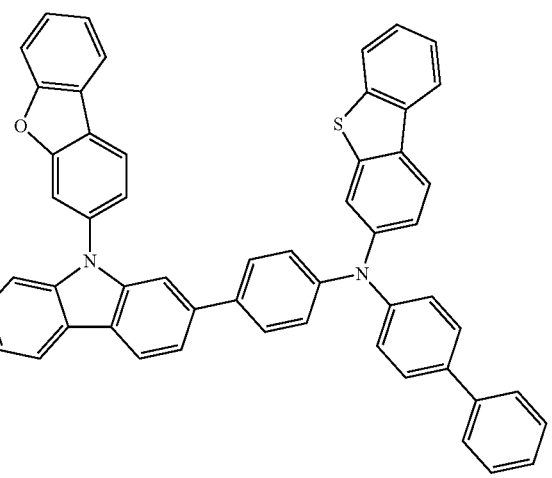
2-22
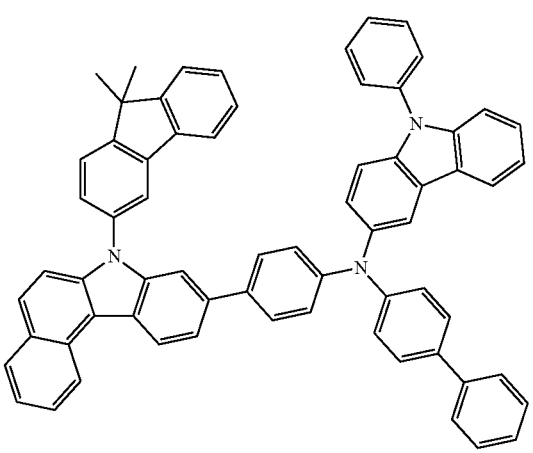
2-23
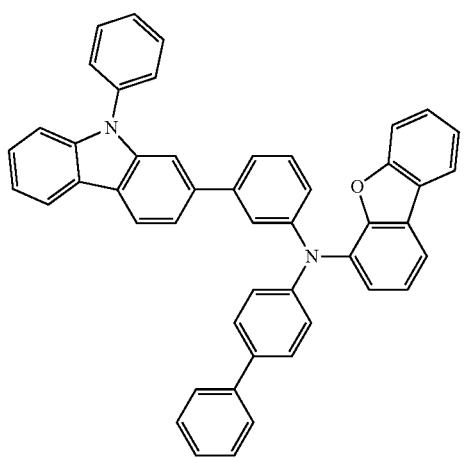

77
-continued
2-24
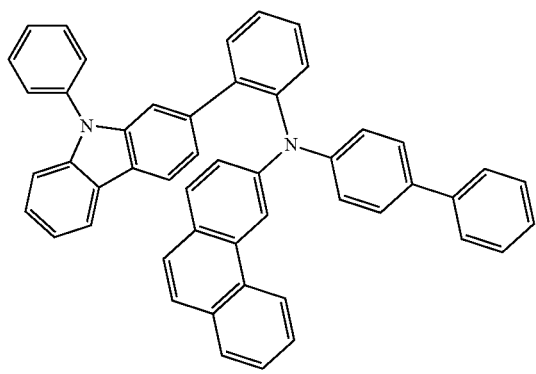
2-25
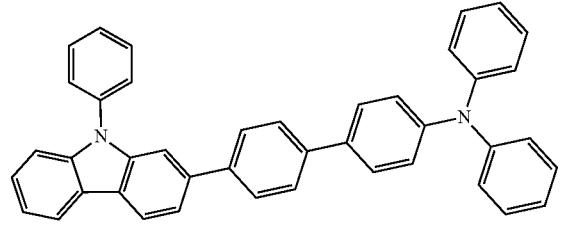
2-26
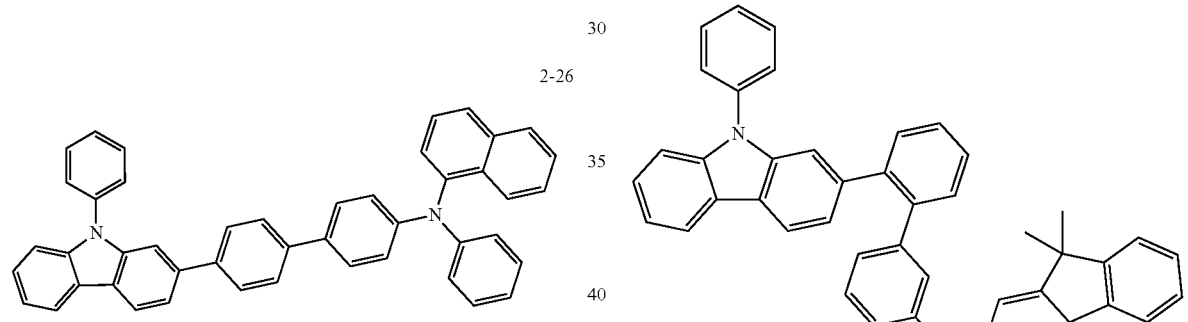
2-27
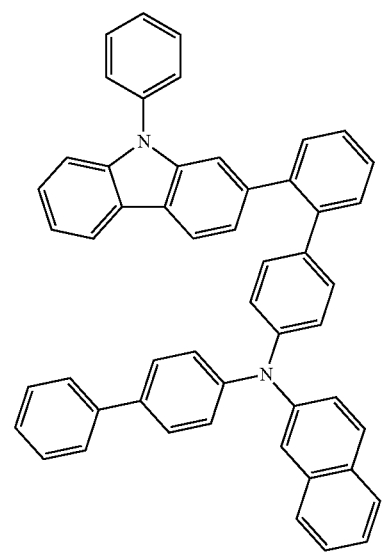
78
-continued
2-28
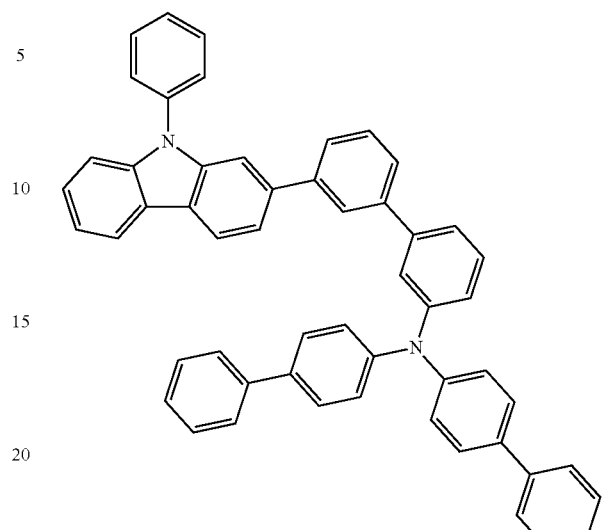
2-29
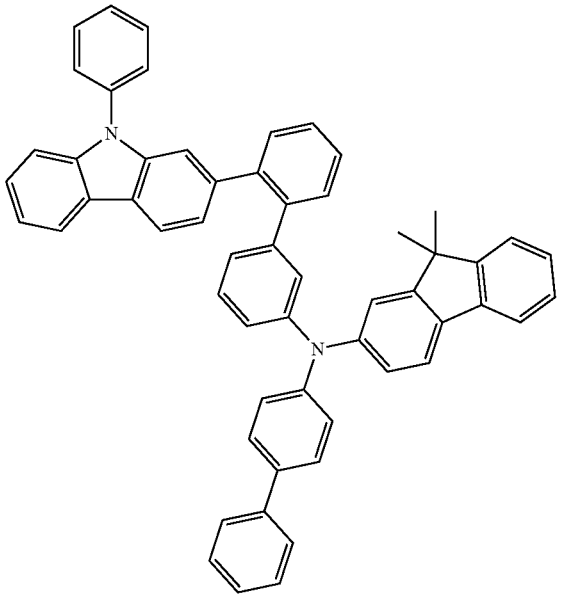
2-30
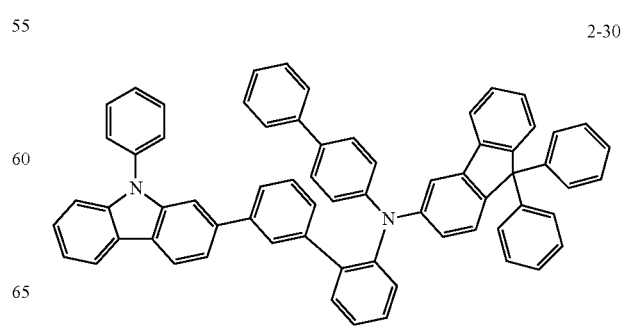

-continued
2-31
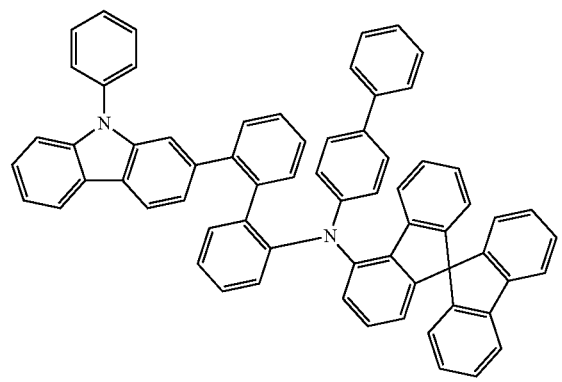
2-32
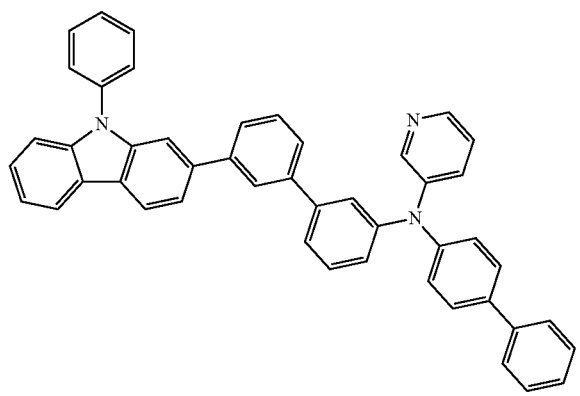
2-33
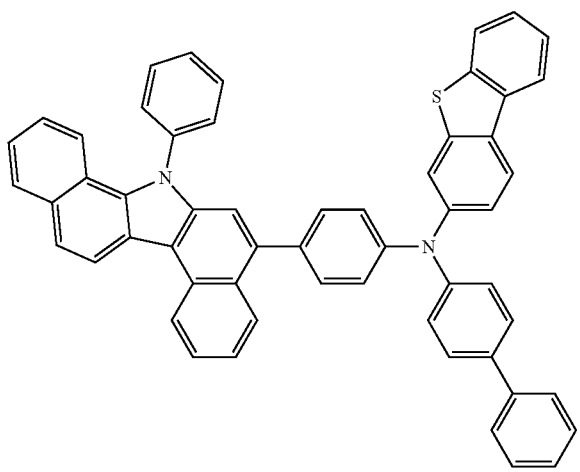
2-34
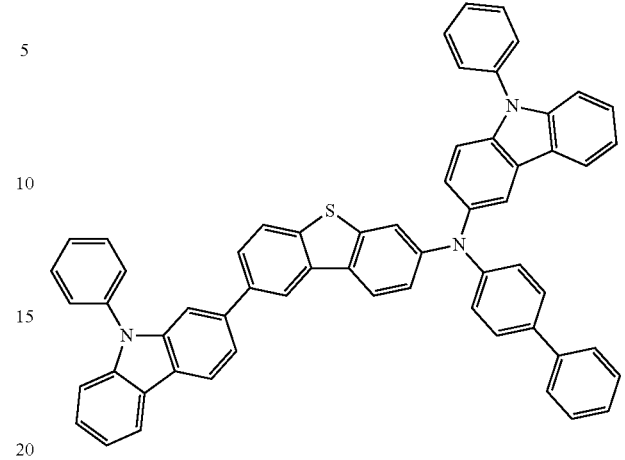
2-35
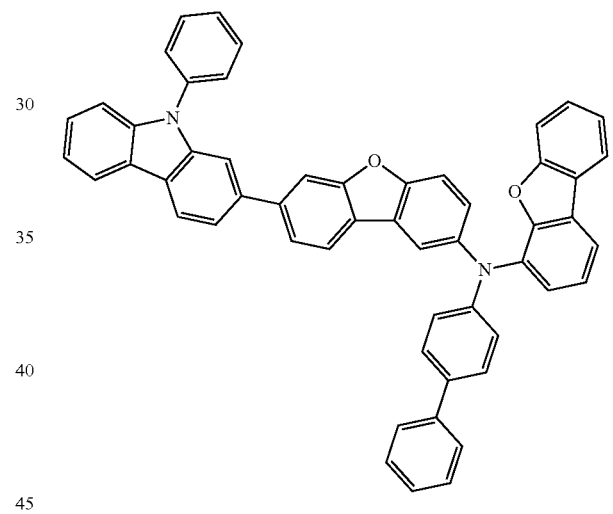
2-36
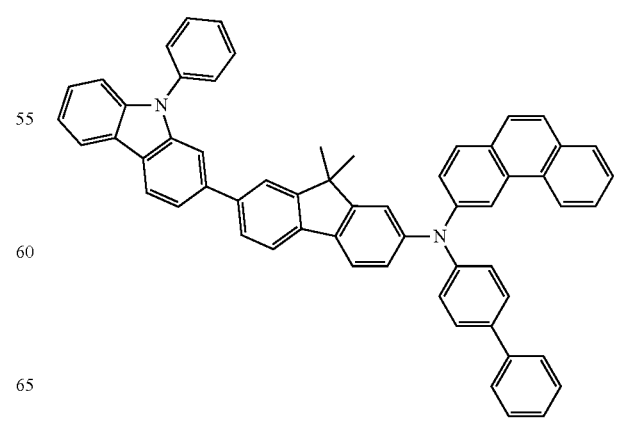

2-37
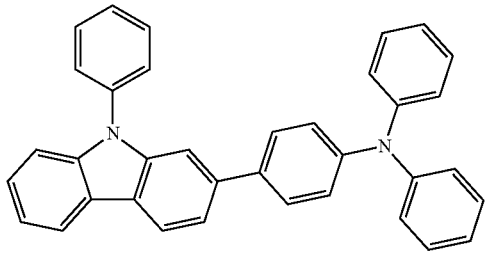
2-38
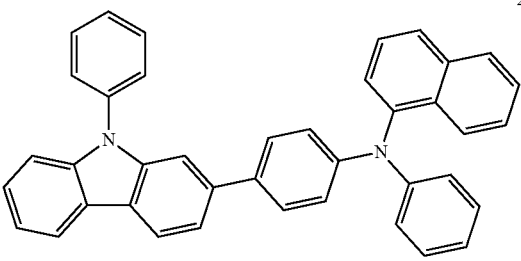
2-39
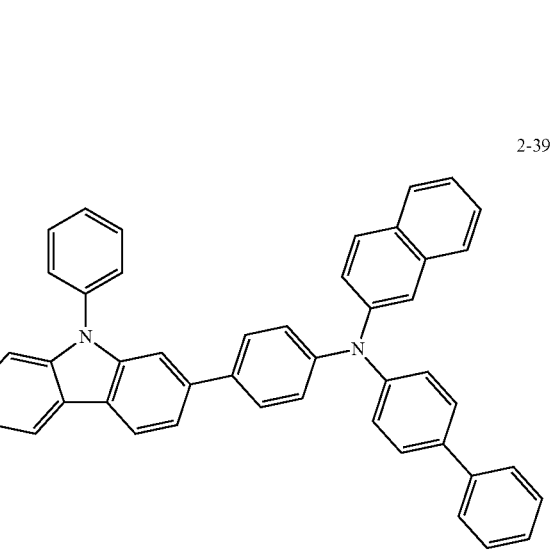
2-40
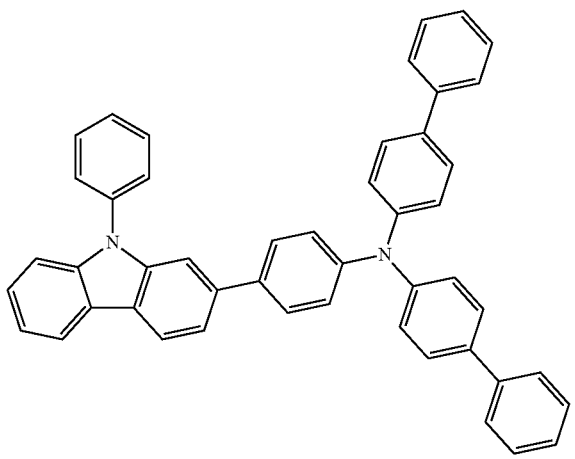
2-41
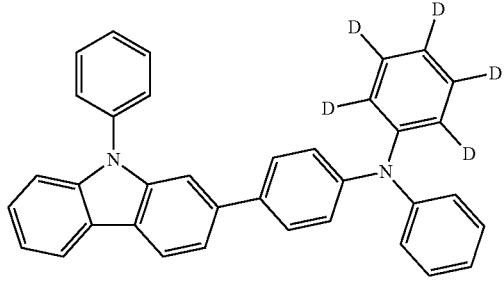
2-42
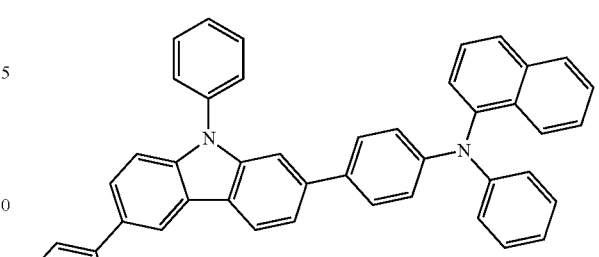
2-43
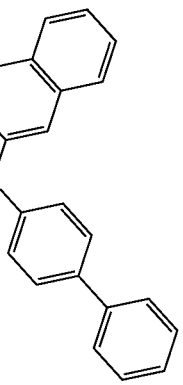

-continued
2-44
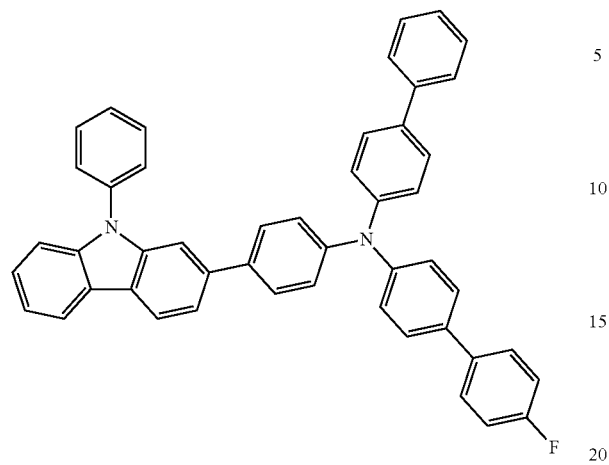
2-45
2-47
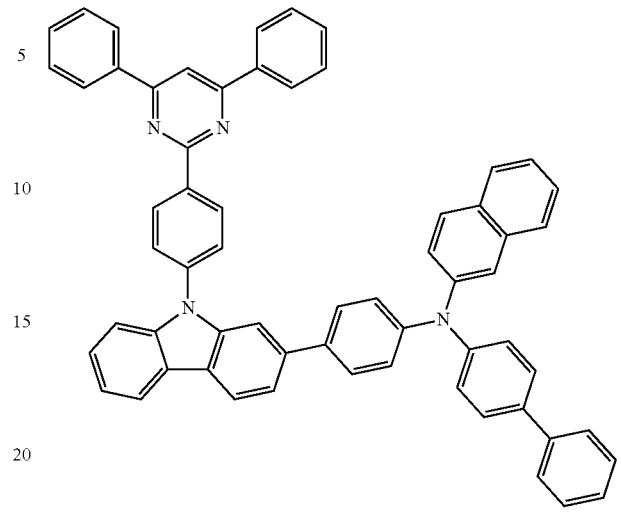
2-48
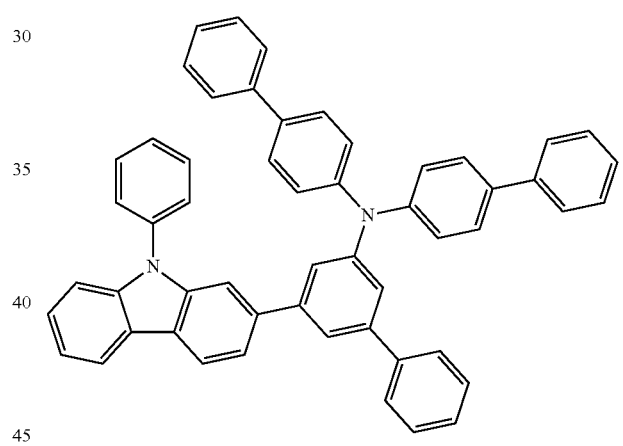
2-46
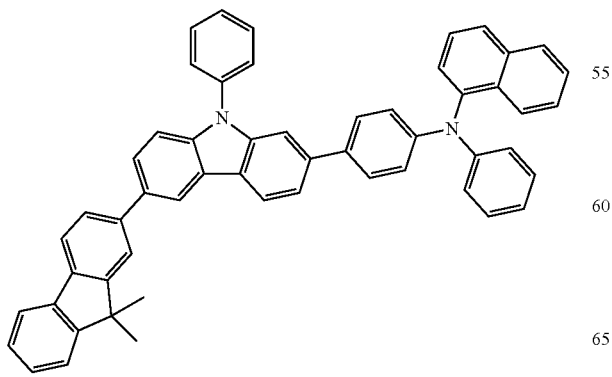
2-49
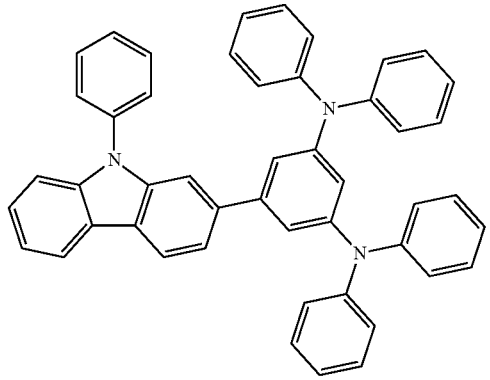

2-50
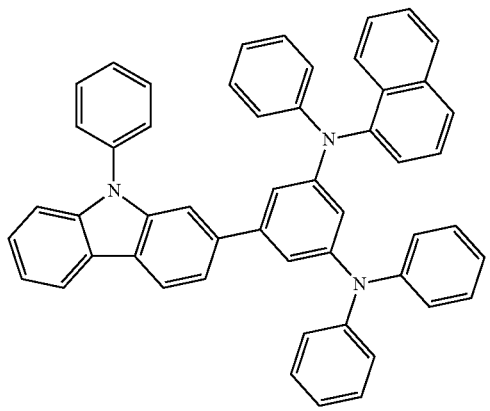
2-53
2-51
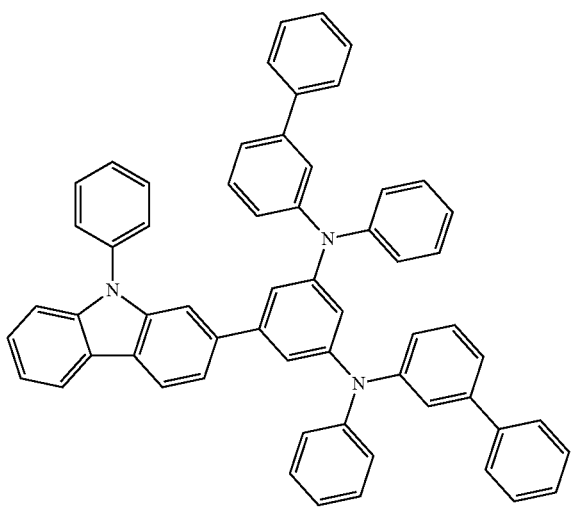
2-54
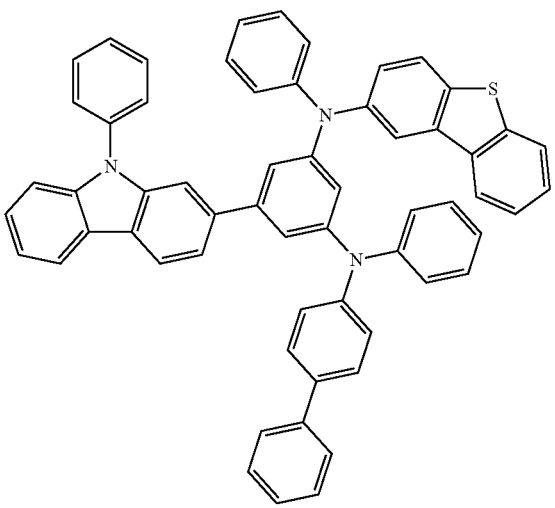
2-52
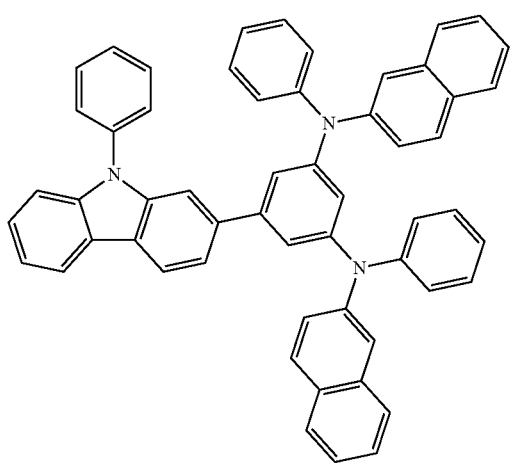
2-55
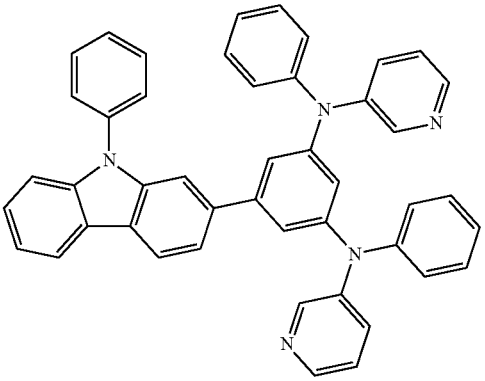

-continued
2-56
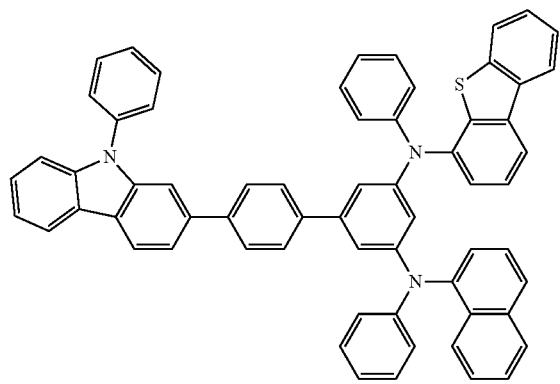
2-59
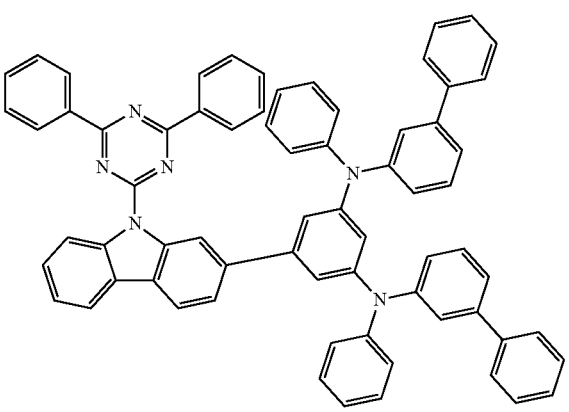
2-57
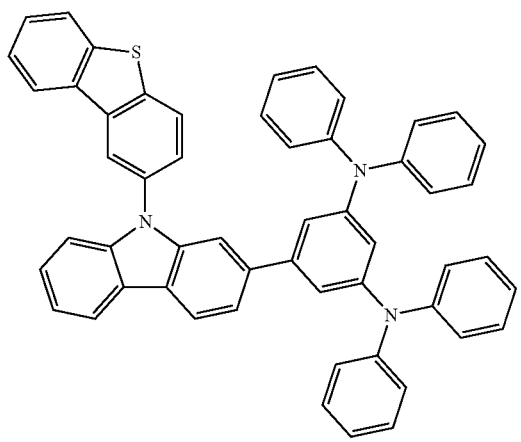
2-60
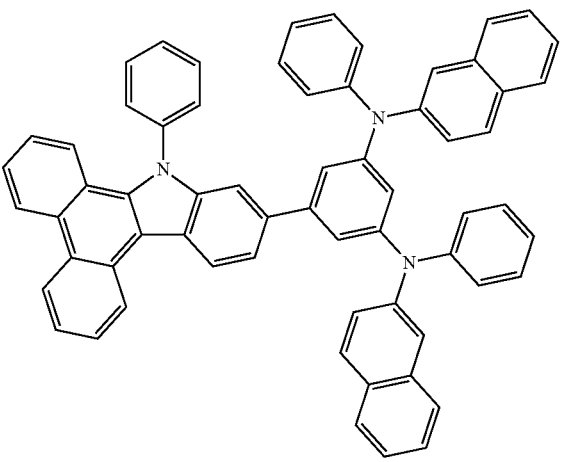
2-58
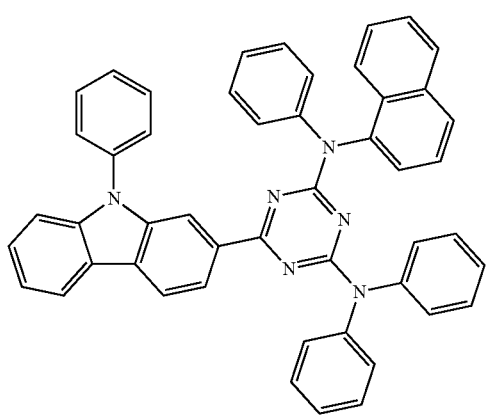
2-61
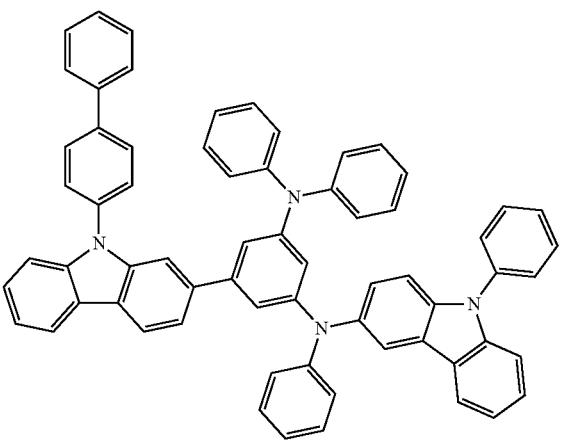

2-62
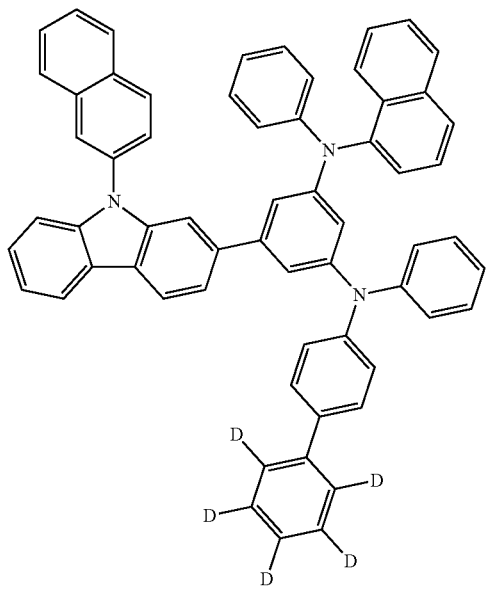
2-65
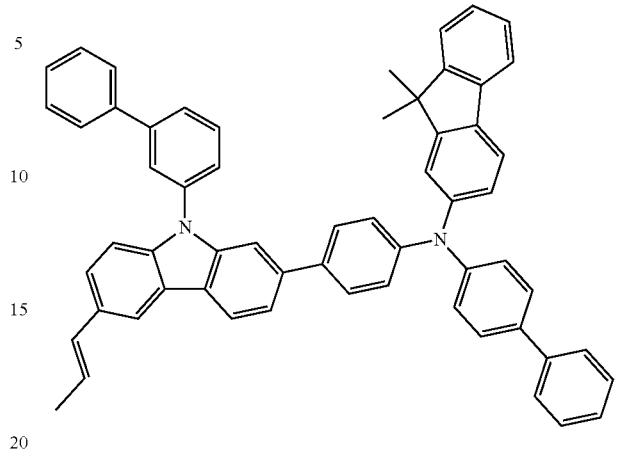
2-63
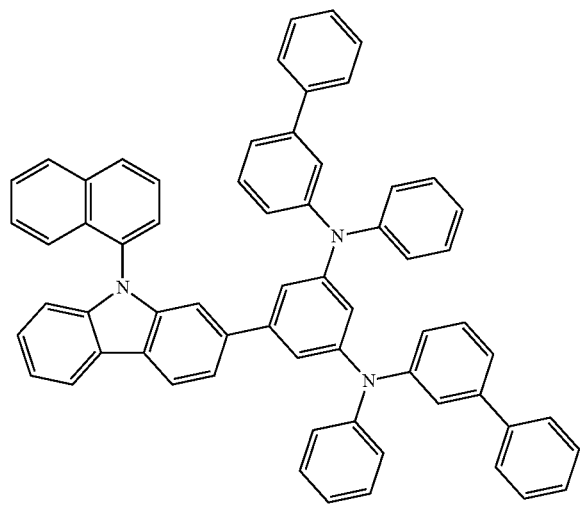
2-66
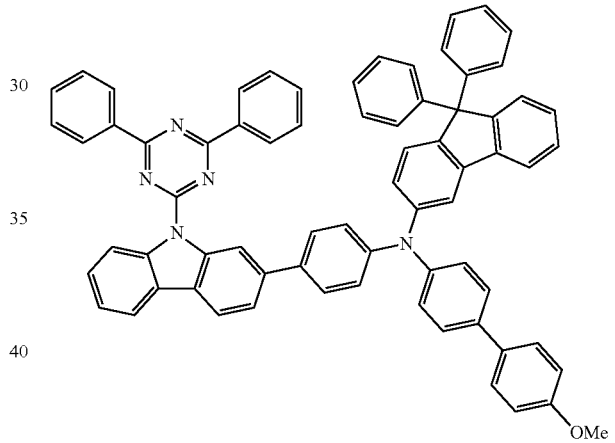
2-64
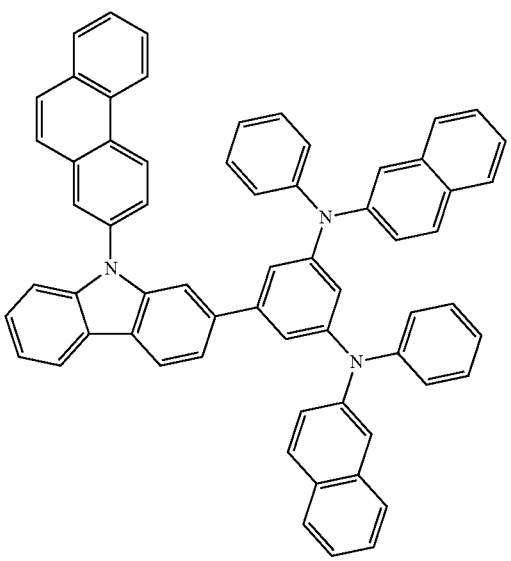
2-67
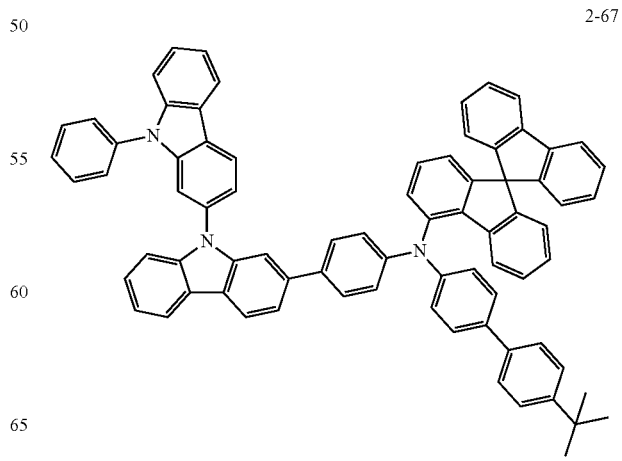

2-68
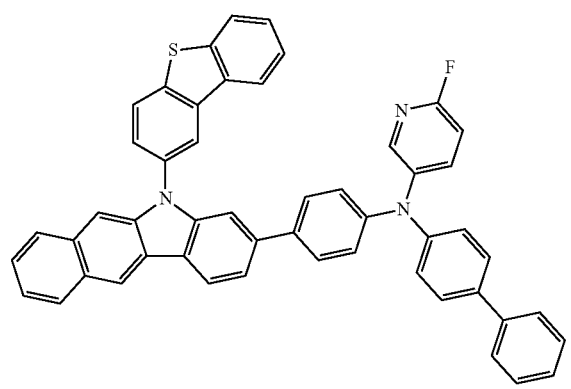
2-71
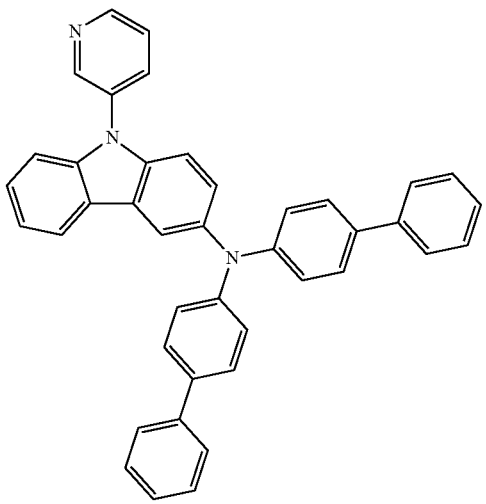
2-69
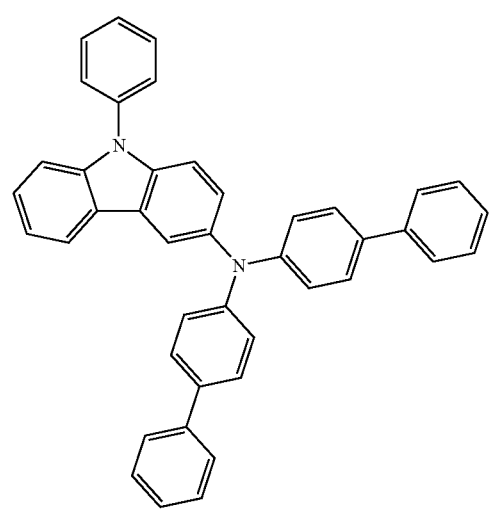
2-70
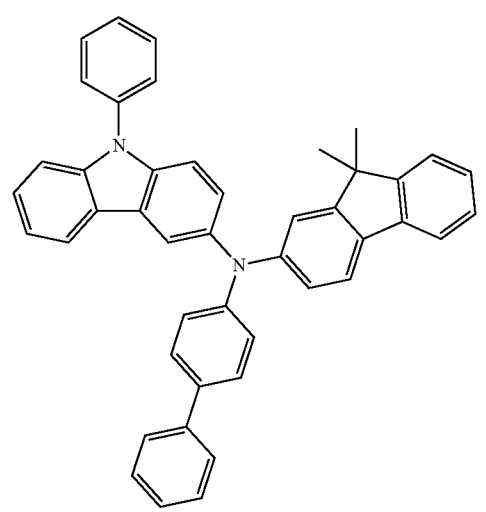
2-72
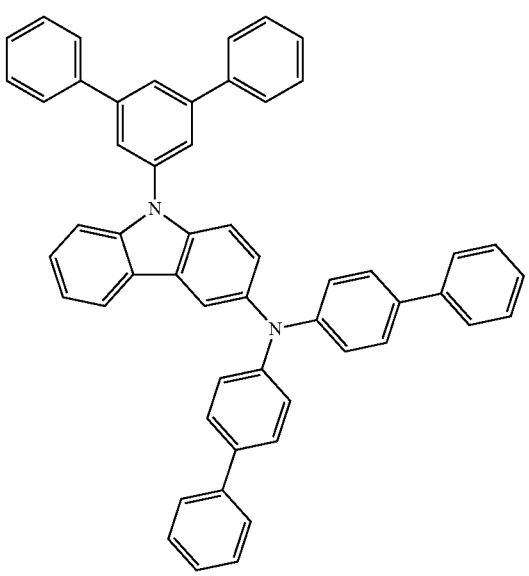

2-73
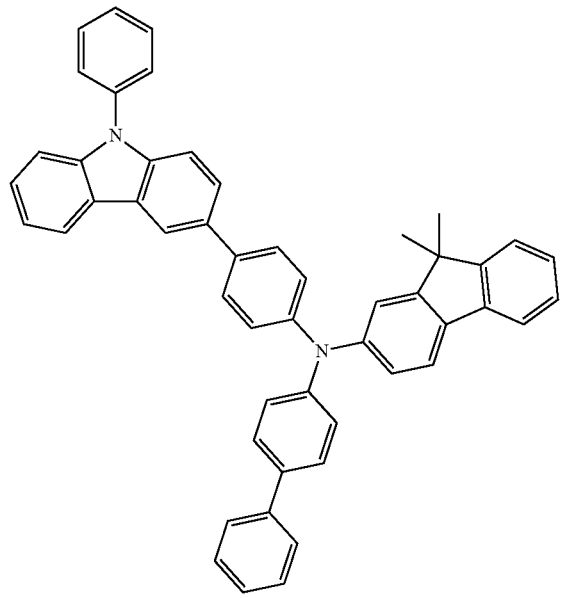
2-75
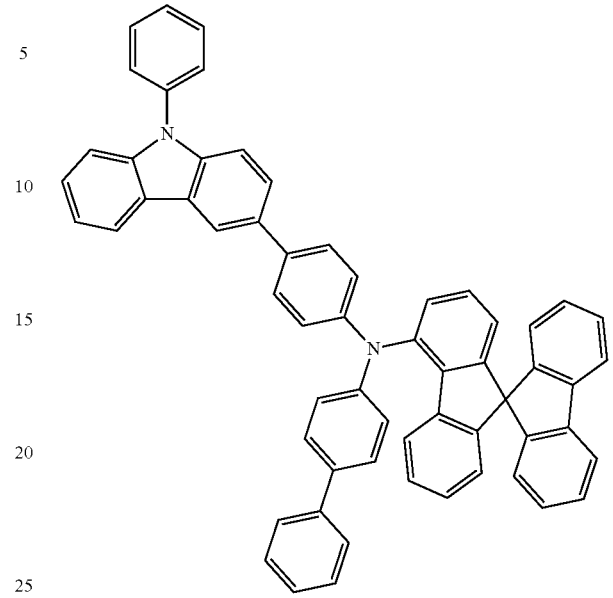
2-76
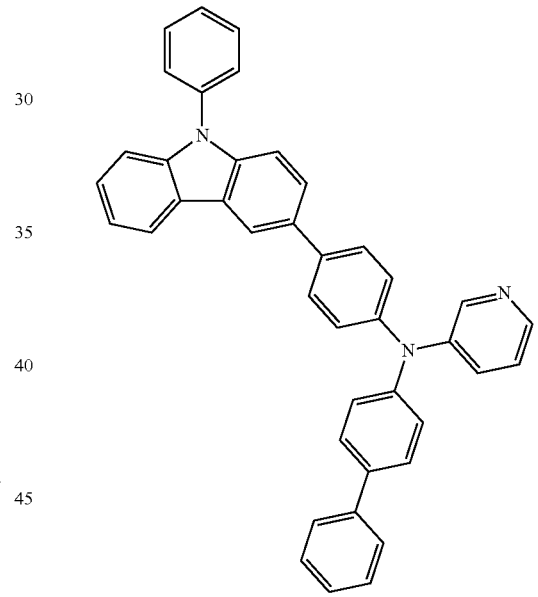
2-74
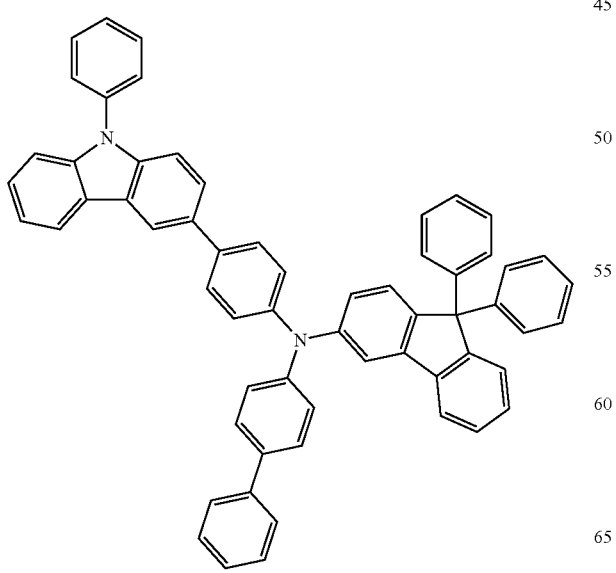
2-77
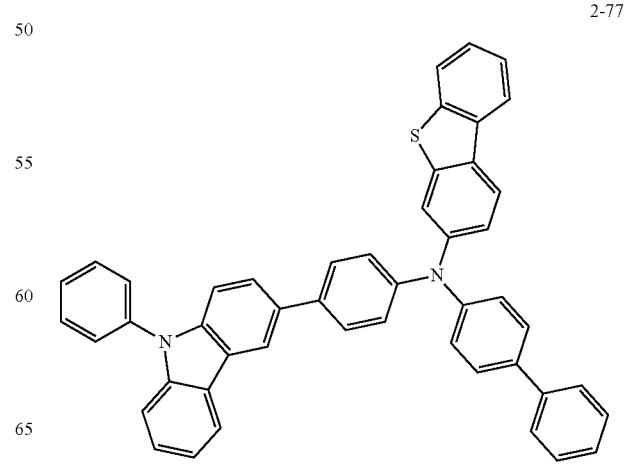

-continued
2-78
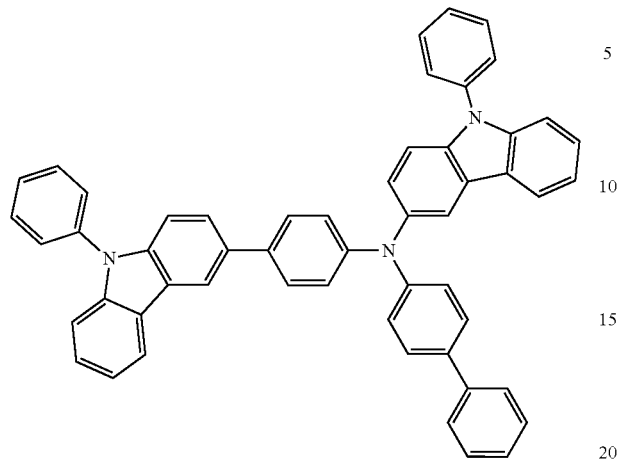
2-80
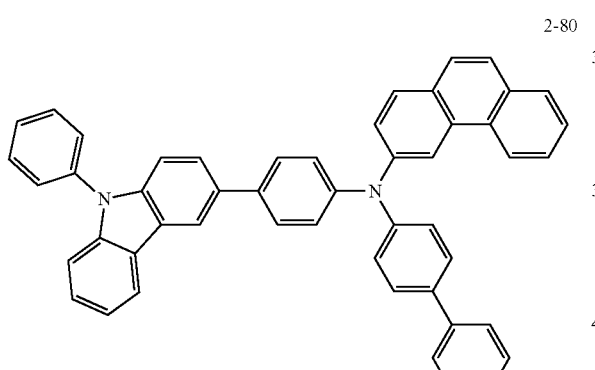
2-81
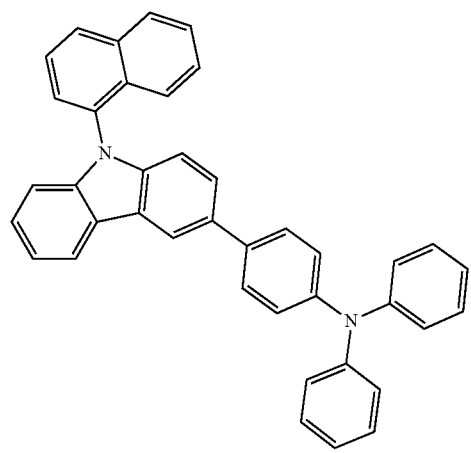
2-82
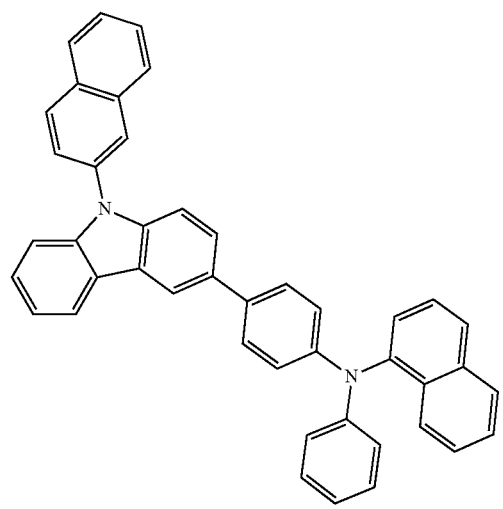
2-83
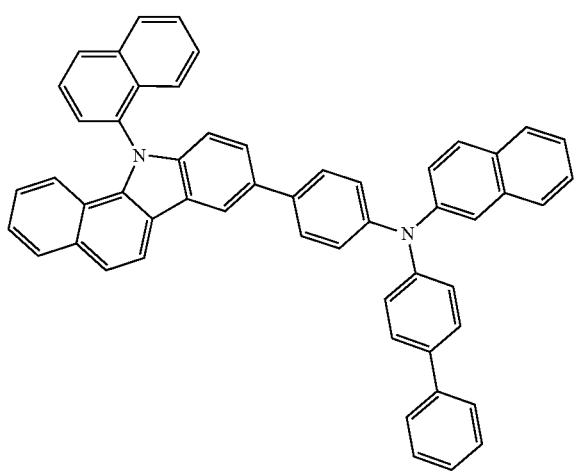
2-84
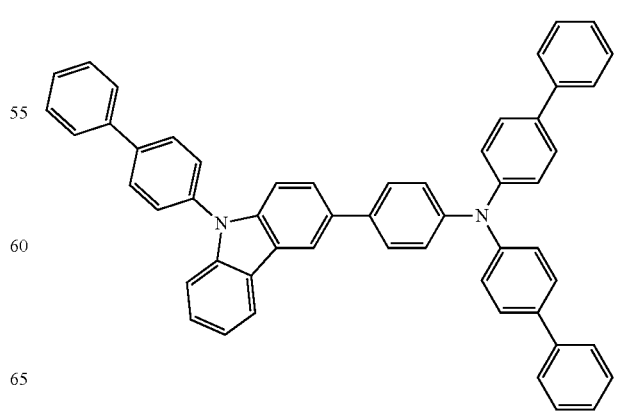

2-85
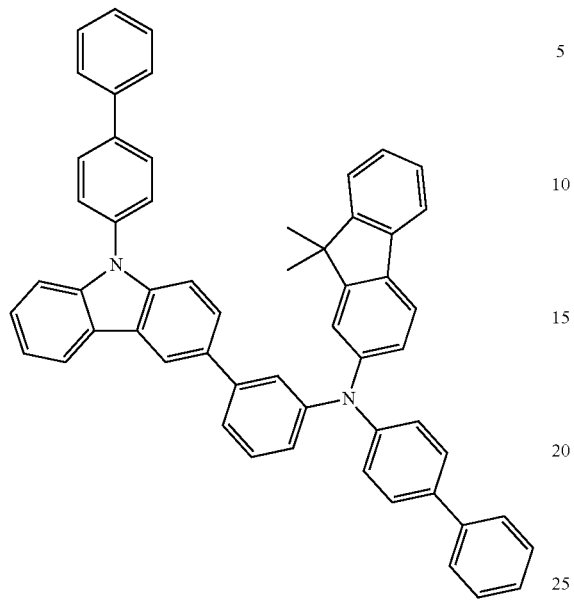
2-87
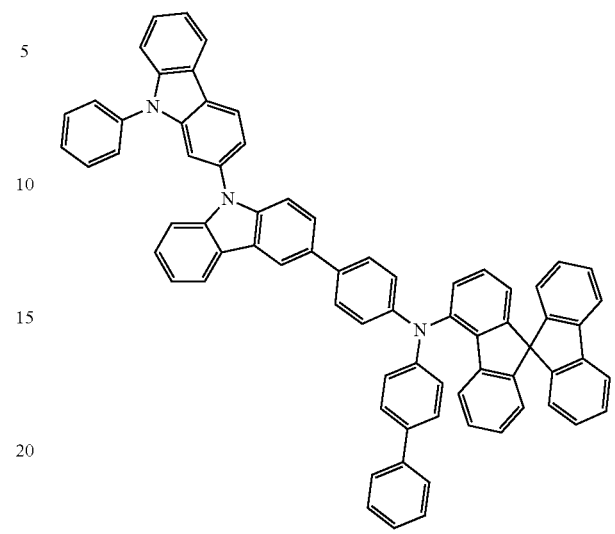
2-88
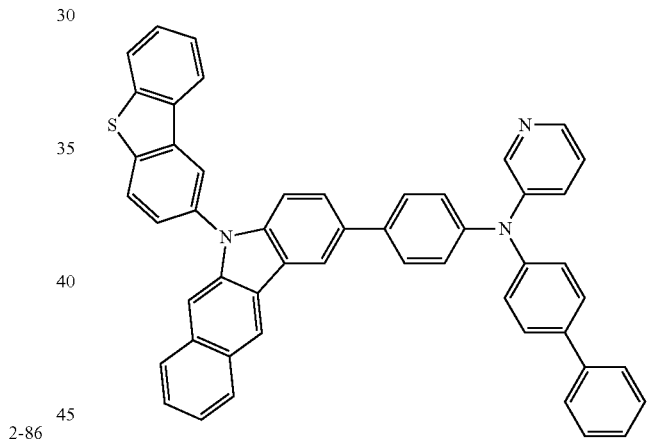
2-86
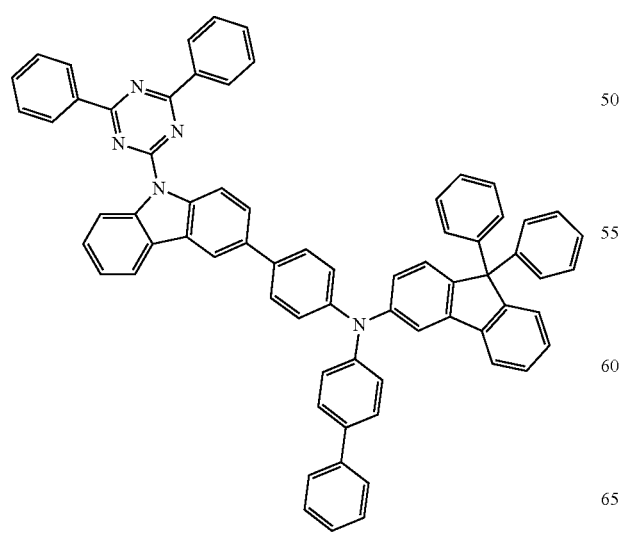
2-89
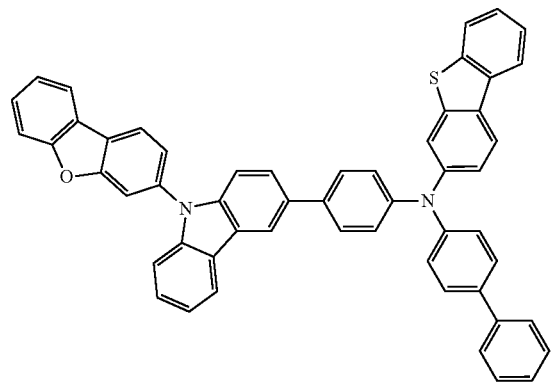

2-90
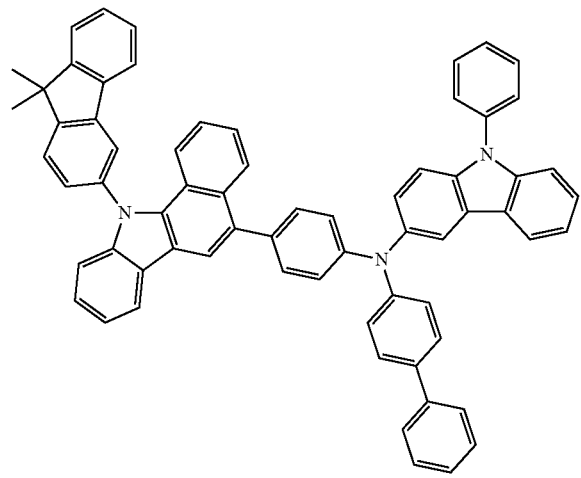
2-91
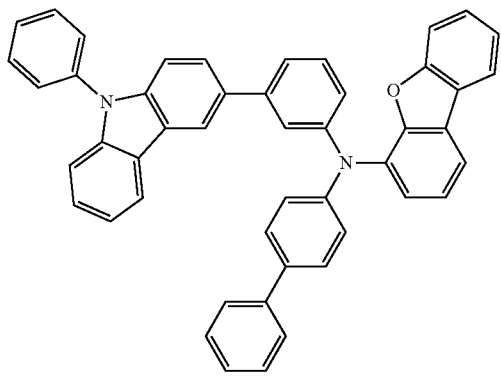
2-92
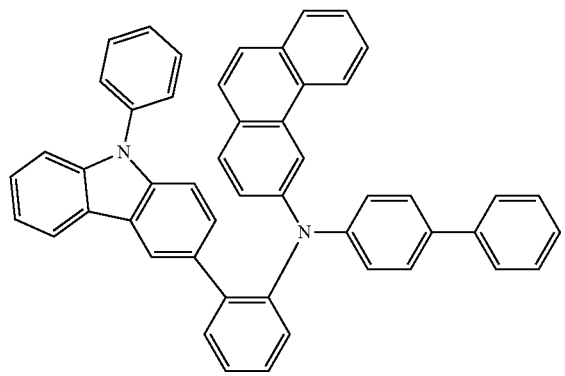
2-93
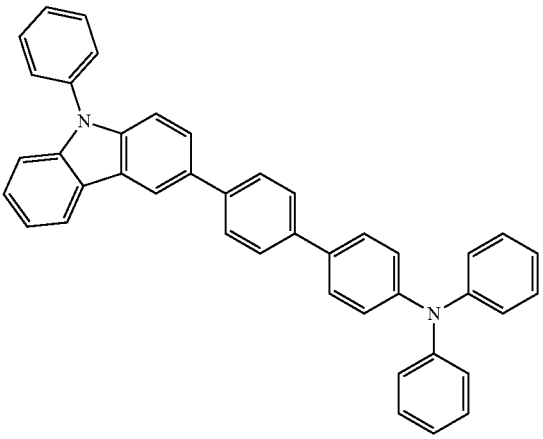
2-94
2-95
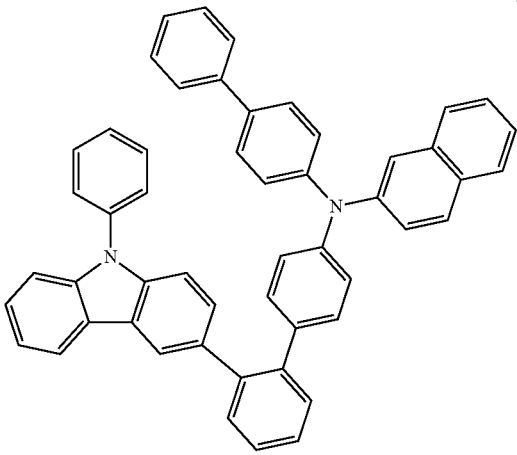

2-96
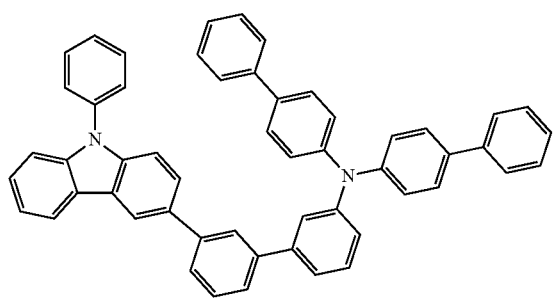
2-99
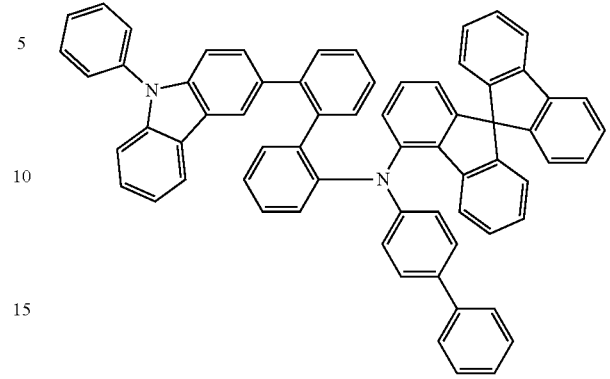
2-97
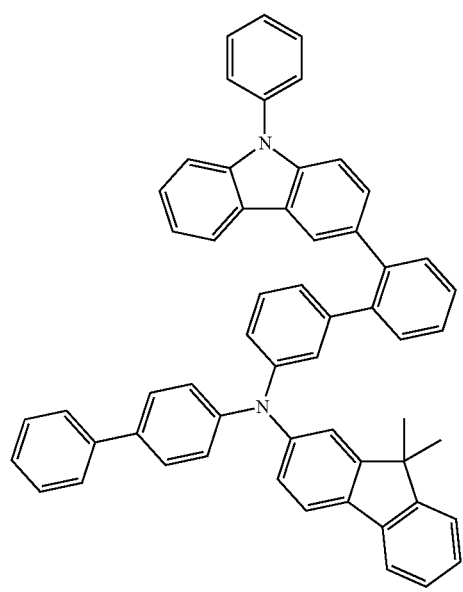
2-100
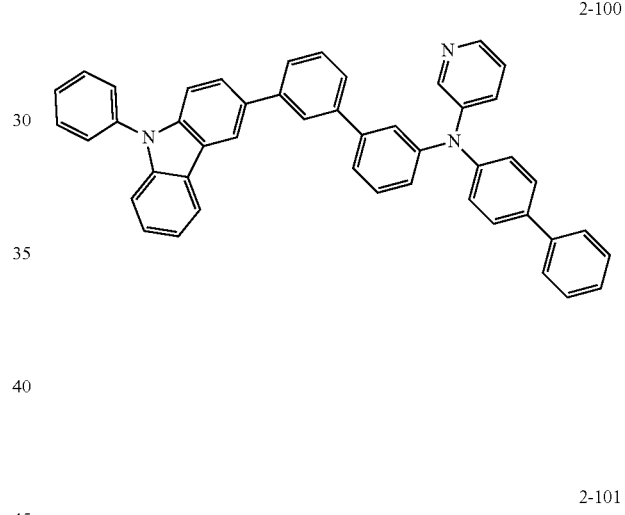
2-98
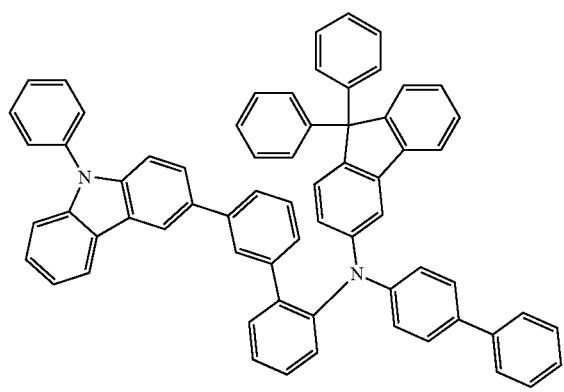
2-101
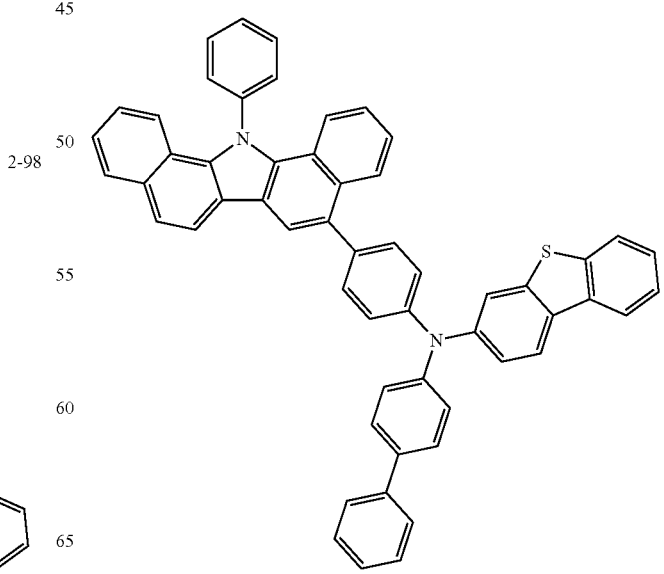

2-102
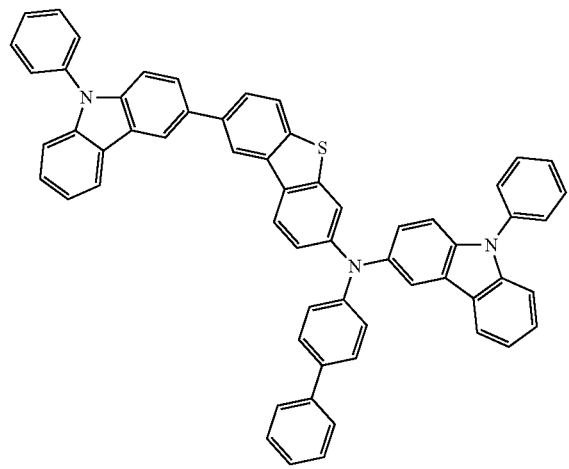
2-105
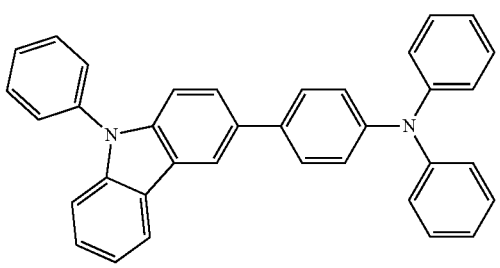
2-103
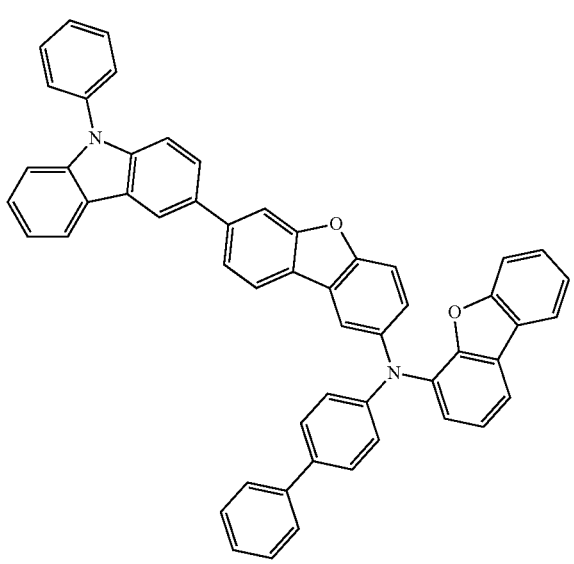
2-106
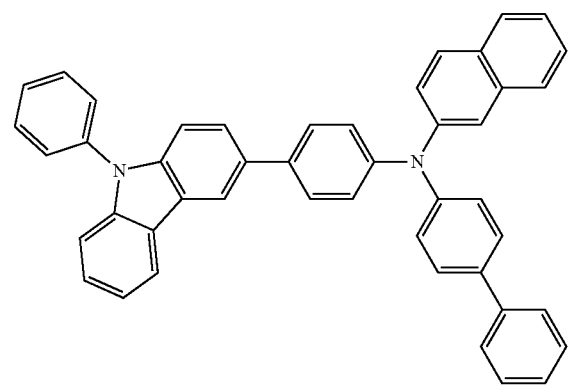
2-107
2-104
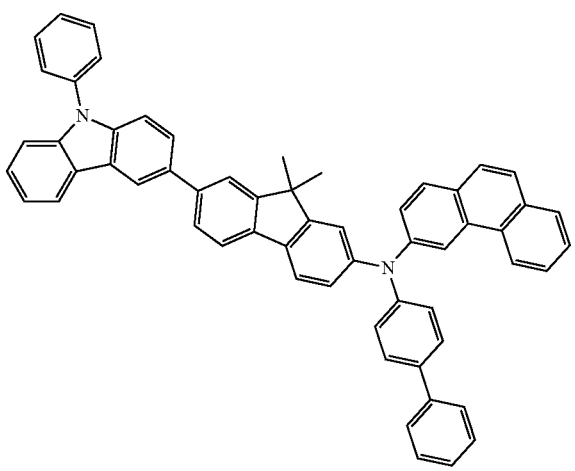
2-108
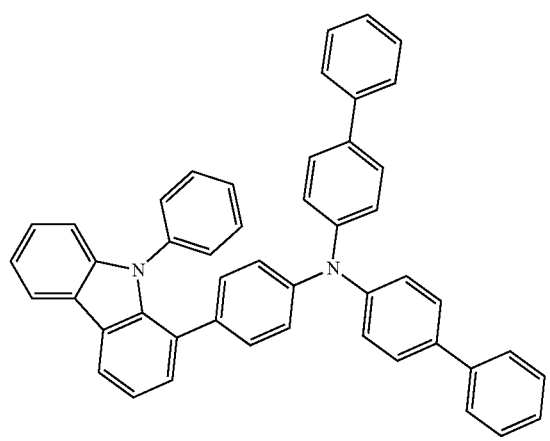

2-109
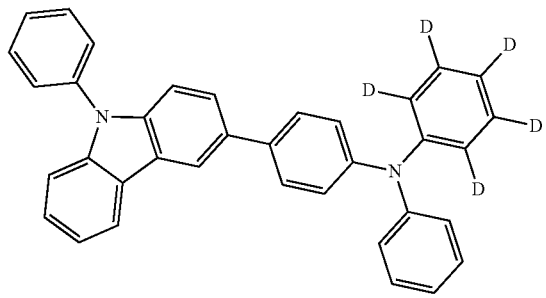
2-110
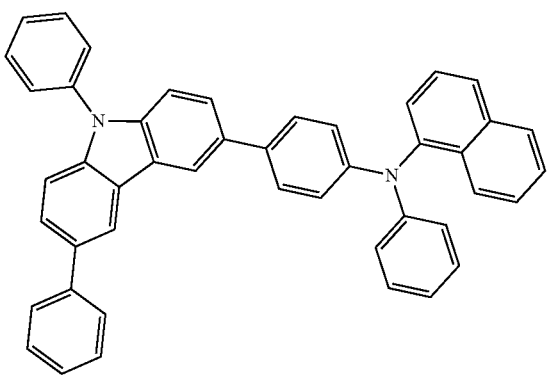
2-111
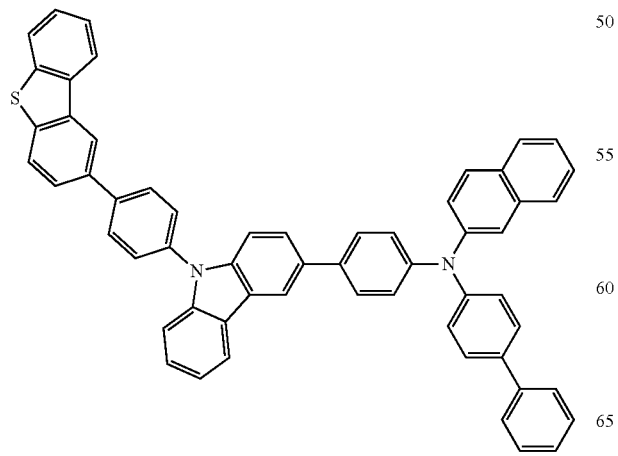
2-112
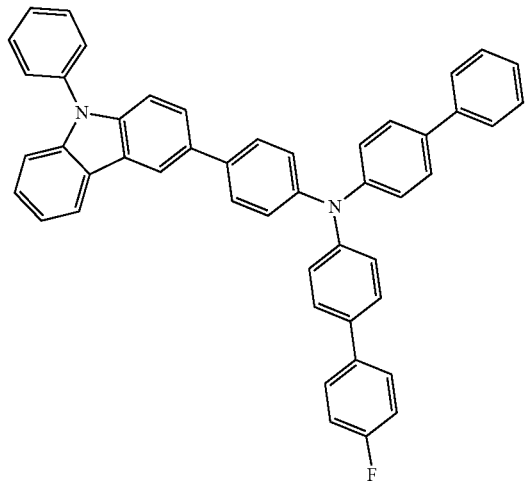
2-113
2-114
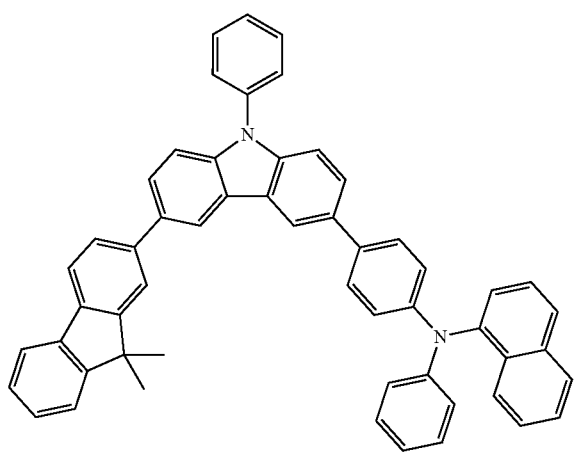

2-115
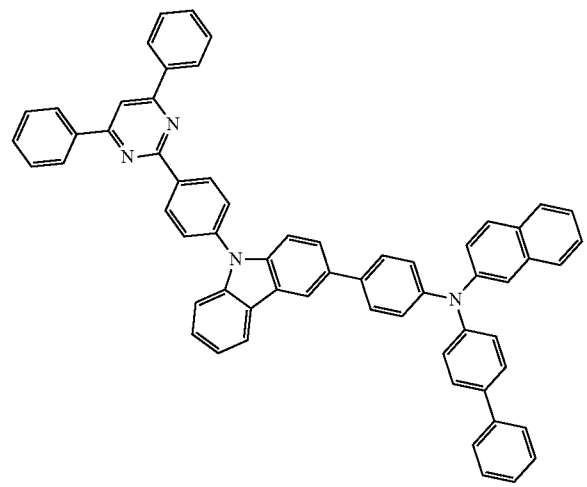
2-116
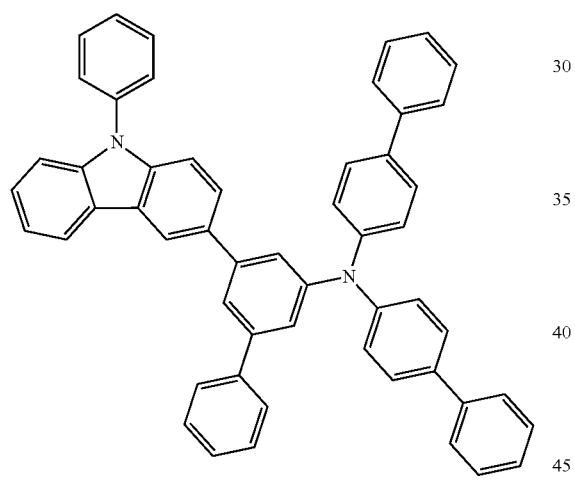
2-117
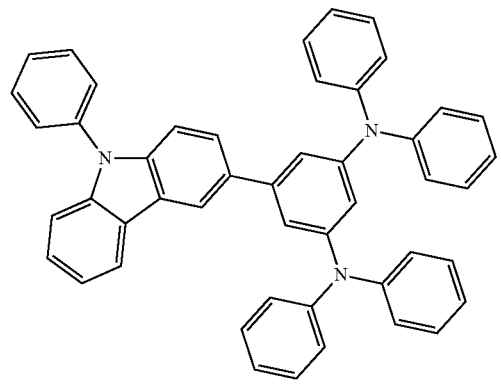
2-118
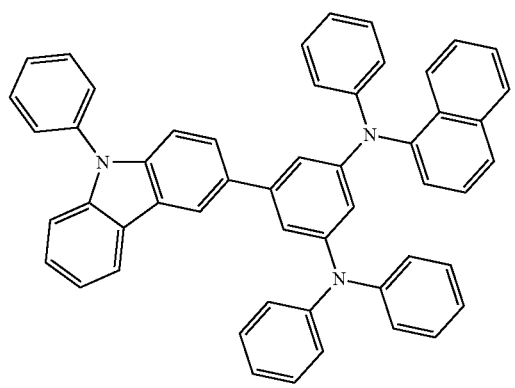
2-119
2-120
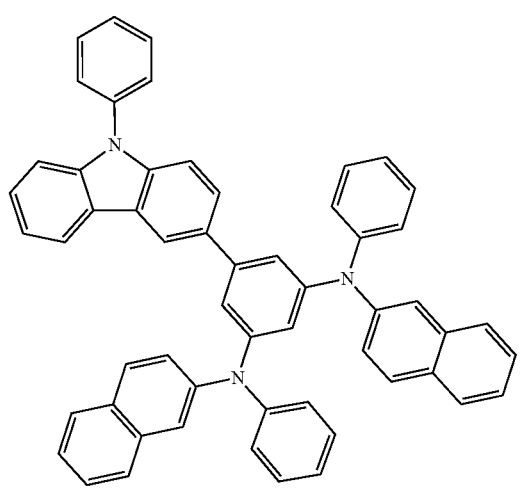

2-121
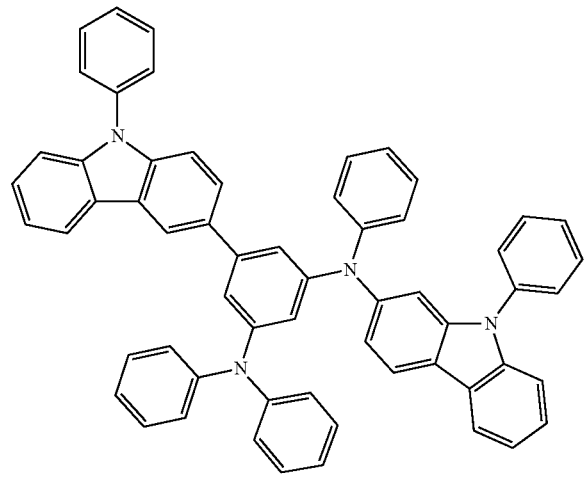
2-122
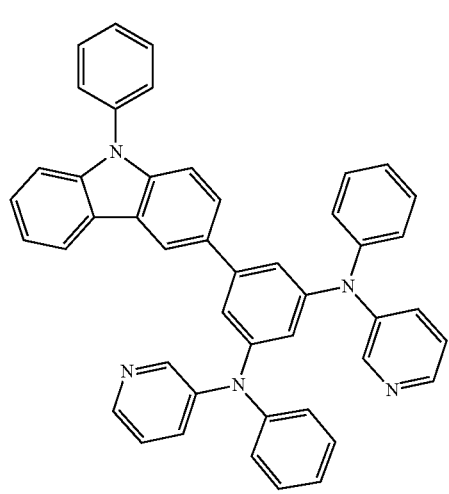
2-123
2-124
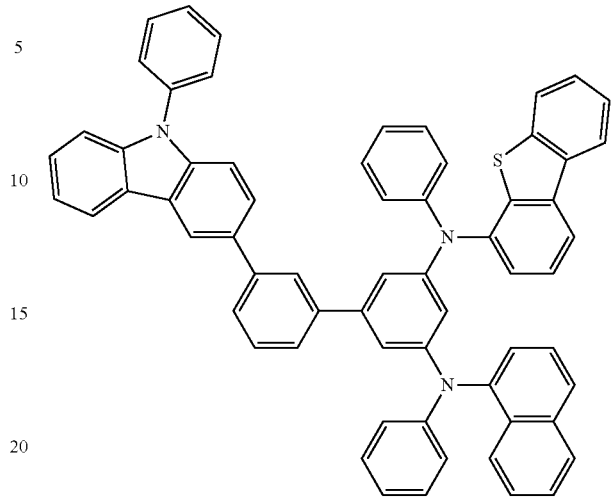
2-125
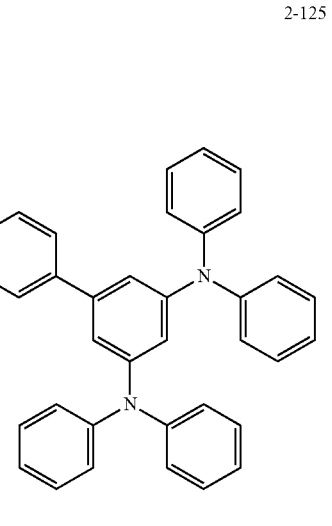
2-126
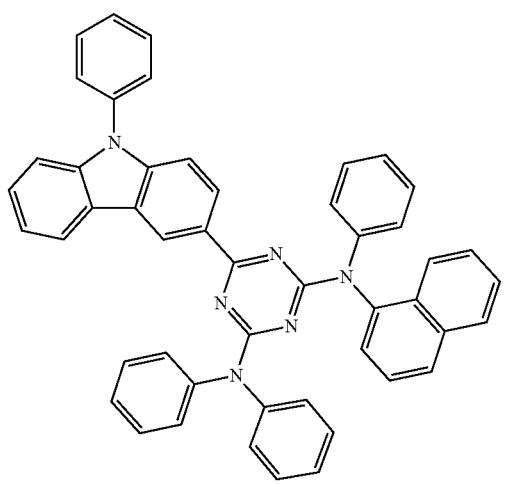

2-127
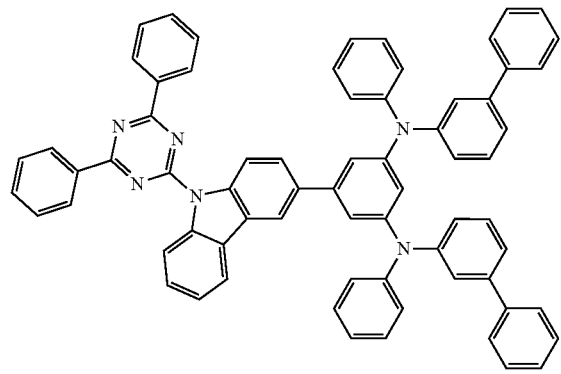
2-128
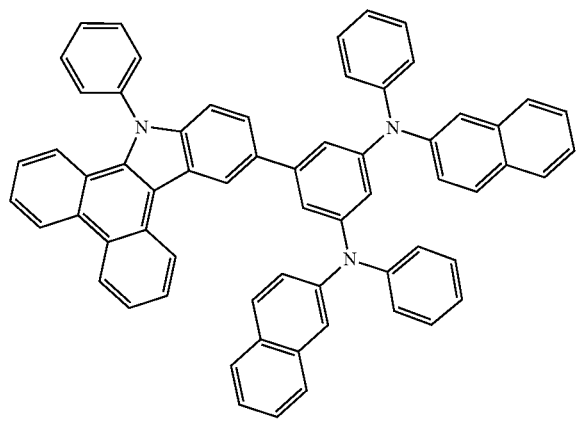
2-129
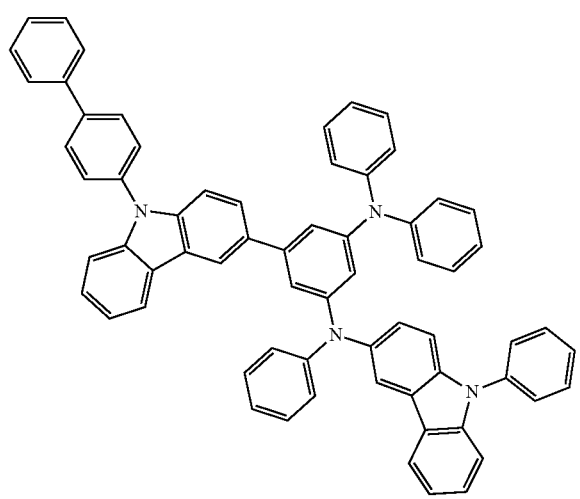
2-130
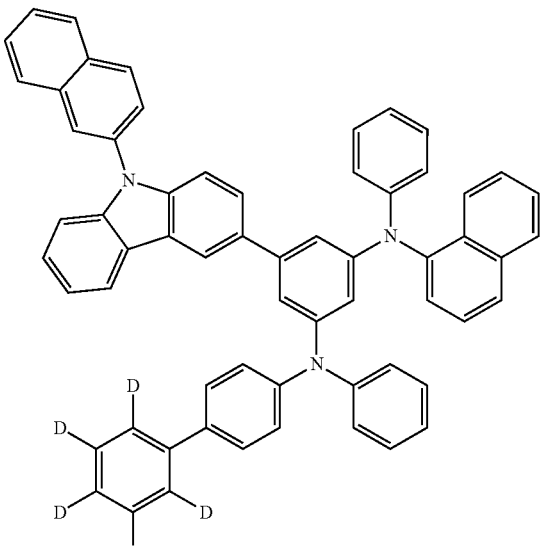
2-131
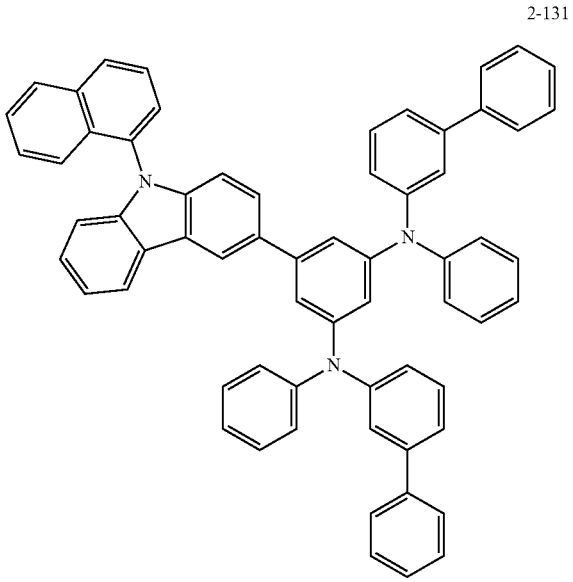
2-132
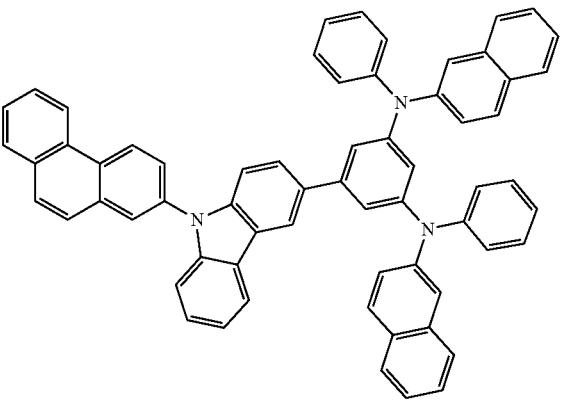

2-133

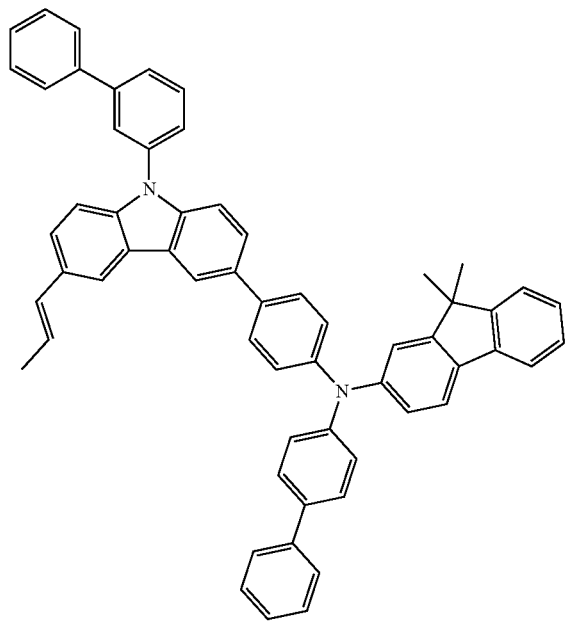

2-134

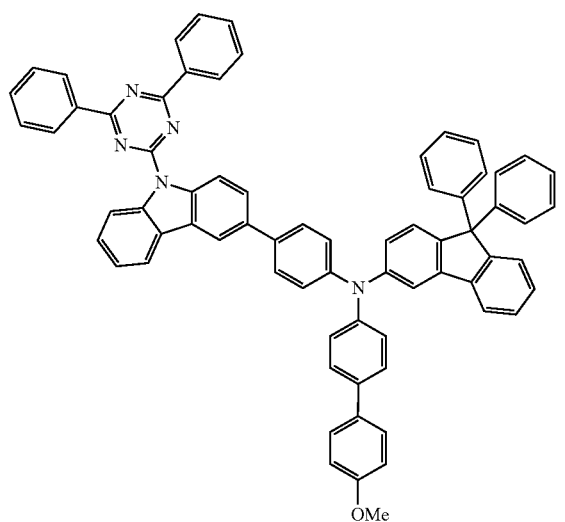

2-135

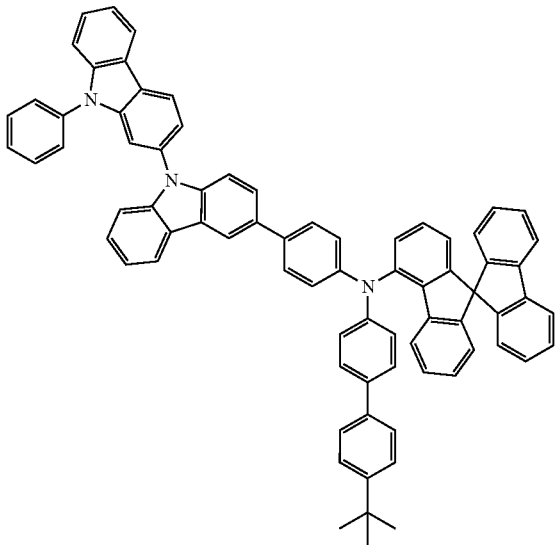

2-136

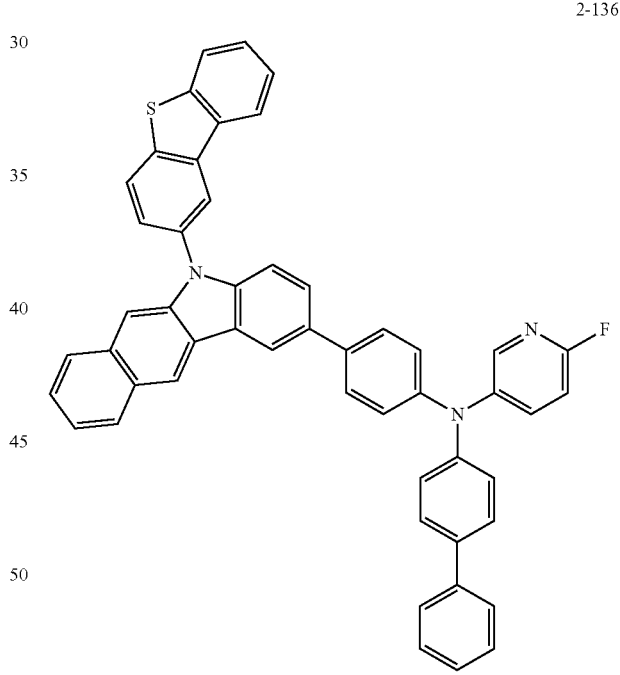

Hereinafter, examples for synthesizing the compounds represented by Formulas 1 and 2 according to the present invention and examples for preparing an organic electric element according to the present invention will be described in detail with reference to examples, but the present invention is not limited to the following examples.

[SYNTHESIS EXAMPLE 1] Formula 1

The compound represented by Formula 1 according to the present invention can be synthesized by reacting Sub 1 and Sub 2 as shown in Reaction Scheme 1, but there is no limitation thereto.

<Reaction Scheme 1>
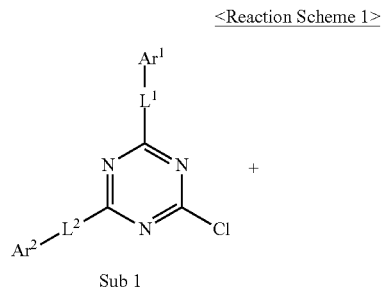
Compounds belong to Sub 1 of Reaction Scheme 1 are as follows, but are not limited thereto.
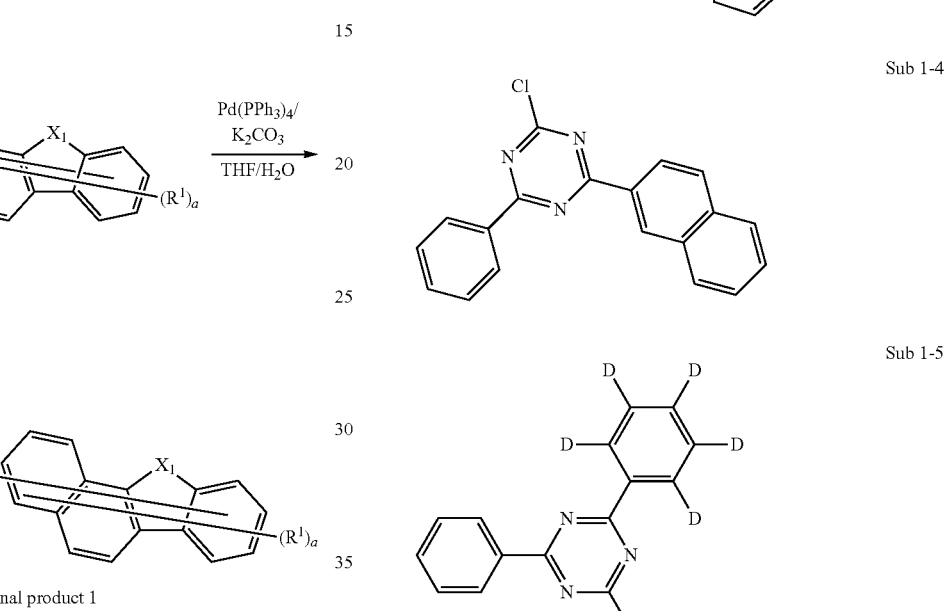
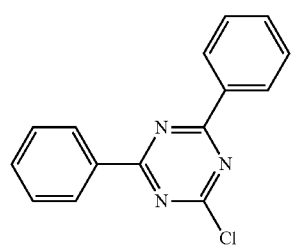
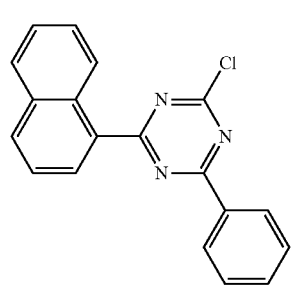
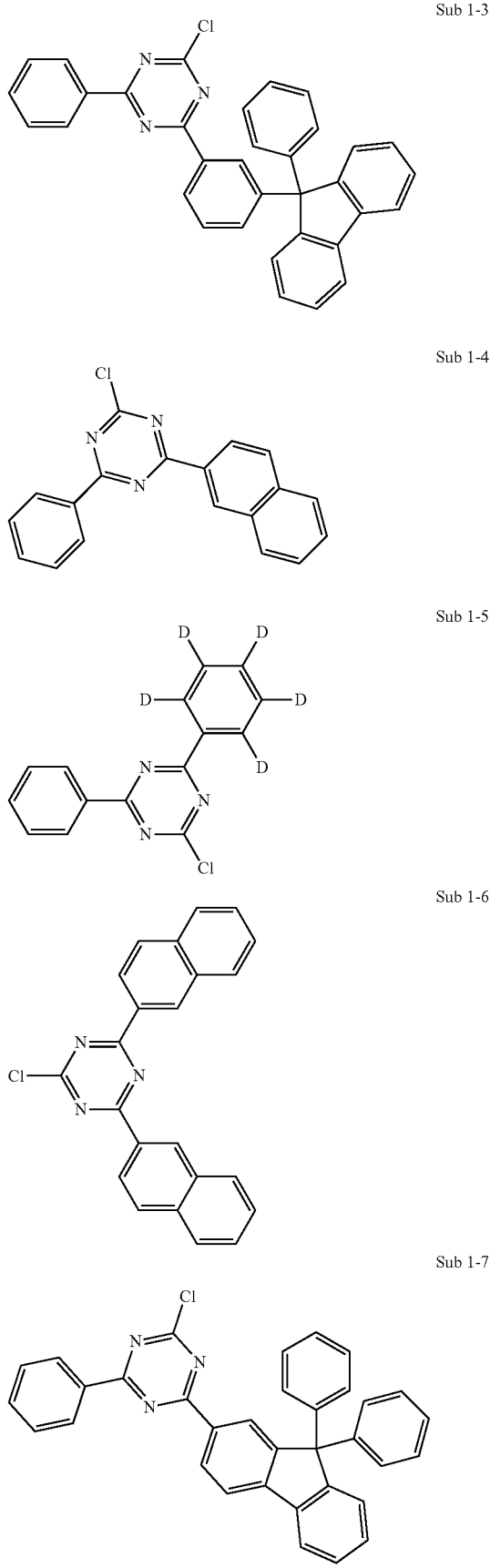

-continued
Sub 1-8
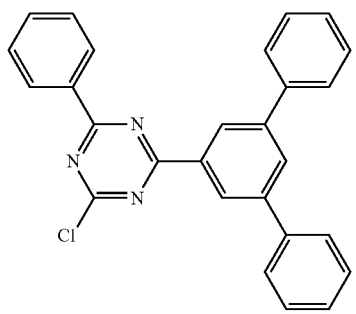
Sub 1-9
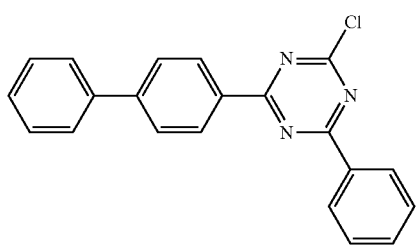
Sub 1-10
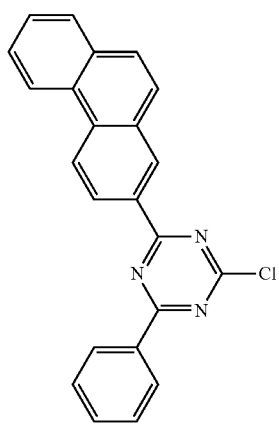
Sub 1-11
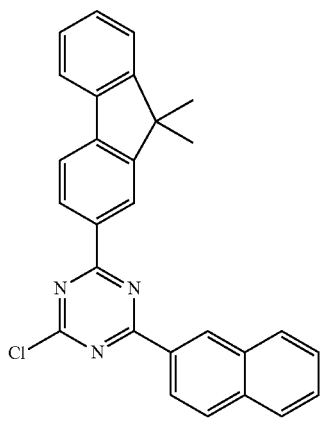
-continued
Sub 1-12
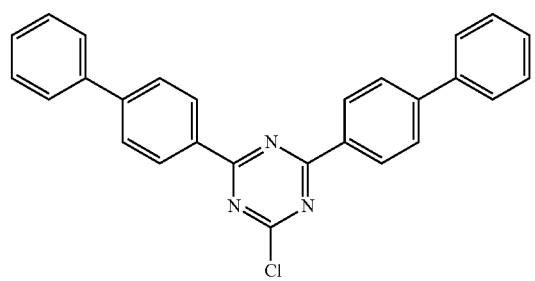
Sub 1-13
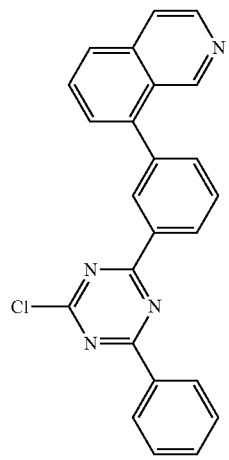
Sub 1-14
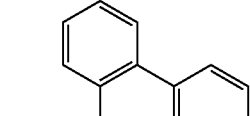
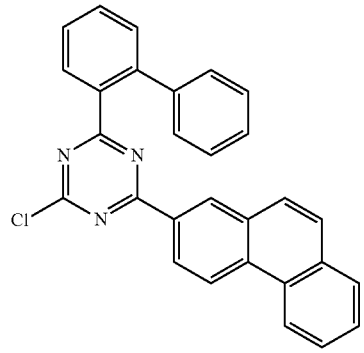
Sub 1-15
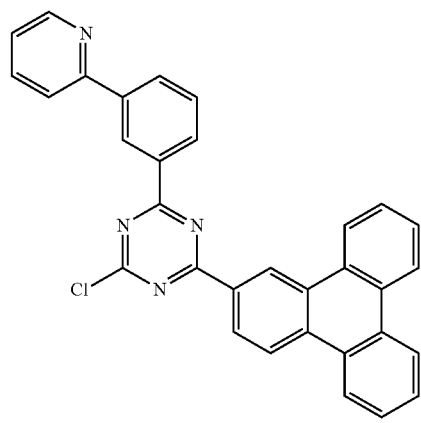

Sub 1-16
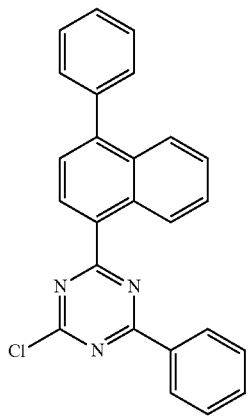
Sub 1-17
Sub 1-18
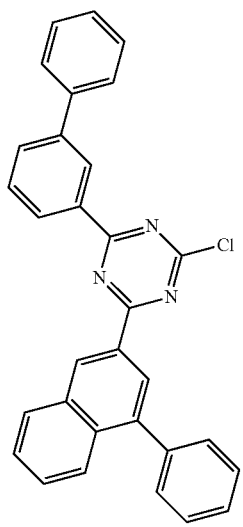
Sub 1-19
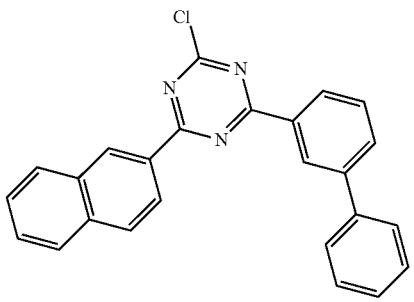
Sub 1-20
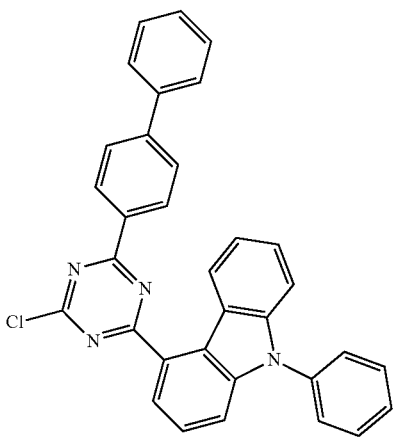
Sub 1-21
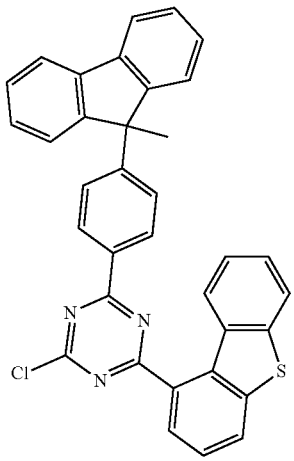
Sub 1-22

Sub 1-23
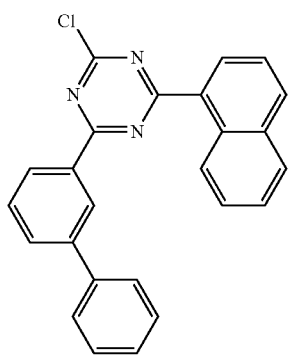
Sub 1-24
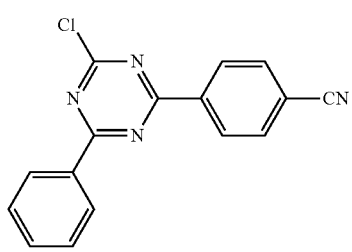
Sub 1-25
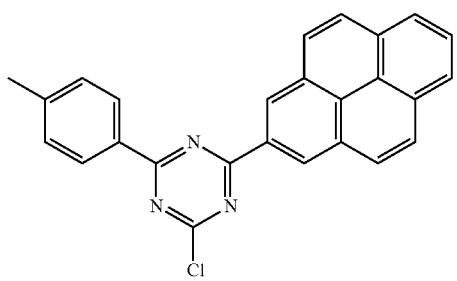
Sub 1-26
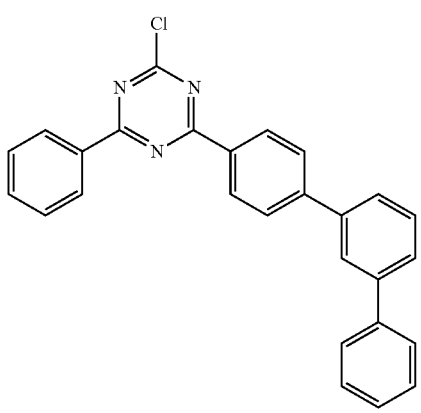
Sub 1-27
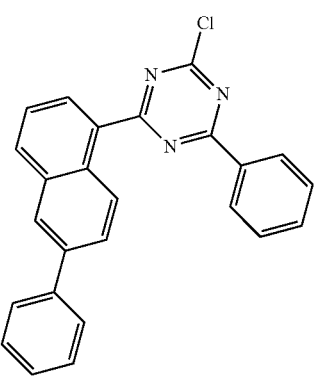
Sub 1-28
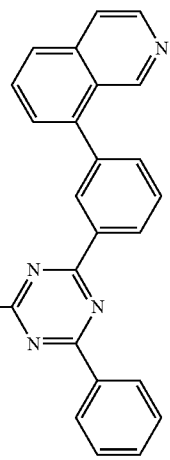
Sub 1-29
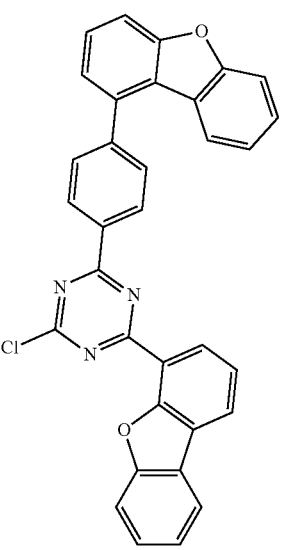

Sub 1-30
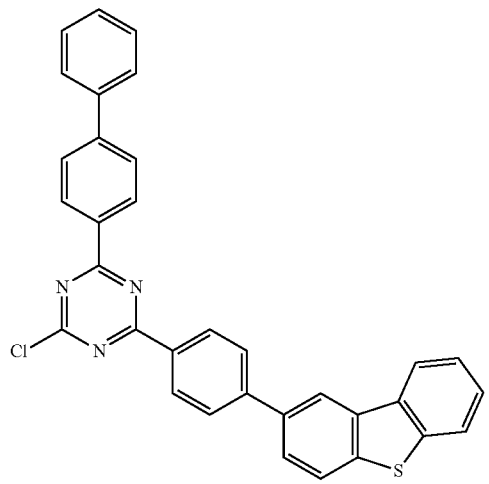
Sub 1-31
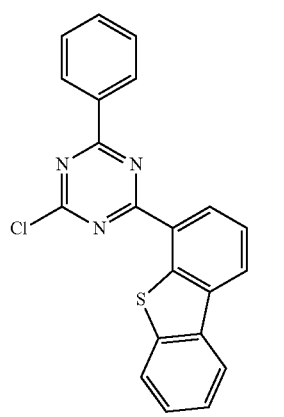
Sub 1-32
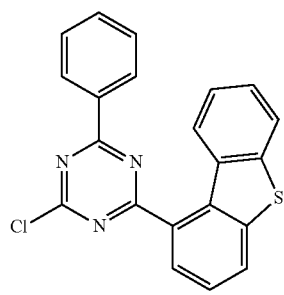
Sub 1-33
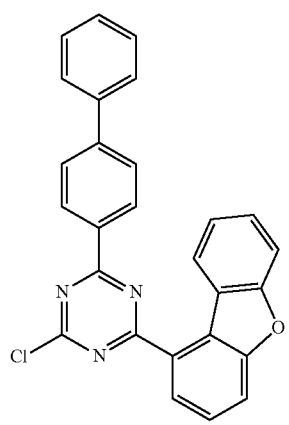
Sub 1-34
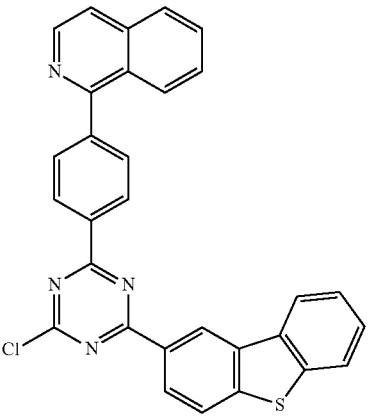
Sub 1-35
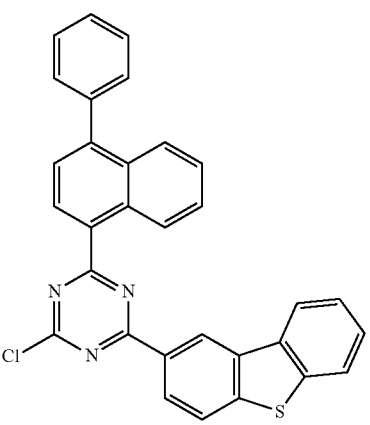
Sub 1-36
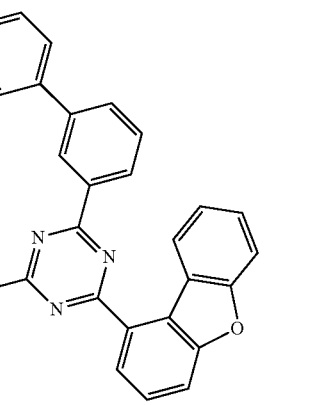
Sub 1-37
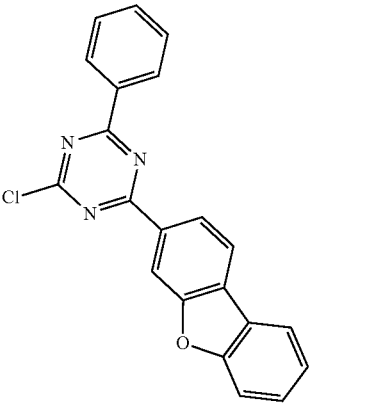

Sub 1-38
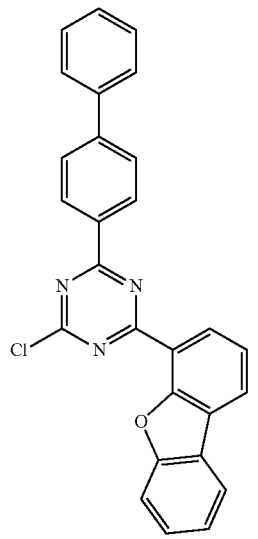
Sub 1-41
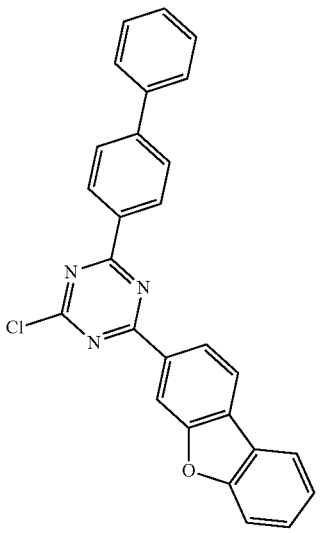
Sub 1-39
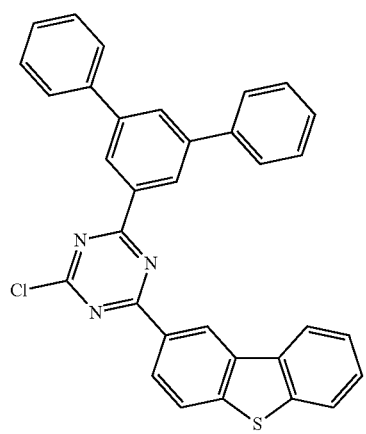
Sub 1-42
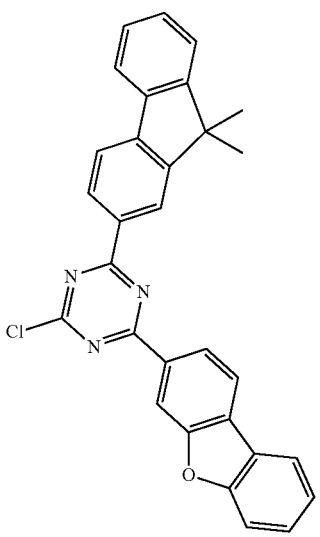
Sub 1-40
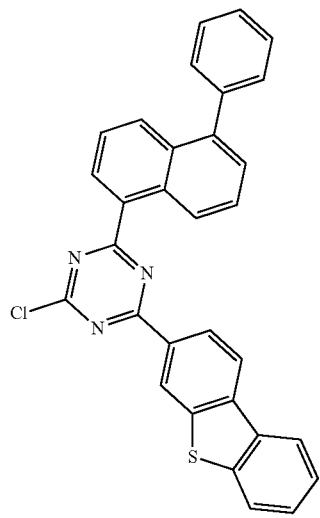
Sub 1-43
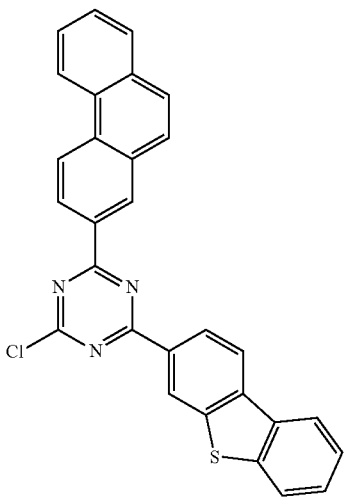

-continued

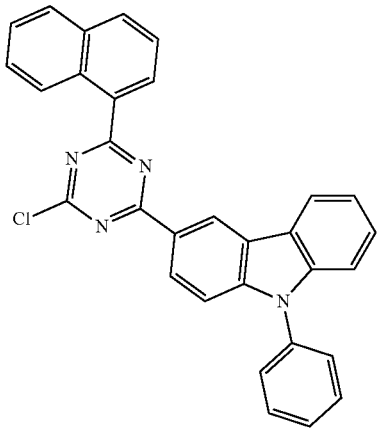

Sub 1-44

FD-MS values of compounds belong to Sub 1 are shown in Table 1 below.

TABLE 1

| Compound | FD-MS | Compound | FD-MS |
| --- | --- | --- | --- |
| Sub 1-1 | m/z = 267.06($C_{15}H_{10}ClN_3$ = 267.72) | Sub 1-2 | m/z = 317.07($C_{19}H_{12}ClN_3$ = 317.78) |
| Sub 1-3 | m/z = 507.15($C_{34}H_{22}ClN_3$ = 508.02) | Sub 1-4 | m/z = 317.07($C_{19}H_{12}ClN_3$ = 317.78) |
| Sub 1-5 | m/z = 272.09($C_{15}H_5D_5ClN_3$ = 272.75) | Sub 1-6 | m/z = 367.09($C_{23}H_{14}ClN_3$ = 367.84) |
| Sub 1-7 | m/z = 507.15($C_{34}H_{22}ClN_3$ = 508.02) | Sub 1-8 | m/z = 419.12($C_{27}H_{18}ClN_3$ = 419.91) |
| Sub 1-9 | m/z = 343.09($C_{21}H_{14}ClN_3$ = 343.81) | Sub 1-10 | m/z = 367.09($C_{23}H_{14}ClN_3$ = 367.84) |
| Sub 1-11 | m/z = 433.13($C_{28}H_{20}ClN_3$ = 433.94) | Sub 1-12 | m/z = 419.12($C_{27}H_{18}ClN_3$ = 419.91) |
| Sub 1-13 | m/z = 394.1($C_{24}H_{15}ClN_4$ = 394.86) | Sub 1-14 | m/z = 443.12($C_{29}H_{18}ClN_3$ = 443.93) |
| Sub 1-15 | m/z = 494.13($C_{32}H_{19}ClN_4$ = 494.98) | Sub 1-16 | m/z = 393.1($C_{25}H_{16}ClN_3$ = 393.87) |
| Sub 1-17 | m/z = 469.13($C_{31}H_{20}ClN_3$ = 469.97) | Sub 1-18 | m/z = 469.13($C_{31}H_{20}ClN_3$ = 469.97) |
| Sub 1-19 | m/z = 393.1($C_{25}H_{16}ClN_3$ = 393.87) | Sub 1-20 | m/z = 508.15($C_{33}H_{21}ClN_4$ = 509.01) |
| Sub 1-21 | m/z = 551.12($C_{35}H_{22}ClN_3S$ = 552.09) | Sub 1-22 | m/z = 423.06($C_{25}H_{14}ClN_3S$ = 423.92) |
| Sub 1-23 | m/z = 393.1($C_{25}H_{16}ClN_3$ = 393.87) | Sub 1-24 | m/z = 292.05($C_{16}H_9ClN_4$ = 292.73) |
| Sub 1-25 | m/z = 405.1($C_{26}H_{16}ClN_3$ = 405.89) | Sub 1-26 | m/z = 419.12($C_{27}H_{18}ClN_3$ = 419.91) |
| Sub 1-27 | m/z = 393.1($C_{25}H_{16}ClN_3$ = 393.87) | Sub 1-28 | m/z = 394.1($C_{24}H_{15}ClN_4$ = 394.86) |
| Sub 1-29 | m/z = 523.11($C_{33}H_{18}ClN_3O_2$ = 523.98) | Sub 1-30 | m/z = 525.11($C_{33}H_{20}ClN_3S$ = 526.05) |
| Sub 1-31 | m/z = 373.04($C_{21}H_{12}ClN_3S$ = 373.86) | Sub 1-32 | m/z = 373.04($C_{21}H_{12}ClN_3S$ = 373.86) |
| Sub 1-33 | m/z = 433.1($C_{27}H_{16}ClN_3O$ = 433.9) | Sub 1-34 | m/z = 500.09($C_{30}H_{17}ClN_4S$ = 501) |
| Sub 1-35 | m/z = 499.09($C_{31}H_{18}ClN_3S$ = 500.02) | Sub 1-36 | m/z = 433.1($C_{27}H_{16}ClN_3O$ = 433.9) |
| Sub 1-37 | m/z = 357.07($C_{21}H_{12}ClN_3O$ = 357.8) | Sub 1-38 | m/z = 433.1($C_{27}H_{16}ClN_3O$ = 433.9) |
| Sub 1-39 | m/z = 525.11($C_{33}H_{20}ClN_3S$ = 526.05) | Sub 1-40 | m/z = 499.09($C_{31}H_{18}ClN_3S$ = 500.02) |
| Sub 1-41 | m/z = 433.1($C_{27}H_{16}ClN_3O$ = 433.9) | Sub 1-42 | m/z = 473.13($C_{30}H_{20}ClN_3O$ = 473.96) |
| Sub 1-43 | m/z = 473.08($C_{29}H_{16}ClN_3S$ = 473.98) | Sub 1-44 | m/z = 482.13($C_{31}H_{19}ClN_4$ = 482.97) |

Compounds belong to Sub 2 of Reaction Scheme 1 are as follows, but are not limited thereto.

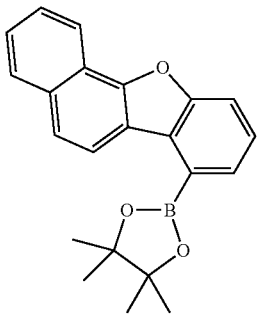

Sub 2-1

Sub 2-2
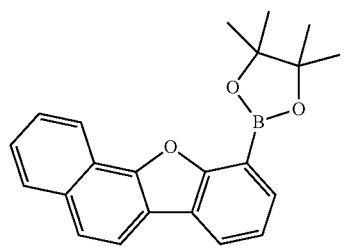
Sub 2-8
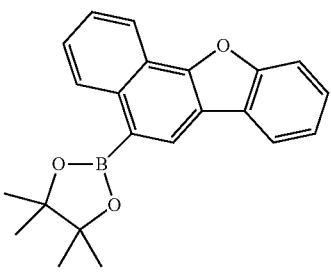
Sub 2-3
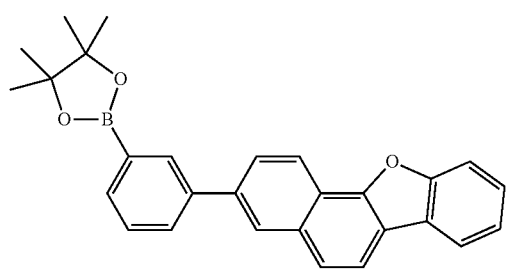
Sub 2-9
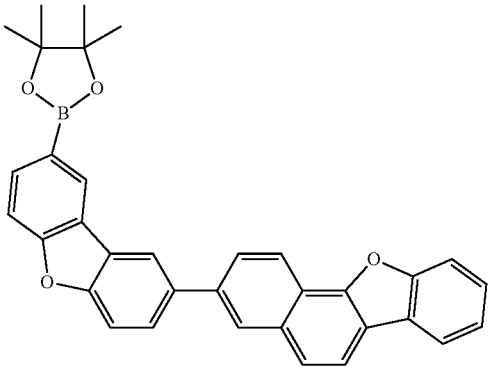
Sub 2-4
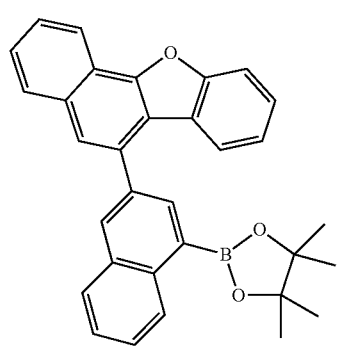
Sub 2-10
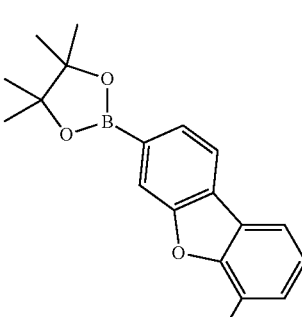
Sub 2-5
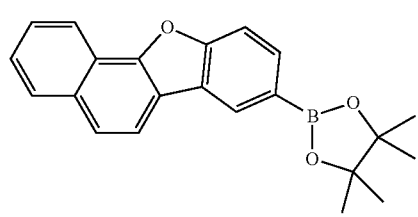
Sub 2-11
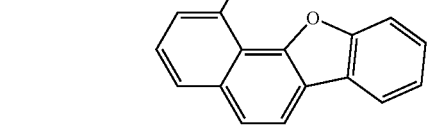
Sub 2-6
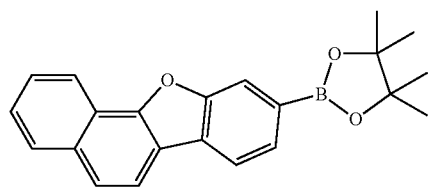
Sub 2-7
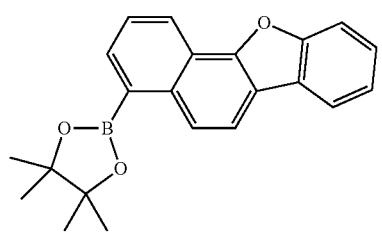
Sub 2-12
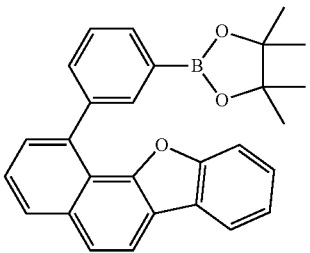

Sub 2-13
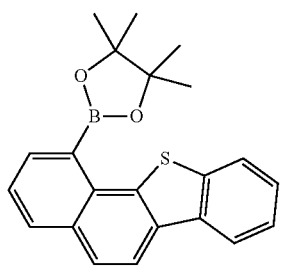
Sub 2-14
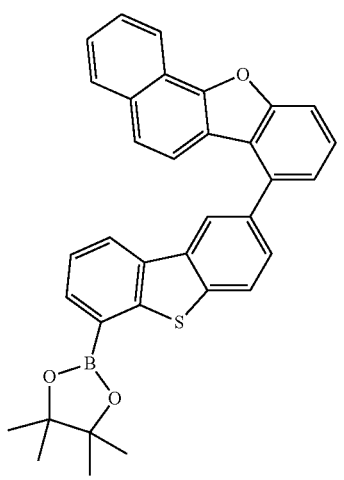
Sub 2-15
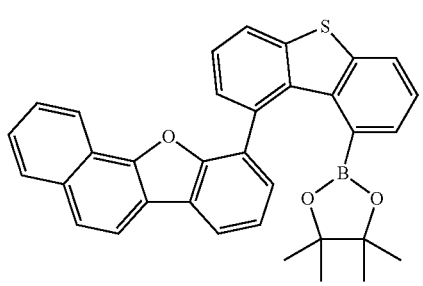
Sub 2-16
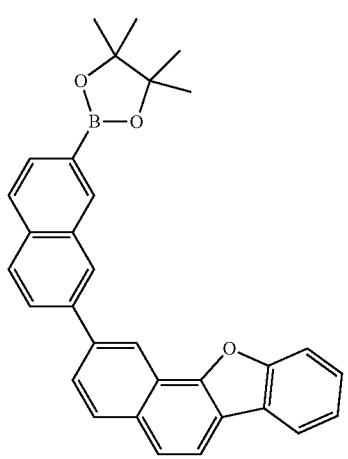
Sub 2-17
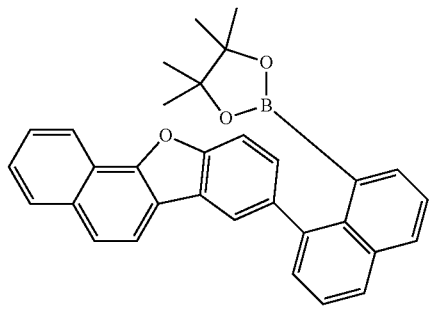
Sub 2-18
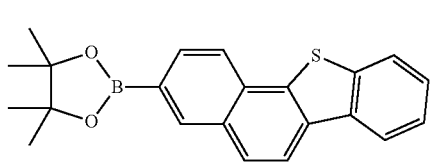
Sub 2-19
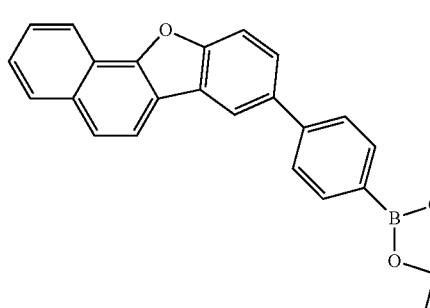
Sub 2-20
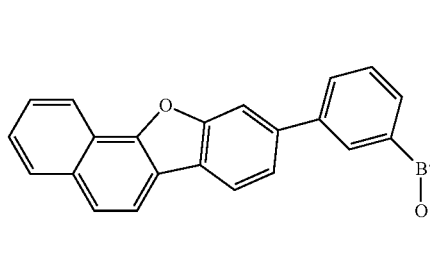
Sub 2-21
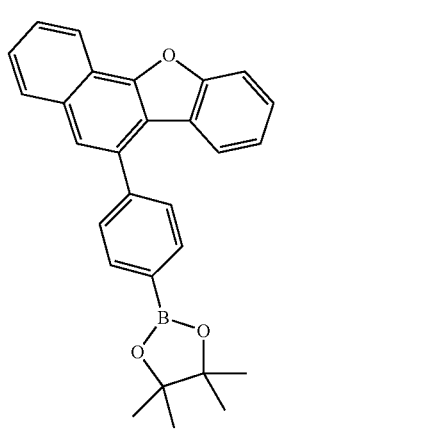

Sub 2-22
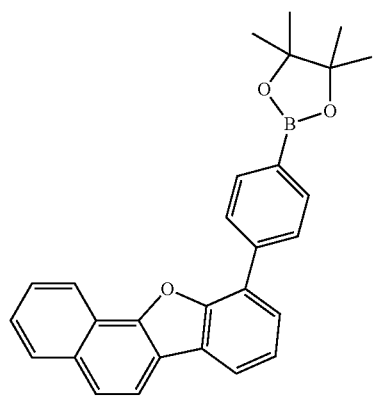
Sub 2-26
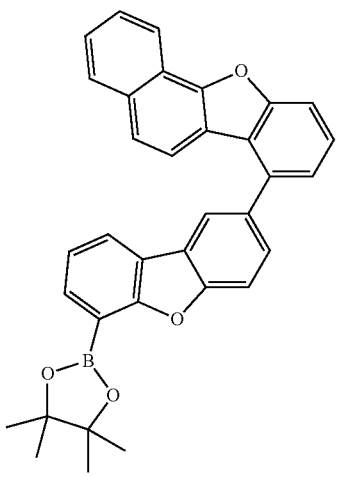
Sub 2-23
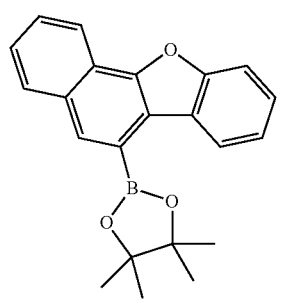
Sub 2-27
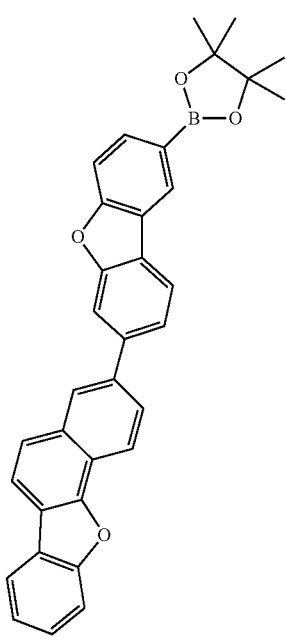
Sub 2-24
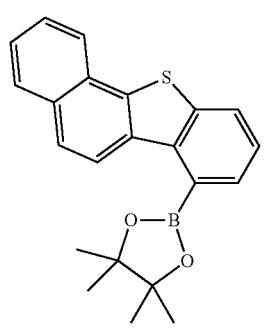
Sub 2-25
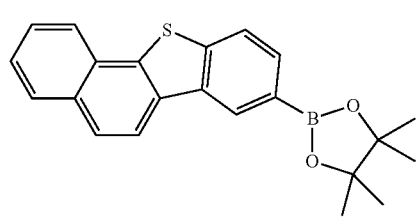
Sub 2-28
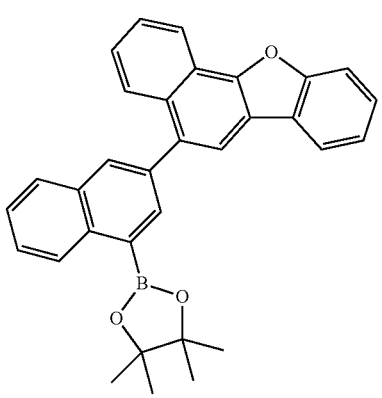

| | |
|---|---|
| Sub 2-29 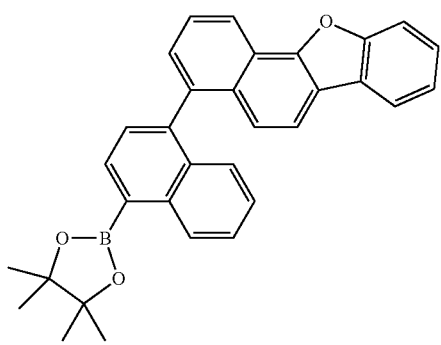 | Sub 2-33 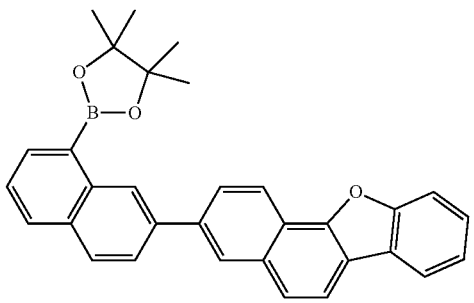 |
| Sub 2-30 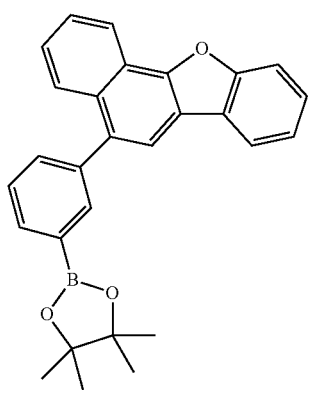 | Sub 2-34 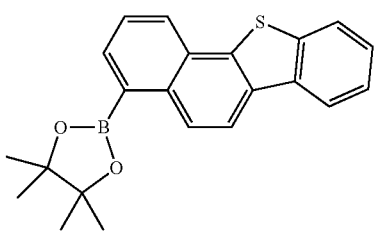 |
| Sub 2-31 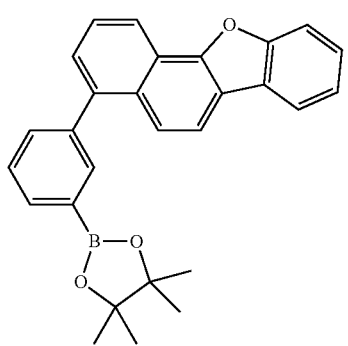 | Sub 2-35 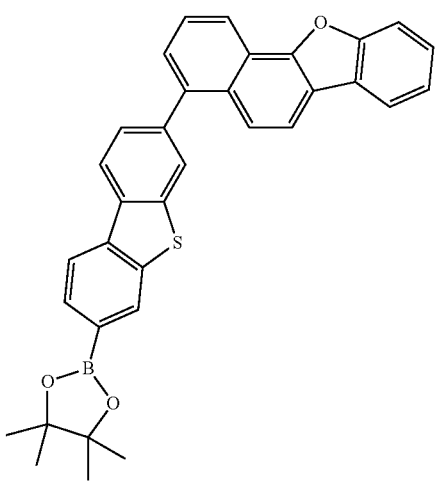 |
| Sub 2-32 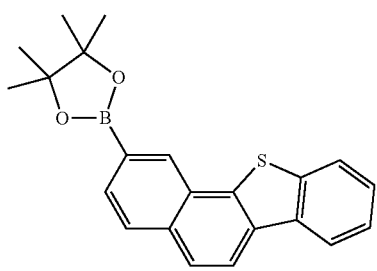 | Sub 2-36 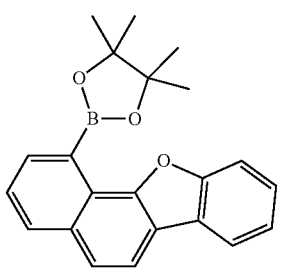 |

-continued
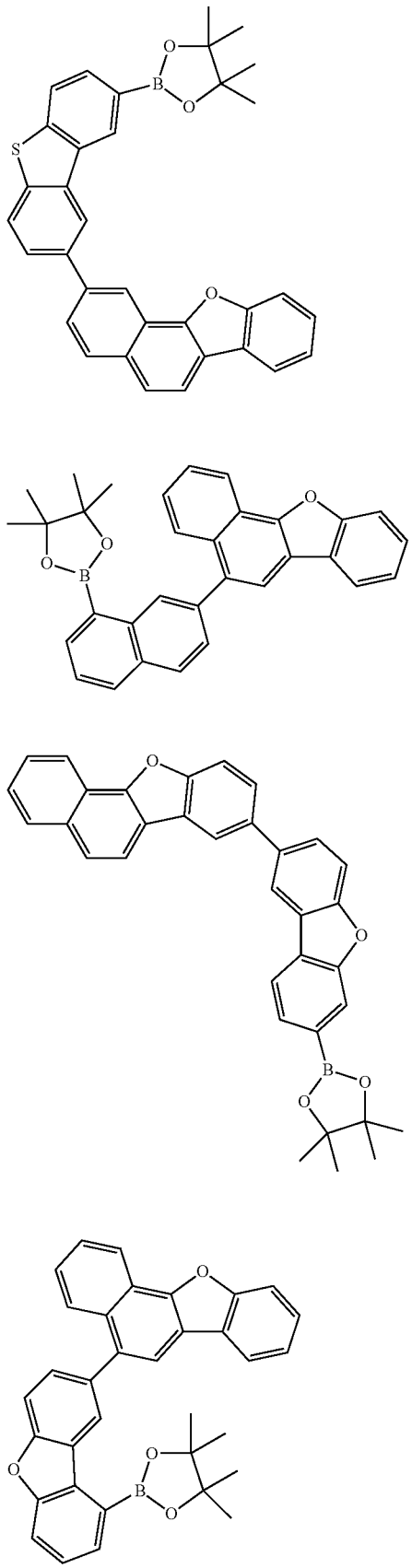
Sub 2-37
Sub 2-38
Sub 2-39
Sub 2-40
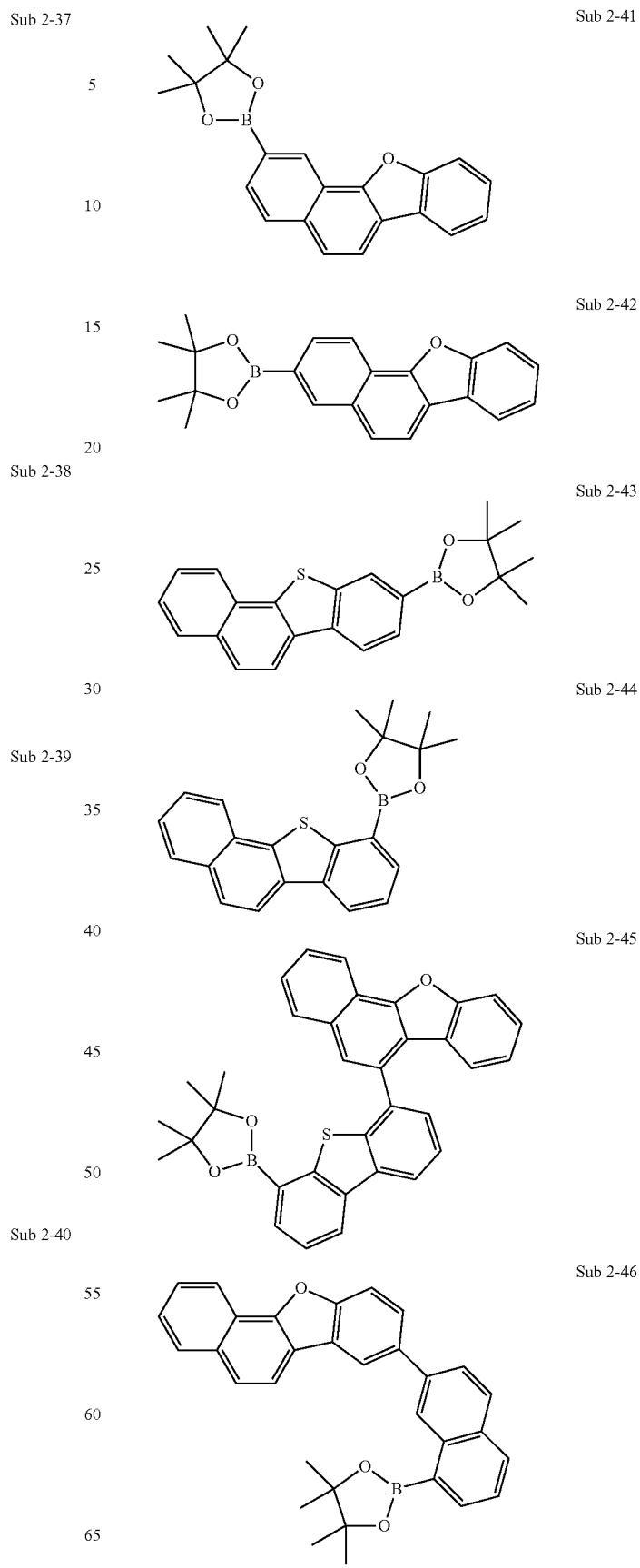
Sub 2-41
Sub 2-42
Sub 2-43
Sub 2-44
Sub 2-45
Sub 2-46

-continued

Sub 2-47

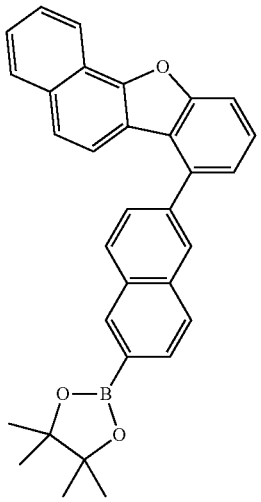

Sub 2-48

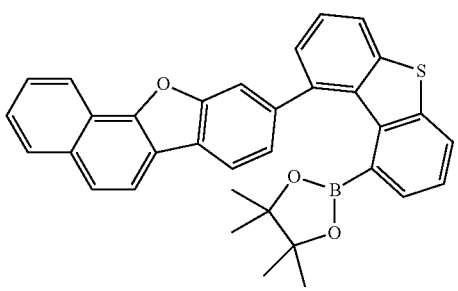

-continued

Sub 2-49

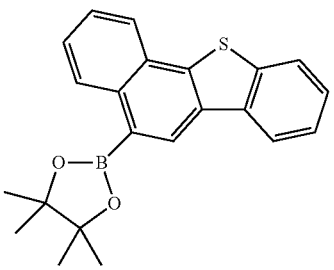

Sub 2-50

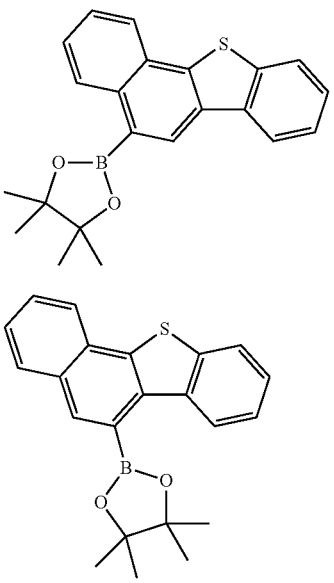

Sub 2-51

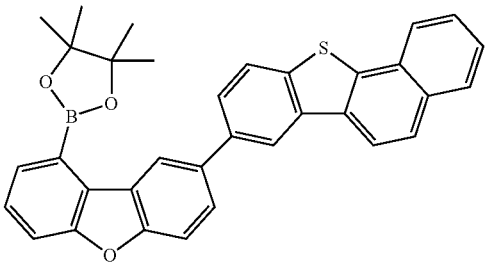

FD-MS values of compounds belong to Sub 2 are shown in Table 2 below.

TABLE 2

| Compound | FD-MS | Compound | FD-MS |
|---|---|---|---|
| Sub 2-1 | m/z = 344.16($C_{22}H_{21}BO_3$ = 344.22) | Sub 2-2 | m/z = 344.16($C_{22}H_{21}BO_3$ = 344.22) |
| Sub 2-3 | m/z = 420.19($C_{28}H_{25}BO_3$ = 420.32) | Sub 2-4 | m/z = 470.21($C_{32}H_{27}BO_3$ = 470.38) |
| Sub 2-5 | m/z = 344.16($C_{22}H_{21}BO_3$ = 344.22) | Sub 2-6 | m/z = 344.16($C_{22}H_{21}BO_3$ = 344.22) |
| Sub 2-7 | m/z = 344.16($C_{22}H_{21}BO_3$ = 344.22) | Sub 2-8 | m/z = 344.16($C_{22}H_{21}BO_3$ = 344.22) |
| Sub 2-9 | m/z = 510.2($C_{34}H_{27}BO_4$ = 510.4) | Sub 2-10 | m/z = 510.2($C_{34}H_{27}BO_4$ = 510.4) |
| Sub 2-11 | m/z = 420.19($C_{28}H_{25}BO_3$ = 420.32) | Sub 2-12 | m/z = 420.19($C_{28}H_{25}BO_3$ = 420.32) |
| Sub 2-13 | m/z = 360.14($C_{22}H_{21}BO_2S$ = 360.28) | Sub 2-14 | m/z = 526.18($C_{34}H_{27}BO_3S$ = 526.46) |
| Sub 2-15 | m/z = 526.18($C_{34}H_{27}BO_3S$ = 526.46) | Sub 2-16 | m/z = 470.21($C_{32}H_{27}BO_3$ = 470.38) |
| Sub 2-17 | m/z = 470.21($C_{32}H_{27}BO_3$ = 470.38) | Sub 2-18 | m/z = 360.14($C_{22}H_{21}BO_2S$ = 360.28) |
| Sub 2-19 | m/z = 420.19($C_{28}H_{25}BO_3$ = 420.32) | Sub 2-20 | m/z = 420.19($C_{28}H_{25}BO_3$ = 420.32) |
| Sub 2-21 | m/z = 420.19($C_{28}H_{25}BO_3$ = 420.32) | Sub 2-22 | m/z = 420.19($C_{28}H_{25}BO_3$ = 420.32) |
| Sub 2-23 | m/z = 344.16($C_{22}H_{21}BO_3$ = 344.22) | Sub 2-24 | m/z = 360.14($C_{22}H_{21}BO_2S$ = 360.28) |
| Sub 2-25 | m/z = 360.14($C_{22}H_{21}BO_2S$ = 360.28) | Sub 2-26 | m/z = 510.2($C_{34}H_{27}BO_4$ = 510.4) |
| Sub 2-27 | m/z = 510.2($C_{34}H_{27}BO_4$ = 510.4) | Sub 2-28 | m/z = 470.21($C_{32}H_{27}BO_3$ = 470.38) |
| Sub 2-29 | m/z = 470.21($C_{32}H_{27}BO_3$ = 470.38) | Sub 2-30 | m/z = 420.19($C_{28}H_{25}BO_3$ = 420.32) |
| Sub 2-31 | m/z = 420.19($C_{28}H_{25}BO_3$ = 420.32) | Sub 2-32 | m/z = 360.14($C_{22}H_{21}BO_2S$ = 360.28) |
| Sub 2-33 | m/z = 470.21($C_{32}H_{27}BO_3$ = 470.38) | Sub 2-34 | m/z = 360.14($C_{22}H_{21}BO_2S$ = 360.28) |
| Sub 2-35 | m/z = 526.18($C_{34}H_{27}BO_3S$ = 526.46) | Sub 2-36 | m/z = 344.16($C_{22}H_{21}BO_3$ = 344.22) |
| Sub 2-37 | m/z = 526.18($C_{34}H_{27}BO_3S$ = 526.46) | Sub 2-38 | m/z = 470.21($C_{32}H_{27}BO_3$ = 470.38) |
| Sub 2-39 | m/z = 510.2($C_{34}H_{27}BO_4$ = 510.4) | Sub 2-40 | m/z = 510.2($C_{34}H_{27}BO_4$ = 510.4) |
| Sub 2-41 | m/z = 344.16($C_{22}H_{21}BO_3$ = 344.22) | Sub 2-42 | m/z = 344.16($C_{22}H_{21}BO_3$ = 344.22) |
| Sub 2-43 | m/z = 360.14($C_{22}H_{21}BO_2S$ = 360.28) | Sub 2-44 | m/z = 360.14($C_{22}H_{21}BO_2S$ = 360.28) |
| Sub 2-45 | m/z = 526.18($C_{34}H_{27}BO_3S$ = 526.46) | Sub 2-46 | m/z = 470.21($C_{32}H_{27}BO_3$ = 470.38) |
| Sub 2-47 | m/z = 470.21($C_{32}H_{27}BO_3$ = 470.38) | Sub 2-48 | m/z = 526.18($C_{34}H_{27}BO_3S$ = 526.46) |
| Sub 2-49 | m/z = 360.14($C_{22}H_{21}BO_2S$ = 360.28) | Sub 2-50 | m/z = 360.14($C_{22}H_{21}BO_2S$ = 360.28) |

1. Synthesis Example of Sub 1

Sub 1 of Reaction Scheme 1 may be synthesized by the reaction route of the following Reaction Scheme 2, but are not limited thereto.

<Reaction Scheme 2>

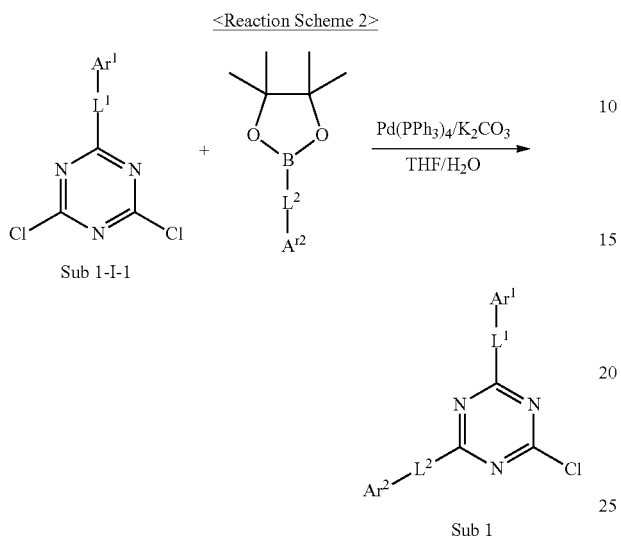

Synthesis example of Sub 1-7

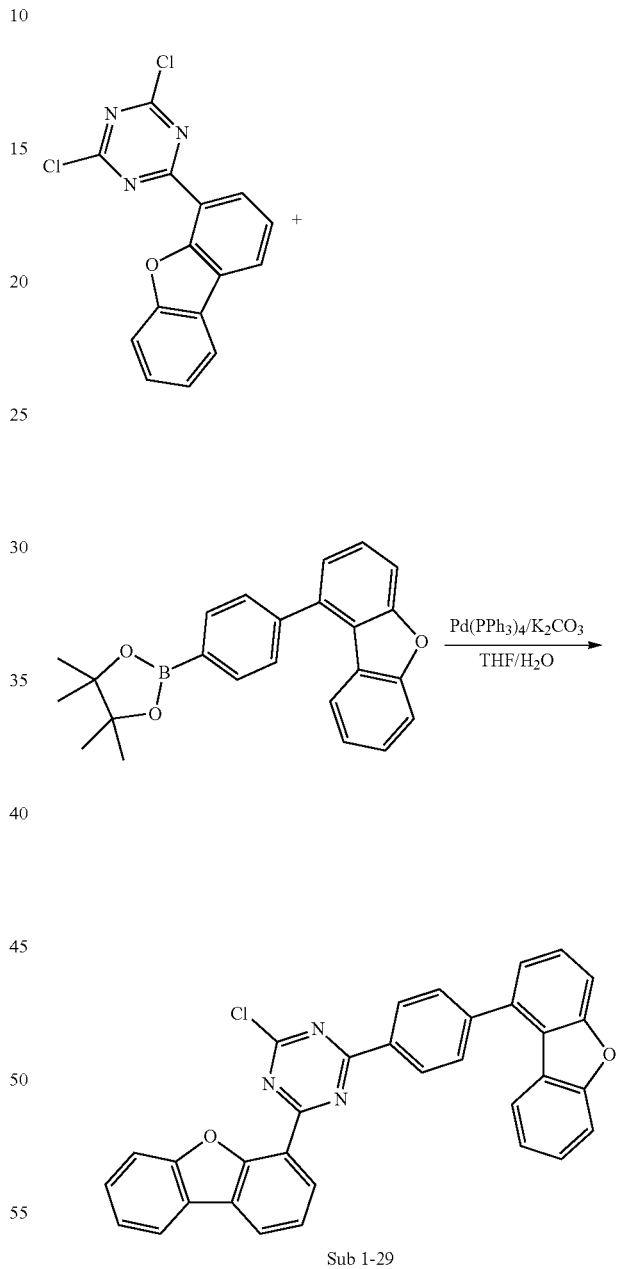

2,4-dichloro-6-phenyl-1,3,5-triazine (30 g, 132.71 mmol) was dissolved in THF 600 mL, and 2-(9,9-diphenyl-9H-fluoren-2-yl)-4,4,5,5-tetramethyl-1,3,2-dioxaborolane (70.77 g, 159.25 mmol), $Pd(PPh_3)_4$ (7.67 g, 6.64 mmol), $K_2CO_3$ (55.02 g, 398.12 mmol) and water (300 ml) were added to the solution. Then, the mixture was stirred under reflux. When the reaction was completed, the reaction product was extracted by ether and water. The organic layer was concentrated and the concentrate was dried over $MgSO_4$ and concentrated. Then, the concentrate was separated by a silica gel column and recrystallized to obtain 51.24 g (yield: 76%) of the product.

Synthesis Example of Sub 1-29

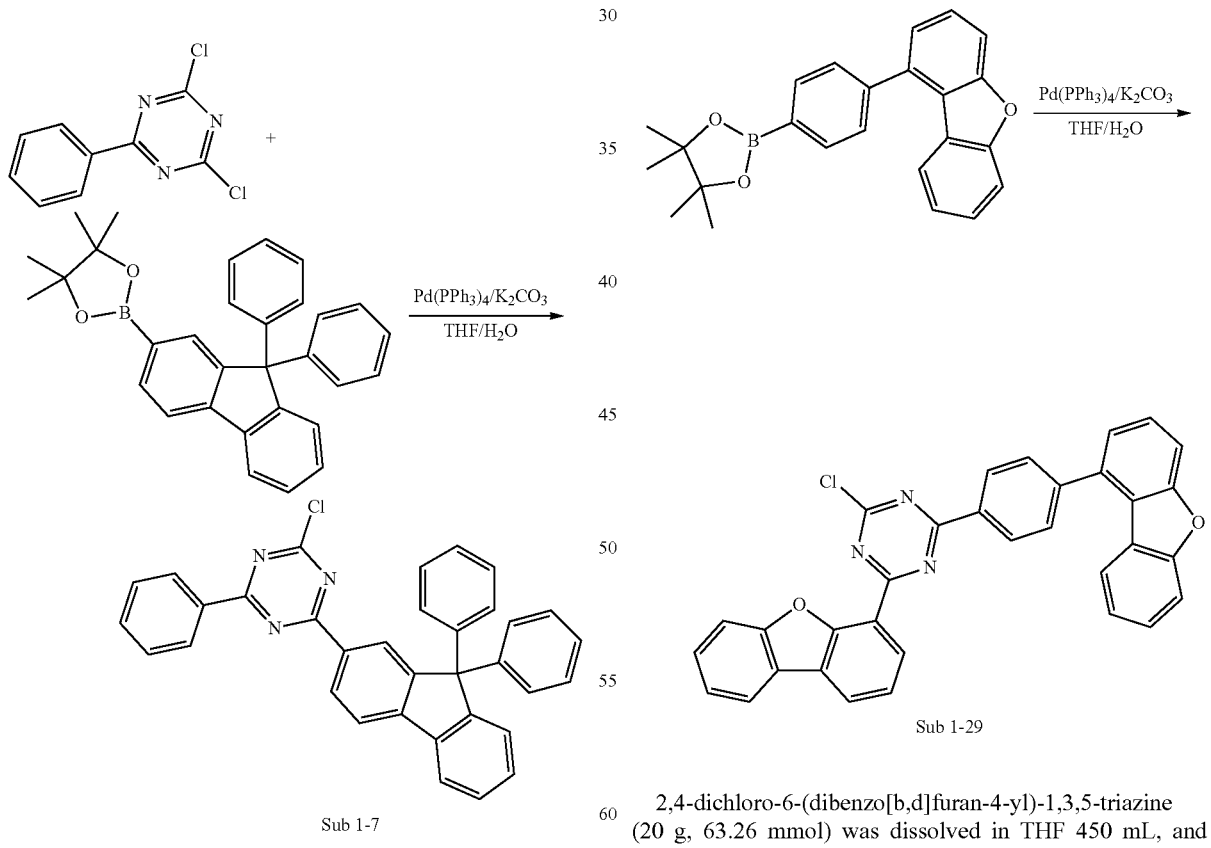

2,4-dichloro-6-(dibenzo[b,d]furan-4-yl)-1,3,5-triazine (20 g, 63.26 mmol) was dissolved in THF 450 mL, and 2-(4-(dibenzo[b,d]furan-1-yl)phenyl)-4,4,5,5-tetramethyl-1,3,2-dioxaborolane (28.11 g, 75.92 mmol), $Pd(PPh_3)_4$ (3.66 g, 3.16 mmol), $K_2CO_3$ (26.23 g, 189.79 mmol) and water 150 mL were added to the solution. Then, the reaction was carried out in the same manner as in the synthesis method of Sub 1-7 to obtain 69.7 g (yield: 73%) of the product.

Synthesis example of Sub 1-39

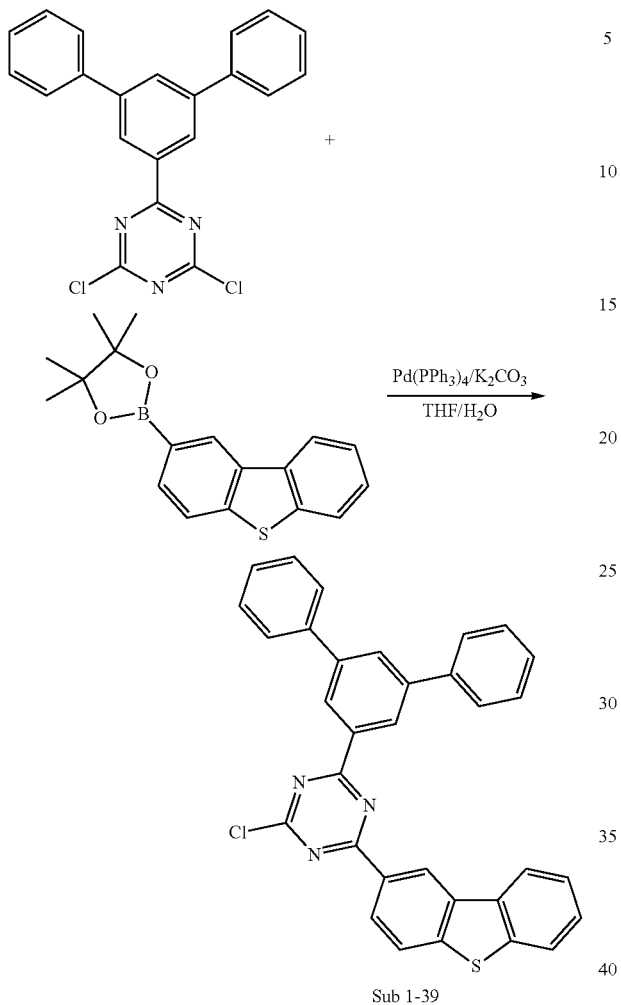

Sub 1-39

2-([1,1':3',1''-terphenyl]-5'-yl)-4,6-dichloro-1,3,5-triazine (17 g, 44.94 mmol) was dissolved in THF 340 mL, and 2-(dibenzo[b,d]thiophen-2-yl)-4,4,5,5-tetramethyl-1,3,2-dioxaborolane (16.73 g, 53.93 mmol), Pd(PPh₃)₄ (2.6 g, 2.25 mmol), K₂CO₃ (18.63 g, 134.83 mmol) and water 170 mL were added to the solution. Then, the reaction was carried out in the same manner as in the synthesis method of Sub 1-7 to obtain 69.7 g (yield: 73%) of the product.

2. Synthesis Example of Sub 2

Sub 2 of Reaction Scheme 1 may be synthesized by the reaction route of the following Reaction Scheme 3, but are not limited thereto.

<Reaction Scheme 3>

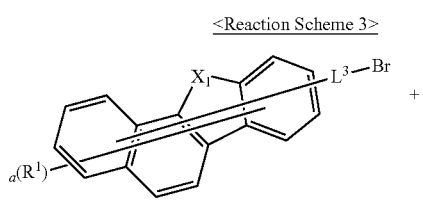

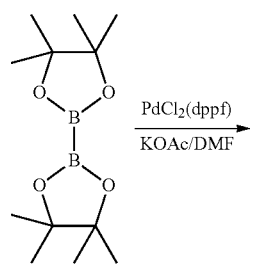

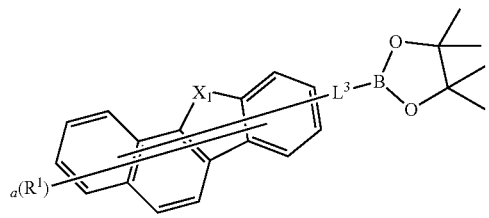

Synthesis example of Sub 2-4

Sub 2-4

Bis(pinacolato)diboron (CAS Registry Number: 73183-34-3) (11.7 g, 46.07 mmol), PdCl₂(dppf) (1.3 g, 1.77 mmol), KOAc (10.4 g, 106.31 mmol) and DMF (300 ml) were added to 6-(4-bromonaphthalen-2-yl)naphtho[1,2-b]benzofuran (15 g, 35.44 mmol). Then, the mixture was stirred under reflux. When the reaction was completed, an organic layer of the reaction product was extracted using CH₂Cl₂ and water. The organic layer was dried over MgSO₄ and concentrated. Then, the concentrate was separated by a silica gel column and recrystallized to obtain 12.83 g (yield: 77%) of the product.

Synthesis Example of Sub 2-25

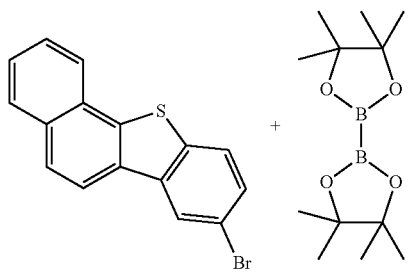

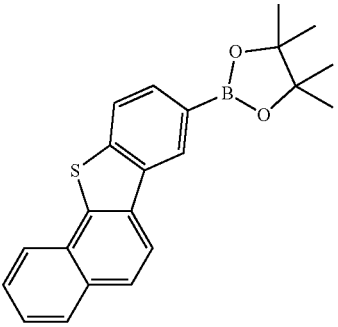

Sub 2-25

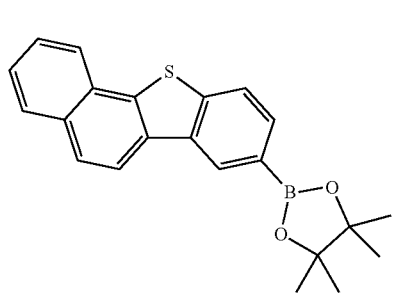

Sub 2-25

Bis(pinacolato)diboron (CAS registry number, 73183-34-3) (26.35 g, 103.76 mmol), PdCl$_2$(dppf) (3.08 g, 4.21 mmol), KOAc (24.77 g, 252.4 mmol) and DMF (500 ml) were added to 8-bromobenzo[b]naphtho[2,1-d]thiophene (25 g, 79.82 mmol). Then, the mixture was stirred under reflux. When the reaction was completed, an organic layer of the reaction product was extracted using CH$_2$Cl$_2$ and water. The organic layer was dried over MgSO$_4$ and concentrated. Then, the concentrate was separated by a silica gel column and recrystallized to obtain 24 g (yield: 83%) of the product.

3. Synthesis Example of Final Products

Synthesis example of 1-13

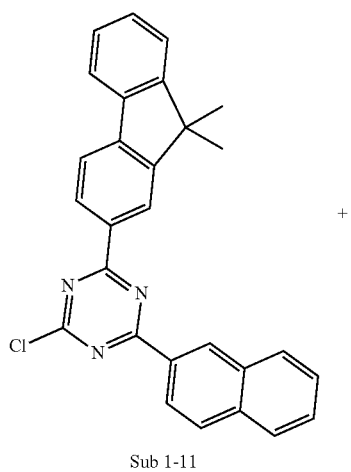

Sub 1-11

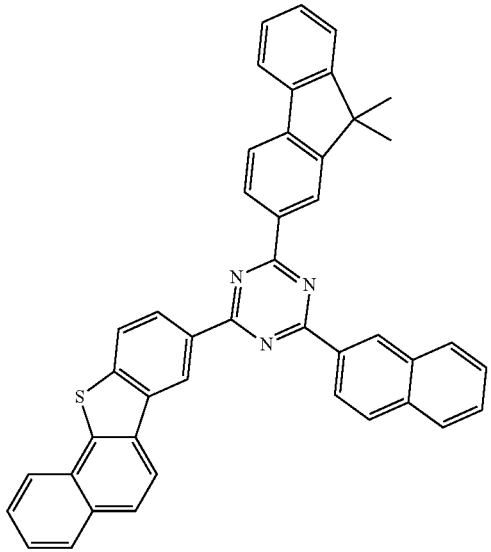

1-13

Sub 1-11 (34.7 g, 80 mmol), Sub 2-25 (30.9 g, 80 mmol), K$_2$CO$_3$ (19.3 g, 140 mmol) and Pd(PPh$_3$)$_4$ (2.8 g, 2.4 mmol) were dissolve in THF and water in a round bottom flask, and the mixture was refluxed at 80° C. for 12 hours. When the reaction was completed, the reaction product was cooled to room temperature, extracted with CH$_2$Cl$_2$ and washed with water. An organic layer was dried over MgSO$_4$ and concentrated. Then, the concentrate was separated by a silica gel column to obtain 37.4 g (yield: 71%) of the product.

Synthesis example of 1-27

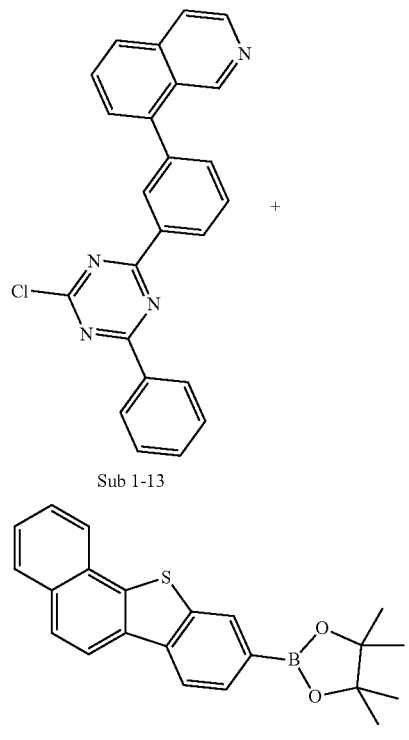

Synthesis Example of 1-34

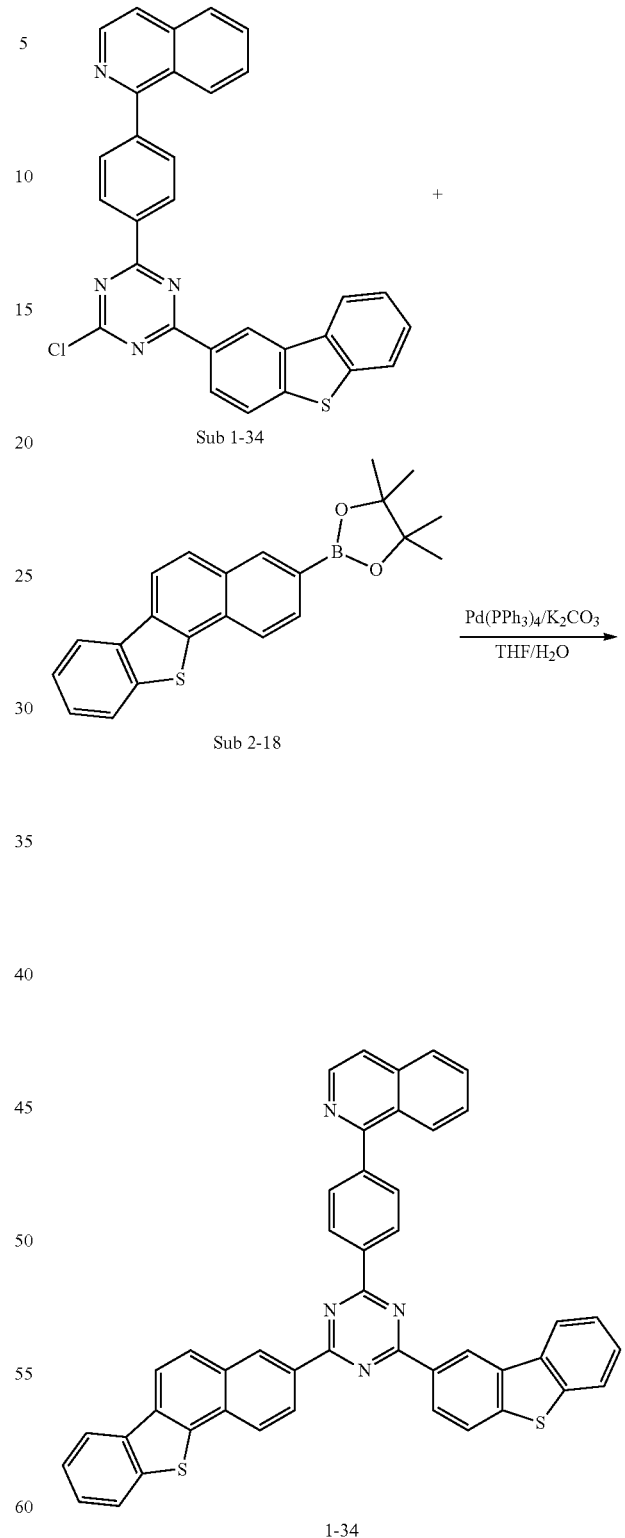

The reaction was carried out in the same manner as in the synthesis method of 1-13, using Sub 1-13 (44.6 g, 80 mmol) instead of Sub 1-11 and Sub 2-43 (30.9 g, 80 mmol) instead of Sub 2-25 to obtain 43.2 g (yield: 69%) of the product.

The reaction was carried out in the same manner as in the synthesis method of 1-13, using Sub 1-34 (42.7 g, 80 mmol) instead of Sub 1-11 and Sub 2-18 (34.9 g, 80 mmol) instead of Sub 2-25 to obtain 42.7 g (yield: 66%) of the product.

Synthesis Example of 1-45

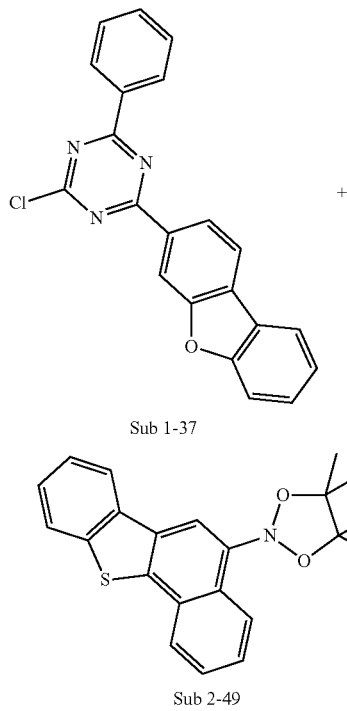

Sub 1-37

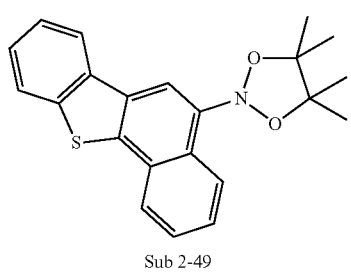

Sub 2-49

1-45

The reaction was carried out in the same manner as in the synthesis method of 1-13, using Sub 1-37 (40.8 g, 80 mmol) instead of Sub 1-11 and Sub 2-49 (43.1 g, 80 mmol) instead of Sub 2-25 to obtain 51.0 g (yield: 72%) of the product.

Synthesis Example of 1-53

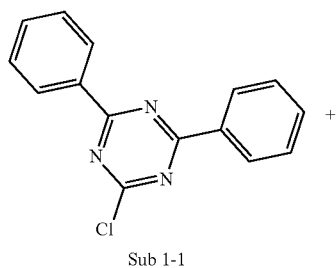

Sub 1-1

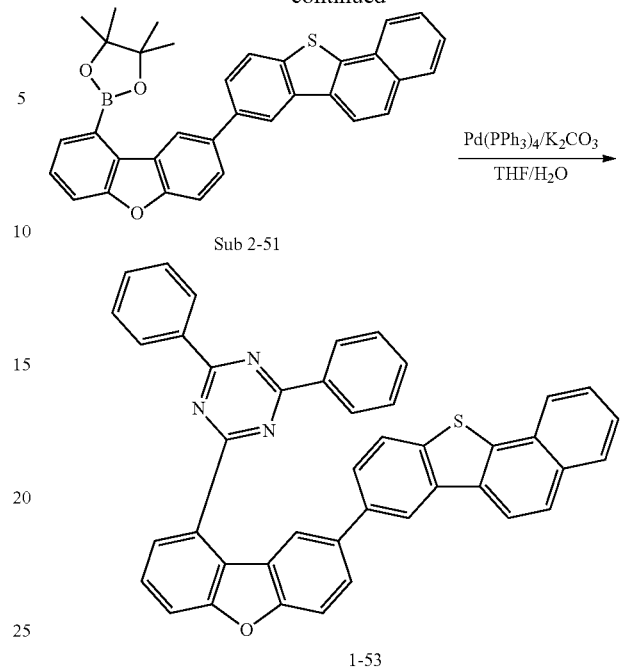

Sub 2-51

1-53

The reaction was carried out in the same manner as in the synthesis method of 1-13, using Sub 1-1 (40.8 g, 80 mmol) instead of Sub 1-11 and Sub 2-51 (37.0 g, 80 mmol) instead of Sub 2-25 to obtain 45.4 g (yield: 70%) of the product.

Synthesis Example of 1-88

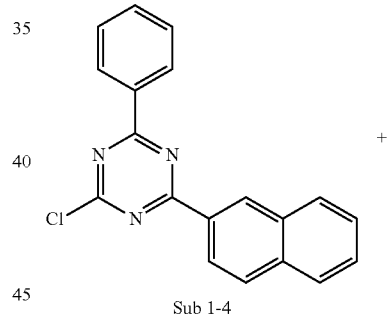

Sub 1-4

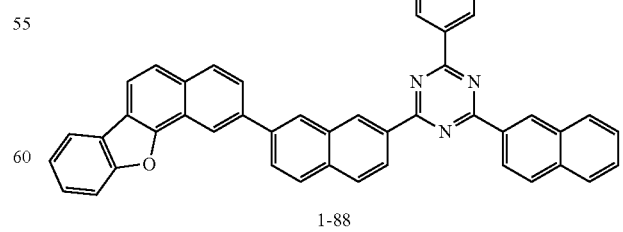

Sub 2-16

1-88

The reaction was carried out in the same manner as in the synthesis method of 1-13, using Sub 1-4 (44.0 g, 80 mmol) instead of Sub 1-11 and Sub 2-16 (29.6 g, 80 mmol) instead of Sub 2-25 to obtain 41.2 g (yield: 68%) of the product.

The FD-MS values of compounds 1-1 to 1-124 of the present invention synthesized by the same method as in Synthesis Example are shown in Table 3 below.

TABLE 3

| Compound | FD-MS | Compound | FD-MS |
|---|---|---|---|
| 1-1 | m/z = 465.13($C_{31}H_{19}N_3S$ = 465.57) | 1-2 | m/z = 575.2($C_{41}H_{25}N_3O$ = 575.67) |
| 1-3 | m/z = 705.22($C_{50}H_{31}N_3S$ = 705.88) | 1-4 | m/z = 540.14($C_{36}H_{20}N_4S$ = 540.64) |
| 1-5 | m/z = 546.19($C_{37}H_{18}D_5N_3S$ = 546.7) | 1-6 | m/z = 549.18($C_{39}H_{23}N_3O$ = 549.63) |
| 1-7 | m/z = 591.18($C_{41}H_{25}N_3S$ = 591.73) | 1-8 | m/z = 465.13($C_{31}H_{19}N_3S$ = 465.57) |
| 1-9 | m/z = 705.22($C_{50}H_{31}N_3S$ = 705.88) | 1-10 | m/z = 617.19($C_{43}H_{27}N_3S$ = 617.77) |
| 1-11 | m/z = 601.22($C_{43}H_{27}N_3O$ = 601.71) | 1-12 | m/z = 565.16($C_{39}H_{23}N_3S$ = 565.69) |
| 1-13 | m/z = 631.21($C_{44}H_{29}N_3S$ = 631.8) | 1-14 | m/z = 499.17($C_{35}H_{21}N_3O$ = 499.57) |
| 1-15 | m/z = 617.19($C_{43}H_{27}N_3S$ = 617.77) | 1-16 | m/z = 603.18($C_{42}H_{25}N_3S$ = 603.74) |
| 1-17 | m/z = 753.28($C_{55}H_{35}N_3O$ = 753.91) | 1-18 | m/z = 592.17($C_{40}H_{24}N_4S$ = 592.72) |
| 1-19 | m/z = 641.19($C_{45}H_{27}N_3S$ = 641.79) | 1-20 | m/z = 692.2($C_{48}H_{28}N_4S$ = 692.84) |
| 1-21 | m/z = 575.2($C_{41}H_{25}N_3O$ = 575.67) | 1-22 | m/z = 591.18($C_{41}H_{25}N_3S$ = 591.73) |
| 1-23 | m/z = 667.21($C_{47}H_{29}N_3S$ = 667.83) | 1-24 | m/z = 575.2($C_{41}H_{25}N_3O$ = 575.67) |
| 1-25 | m/z = 591.18($C_{41}H_{25}N_3S$ = 591.73) | 1-26 | m/z = 575.2($C_{41}H_{25}N_3O$ = 575.67) |
| 1-27 | m/z = 592.17($C_{40}H_{24}N_4S$ = 592.72) | 1-28 | m/z = 575.2($C_{41}H_{25}N_3O$ = 575.67) |
| 1-29 | m/z = 706.22($C_{49}H_{30}N_4S$ = 706.87) | 1-30 | m/z = 733.22($C_{51}H_{31}N_3OS$ = 733.89) |
| 1-31 | m/z = 621.13($C_{41}H_{23}N_3S_2$ = 621.78) | 1-32 | m/z = 555.14($C_{37}H_{21}N_3S$ = 555.66) |
| 1-33 | m/z = 615.19($C_{43}H_{25}N_3O_2$ = 615.69) | 1-34 | m/z = 698.16($C_{46}H_{26}N_4S_2$ = 698.86) |
| 1-35 | m/z = 697.16($C_{47}H_{27}N_3S_2$ = 697.87) | 1-36 | m/z = 615.19($C_{43}H_{25}N_3O_2$ = 615.69) |
| 1-37 | m/z = 707.2($C_{49}H_{29}N_3OS$ = 707.85) | 1-38 | m/z = 681.19($C_{47}H_{27}N_3OS$ = 681.81) |
| 1-39 | m/z = 631.17($C_{43}H_{25}N_3OS$ = 631.75) | 1-40 | m/z = 655.23($C_{46}H_{29}N_3O_2$ = 655.76) |
| 1-41 | m/z = 671.15($C_{45}H_{25}N_3S_2$ = 671.84) | 1-42 | m/z = 631.17($C_{43}H_{25}N_3OS$ = 631.75) |
| 1-43 | m/z = 571.12($C_{37}H_{21}N_3S_2$ = 571.72) | 1-44 | m/z = 631.17($C_{43}H_{25}N_3OS$ = 631.75) |
| 1-45 | m/z = 555.14($C_{37}H_{21}N_3OS$ = 555.66) | 1-46 | m/z = 721.18($C_{49}H_{27}N_3O_2S$ = 721.83) |
| 1-47 | m/z = 690.24($C_{49}H_{30}N_4O$ = 690.81) | 1-48 | m/z = 681.19($C_{47}H_{27}N_3OS$ = 681.81) |
| 1-49 | m/z = 647.15($C_{43}H_{25}N_3S_2$ = 647.81) | 1-50 | m/z = 697.16($C_{47}H_{27}N_3S_2$ = 697.87) |
| 1-51 | m/z = 707.2($C_{49}H_{29}N_3OS$ = 707.85) | 1-52 | m/z = 756.23($C_{53}H_{32}N_4S$ = 756.93) |
| 1-53 | m/z = 631.17($C_{43}H_{25}N_3OS$ = 631.75) | 1-54 | m/z = 631.17($C_{43}H_{25}N_3OS$ = 631.75) |
| 1-55 | m/z = 631.17($C_{43}H_{25}N_3OS$ = 631.75) | 1-56 | m/z = 681.19($C_{47}H_{27}N_3OS$ = 681.81) |
| 1-57 | m/z = 681.19($C_{47}H_{27}N_3OS$ = 681.81) | 1-58 | m/z = 874.28($C_{61}H_{38}N_4OS$ = 875.06) |
| 1-59 | m/z = 707.2($C_{49}H_{29}N_3OS$ = 707.85) | 1-60 | m/z = 905.3($C_{66}H_{39}N_3O_2$ = 906.06) |
| 1-61 | m/z = 615.19($C_{43}H_{25}N_3O_2$ = 615.69) | 1-62 | m/z = 757.22($C_{53}H_{31}N_3OS$ = 757.91) |
| 1-63 | m/z = 713.25($C_{49}H_{35}N_3OS$ = 713.9) | 1-64 | m/z = 721.18($C_{49}H_{27}N_3O_2S$ = 721.83) |
| 1-65 | m/z = 753.14($C_{49}H_{27}N_3S_3$ = 753.96) | 1-66 | m/z = 737.18($C_{49}H_{27}N_3O_3S$ = 737.83) |
| 1-67 | m/z = 681.19($C_{47}H_{27}N_3OS$ = 681.81) | 1-68 | m/z = 707.2($C_{49}H_{29}N_3OS$ = 707.85) |
| 1-69 | m/z = 657.19($C_{45}H_{27}N_3OS$ = 657.79) | 1-70 | m/z = 615.19($C_{43}H_{25}N_3O_2$ = 615.69) |
| 1-71 | m/z = 773.2($C_{53}H_{31}N_3S_2$ = 773.97) | 1-72 | m/z = 707.2($C_{49}H_{29}N_3OS$ = 707.85) |
| 1-73 | m/z = 796.23($C_{55}H_{32}N_4OS$ = 796.95) | 1-74 | m/z = 631.17($C_{43}H_{25}N_3OS$ = 631.75) |
| 1-75 | m/z = 631.17($C_{43}H_{25}N_3OS$ = 631.75) | 1-76 | m/z = 787.18($C_{53}H_{29}N_3OS_2$ = 787.96) |
| 1-77 | m/z = 641.19($C_{45}H_{27}N_3S$ = 641.79) | 1-78 | m/z = 752.26($C_{34}H_{32}N_4O$ = 752.88) |
| 1-79 | m/z = 641.19($C_{45}H_{27}N_3S$ = 641.79) | 1-80 | m/z = 717.22($C_{51}H_{31}N_3S$ = 717.89) |
| 1-81 | m/z = 718.22($C_{50}H_{30}N_4S$ = 718.88) | 1-82 | m/z = 625.22($C_{45}H_{27}N_3O$ = 625.73) |
| 1-83 | m/z = 641.19($C_{45}H_{27}N_3S$ = 641.79) | 1-84 | m/z = 625.22($C_{45}H_{27}N_3O$ = 625.73) |
| 1-85 | m/z = 675.23($C_{49}H_{29}N_3O$ = 675.79) | 1-86 | m/z = 641.19($C_{45}H_{27}N_3S$ = 641.79) |
| 1-87 | m/z = 641.19($C_{45}H_{27}N_3S$ = 641.79) | 1-88 | m/z = 625.22($C_{45}H_{27}N_3O$ = 625.73) |
| 1-89 | m/z = 717.22($C_{51}H_{31}N_3S$ = 717.89) | 1-90 | m/z = 717.22($C_{51}H_{31}N_3S$ = 717.89) |
| 1-91 | m/z = 817.31($C_{60}H_{39}N_3O$ = 817.99) | 1-92 | m/z = 717.22($C_{51}H_{31}N_3S$ = 717.89) |
| 1-93 | m/z = 823.21($C_{57}H_{33}N_3S_2$ = 824.03) | 1-94 | m/z = 715.23($C_{51}H_{29}N_3O_2$ = 715.81) |
| 1-95 | m/z = 731.2($C_{51}H_{29}N_3OS$ = 731.87) | 1-96 | m/z = 807.23($C_{57}H_{33}N_3OS$ = 807.97) |
| 1-97 | m/z = 791.26($C_{57}H_{33}N_3O_2$ = 791.91) | 1-98 | m/z = 823.21($C_{57}H_{33}N_3S_2$ = 824.03) |
| 1-99 | m/z = 913.22($C_{63}H_{35}N_3OS_2$ = 914.11) | 1-100 | m/z = 823.21($C_{57}H_{33}N_3S_2$ = 824.03) |
| 1-101 | m/z = 707.2($C_{49}H_{29}N_3OS$ = 707.85) | 1-102 | m/z = 681.19($C_{47}H_{27}N_3OS$ = 681.81) |
| 1-103 | m/z = 757.22($C_{53}H_{31}N_3OS$ = 757.91) | 1-104 | m/z = 707.2($C_{49}H_{29}N_3OS$ = 707.85) |
| 1-105 | m/z = 731.2($C_{51}H_{29}N_3OS$ = 731.87) | 1-106 | m/z = 831.23($C_{59}H_{33}N_3OS$ = 831.99) |
| 1-107 | m/z = 707.2($C_{49}H_{29}N_3OS$ = 707.85) | 1-108 | m/z = 757.22($C_{53}H_{31}N_3OS$ = 757.91) |
| 1-109 | m/z = 681.19($C_{47}H_{27}N_3OS$ = 681.81) | 1-110 | m/z = 681.19($C_{47}H_{27}N_3OS$ = 681.81) |
| 1-111 | m/z = 783.23($C_{55}H_{33}N_3OS$ = 783.95) | 1-112 | m/z = 807.23($C_{57}H_{33}N_3OS$ = 807.97) |
| 1-113 | m/z = 757.22($C_{53}H_{31}N_3OS$ = 757.91) | 1-114 | m/z = 707.2($C_{49}H_{29}N_3OS$ = 707.85) |
| 1-115 | m/z = 783.23($C_{55}H_{33}N_3OS$ = 783.95) | 1-116 | m/z = 783.23($C_{55}H_{33}N_3OS$ = 783.95) |
| 1-117 | m/z = 841.27($C_{61}H_{35}N_3O_2$ = 841.97) | 1-118 | m/z = 807.23($C_{57}H_{33}N_3OS$ = 807.97) |
| 1-119 | m/z = 757.22($C_{53}H_{31}N_3OS$ = 757.91) | 1-120 | m/z = 843.29($C_{61}H_{37}N_3O_2$ = 843.99) |
| 1-121 | m/z = 691.23($C_{49}H_{29}N_3O_2$ = 691.79) | 1-122 | m/z = 907.27($C_{65}H_{37}N_3OS$ = 908.09) |
| 1-123 | m/z = 867.29($C_{63}H_{37}N_3O_2$ = 868.01) | 1-124 | m/z = 775.21($C_{53}H_{30}FN_3OS$ = 775.9) |

[Synthesis Example 2] Synthesis Example Formula 2
The compound (Final product 2) represented by Formula 2 of the present invention may be prepared by reacting Sub 3 and Sub 4 as shown in Reaction Scheme 4 below, but is not limited thereto.
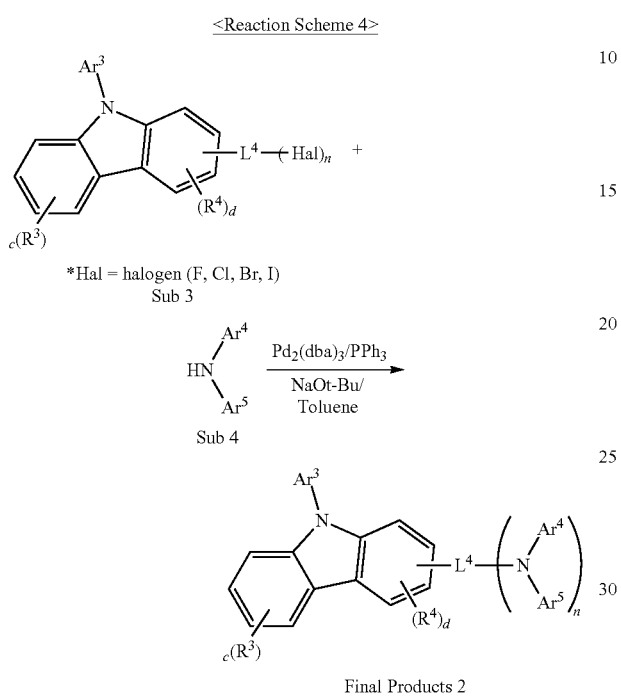
Final Products 2
The compounds belonging to Sub 3 of Reaction Scheme 4 are as follows, but are not limited thereto.
Sub 3-1
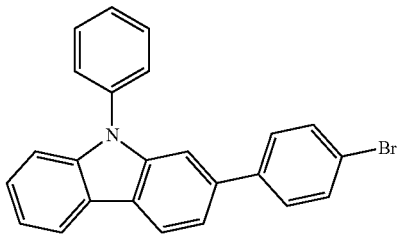
Sub 3-2
Sub 3-3
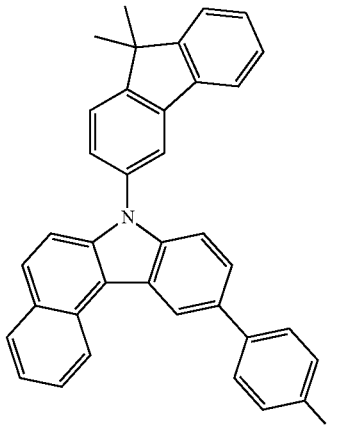
Sub 3-4
Sub 3-5
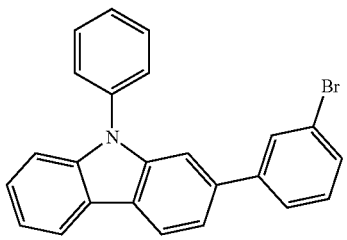
Sub 3-6
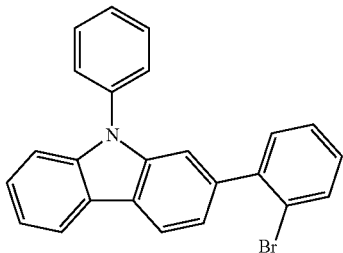
Sub 3-7
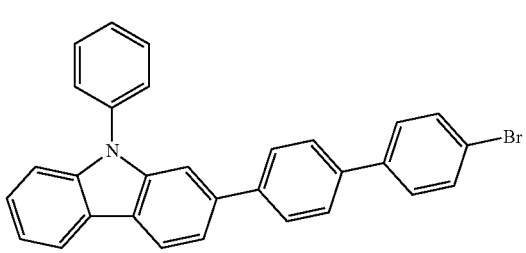

Sub 3-8
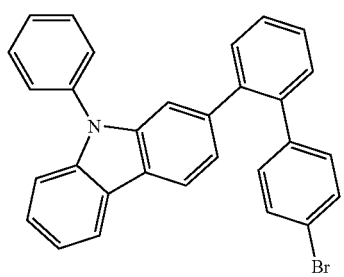
Sub 3-9
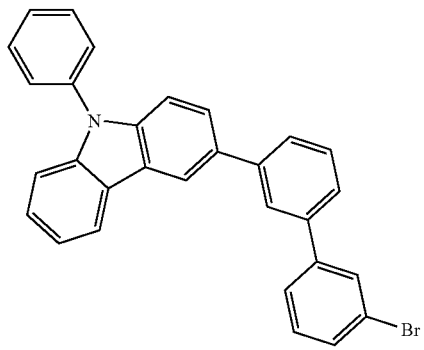
Sub 3-10
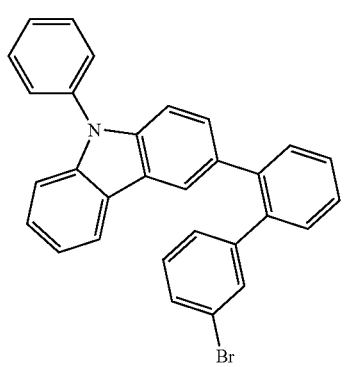
Sub 3-11
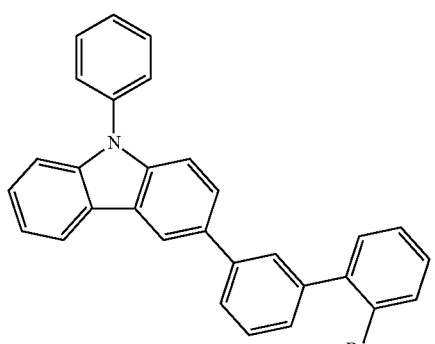
Sub 3-12
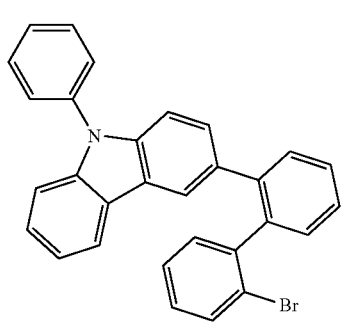
Sub 3-13
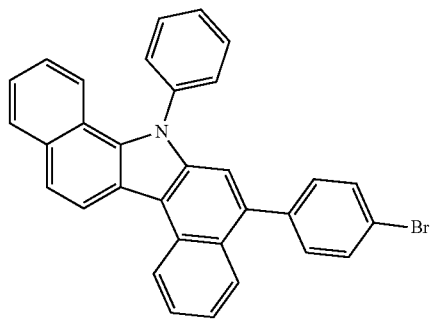
Sub 3-14
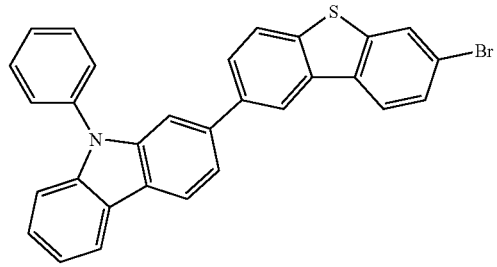
Sub 3-15
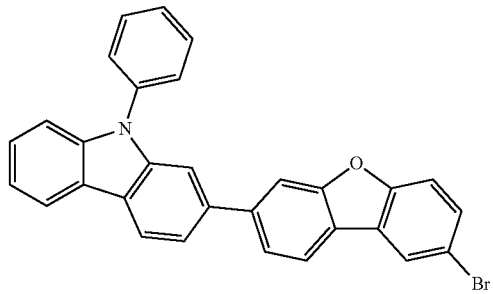
Sub 3-16
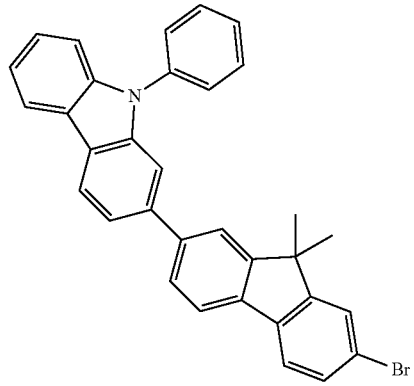

Sub 3-17
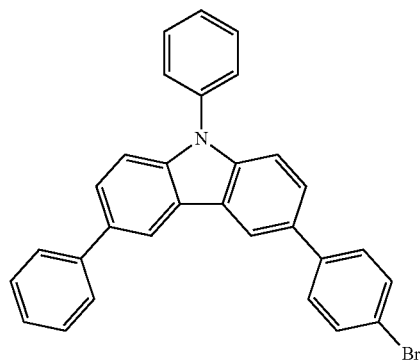
Sub 3-18
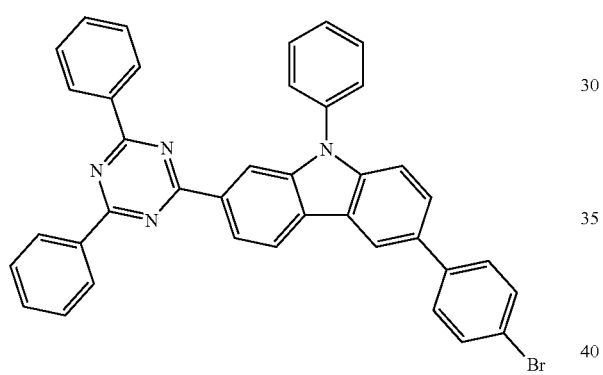
Sub 3-19
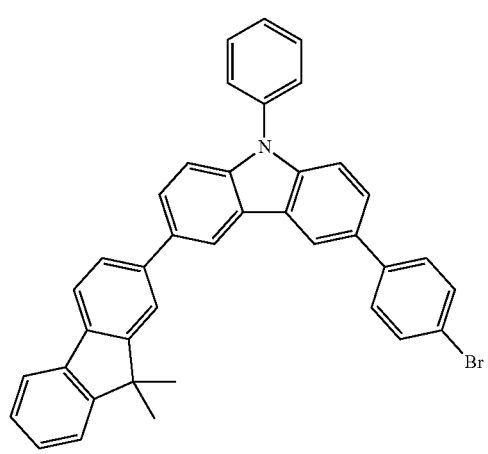
Sub 3-20
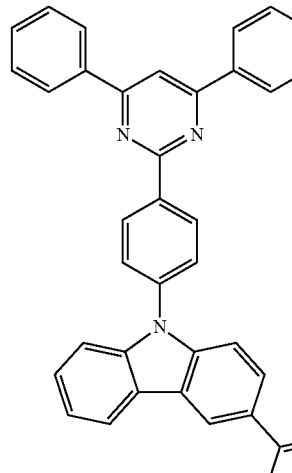
Sub 3-21
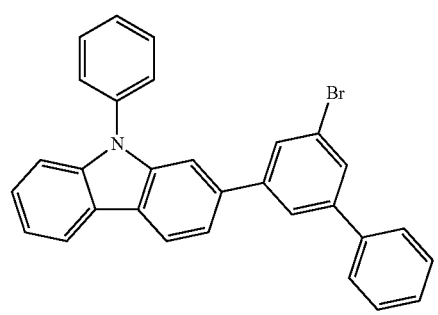
Sub 3-22
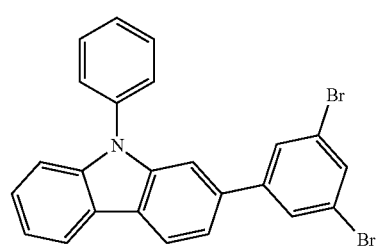
Sub 3-23
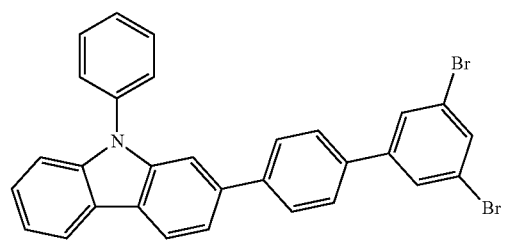

Sub 3-24
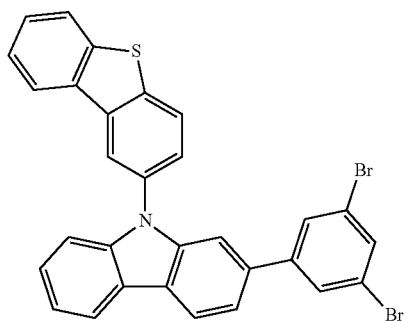
Sub 3-28
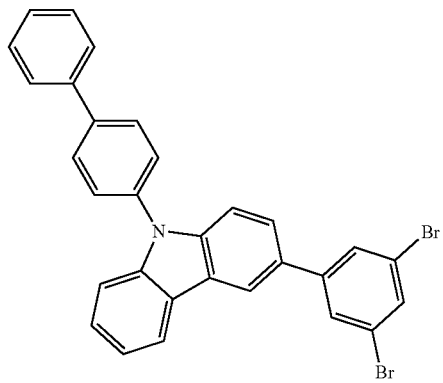
Sub 3-25
Sub 3-29
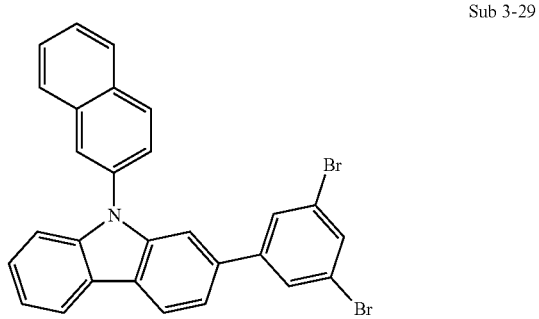
Sub 3-26
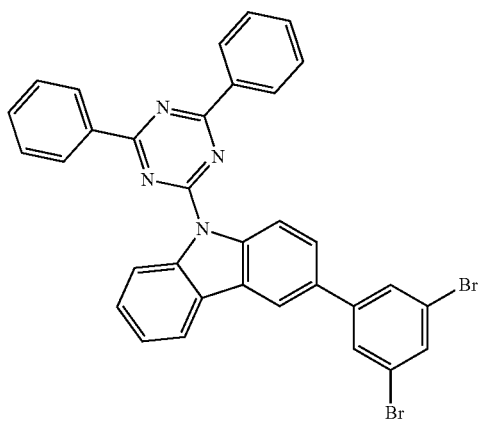
Sub 3-30
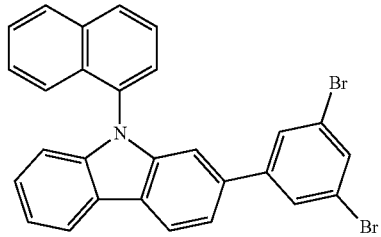
Sub 3-27
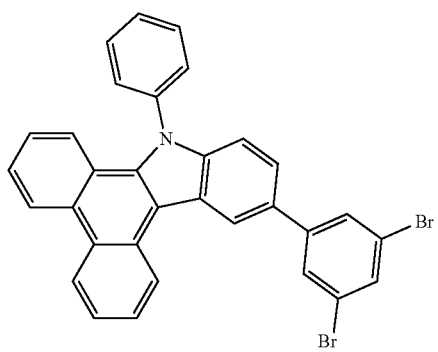
Sub 3-31
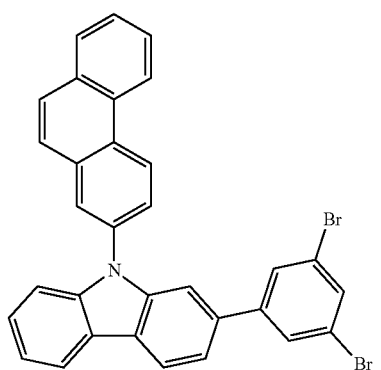

Sub 3-32

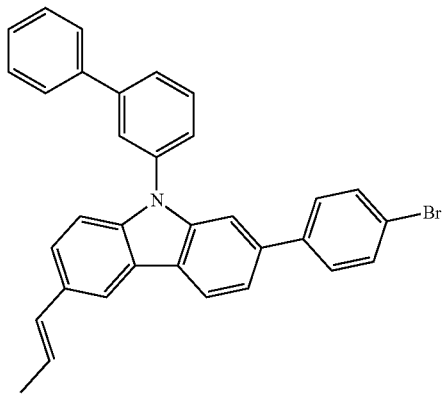

Sub 4-4

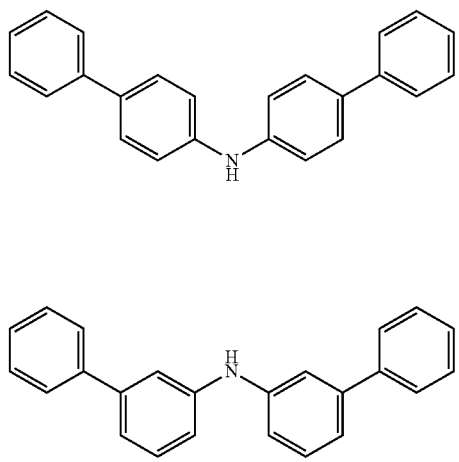

Sub 4-5

The FD-MS values of the compounds belonging to Sub 3 are shown in Table 4 below.

TABLE 4

| Compound | FD-MS | Compound | FD-MS |
| --- | --- | --- | --- |
| Sub 3-1 | m/z = 321.02($C_{18}H_{12}BrN$ = 322.21) | Sub 3-2 | m/z = 321.02($C_{18}H_{12}BrN$ = 322.21) |
| Sub 3-3 | m/z = 397.05($C_{24}H_{16}BrN$ = 398.30) | Sub 3-4 | m/z = 563.12($C_{37}H_{26}BrN$ = 564.53) |
| Sub 3-5 | m/z = 397.05($C_{24}H_{16}BrN$ = 398.30) | Sub 3-6 | m/z = 397.05($C_{24}H_{16}BrN$ = 398.30) |
| Sub 3-7 | m/z = 473.08($C_{30}H_{20}BrN$ = 474.40) | Sub 3-8 | m/z = 473.08($C_{30}H_{20}BrN$ = 474.40) |
| Sub 3-9 | m/z = 473.08($C_{30}H_{20}BrN$ = 474.40) | Sub 3-10 | m/z = 473.08($C_{30}H_{20}BrN$ = 474.40) |
| Sub 3-11 | m/z = 473.08($C_{30}H_{20}BrN$ = 474.40) | Sub 3-12 | m/z = 473.08($C_{30}H_{20}BrN$ = 474.40) |
| Sub 3-13 | m/z = 497.08($C_{32}H_{20}BrN$ = 498.42) | Sub 3-14 | m/z = 503.03($C_{30}H_{18}BrNS$ = 504.45) |
| Sub 3-15 | m/z = 487.06($C_{30}H_{18}BrNO$ = 488.38) | Sub 3-16 | m/z = 513.11($C_{33}H_{24}BrN$ = 514.47) |
| Sub 3-17 | m/z = 473.08($C_{30}H_{20}BrN$ = 474.40) | Sub 3-18 | m/z = 628.13($C_{39}H_{25}BrN_4$ = 629.56) |
| Sub 3-19 | m/z = 589.14($C_{39}H_{28}BrN$ = 590.56) | Sub 3-20 | m/z = 627.13($C_{40}H_{26}BrN_3$ = 628.57) |
| Sub 3-21 | m/z = 473.08($C_{30}H_{20}BrN$ = 474.40) | Sub 3-22 | m/z = 474.96($C_{24}H_{15}Br_2N$ = 477.20) |
| Sub 3-23 | m/z = 550.99($C_{30}H_{19}Br_2N$ = 553.30) | Sub 3-24 | m/z = 580.94($C_{30}H_{17}Br_2N$ = 580.34) |
| Sub 3-25 | m/z = 477.94($C_{21}H_{12}Br_2N_4$ = 480.16) | Sub 3-26 | m/z = 630.01($C_{33}H_{20}Br_2N_4$ = 632.36) |
| Sub 3-27 | m/z = 574.99($C_{32}H_{19}Br_2N$ = 577.32) | Sub 3-28 | m/z = 550.99($C_{30}H_{19}Br_2N$ = 553.30) |
| Sub 3-29 | m/z = 524.97($C_{28}H_{17}Br_2N$ = 527.26) | Sub 3-30 | m/z = 524.97($C_{28}H_{17}Br_2N$ = 527.26) |
| Sub 3-31 | m/z = 574.99($C_{32}H_{19}Br_2N$ = 577.32) | Sub 3-32 | m/z = 513.11($C_{33}H_{24}BrN$ = 514.47) |

The compounds belonging to Sub 4 of Reaction Scheme 4 are as follows, but are not limited thereto.

Sub 4-1

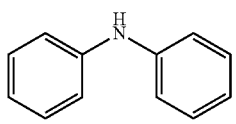

Sub 4-6

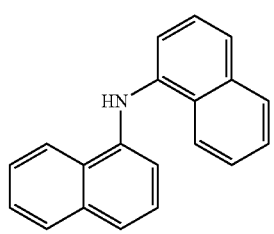

Sub 4-2

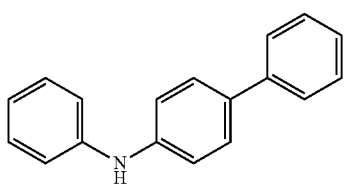

Sub 4-3

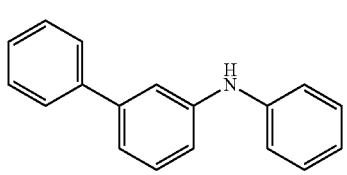

Sub 4-7

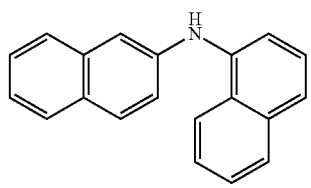

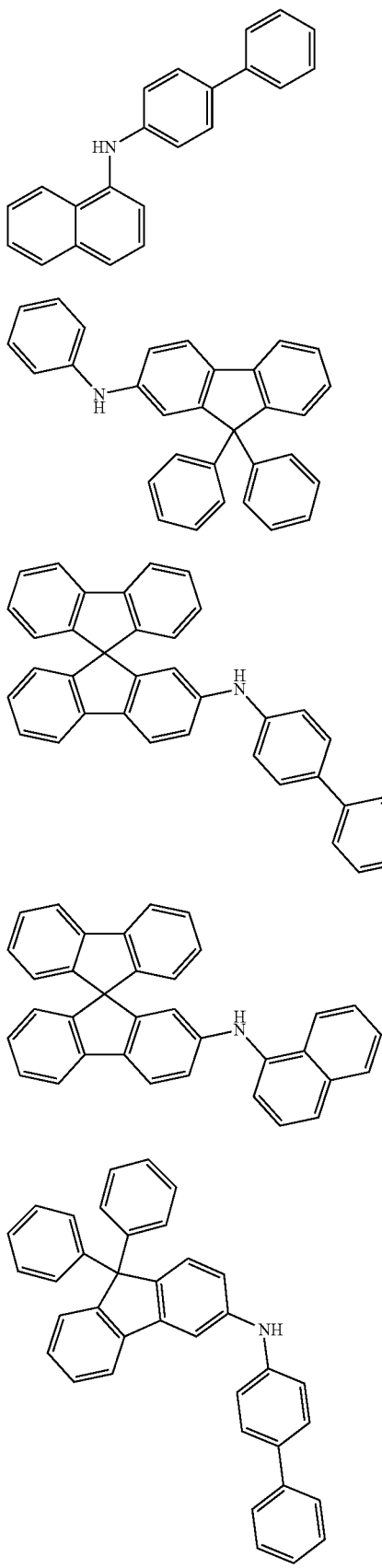
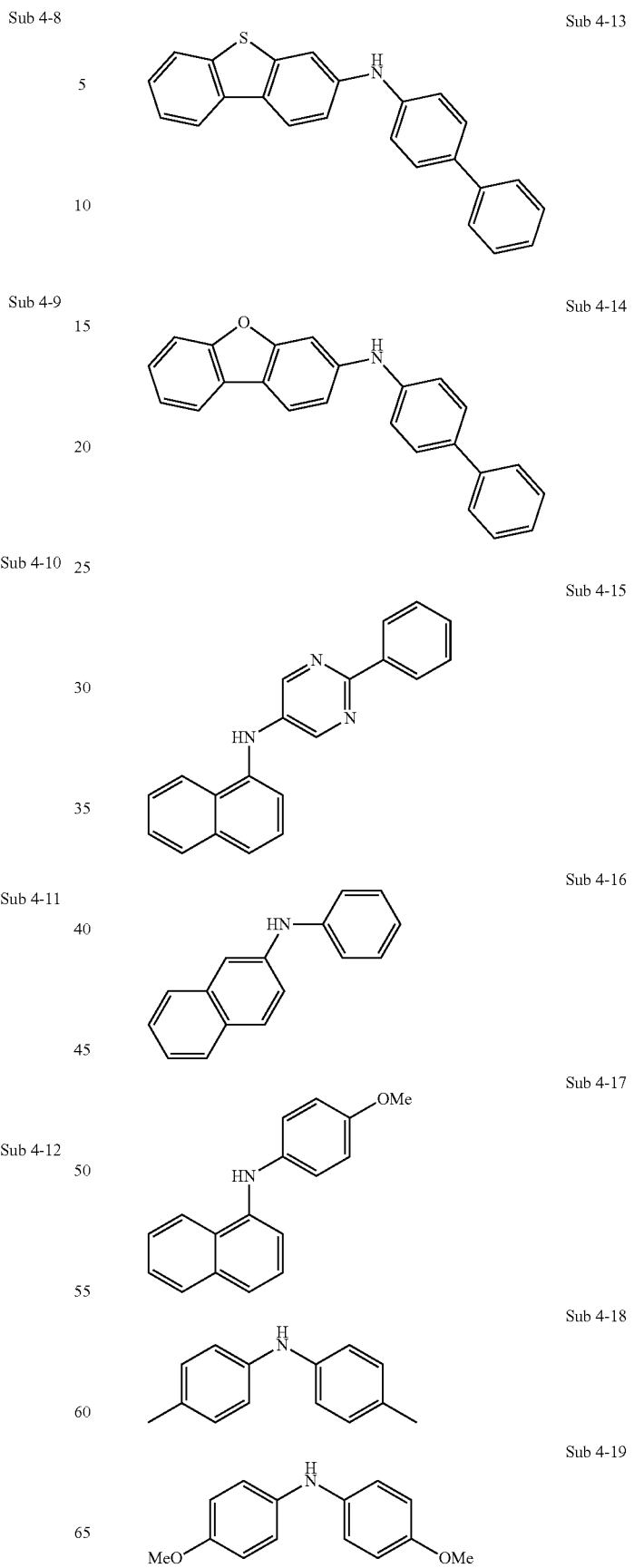

| | |
|---|---|
| Sub 4-20 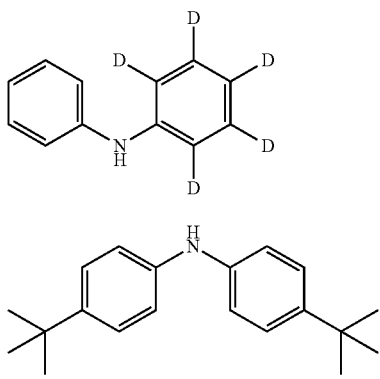 | Sub 4-27 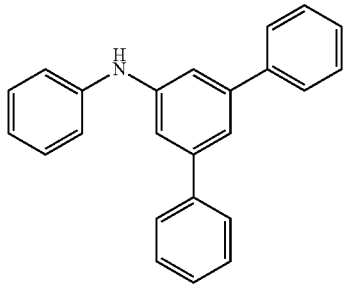 |
| Sub 4-21 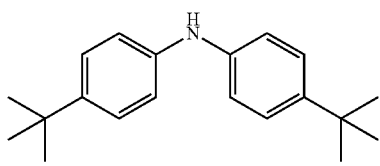 | Sub 4-28 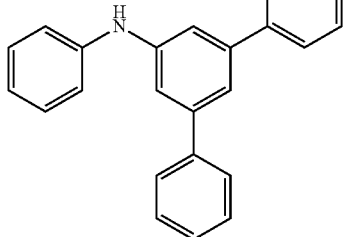 |
| Sub 4-22 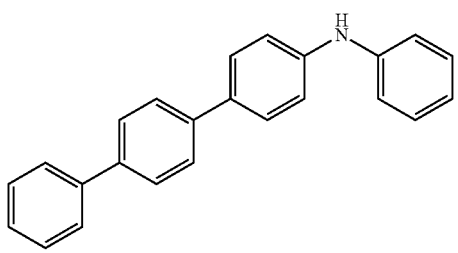 | |
| Sub 4-23 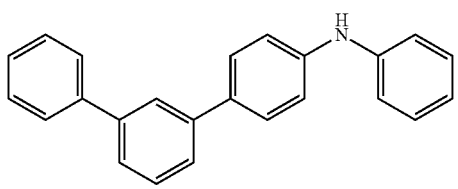 | Sub 4-29 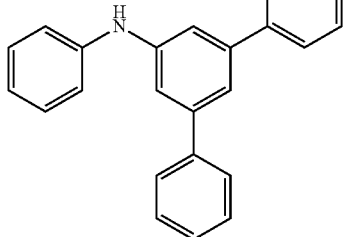 |
| Sub 4-24 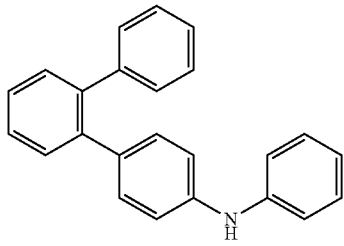 | Sub 4-30 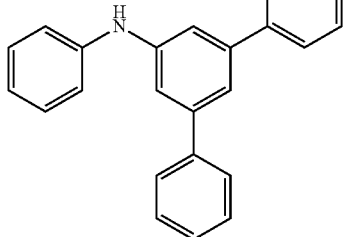 |
| Sub 4-25 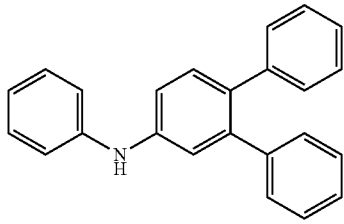 | Sub 4-31 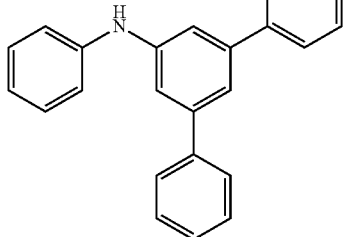 |
| Sub 4-26 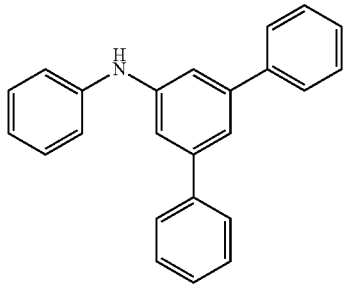 | |

Sub 4-32
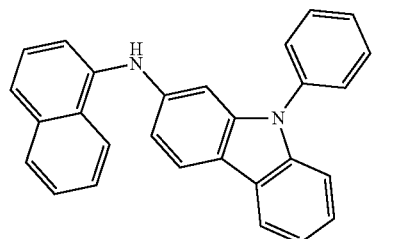
Sub 2-33
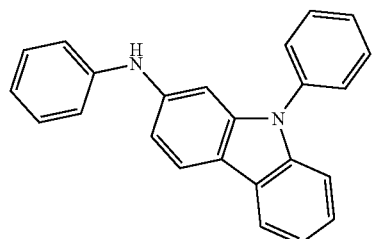
Sub 2-34
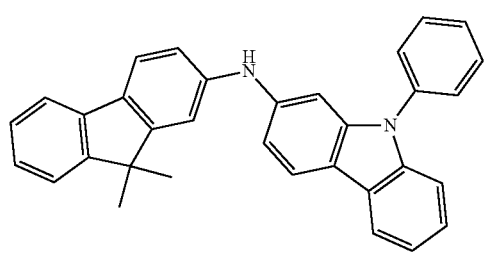
Sub 4-35
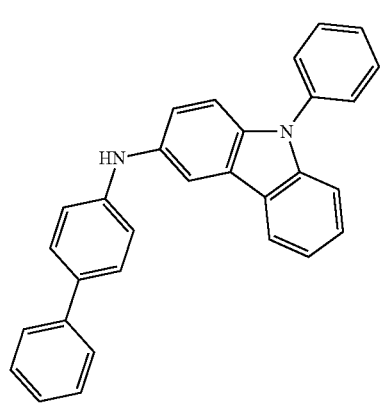
Sub 4-36
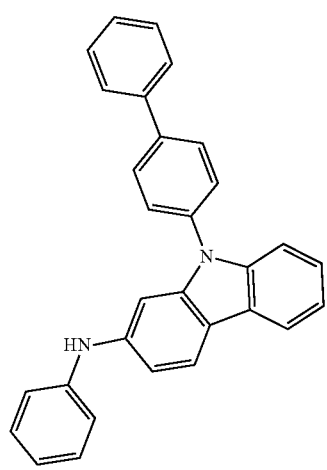
Sub 4-37
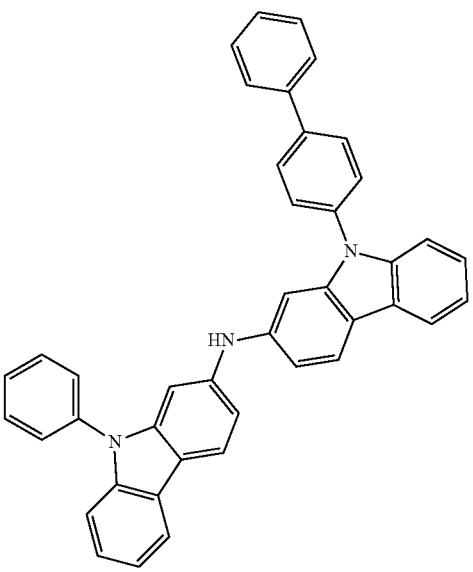
Sub 4-38
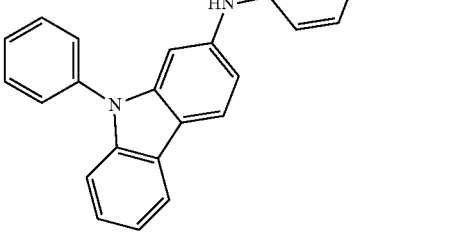
Sub 4-39
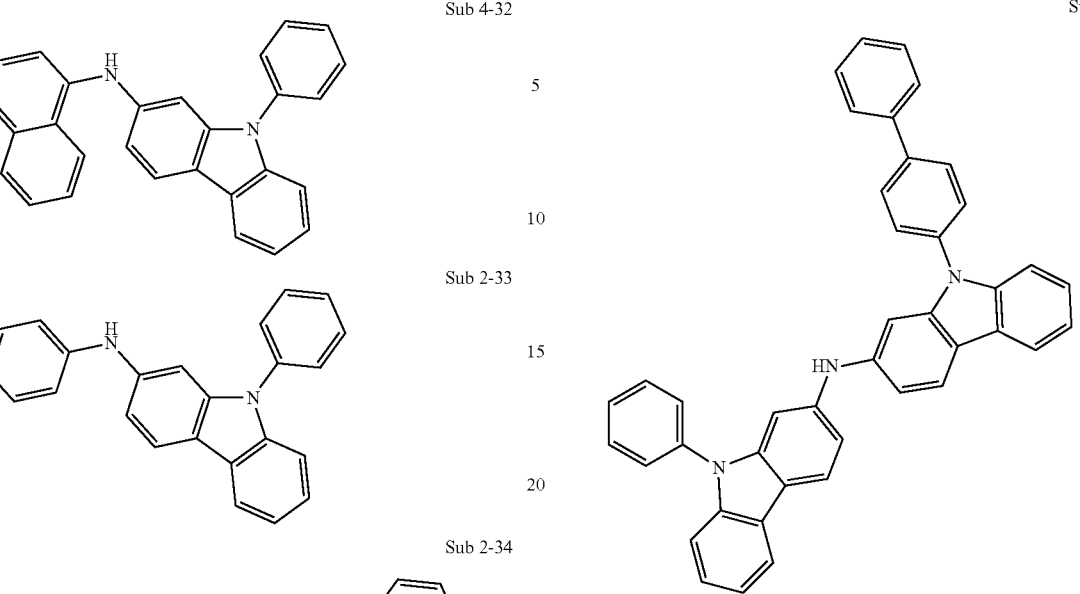

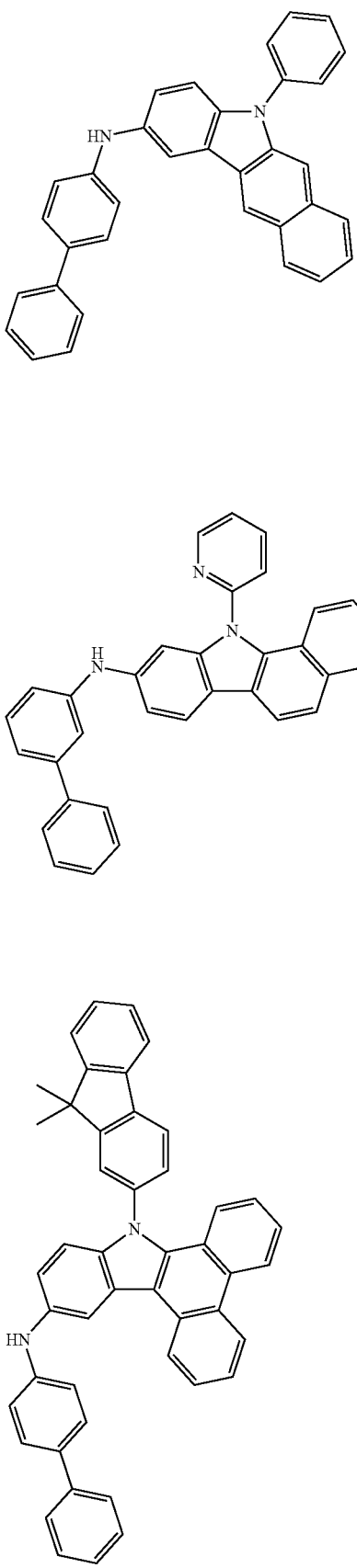
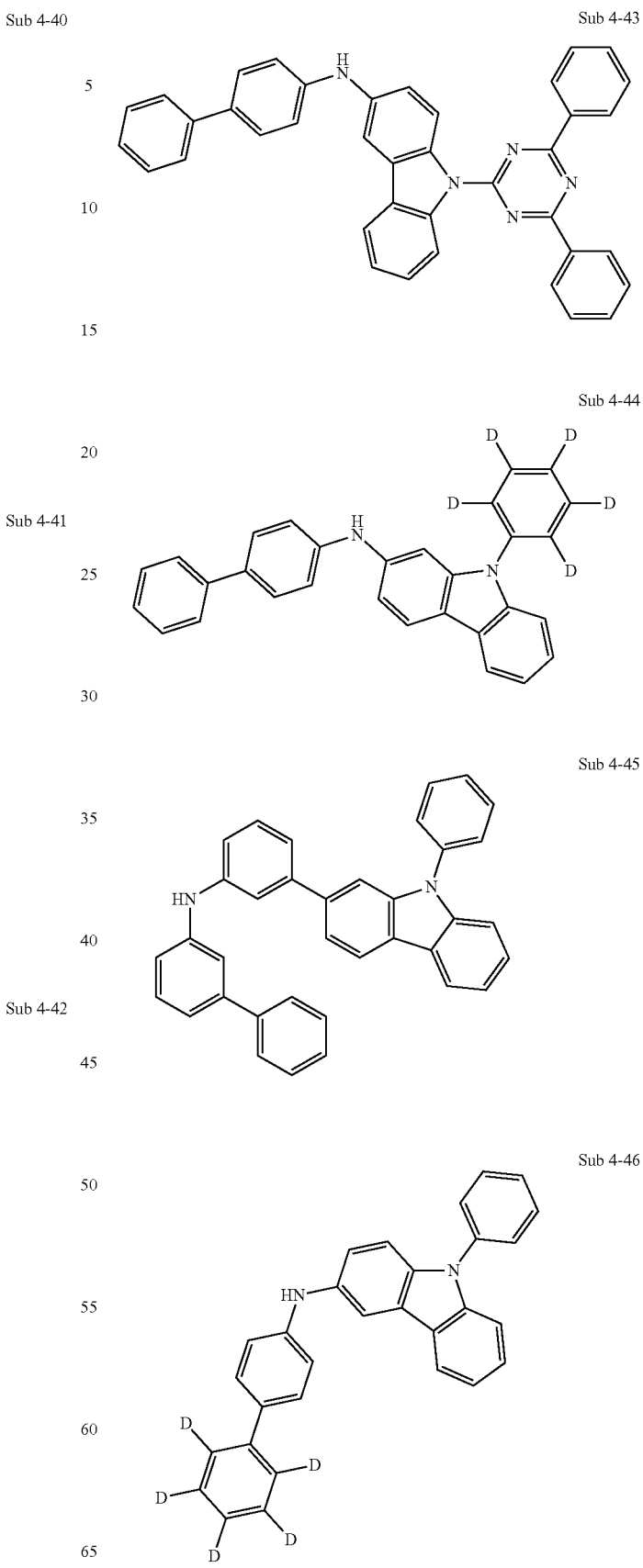

The FD-MS values of the compounds belonging to Sub 4 are shown in Table 5 below.

TABLE 5

| Compound | FD-MS | Compound | FD-MS |
|---|---|---|---|
| Sub 4-1 | m/z = 169.09($C_{12}H_{11}N$ = 169.22) | Sub 4-2 | m/z = 245.12($C_{18}H_{15}N$ = 245.32) |
| Sub 4-3 | m/z = 245.12($C_{18}H_{15}N$ = 245.32) | Sub 4-4 | m/z = 321.15($C_{24}H_{19}N$ = 321.41) |
| Sub 4-5 | m/z = 321.15 ($C_{24}H_{19}N$ = 321.41) | Sub 4-6 | m/z = 269.12($C_{20}H_{15}N$ = 269.34) |
| Sub 4-7 | m/z = 269.12($C_{20}H_{15}N$ = 269.34) | Sub 4-8 | m/z = 295.14($C_{22}H_{17}N$ = 295.38) |
| Sub 4-9 | m/z = 409.18($C_{31}H_{23}N$ = 409.52) | Sub 4-10 | m/z = 483.20($C_{37}H_{25}N$ = 483.60) |
| Sub 4-11 | m/z = 459.20($C_{35}H_{25}N$ = 459.58) | Sub 4-12 | m/z = 485.21($C_{37}H_{27}N$ = 485.62) |
| Sub 4-13 | m/z = 275.08($C_{18}H_{13}NS$ = 275.37) | Sub 4-14 | m/z = 335.13($C_{24}H_{17}NO$ = 335.40) |
| Sub 4-15 | m/z = 297.13($C_{29}H_{15}N_3$ = 297.35) | Sub 4-16 | m/z = 219.10($C_{16}H_{13}N$ = 219.28) |
| Sub 4-17 | m/z = 249.12($C_{17}H_{15}NO$ = 249.31) | Sub 4-18 | m/z = 197.12($C_{14}H_{15}N$ = 197.28) |
| Sub 4-19 | m/z = 229.11($C_{14}H_{15}NO_2$ = 229.27) | Sub 4-20 | m/z = 174.12($C_{12}H_6D_5N$ = 174.25) |
| Sub 4-21 | m/z = 281.21($C_{20}H_{27}N$ = 281.44) | Sub 4-22 | m/z = 321.15($C_{24}H_{19}N$ = 321.41) |
| Sub 4-23 | m/z = 321.15($C_{24}H_{19}N$ = 321.41) | Sub 4-24 | m/z = 321.15($C_{24}H_{19}N$ = 321.41) |
| Sub 4-25 | m/z = 321.15($C_{24}H_{19}N$ = 321.41) | Sub 4-26 | m/z = 321.15($C_{24}H_{19}N$ = 321.41) |
| Sub 4-27 | m/z = 297.13($C_{29}H_{15}N_3$ = 297.35) | Sub 4-28 | m/z = 499.20($C_{36}H_{25}N_3$ = 499.60) |
| Sub 4-29 | m/z = 499.20($C_{38}H_{22}N_2$ = 410.51) | Sub 4-30 | m/z = 424.16($C_{30}H_{20}N_2O$ = 424.49) |
| Sub 4-31 | m/z = 440.13($C_{30}H_{20}N_2S$ = 440.56) | Sub 4-32 | m/z = 384.16($C_{28}H_{20}N_2$ = 384.47) |
| Sub 4-33 | m/z = 334.15($C_{24}H_{18}N_2$ = 334.41) | Sub 4-34 | m/z = 450.21($C_{33}H_{26}N_2$ = 450.57) |
| Sub 4-35 | m/z = 410.18($C_{39}H_{22}N_2$ = 410.51) | Sub 4-36 | m/z = 410.18($C_{30}H_{22}N_2$ = 410.51) |
| Sub 4-37 | m/z = 575.24($C_{42}H_{29}N_3$ = 575.70) | Sub 4-38 | m/z = 574.24($C_{43}H_{30}N_2$ = 574.71) |
| Sub 4-39 | m/z = 460.19($C_{34}H_{24}N_2$ = 460.57) | Sub 4-40 | m/z = 460.19($C_{34}H_{24}N_2$ = 460.57) |
| Sub 4-41 | m/z = 461.19($C_{33}H_{23}N_3$ = 461.56) | Sub 4-42 | m/z = 626.27($C_{47}H_{34}N_2$ = 626.79) |
| Sub 4-43 | m/z = 565.23($C_{39}H_{27}N_5$ = 565.67) | Sub 4-44 | m/z = 415.21($C_{30}H_{17}D_5N_2$ = 415.54) |
| Sub 4-45 | m/z = 486.21($C_{36}H_{26}N_2$ = 486.61) | Sub 4-46 | m/z = 415.21($C_{30}H_{17}D_5N_2$ = 415.54) |

1. Synthesis Example of Sub 3

Sub 3 may be synthesized by the reaction route of the following Reaction Scheme 4-1, but are not limited thereto.

Synthesis Example of Sub 3-c(1)

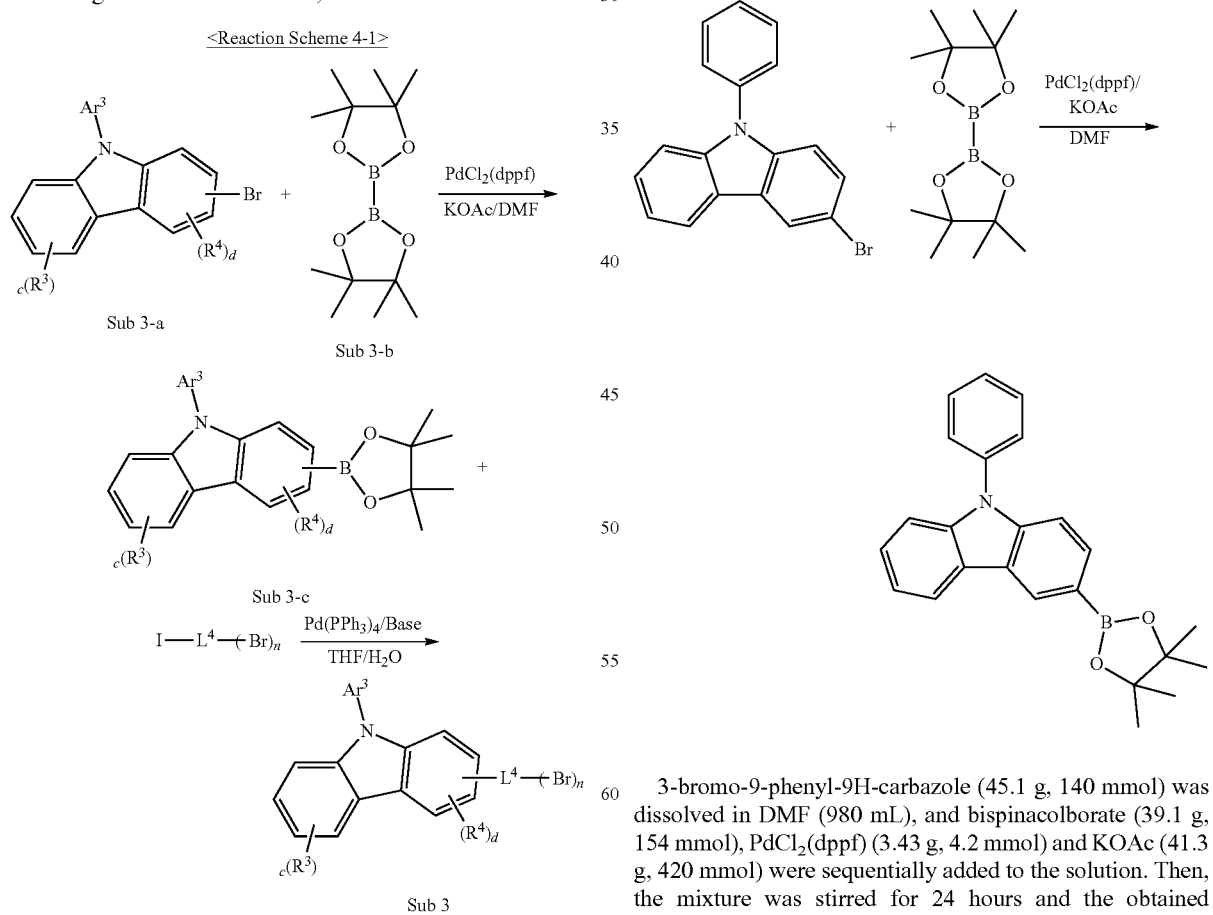

3-bromo-9-phenyl-9H-carbazole (45.1 g, 140 mmol) was dissolved in DMF (980 mL), and bispinacolborate (39.1 g, 154 mmol), $PdCl_2(dppf)$ (3.43 g, 4.2 mmol) and KOAc (41.3 g, 420 mmol) were sequentially added to the solution. Then, the mixture was stirred for 24 hours and the obtained intermediate was separated by a silica gel column and recrystallized to obtain 35.2 g (yield: 68%) of a final compound.

Synthesis Example of Sub 3-c(2)

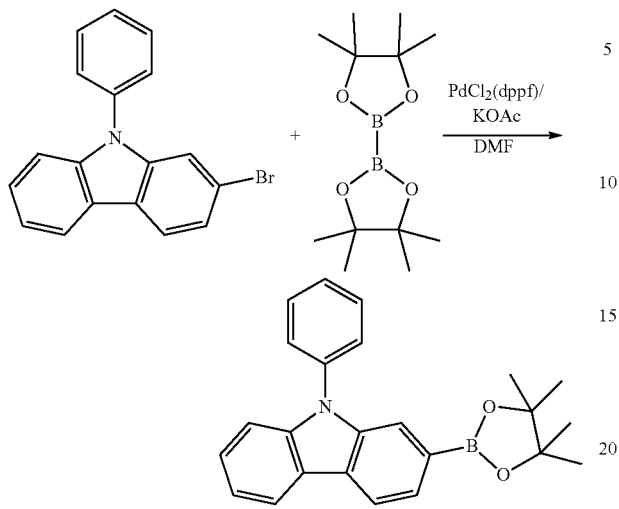

2-bromo-9-phenyl-9H-carbazole (76.78 g, 238.3 mmol) was dissolved in DMF (980 mL), and b bis(pinacolato) diboron (66.57 g, 262.1 mmol), Pd(dppf)Cl$_2$ (5.84 g, 7.1 mmol) and KOAc (70.16 g, 714.9 mmol) were added to the solution. Then, the mixture was stirred for 24 hours and the obtained intermediate was separated by a silica gel column and recrystallized to obtain 73.92 g (yield: 84%) of a final compound.

Synthesis Example of Sub 3-3

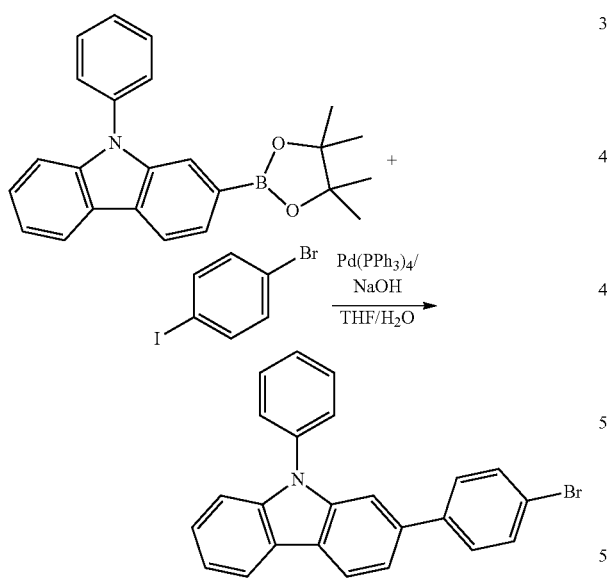

After Sub 3-c(2) (29.5 g, 80 mmol) was dissolved in THF 360 mL, 1-bromo-4-iodobenzene (23.8 g, 84 mmol), Pd(PPh$_3$)$_4$ (2.8 g, 2.4 mmol), NaOH (9.6 g, 240 mmol) and water 180 mL were added to the solution and the mixture was stirred under reflux. When the reaction was completed, the reaction product was extracted using ether and water. The organic layer was dried over MgSO$_4$ and concentrated. Then, the concentrate was separated by a silica gel column and recrystallized to obtain 22.9 g (yield: 72%) of the product.

Synthesis Example of Sub 3-5

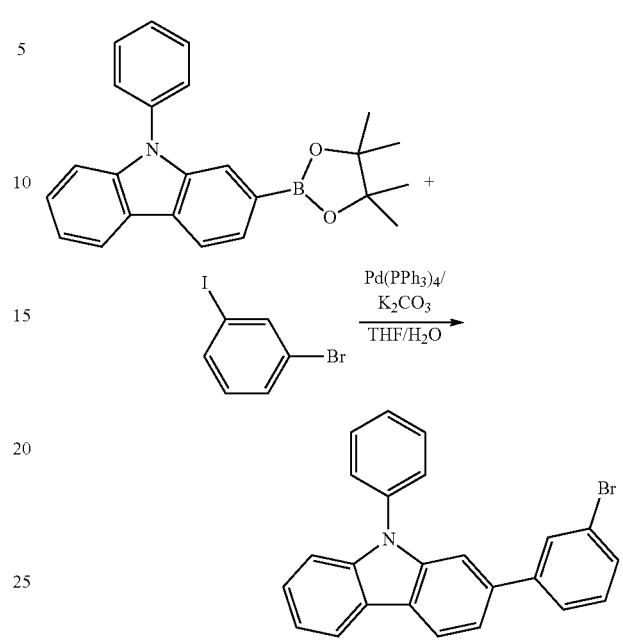

After Sub 3-c(2) (73.92 g, 200.2 mmol) was dissolved in THF 880 mL, 1-bromo-2-iodobenzene (85.0 g, 300.3 mmol), Pd(PPh$_3$)$_4$ (11.6 g, 10 mmol), K$_2$CO$_3$ (83 g, 600.6 mmol) and water 440 mL were added to the solution and the mixture was stirred under reflux. When the reaction was completed, the reaction product was extracted using ether and water. The organic layer was dried over MgSO$_4$ and concentrated. Then, the concentrate was separated by a silica gel column and recrystallized to obtain 55.8 g (yield: 70%) of the product.

Synthesis Example of Sub 3-10

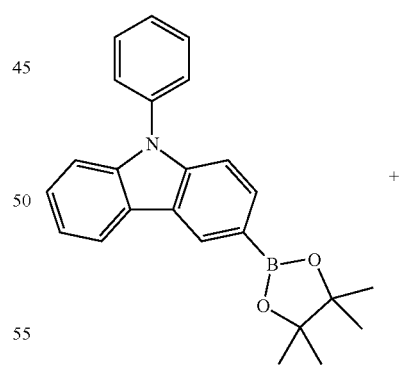

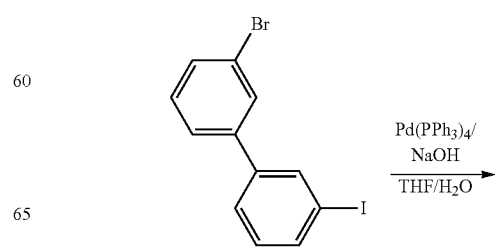

-continued

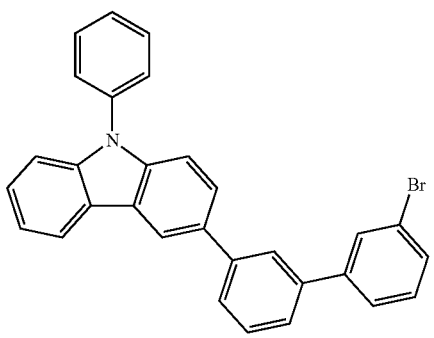

After Sub 3-c(1) (29.5 g, 80 mmol) was dissolved in THF 360 mL, 3-bromo-3'-iodo-1,1'-biphenyl (30.16 g, 84 mmol), Pd(PPh$_3$)$_4$ (2.8 g, 2.4 mmol), NaOH (9.6 g, 240 mmol) and water 180 mL were added to the solution and the mixture was stirred under reflux. When the reaction was completed, the reaction product was extracted using ether and water. The organic layer was dried over MgSO$_4$ and concentrated. Then, the concentrate was separated by a silica gel column and recrystallized to obtain 26.56 g (yield: 70%) of the product.

Synthesis Example of Sub 3-15

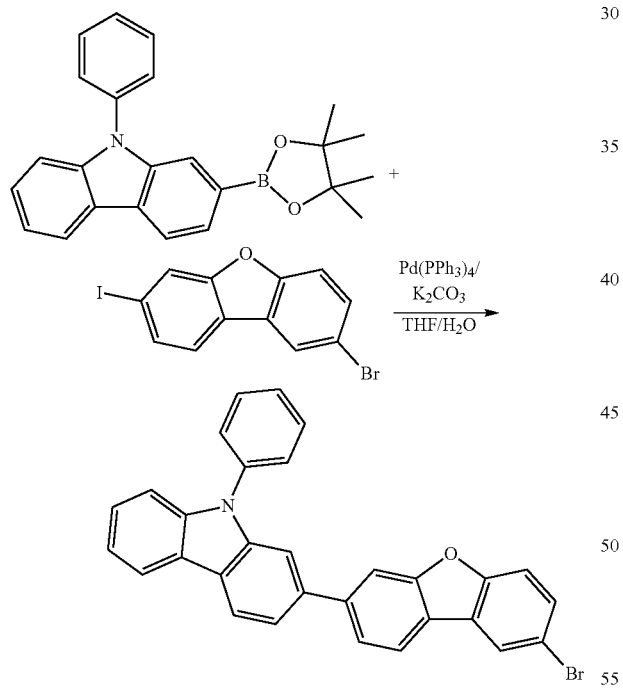

After Sub 3-c(2) (73.92 g, 200.2 mmol) was dissolved in THF 880 mL, 2-bromo-7-iododibenzo[b,d]furan (112.0 g, 300.3 mmol), Pd(PPh$_3$)$_4$ (11.6 g, 10 mmol), K$_2$CO$_3$ (83 g, 600.6 mmol) and water 440 mL were added to the solution and the mixture was stirred under reflux. When the reaction was completed, the reaction product was extracted using ether and water. The organic layer was dried over MgSO$_4$ and concentrated. Then, the concentrate was separated by a silica gel column and recrystallized to obtain 72.4 g (yield: 74%) of the product.

Synthesis Example of Sub 3-22

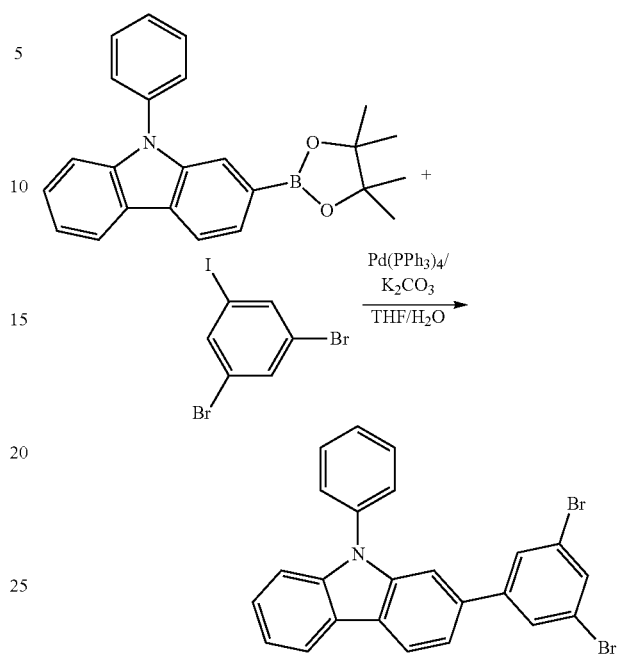

After Sub 3-c(2) (73.92 g, 200.2 mmol) was dissolved in THF 880 mL, 1,3-dibromo-5-iodobenzene (108.65 g, 300.3 mmol), Pd(PPh$_3$)$_4$ (11.6 g, 10 mmol), K$_2$CO$_3$ (83 g, 600.6 mmol) and water 440 mL were added to the solution and the mixture was stirred under reflux. When the reaction was completed, the reaction product was extracted using ether and water. The organic layer was dried over MgSO$_4$ and concentrated. Then, the concentrate was separated by a silica gel column and recrystallized to obtain 69.7 g (yield: 73%) of the product.

2. Synthesis Example of Sub 4

Sub 4 of Reaction Scheme 4 may be synthesized by the reaction route of the following Reaction Scheme 4-2, but are not limited thereto.

<Reaction Scheme 4-2>

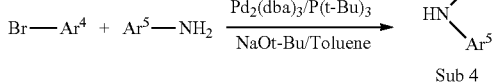

Synthesis Example of Sub 4-1

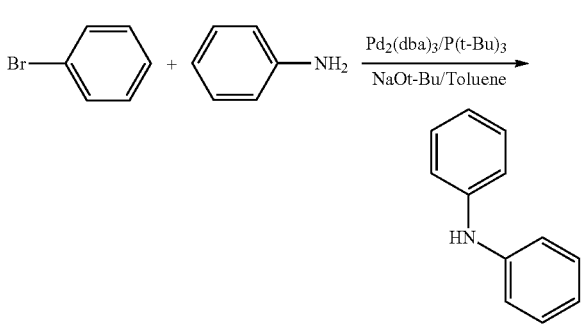

Bromobenzene (37.1 g, 236.2 mmol) was dissolve in toluene (2200 mL) in a round bottom flask, and aniline (20 g, 214.8 mmol), Pd$_2$(dba)$_3$ (9.83 g, 10.7 mmol), P(t-Bu)$_3$ (4.34 g, 21.5 mmol) and NaOt-Bu (62 g, 644.3 mmol) were added sequentially to the solution. Then, the mixture was stirred at 100° C. When the reaction was completed, the reaction product was extracted using ether and water. The organic layer was dried over MgSO$_4$ and concentrated. Then, the concentrate was separated by a silica gel column and recrystallized to obtain 28 g (yield: 77%) of the product.

Synthesis Example of Sub 4-13

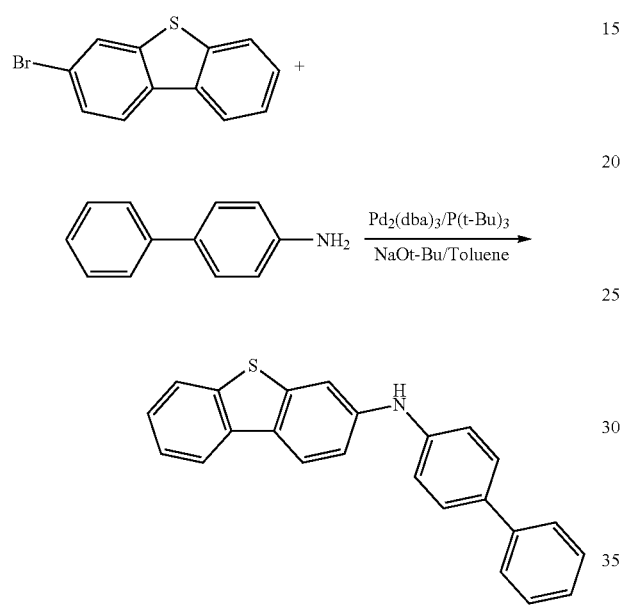

3-bromodibenzo[b,d]thiophene (42.8 g, 162.5 mmol) was dissolve in toluene(1550 mL) in a round bottom flask, and [1,1'-biphenyl]-4-amine (25 g, 147.7 mmol), Pd$_2$(dba)$_3$ (6.76 g, 7.4 mmol), P(t-Bu)$_3$ (3 g, 14.8 mmol) and NaOt-Bu (42.6 g, 443.2 mmol) were added to the solution. Then, the mixture was stirred at 100° C.

When the reaction was completed, the reaction product was extracted using ether and water. The organic layer was dried over MgSO$_4$ and concentrated. Then, the concentrate was separated by a silica gel column and recrystallized to obtain 37.9 g (yield: 73%) of the product.

3. Synthesis Example of Final Products

Synthesis Example of 2-10

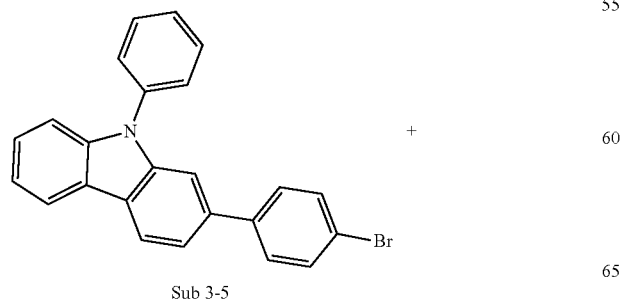

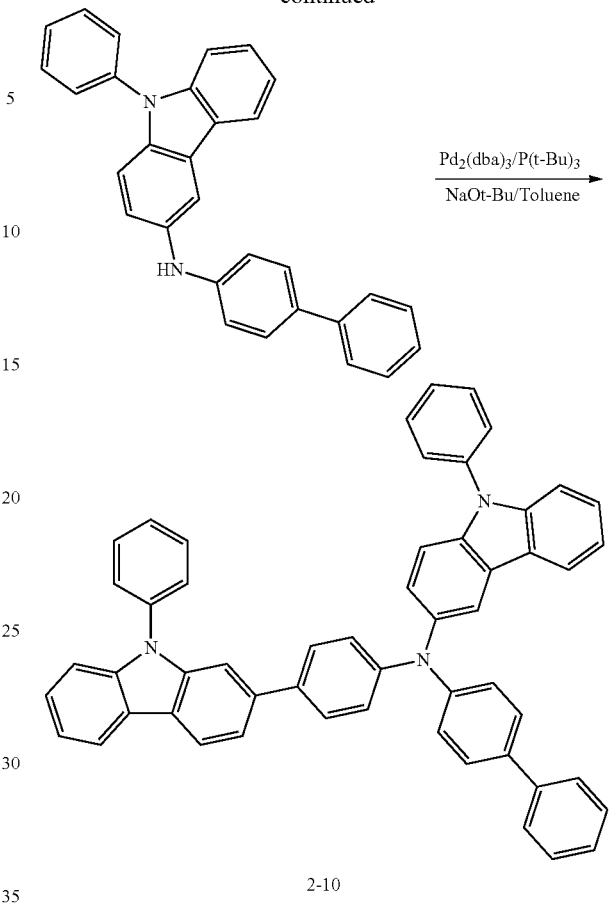

2-10

Sub 3-5 (20.7 g, 52.0 mmol) was dissolve in toluene(500 mL) in a round bottom flask, and Sub 4-35 (24.5 g, 59.8 mmol), Pd$_2$(dba)$_3$ (2.4 g, 2.6 mmol), P(t-Bu)$_3$ (1.05 g, 5.2 mmol) and NaOt-Bu (13.6 g, 141.8 mmol) were added to the solution. Then, the mixture was stirred at 100° C. When the reaction was completed, the reaction product was extracted using CH$_2$Cl$_2$ and water. The organic layer was dried over MgSO$_4$ and concentrated. Then, the concentrate was separated by a silica gel column and recrystallized to obtain 26.48 g (yield: 70%) of the product.

Synthesis Example of 2-37

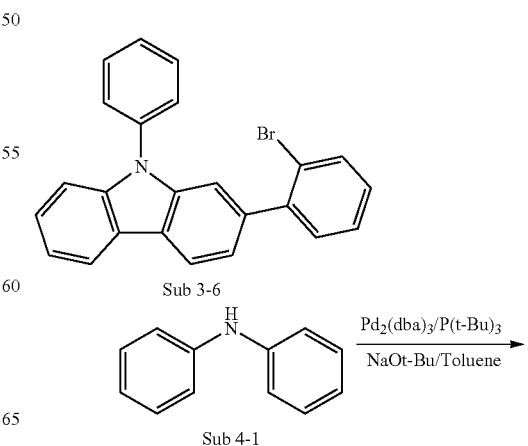

-continued

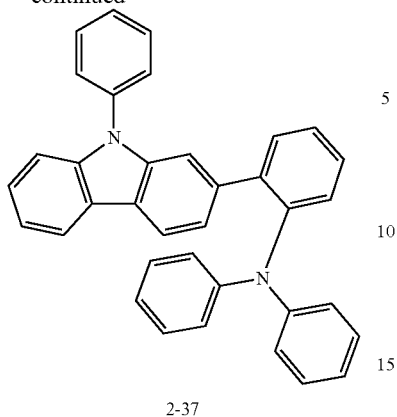
2-37

Sub 3-6 (20.7 g, 52.0 mmol) was dissolved in toluene (500 mL), and Sub 4-1 (8.0 g, 47.3 mmol), Pd$_2$(dba)$_3$ (2.4 g, 2.6 mmol), P(t-Bu)$_3$ (1.05 g, 5.2 mmol) and NaOt-Bu (13.6 g, 141.8 mmol) were added to the solution. Then, the reaction was carried out in the same manner as in the synthesis method of 2-10 to obtain 16.1 g (yield: 70%) of the product.

Synthesis Example of 2-54

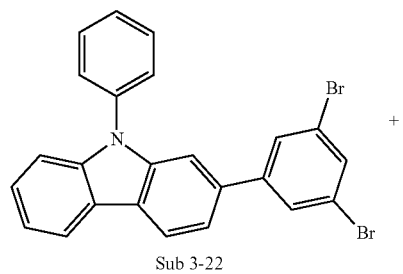
Sub 3-22

+

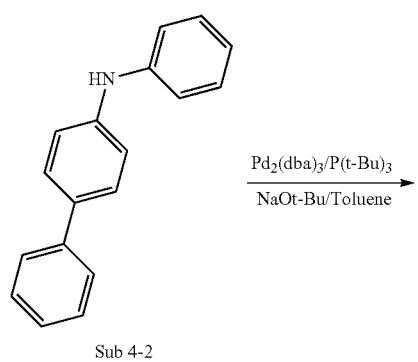
Sub 4-2

-continued

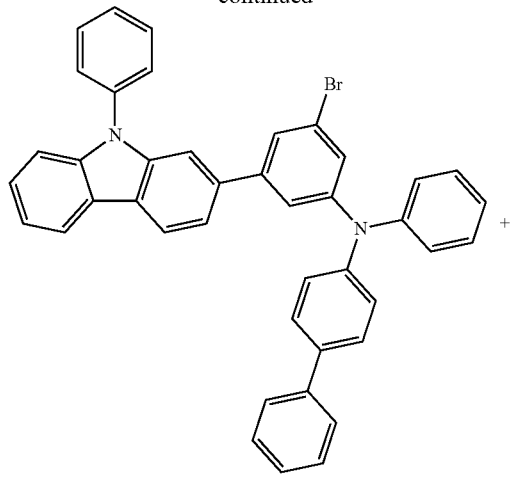
Inter_A-1

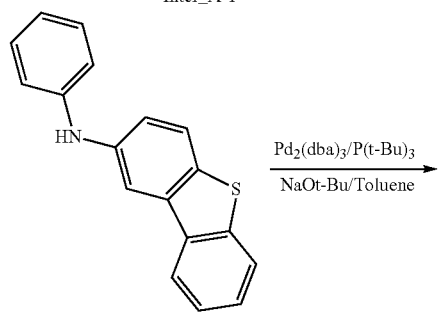
Sub 4-13

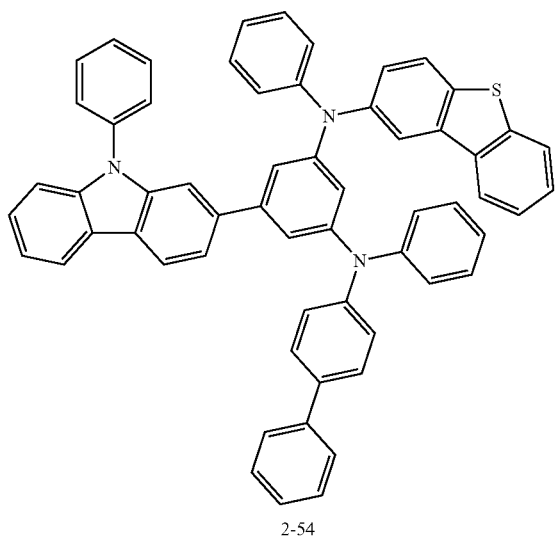 [SMILES: c1ccc(-c2ccc(N(c3ccccc3)c3cc(-c4ccc5c6ccccc6n(-c6ccccc6)c5c4)cc(N(c4ccccc4)c4ccc5sc6ccccc6c5c4)c3)cc2)cc1]
2-54

(1) Synthesis of Inter_A-1

Sub 3-22 (24.8 g, 52.0 mmol) was dissolved in toluene (500 mL), and Sub 4-2 (11.6 g, 47.3 mmol), Pd$_2$(dba)$_3$ (2.4 g, 2.6 mmol), P(t-Bu)$_3$ (1.05 g, 5.2 mmol) and NaOt-Bu (13.6 g, 141.8 mmol) were added to the solution. Then, the reaction was carried out in the same manner as in the synthesis method of 2-10 to obtain 25.01 g (yield: 62%) of the product Inter_A-1.

(2) Synthesis of 2-54

Inter_A-1 (20.5 g, 32 mmol) was dissolved in toluene (305 mL), and Sub 4-13 (10.1 g, 36.7 mmol), Pd$_2$(dba)$_3$ (1.5 g, 1.6 mmol), P(t-Bu)$_3$ (0.65 g, 3.2 mmol) and NaOt-Bu (8.4 g, 87.2 mmol) were added to the solution. Then, the reaction was carried out in the same manner as in the synthesis method of 2-10 to obtain 19.7 g (yield: 74%) of the product 2-54.

Synthesis Example of 2-73

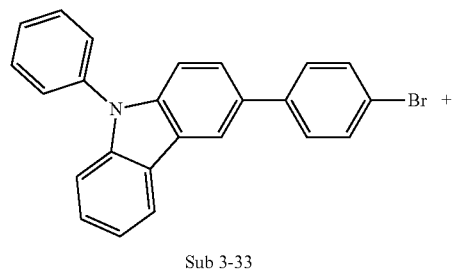

Sub 3-33

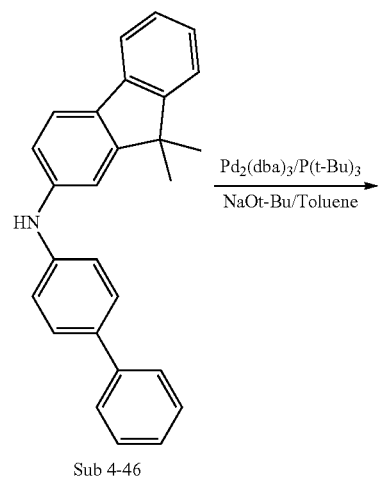

Sub 4-46

Synthesis Example of 2-86

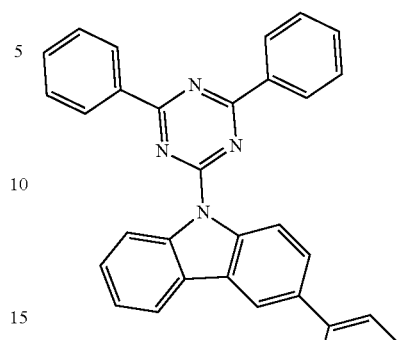

Sub 3-34

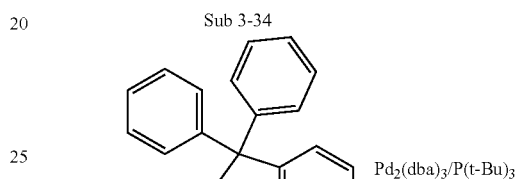

Sub 4-12

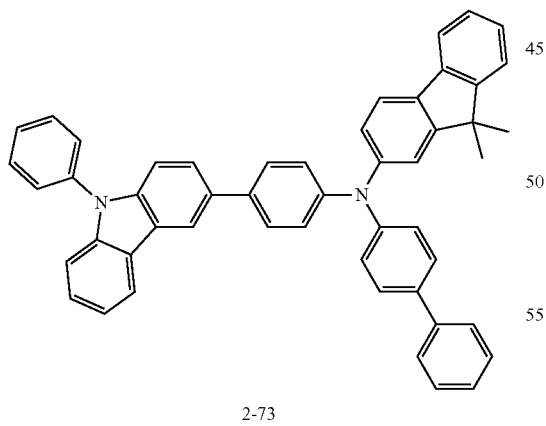

2-73

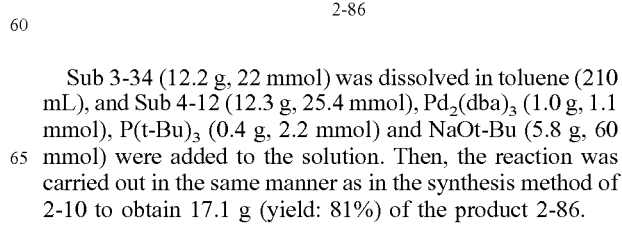

2-86

Sub 3-33 (8.73 g, 22 mmol) was dissolved in toluene (210 mL), and Sub 4-46 (9.1 g, 25.2 mmol), $Pd_2(dba)_3$ (1 g, 1.1 mmol), $P(t-Bu)_3$ (0.4 g, 2.2 mmol) and NaOt-Bu (5.74 g, 60 mmol) were added to the solution. Then, the reaction was carried out in the same manner as in the synthesis method of 2-10 to obtain 12.7 g (yield: 85%) of the product 2-73.

Sub 3-34 (12.2 g, 22 mmol) was dissolved in toluene (210 mL), and Sub 4-12 (12.3 g, 25.4 mmol), $Pd_2(dba)_3$ (1.0 g, 1.1 mmol), $P(t-Bu)_3$ (0.4 g, 2.2 mmol) and NaOt-Bu (5.8 g, 60 mmol) were added to the solution. Then, the reaction was carried out in the same manner as in the synthesis method of 2-10 to obtain 17.1 g (yield: 81%) of the product 2-86.

Synthesis Example of 2-128

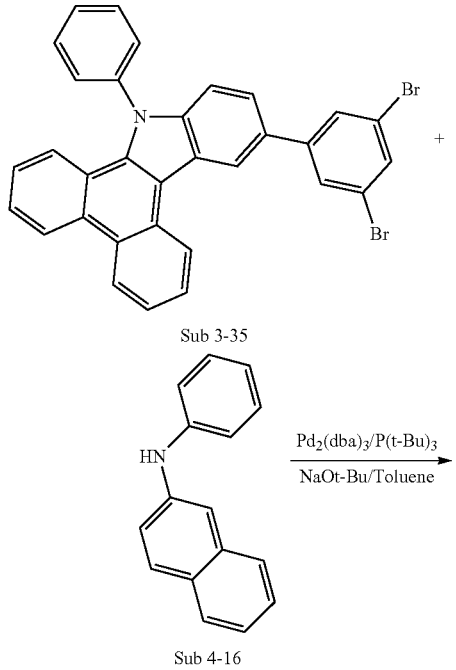

Sub 3-35

Sub 4-16

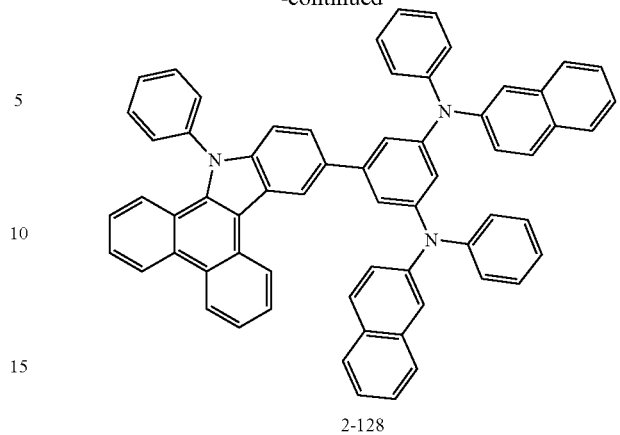

2-128

Sub 3-35 (13.9 g, 24.1 mmol) was dissolved in toluene (260 mL), and Sub 4-16 (12.1 g, 55.4 mmol), $Pd_2(dba)_3$ (2.2 g, 2.4 mmol), $P(t-Bu)_3$ (1 g, 4.8 mmol) and NaOt-Bu (8.3 g, 86.7 mmol) were added to the solution. Then, the reaction was carried out in the same manner as in the synthesis method of 2-10 to obtain 16.5 g (yield: 80%) of the product 2-128.

The FD-MS values of the compounds 2-1 to 2-136 of the present invention synthesized by the above synthesis method are shown in Table 6 below.

TABLE 6

| Compound | FD-MS | Compound | FD-MS |
|---|---|---|---|
| 2-1 | m/z = 562.24($C_{42}H_{30}N_2$ = 562.72) | 2-2 | m/z = 602.27($C_{45}H_{34}N_2$ = 602.78) |
| 2-3 | m/z = 563.24($C_{41}H_{29}N_3$ = 563.70) | 2-4 | m/z = 714.30($C_{54}H_{38}N_2$ = 714.91) |
| 2-5 | m/z = 678.30($C_{51}H_{38}N_2$ = 678.88) | 2-6 | m/z = 802.33($C_{61}H_{42}N_2$ = 803.02) |
| 2-7 | m/z = 800.32($C_{61}H_{40}N_2$ = 801.01) | 2-8 | m/z = 563.24($C_{41}H_{29}N_3$ = 563.70) |
| 2-9 | m/z = 668.23($C_{48}H_{32}N_2S$ = 668.86) | 2-10 | m/z = 727.30($C_{54}H_{37}N_3$ = 727.91) |
| 2-11 | m/z = 652.25($C_{48}H_{32}N_2O$ = 652.80) | 2-12 | m/z = 662.27($C_{50}H_{34}N_2$ = 662.84) |
| 2-13 | m/z = 536.23($C_{40}H_{28}N_2$ = 536.68) | 2-14 | m/z = 586.24($C_{44}H_{30}N_2$ = 586.74) |
| 2-15 | m/z = 712.29($C_{54}H_{36}N_2$ = 712.90) | 2-16 | m/z = 714.30($C_{54}H_{38}N_2$ = 714.91) |
| 2-17 | m/z = 754.33($C_{57}H_{42}N_2$ = 754.98) | 2-18 | m/z = 957.38($C_{70}H_{47}N_5$ = 958.18) |
| 2-19 | m/z = 965.38($C_{73}H_{47}N_3$ = 966.20) | 2-20 | m/z = 719.24($C_{51}H_{33}N_3S$ = 719.91) |
| 2-21 | m/z = 758.24($C_{54}H_{34}N_2OS$ = 758.94) | 2-22 | m/z = 893.38($C_{67}H_{47}N_3$ = 894.13) |
| 2-23 | m/z = 652.25($C_{48}H_{32}N_2O$ = 652.80) | 2-24 | m/z = 662.27($C_{50}H_{34}N_2$ = 662.84) |
| 2-25 | m/z = 562.24($C_{42}H_{30}N_2$ = 562.72) | 2-26 | m/z = 612.26($C_{46}H_{32}N_2$ = 612.78) |
| 2-27 | m/z = 688.29($C_{52}H_{36}N_2$ = 688.87) | 2-28 | m/z = 714.30($C_{54}H_{38}N_2$ = 714.91) |
| 2-29 | m/z = 754.33($C_{57}H_{42}N_2$ = 754.98) | 2-30 | m/z = 878.37($C_{67}H_{46}N_2$ = 879.12) |
| 2-31 | m/z = 876.35($C_{67}H_{44}N_2$ = 877.10) | 2-32 | m/z = 639.27($C_{47}H_{33}N_3$ = 369.80) |
| 2-33 | m/z = 768.26($C_{56}H_{36}N_2S$ = 768.98) | 2-34 | m/z = 833.29($C_{60}H_{39}N_3S$ = 834.05) |
| 2-35 | m/z = 742.26($C_{54}H_{34}N_2O_5$ = 742.88) | 2-36 | m/z = 778.333($C_{59}H_{42}N_2$ = 779.00) |
| 2-37 | m/z = 486.21($C_{36}H_{26}N_2$ = 486.62) | 2-38 | m/z = 536.23($C_{40}H_{28}N_2$ = 536.68) |
| 2-39 | m/z = 612.26($C_{46}H_{32}N_2$ = 612.78) | 2-40 | m/z = 638.27($C_{48}H_{34}N_2$ = 638.81) |
| 2-41 | m/z = 491.24($C_{36}H_{21}D_5N_2$ = 491.65) | 2-42 | m/z = 612.26($C_{46}H_{32}N_2$ = 612.78) |
| 2-43 | m/z = 794.28($C_{58}H_{38}N_2S$ = 795.02) | 2-44 | m/z = 656.26($C_{48}H_{33}FN_2$ = 656.80) |
| 2-45 | m/z = 717.29($C_{51}H_{35}N_5$ = 717.88) | 2-46 | m/z = 728.32($C_{55}H_{40}N_2$ = 728.94) |
| 2-47 | m/z = 842.34($C_{62}H_{42}N_4$ = 843.05) | 2-48 | m/z = 714.30($C_{54}H_{38}N_2$ = 714.91) |
| 2-49 | m/z = 653.28($C_{48}H_{35}N_3$ = 653.81) | 2-50 | m/z = 703.30($C_{52}H_{37}N_3$ = 703.87) |
| 2-51 | m/z = 805.35($C_{60}H_{43}N_3$ = 806.00) | 2-52 | m/z = 753.31($C5_6H_{39}N_3$ = 753.93) |
| 2-53 | m/z = 818.34($C_{60}H_{42}N_4$ = 819.00) | 2-54 | m/z = 835.30($C_{60}H_{41}N_3S$ = 836.05) |
| 2-55 | m/z = 655.27($C_{46}H_{33}N_5$ = 655.79) | 2-56 | m/z = 885.32($C_{64}H_{43}N_3S$ = 886.11) |
| 2-57 | m/z = 759.27($C_{54}H_{37}N_3S$ = 759.96) | 2-58 | m/z = 706.28($C_{49}H_{34}N_6$ = 706.83) |
| 2-59 | m/z = 960.39($C_{69}H_{48}N_6$ = 961.16) | 2-60 | m/z = 853.35($C_{64}H_{43}N_3$ = 854.05) |
| 2-61 | m/z = 894.37($C_{66}H_{46}N_4$ = 895.10) | 2-62 | m/z = 834.38($C_{62}H_{38}D_5N_3$ = 835.06) |
| 2-63 | m/z = 855.36($C_{64}H_{45}N_3$ = 856.06) | 2-64 | m/z = 853.35($C_{64}H_{43}N_3$ = 854.05) |
| 2-65 | m/z = 794.37($C_{60}H_{46}N_2$ = 795.04) | 2-66 | m/z = 987.39($C_{71}H_{49}N_5O$ = 988.21) |
| 2-67 | m/z = 1021.44($C_{77}H_{55}N_3$ = 1022.31) | 2-68 | m/z = 737.23($C_{51}H_{32}FN_3S$ = 737.90) |
| 2-69 | m/z = 562.24($C_{42}H_{30}N_2$ = 562.72) | 2-70 | m/z = 602.27($C_{45}H_{34}N_2$ = 602.78) |
| 2-71 | m/z = 563.24($C_{41}H_{29}N_3$ = 563.70) | 2-72 | m/z = 714.30($C_{54}H_{38}N_2$ = 714.91) |
| 2-73 | m/z = 678.30($C_{51}H_{38}N_2$ = 678.88) | 2-74 | m/z = 802.33($C_{61}H_{42}N_2$ = 803.02) |
| 2-75 | m/z = 800.32($C_{61}H_{40}N_2$ = 801.01) | 2-76 | m/z = 563.24($C_{41}H_{29}N_3$ = 563.70) |
| 2-77 | m/z = 668.23($C_{48}H_{32}N_2S$ = 668.86) | 2-78 | m/z = 727.30($C_{54}H_{37}N_3$ = 727.91) |
| 2-79 | m/z = 652.25($C_{48}H_{32}N_2O$ = 652.80) | 2-80 | m/z = 662.27($C_{50}H_{34}N_2$ = 662.84) |

TABLE 6-continued

| Compound | FD-MS | Compound | FD-MS |
|---|---|---|---|
| 2-81 | m/z = 536.23($C_{40}H_{28}N_2$ = 536.68) | 2-82 | m/z = 586.24($C_{44}H_{30}N_2$ = 586.74) |
| 2-83 | m/z = 712.29($C_{54}H_{36}N_2$ = 712.90) | 2-84 | m/z = 714.30($C_{54}H_{38}N_2$ = 714.91) |
| 2-85 | m/z = 754.33($C_{57}H_{42}N_2$ = 754.98) | 2-86 | m/z = 957.38($C_{70}H_{47}N_5$ = 958.18) |
| 2-87 | m/z = 965.38($C_{73}H_{47}N_3$ = 966.20) | 2-88 | m/z = 719.24($C_{51}H_{33}N_3S$ = 719.91) |
| 2-89 | m/z = 758.24($C_{54}H_{34}N_2OS$ = 758.94) | 2-90 | m/z = 893.38($C_{67}H_{47}N_3$ = 894.13) |
| 2-91 | m/z = 652.25($C_{48}H_{32}N_2O$ = 652.80) | 2-92 | m/z = 662.27($C_{50}H_{34}N_2$ = 662.84) |
| 2-93 | m/z = 562.24($C_{42}H_{30}N_2$ = 562.72) | 2-94 | m/z = 612.26($C_{46}H_{32}N_2$ = 612.78) |
| 2-95 | m/z = 688.29($C_{52}H_{36}N_2$ = 688.87) | 2-96 | m/z = 714.30($C_{54}H_{38}N_2$ = 714.91) |
| 2-97 | m/z = 754.33($C_{57}H_{42}N_2$ = 754.98) | 2-98 | m/z = 878.37($C_{67}H_{46}N_2$ = 879.12) |
| 2-99 | m/z = 876.35($C_{67}H_{44}N_2$ = 877.10) | 2-100 | m/z = 639.27($C_{47}H_{33}N_3$ = 369.80) |
| 2-101 | m/z = 768.26($C_{56}H_{36}N_2S$ = 768.98) | 2-102 | m/z = 833.29($C_{60}H_{39}N_3S$ = 834.05) |
| 2-103 | m/z = 742.26($C_{54}H_{34}N_2O_s$ = 742.88) | 2-104 | m/z = 778.333($C_{59}H_{42}N_2$ = 779.00) |
| 2-105 | m/z = 486.21($C_{36}H_{26}N_2$ = 486.62) | 2-106 | m/z = 536.23($C_{40}H_{28}N_2$ = 536.68) |
| 2-107 | m/z = 612.26($C_{46}H_{32}N_2$ = 612.78) | 2-108 | m/z = 638.27($C_{48}H_{34}N_2$ = 638.81) |
| 2-109 | m/z = 491.24($C_{36}H_{21}D_5N_2$ = 491.65) | 2-110 | m/z = 612.26($C_{46}H_{32}N_2$ = 612.78) |
| 2-111 | m/z = 794.28($C_{58}H_{38}N_2S$ = 795.02) | 2-112 | m/z = 656.26($C_{48}H_{33}FN_2$ = 656.80) |
| 2-113 | m/z = 717.29($C_{51}H_{35}N_5$ = 717.88) | 2-114 | m/z = 728.32($C_{55}H_{40}N_2$ = 728.94) |
| 2-115 | m/z = 842.34($C_{62}H_{42}N_4$ = 843.05) | 2-116 | m/z = 714.30($C_{54}H_{38}N_2$ = 714.91) |
| 2-117 | m/z = 653.28($C_{48}H_{35}N_3$ = 653.81) | 2-118 | m/z = 703.30($C_{52}H_{37}N_3$ = 703.87) |
| 2-119 | m/z = 805.35($C_{60}H_{43}N_3$ = 806.00) | 2-120 | m/z = 753.31($C_{56}H_{39}N_3$ = 753.93) |
| 2-121 | m/z = 818.34($C_{60}H_{42}N_4$ = 819.00) | 2-122 | m/z = 835.30($C_{60}H_{41}N_3S$ = 836.05) |
| 2-123 | m/z = 655.27($C_{46}H_{33}N_5$ = 655.79) | 2-124 | m/z = 885.32($C_{64}H_{43}N_3S$ = 886.11) |
| 2-125 | m/z = 759.27($C_{54}H_{37}N_3S$ = 759.96) | 2-126 | m/z = 706.28($C_{49}H_{34}N_6$ = 706.83) |
| 2-127 | m/z = 960.39($C_{69}H_{48}N_6$ = 961.16) | 2-128 | m/z = 853.35($C_{64}H_{43}N_3$ = 854.05) |
| 2-129 | m/z = 894.37($C_{66}H_{46}N_4$ = 895.10) | 2-130 | m/z = 834.38($C_{62}H_{38}D_5N_3$ = 835.06) |
| 2-131 | m/z = 855.36($C_{64}H_{45}N_3$ = 856.06) | 2-132 | m/z = 853.35($C_{64}H_{43}N_3$ = 854.05) |
| 2-133 | m/z = 794.37($C_{60}H_{46}N_2$ = 795.04) | 2-134 | m/z = 987.39($C_{71}H_{49}N_5O$ = 988.21) |
| 2-135 | m/z = 1021.44($C_{77}H_{55}N_3$ = 1022.31) | 2-136 | m/z = 737.23($C_{51}H_{32}FN_3S$ = 737.90) |

Manufacturing and Evaluation of Organic Electric Element

EXAMPLE 1

Red OLED

On the ITO layer (anode) formed on the glass substrate, 4,4',4''-tris[2-naphthyl(phenyl)amino]triphenylamine (hereinafter, abbreviated as "2-TNATA") was vacuum deposited to a thickness of 60 nm to form a hole injection layer. Then, N,N'-bis(1-naphthalenyl)-N,N'-bis-phenyl-(1,1'-biphenyl)-4,4'-diamine (hereinafter abbreviated as "NPB") was vacuum deposited to a thickness of 60 nm to form a hole transport layer.

Next, a light emitting layer having a thickness of 30 nm was deposited on the hole transport layer by using the compound 1-10 of the present invention as a host material, bis-(1-phenylisoquinolyl)iridium(III)acetylacetonate (hereinafter, abbreviated as "(piq)$_2$Ir(acac)") as a dopant material, wherein the weight ratio of the host and the dopant was 95:5.

Next, (1,1'-bisphenyl-4-olato)bis(2-methyl-8-quinolinolato)aluminum (hereinafter, "BAlq") was vacuum-deposited to a thickness of 10 nm on the light emitting layer to form a hole blocking layer, and bis(10-hydroxybenzo[h]quinolinato)beryllium (hereinafter, "BeBq$_2$") was vacuum-deposited to a thickness of 40 nm on the hole blocking layer to form a an electron transport layer. Thereafter, LiF was deposited to a thickness of 0.2 nm to form an electron injection layer on the electron transport layer, and then Al was deposited to a thickness of 150 nm to form a cathode on the electron injection layer. In this way, OLED was manufactured.

EXAMPLE 2 to EXAMPLE 15

The organic electroluminescent elements were manufactured in the same manner as described in Example 1 except that compounds of the present invention described in the following Table 7 instead of compound 1-10 of the present invention were used as host material of the light emitting layer.

COMPARATIVE EXAMPLE 1 to COMPARATIVE EXAMPLE 4

The organic electroluminescent element was manufactured in the same manner as described in Example 1 except that one of the following Comparative Compounds 1 to 4 instead of compound 1-10 of the present invention was used as host material of the light emitting layer.

<Comp. Compd 1>

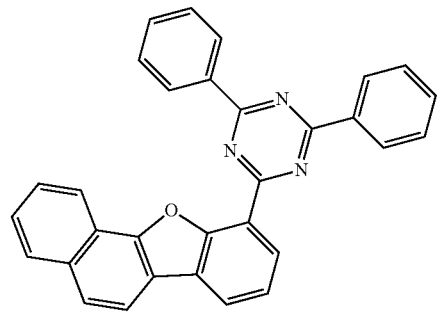

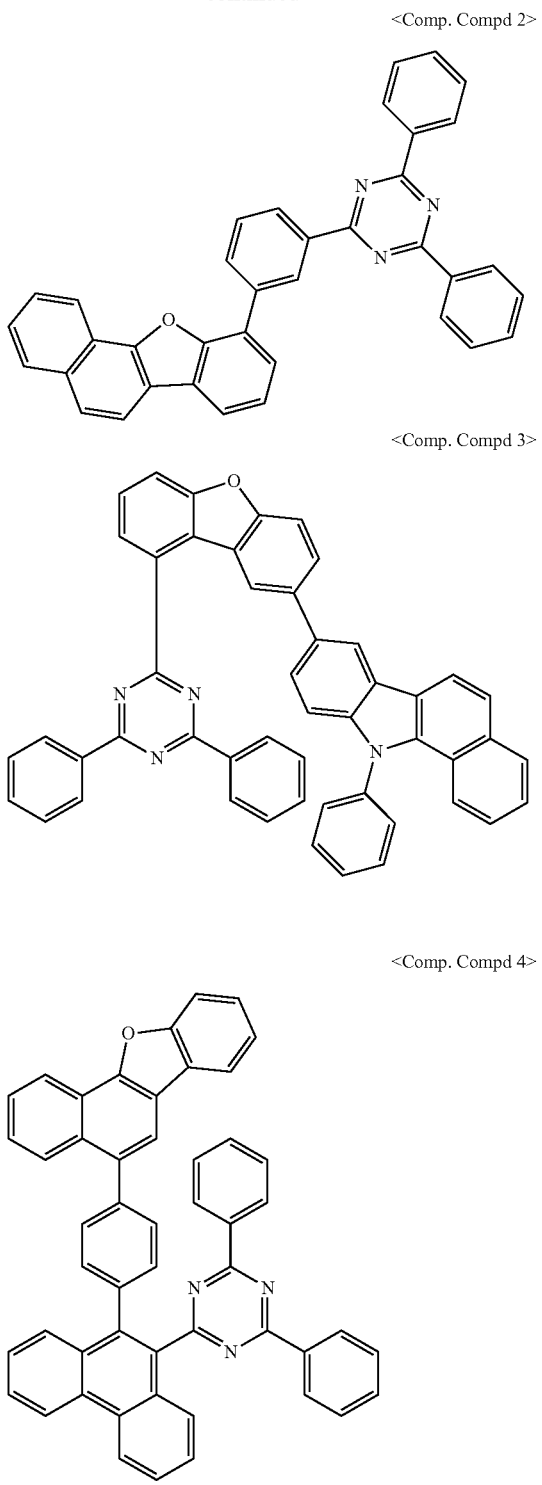

<Comp. Compd 2>

<Comp. Compd 3>

<Comp. Compd 4>

Electroluminescence characteristics were measured with a PR-650 (Photoresearch) by applying a forward bias DC voltage to the OLEDs prepared in Examples 1 to 15 of the present invention and Comparative Examples 1 to 4. T(95) life time was measured using a life time measuring apparatus manufactured by Mc science Inc. at reference brightness of 2500 cd/m². The measurement results are shown in the table 7 below.

TABLE 7

| Compound | | Voltage (V) | Current Density (mA/cm²) | Brightness (cd/m²) | Efficiency (cd/A) | Lifetime T(95) |
|---|---|---|---|---|---|---|
| comp. Ex(1) | comp. Com 1 | 5.9 | 15.8 | 2500 | 15.8 | 99.3 |
| comp. Ex(2) | comp. Com 2 | 6.4 | 18.4 | 2500 | 13.6 | 91.7 |
| comp. Ex(3) | comp. Com 3 | 6.2 | 13.8 | 2500 | 18.1 | 104.6 |
| comp. Ex(4) | comp. Com 4 | 6.1 | 15.5 | 2500 | 16.1 | 101.1 |
| Ex. (1) | Com. (1-10) | 5.5 | 11.4 | 2500 | 22 | 123.5 |
| Ex. (2) | Com. (1-22) | 5.6 | 11.1 | 2500 | 22.5 | 131.9 |
| Ex. (3) | Com. (1-24) | 5.4 | 11.8 | 2500 | 21.1 | 121 |
| Ex. (4) | Com. (1-32) | 5.5 | 11.7 | 2500 | 21.3 | 121.9 |
| Ex. (5) | Com. (1-35) | 5.4 | 11.8 | 2500 | 21.1 | 127.2 |
| Ex. (6) | Com. (1-44) | 5.4 | 11.1 | 2500 | 22.6 | 120.4 |
| Ex. (7) | Com. (1-45) | 5.4 | 10.8 | 2500 | 23.1 | 128.5 |
| Ex. (8) | Com. (1-53) | 5.8 | 11.3 | 2500 | 22.1 | 126.4 |
| Ex. (9) | Com. (1-56) | 5.7 | 11.7 | 2500 | 21.3 | 130.2 |
| Ex. (10) | Com. (1-62) | 5.7 | 10.6 | 2500 | 23.5 | 133.8 |
| Ex. (11) | Com. (1-65) | 5.5 | 10.5 | 2500 | 23.7 | 132.5 |
| Ex. (12) | Com. (1-80) | 5.5 | 10.3 | 2500 | 24.2 | 129.6 |
| Ex. (13) | Com. (1-82) | 5.6 | 10.5 | 2500 | 23.9 | 132 |
| Ex. (14) | Com. (1-84) | 5.5 | 10.3 | 2500 | 24.3 | 130.3 |
| Ex. (15) | Com. (1-112) | 5.5 | 11.8 | 2500 | 21.2 | 134.5 |

From Table 7 above, it can be seen that the electric element using the compound of the present invention as a phosphorescent red host material of the light emitting layer has a lower driving voltage and significantly improved efficiency and lifespan compared to the case where Comparative Compounds 1 to 4 are used.

Comparative Compounds 1 to 4 and the compounds of the present invention are similar in that their basic skeleton contains a heterocycle in which triazine and aromatic rings are condensed. However, Comparative Compound 1 is different from the present invention in that triazine and 2,1-benzonaphthofuran (benzo[b]naphtho[2,1-d]furan) are directly bonded and Comparative Compound 2 is different from the present invention in that triazine and 2,1-benzonaphthofuran are connected with a phenyl linker. In addition, Comparative Compound 3 is similar to the compound of the present invention in that it has a three-membered ring as linking group between the triazine and four-membered ring, but it is different in that the hetero element of the four-membered heterocyclic ring connected to the triazine through the linker is N. Comparative Compound 5 is different from the present invention in that a phenyl-phenanthrene as linking group is introduced between 2,1-benzonaphthofuran and triazine, and triazine is attached to the ortho position of the phenanthrene.

Comparing Comparative Examples 1 to 4, it can be seen that the driving voltage, efficiency, and lifespan are greatly changed when having a single bond or a polycyclic ring as a linking group between triazine and 2,1-benzonaphthofuran (benzo[b]naphtho[2,1-d]furan) or 2,1-benzonaphthothiophene (benzo[b]naphtho[2,1-d]thiophene). From this, it can be seen that the difference in the skeleton of the compound and the linking group affects the electrical properties of the element.

In the compound represented by Formula 1-A of the present invention, triazine is bonded to the naphthalene, and a single bond or a linking group of a condensed ring is introduced, thereby having an appropriate T1 value and a LUMO value. As a result, it seems that the element characteristics of the present invention are significantly improved than those of Comparative Examples 1 to 4.

And, the lifetime of the element was improved in Example 15 of the present invention. From this, it can be seen that the characteristics of the organic electric element are improved when a substituent other than hydrogen is bonded to 2,1-benzonaphthofuran or 2,1-benzonaphthothiophene. It seems that this is because a three-dimensional structure is formed as the substituents are bonded, so that the deposition temperature is lowered, the the glass transition temperature(Tg) increases as the molecular weight increases, so that decomposition during evaporation is suppressed and thermal stability is increased.

Therefore, it seems that the energy level (HOMO, LUMO, T1, etc.) of the compound may be different depending on the position at which the triazine is bonded to a 4-membered ring such as 2,1-benzonaphthofuran or 2,1-benzonaphthothiophene, the presence and absence of a linking group and its type, and whether a substituent is bonded. The element characteristics were improved when the compound of the present invention was used, compared to the case where the comparative compound was used. It seems that this is because compound of the present invention has a LUMO value for easy electron transfer to the light emitting layer and a T1 value for efficient energy transfer to the dopant. In particular, it can be seen that the compound represented by Formula 1-A of the present invention is suitable as a red host material in terms of the element performance.

EXAMPLE 16

Mixed Phosphorescent Host of a Light Emitting Layer

On the ITO layer (anode) formed on the glass substrate, 2-TNATA was vacuum deposited to a thickness of 60 nm to form a hole injection layer. Then, NPB was vacuum deposited to a thickness of 55 nm to form a hole transport layer.

Next, a light emitting layer with a thickness of 30 nm was formed on the hole transport layer, wherein a mixture of a compound 1-10 of the present invention (host 1) and a compound 2-9 of the present invention (host 2) in a weight ratio of 3: 7 was used as a host and (piq)2Ir(acac) was used as a dopant and the host and dopant were used in a weight ratio of 95:5.

Next, a film of BAlq was vacuum-deposited with a thickness of 5 nm on the light emitting layer to form a hole blocking layer and $BeBq_2$ was deposited on the hole blocking layer to form an electron transport layer having a thickness of 45 nm. Next, LiF on the electron transport layer was deposited to a thickness of 0.2 nm and then Al was deposited to a thickness of 150 nm to form a cathode. In this way, the OLED was manufactured.

EXAMPLE 17 to EXAMPLE 75

The organic electroluminescent elements were manufactured in the same manner as described in Example 16, except that a mixture of the first host compound(host 1) and the second host compound(host 2) described in the following Table 8 was used as host material of the light emitting layer.

COMPARATIVE EXAMPLE 5 to COMPARATIVE EXAMPLE 8

The OLEDs were manufactured in the same manner as described in Example 16, except that a single compound 1-22, compound 1-32, compound 1-49 or compound 1-194 as listed in the following Table 8 was used as a host of the light emitting layer, respectively.

COMPARATIVE EXAMPLE 9 and COMPARATIVE EXAMPLE 10

The OLEDs were manufactured in the same manner as described in Example 16 except that the the mixture of Comparative compounds 5 and 6 or the mixture of Comparative compounds 5 and 7 as listed in the following Table 8 were uses as a host of a light emitting layer, respectively.

Electroluminescence characteristics were measured with a PR-650 (Photoresearch) by applying a forward bias DC voltage to the OLEDs prepared in Examples 16 to 75 of the present invention and Comparative Examples 5 to 10. T(95) life time was measured using a life time measuring apparatus manufactured by Mc science Inc. at reference brightness of 2500 cd/m². The measurement results are shown in the table 8 below.

<Comp. Compd 5>

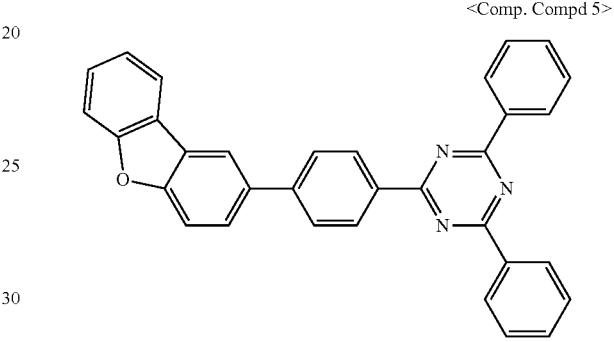

<Comp. Compd 6>

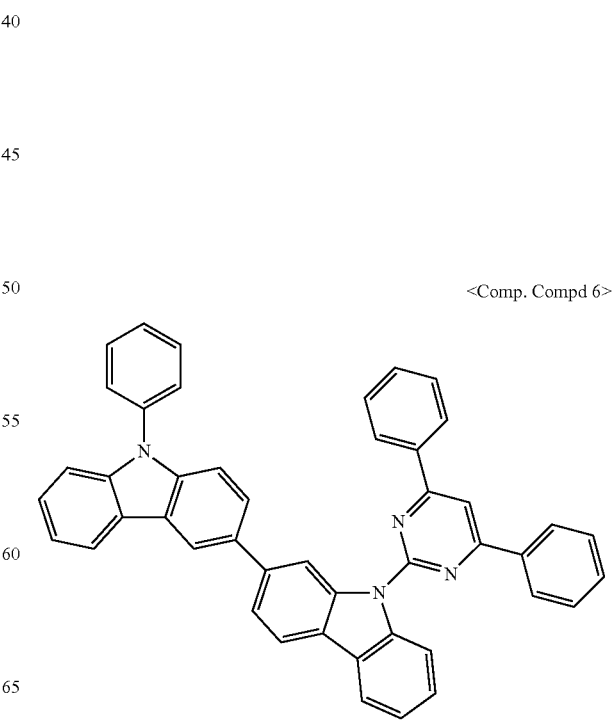

-continued

<Comp. Compd 7>

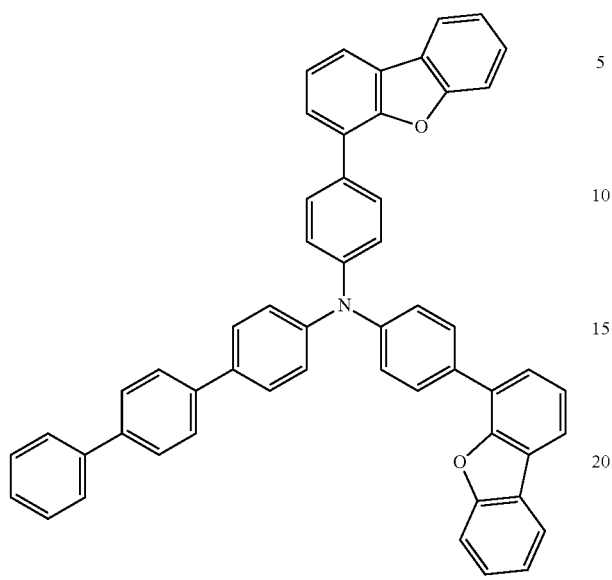

TABLE 8

| | Compound | Compound | Voltage (V) | Current Density (mA/cm$^2$) | Brightness (cd/m$^2$) | Efficiency (cd/A) | Lifetime T(95) |
|---|---|---|---|---|---|---|---|
| comp. Ex(5) | Com. (1-22) | | 5.7 | 13.6 | 2500.0 | 18.4 | 111.0 |
| comp. Ex(6) | Com. (1-32) | | 5.9 | 11.2 | 2500.0 | 22.3 | 122.6 |
| comp. Ex(7) | Com. (1-49) | | 5.9 | 11.5 | 2500.0 | 21.8 | 119.1 |
| comp. Ex(8) | Com. (1-94) | | 5.8 | 13.4 | 2500.0 | 18.7 | 111.1 |
| comp. Ex(9) | Comp. compd 5 | Comp. compd 6 | 5.7 | 10.8 | 2500.0 | 23.1 | 120.4 |
| comp. Ex(10) | Comp. compd 5 | Comp. compd 7 | 5.6 | 10.9 | 2500.0 | 22.9 | 121.7 |
| Ex. (16) | Com. (1-10) | Com. (2-9) | 5.0 | 8.4 | 2500.0 | 29.8 | 133.2 |
| Ex. (17) | Com. (1-22) | | 5.1 | 7.6 | 2500.0 | 33.0 | 138.9 |
| Ex. (18) | Com. (1-24) | | 4.9 | 8.1 | 2500.0 | 30.9 | 136.7 |
| Ex. (19) | Com. (1-32) | | 5.0 | 8.1 | 2500.0 | 30.9 | 132.8 |
| Ex. (20) | Com. (1-35) | | 5.1 | 8.3 | 2500.0 | 30.1 | 131.5 |
| Ex. (21) | Com. (1-44) | | 5.0 | 7.7 | 2500.0 | 32.3 | 133.3 |
| Ex. (22) | Com. (1-45) | | 4.9 | 7.5 | 2500.0 | 33.3 | 138.2 |
| Ex. (23) | Com. (1-49) | | 5.0 | 8.4 | 2500.0 | 29.8 | 136.2 |
| Ex. (24) | Com. (1-62) | | 5.1 | 7.6 | 2500.0 | 32.7 | 135.4 |
| Ex. (25) | Com. (1-80) | | 5.0 | 7.6 | 2500.0 | 32.8 | 139.7 |
| Ex. (26) | Com. (1-82) | | 5.1 | 7.4 | 2500.0 | 33.7 | 134.5 |
| Ex. (27) | Com. (1-84) | | 5.1 | 7.4 | 2500.0 | 34.0 | 134.8 |
| Ex. (28) | Com. (1-94) | | 5.1 | 7.5 | 2500.0 | 33.2 | 138.7 |
| Ex. (29) | Com. (1-110) | | 5.0 | 8.4 | 2500.0 | 29.9 | 132.4 |
| Ex. (30) | Com. (1-113) | | 5.0 | 8.0 | 2500.0 | 31.1 | 136.7 |
| Ex. (31) | Com. (1-10) | Com. (2-28) | 5.0 | 8.7 | 2500.0 | 28.6 | 135.7 |
| Ex. (32) | Com. (1-22) | | 5.1 | 7.9 | 2500.0 | 31.6 | 141.0 |
| Ex. (33) | Com. (1-24) | | 4.9 | 8.5 | 2500.0 | 29.5 | 138.4 |
| Ex. (34) | Com. (1-32) | | 5.0 | 8.6 | 2500.0 | 29.2 | 137.7 |
| Ex. (35) | Com. (1-35) | | 5.0 | 8.6 | 2500.0 | 29.1 | 139.0 |
| Ex. (36) | Com. (1-44) | | 5.0 | 8.1 | 2500.0 | 30.9 | 135.5 |
| Ex. (37) | Com. (1-45) | | 4.9 | 8.0 | 2500.0 | 31.4 | 140.2 |
| Ex. (38) | Com. (1-49) | | 5.0 | 8.9 | 2500.0 | 28.0 | 134.0 |
| Ex. (39) | Com. (1-62) | | 5.1 | 7.9 | 2500.0 | 31.6 | 139.9 |
| Ex. (40) | Com. (1-80) | | 5.1 | 7.9 | 2500.0 | 31.6 | 139.8 |
| Ex. (41) | Com. (1-82) | | 5.1 | 7.8 | 2500.0 | 32.0 | 136.1 |
| Ex. (42) | Com. (1-84) | | 5.0 | 8.1 | 2500.0 | 30.9 | 138.1 |
| Ex. (43) | Com. (1-94) | | 5.1 | 8.0 | 2500.0 | 31.3 | 141.6 |
| Ex. (44) | Com. (1-110) | | 5.0 | 8.9 | 2500.0 | 28.1 | 135.4 |
| Ex. (45) | Com. (1-113) | Com. (2-28) | 5.1 | 8.5 | 2500.0 | 29.3 | 138.7 |
| Ex. (46) | Com. (1-10) | Com. (2-54) | 5.0 | 9.5 | 2500.0 | 26.4 | 140.3 |
| Ex. (47) | Com. (1-22) | | 5.0 | 8.3 | 2500.0 | 30.2 | 143.6 |
| Ex. (48) | Com. (1-24) | | 4.9 | 8.9 | 2500.0 | 28.0 | 138.0 |
| Ex. (49) | Com. (1-32) | | 4.8 | 9.0 | 2500.0 | 27.9 | 136.0 |
| Ex. (50) | Com. (1-35) | | 4.9 | 9.2 | 2500.0 | 27.2 | 136.7 |
| Ex. (51) | Com. (1-44) | | 4.8 | 8.4 | 2500.0 | 29.8 | 137.5 |
| Ex. (52) | Com. (1-45) | | 4.8 | 8.4 | 2500.0 | 29.9 | 143.0 |

TABLE 8-continued

|  | Compound | Compound | Voltage (V) | Current Density (mA/cm²) | Brightness (cd/m²) | Efficiency (cd/A) | Lifetime T(95) |
|---|---|---|---|---|---|---|---|
| Ex. (53) | Com. (1-49) |  | 5.0 | 9.6 | 2500.0 | 26.1 | 136.1 |
| Ex. (54) | Com. (1-62) |  | 5.0 | 8.5 | 2500.0 | 29.2 | 139.8 |
| Ex. (55) | Com. (1-80) |  | 4.9 | 8.4 | 2500.0 | 29.8 | 140.5 |
| Ex. (56) | Com. (1-82) |  | 5.0 | 8.2 | 2500.0 | 30.4 | 140.7 |
| Ex. (57) | Com. (1-84) |  | 4.9 | 8.4 | 2500.0 | 29.8 | 142.1 |
| Ex. (58) | Com. (1-94) |  | 5.0 | 8.2 | 2500.0 | 30.3 | 141.5 |
| Ex. (59) | Com. (1-110) |  | 4.9 | 9.1 | 2500.0 | 27.5 | 139.4 |
| Ex. (60) | Com. (1-113) |  | 5.0 | 9.0 | 2500.0 | 27.7 | 136.9 |
| Ex. (61) | Com. (1-10) | Com. (2-117) | 4.9 | 9.7 | 2500.0 | 25.7 | 141.4 |
| Ex. (62) | Com. (1-22) |  | 4.9 | 8.9 | 2500.0 | 28.2 | 145.3 |
| Ex. (63) | Com. (1-24) |  | 4.8 | 9.5 | 2500.0 | 26.2 | 138.7 |
| Ex. (64) | Com. (1-32) |  | 4.9 | 9.5 | 2500.0 | 26.3 | 142.6 |
| Ex. (65) | Com. (1-35) |  | 4.8 | 9.6 | 2500.0 | 26.0 | 141.1 |
| Ex. (66) | Com. (1-44) |  | 4.9 | 8.7 | 2500.0 | 28.7 | 138.5 |
| Ex. (67) | Com. (1-45) |  | 4.8 | 8.8 | 2500.0 | 28.3 | 144.7 |
| Ex. (68) | Com. (1-49) |  | 4.9 | 9.7 | 2500.0 | 25.7 | 141.0 |
| Ex. (69) | Com. (1-62) |  | 5.0 | 9.1 | 2500.0 | 27.6 | 145.5 |
| Ex. (70) | Com. (1-80) |  | 4.9 | 8.8 | 2500.0 | 28.6 | 144.3 |
| Ex. (71) | Com. (1-82) |  | 4.9 | 8.6 | 2500.0 | 29.1 | 144.5 |
| Ex. (72) | Com. (1-84) |  | 5.0 | 8.9 | 2500.0 | 28.2 | 144.0 |
| Ex. (73) | Com. (1-94) |  | 5.0 | 8.8 | 2500.0 | 28.4 | 142.6 |
| Ex. (74) | Com. (1-110) |  | 4.8 | 9.9 | 2500.0 | 25.3 | 139.0 |
| Ex. (75) | Com. (1-113) |  | 5.0 | 9.3 | 2500.0 | 27.0 | 142.0 |

From Table 8, it can be seen that the driving voltage, efficiency and lifetime were remarkably improved when the mixture of the compounds for an organic electroluminescent element of the present invention represented by Formula 1 and Formula 2 was used as a phosphorescent host (Examples 16 to 75), compared to element using a single material (Comparative Examples 5 to 8), a mixture of Comparative Compounds 5 and 6 (Comparative Examples 9), a mixture of Comparative Compounds 5 to 7 (Comparative Examples 10).

That is, the characteristics of the element were improved further improved when a mixture of two types of comparative compounds was used compared to when the compound of the present invention was used alone, the driving voltage was lowered and efficiency was remarkably improved when the mixture of the compounds of Formulas 1 and 2 of the present invention was used as host compared to when a mixture of two types of comparative compounds was used.

From these results, the inventors of the present invention believed that a mixture of compounds of Formulas 1 and 2 has novel characteristics other than those of each compound, and thus the PL lifetime for each of these compounds and mixtures were measured. As a result, it was confirmed that a new PL wavelength for the mixture of compounds of Formula 1 and 2 of the present invention was formed unlike a single compound.

It seems that this is because when a mixture of compounds of the present invention is used, electrons and holes move or energy is transferred through a new region (exciplex) having a new energy level formed by mixing as well as the energy level of each substance, as a result, efficiency and lifetime are increased. This is an important example in which the mixed thin film shows exciplex energy transfer and light emission processes when the mixture of the present invention is used.

In addition, when a mixture of a polycyclic compound of Formula 1 which has a high T1 value with high stability to not only electrons but also holes and compound of Formula 2 which has strong hole properties was used, the electron blocking ability is improved and more holes move quickly and easily in the light emitting layer due to the high T1 and high LUMO energy value. As a result, the charge balance in the light emitting layer increases, and thus light emission occurs well inside the light-emitting layer, not the interface of the hole transport layer. As a result, the deterioration in the interface of ahole transport layer is also reduced, thereby maximizing the driving voltage, efficiency and lifetime of the element. Therefore, when the mixture of compounds of Formulas 1 and 2 was used, the overall performance of the element was improved due to electrochemical synergy.

In particular, it seems that the electrical properties of the element were improved when the compound of Formula 1 of the present invention was used since the compound has a narrower bandgap as the conjugation length increases, and thus absorption and emission occur at longer wavelengths, wherein the compound of Formula 1 of the present invention comprises a 4-membered ring in which benzene ring is further fused to dibenzothiophene (DBT) or dibenzofuran (DBF).

In addition, when charges are transferred, Joule heating is generated, which affects the lifespan. The compounds of the present invention having a glass transition temperature higher than those of Comparative Compounds 5 to 7 have excellent thermal stability, so the lifespan of the element is improved.

EXAMPLE 76 and EXAMPLE 77

An OLED was manufactured in the same manner as in Example 16, except that Compound 1-45 and Compound 2-54 of the present invention were used in a weight ratio of 7:3 or 5:5 as shown in Table 9 below.

EXAMPLE 78 and EXAMPLE 79

An OLED was manufactured in the same manner as in Example 16, except that Compound 1-82 and Compound 2-117 of the present invention were used in a weight ratio of 7:3 or 5:5 as shown in Table 9 below.

Electroluminescence characteristics were measured with a PR-650 (Photoresearch) by applying a forward bias DC voltage to the OLEDs prepared in Examples 76 to 79 of the present invention. T(95) life time was measured using a life time measuring apparatus manufactured by Mc science Inc. at reference brightness of 2500 cd/m². The measurement results are shown in the table 9 below. Examples 52 and 71 show the results of measuring the elements characteristics when host 1 and host 2 were mixed in a ratio of 3:7 and used as a host in as Table 8.

TABLE 9

|  | Host 1 | Host 2 | Mixing ratio (Host 1:Host 2) | Voltage (V) | Current Density (mA/cm$^2$) | Brightness (cd/m$^2$) | Efficiency (cd/A) | Lifetime T(95) |
|---|---|---|---|---|---|---|---|---|
| Ex. (76) | 1-45 | 2-54 | 7:3 | 5.3 | 9.9 | 2500.0 | 25.2 | 138.2 |
| Ex. (77) |  |  | 5:5 | 5.0 | 9.3 | 2500.0 | 26.9 | 142.4 |
| Ex. (52) |  |  | 3:7 | 4.8 | 8.4 | 2500.0 | 29.9 | 143.0 |
| Ex. (78) | 1-82 | 2-117 | 7:3 | 5.2 | 10.1 | 2500.0 | 24.8 | 137.4 |
| Ex. (79) |  |  | 5:5 | 4.9 | 9.9 | 2500.0 | 25.3 | 139.9 |
| Ex. (71) |  |  | 3:7 | 4.9 | 8.6 | 2500.0 | 29.1 | 144.5 |

Table 9 shows the results of measuring element characteristics when a mixture in which the mixing ratio of the compound of Formula 1 (first host) and the compound of Formula 2 (second host) of the present invention was different (7:3, 5:5, 3:7) was used as host.

Referring to Table 9, when the mixing ratio of the first host and the second host was 3:7, the driving voltage was the lowest and the efficiency and lifespan were the best. As the amount of the first host was increased, the driving voltage was increased, and the efficiency and lifespan were lowered.

From this, it can be seen that efficiency and lifetime are improved because the charge balance in the light emitting layer is maximized as the amount of the compound represented by Formula 2, which has relatively stronger hole characteristics than that of Formula 1, is increased.

Although the exemplary embodiments of the present invention have been described for illustrative purposes, those skilled in the art to which the present invention pertains will be capable of various modifications without departing from the essential characteristics of the present invention. Therefore, the embodiments disclosed in this specification are not intended to limit the present invention, but to illustrate the present invention, and the spirit and scope of the present invention are not limited by the embodiments. The scope of the present invention shall be construed on the basis of the accompanying claims, and it shall be construed that all of the technical ideas included within the scope equivalent to the claims belong to the present invention.

The invention claimed is:

1. An organic electric element comprising a first electrode, a second electrode, and an organic material layer formed between the first electrode and the second electrode, wherein the organic material layer comprises a phosphorescent light emitting layer, and the phosphorescent light emitting layer comprises a first host compound of Formula 1 and a second host compound of Formula 2:

[Formula 1]

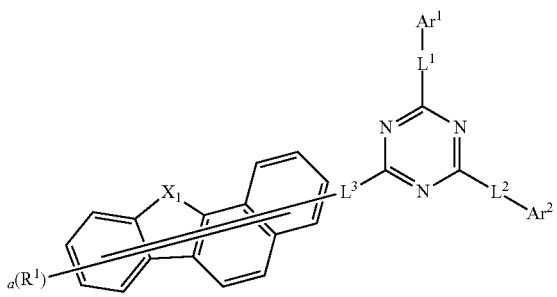

-continued

[Formula 2]

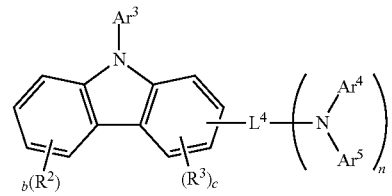

wherein:

$X_1$ is O or S, $Ar^1$ to $Ar^5$ are each independently selected from the group consisting of a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a $C_1$-$C_{50}$ alkyl group, a $C_2$-$C_{20}$ alkenyl group, and a $C_2$-$C_{20}$ alkynyl group, and $Ar^4$ and $Ar^5$ may be bonded to each other to form a ring, $L^1$ to $L^4$ are each independently selected from the group consisting of a single bond, a $C_6$-$C_{60}$ arylene group, a fluorenylene group, a $C_2$-$C_{60}$ heterocyclic group comprising at least one heteroatom selected from the group consisting of O, N, S, Si and P, and a $C_3$-$C_{60}$ aliphatic ring, $R^1$ to $R^3$ are each independently selected from the group consisting of hydrogen, deuterium, halogen, a cyano group, a $C_6$-$C_{60}$ aryl group, a fluorenyl group, a $C_2$-$C_{60}$ heterocyclic group comprising at least one heteroatom selected from the group consisting of O, N, S, Si and P, a $C_3$-$C_{60}$ aliphatic ring, a $C_1$-$C_{50}$ alkyl group, a $C_2$-$C_{20}$ alkenyl group, and a $C_2$-$C_{20}$ alkynyl group, and adjacent groups may be bonded to each other to form a ring, a is an integer of 0-9, b is an integer of 0-4, c is an integer of 0-3, and where each of these is an integer of 2 or more, each of a plurality of $R^1$s, each of a plurality of $R^2$s, and each of a plurality of $R^3$s are the same as or different from each other, n is an integer of 1-3, and where n is an integer of 2 or more, each of a plurality of $Ar^4$s, and each of a plurality of $Ar^5$s are the same as or different from each other, wherein $Ar^1$ to $Ar^5$, $L^1$ to $L^4$, and $R^1$ to $R^3$ are optionally substituted with one or more of deuterium, halogen, a cyano group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group comprising at least one heteroatom selected from the group consisting of O, N, S, Si and P, and a $C_3$-$C_{20}$ aliphatic ring.

2. The organic electric element of claim 1, wherein $L^1$ to $L^4$ are each independently represented by one of Formulas b-1 to b-13:
<Formula b-1>
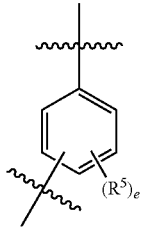
<Formula b-2>
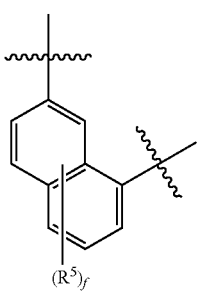
<Formula b-3>
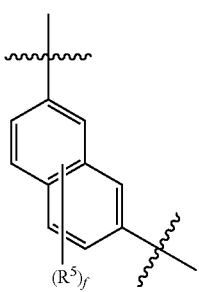
<Formula b-4>
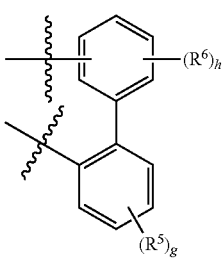
<Formula b-5>
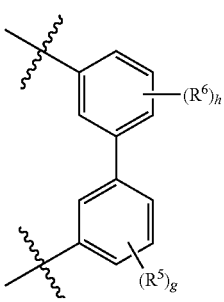
<Formula b-6>
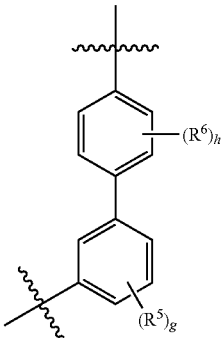
<Formula b-7>
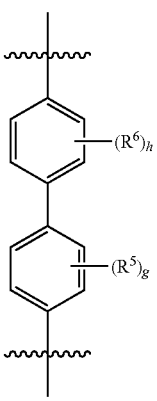
<Formula b-8>
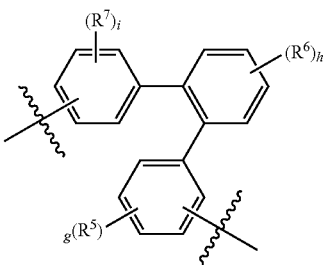
<Formula b-9>
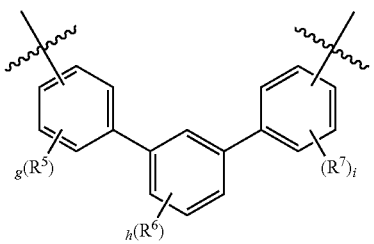
<Formula b-10>
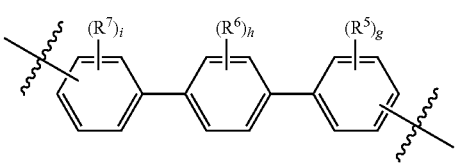
<Formula b-11>
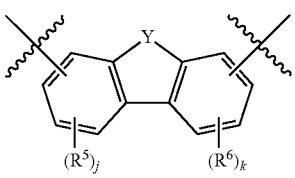

-continued

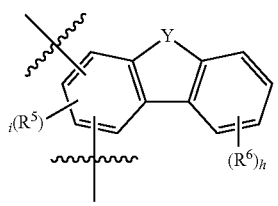
<Formula b-12>

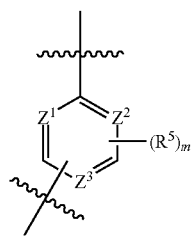
<Formula b-13> wherein:

$R^5$ to $R^7$ are each independently selected from the group consisting of hydrogen, deuterium, halogen, a cyano group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_1$-$C_{20}$ alkyl group, a $C_2$-$C_{20}$ alkenyl group, and a $C_2$-$C_{20}$ alkynyl group, and adjacent groups may be bonded to each other to form a ring, Y is N-($L^a$-$Ar^a$), O, S or C(R') (R"), $Z^1$ to $Z^3$ are each independently C, C(R') or N, and at least one of $Z^1$ to $Z^3$ is N, f is an integer of 0-6, e, g, h and i are each an integer of 0-4, j and k are each an integer of 0-3, l is an integer of 0-2, m is an integer of 0-3, and where each of these is an integer of 2 or more, each of a plurality of $R^5$s, each of a plurality of Res, and each of a plurality of $R^7$s are the same as or different from each other, R' and R" are each independently selected from the group consisting of hydrogen, deuterium, halogen, a cyano group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_1$-$C_{20}$ alkyl group, a $C_2$-$C_{20}$ alkenyl group, and a $C_2$-$C_{20}$ alkynyl group, R' and R" in C(R') (R") may be linked to each other to form a ring, and adjacent R's in C(R') may be linked to each other to form a ring, $Ar^a$ is selected from the group consisting of a $C_6$-$C_{20}$ aryl group, a fluorenyl group, a $C_2$-$C_{20}$ heterocyclic group comprising at least one heteroatom selected from the group consisting of O, N, S, Si and P, and a $C_3$-$C_{20}$ aliphatic ring, $L^a$ is selected from the group consisting of a single bond, a $C_6$-$C_{20}$ arylene group, a fluorenylene group, a $C_2$-$C_{20}$ heterocyclic group comprising at least one heteroatom selected from the group consisting of O, N, S, Si and P, and a $C_3$-$C_{20}$ aliphatic ring.

3. The organic electric element of claim 1, wherein Formula 1 is represented by one of Formula 1-A to Formula 1-E:

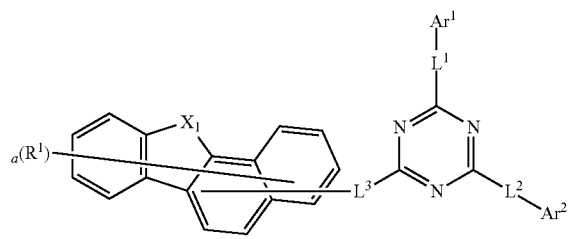
<Formula 1-A>

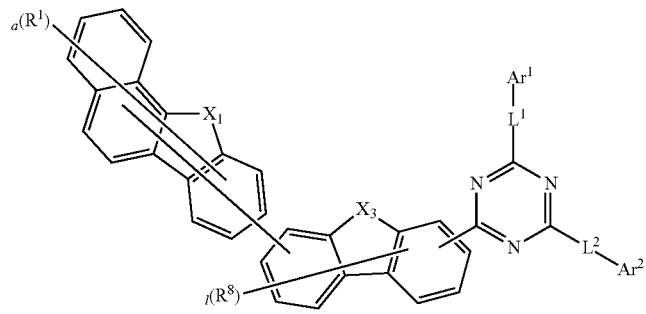
<Formula 1-B>

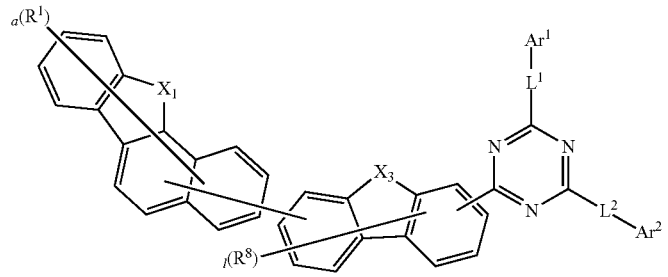
<Formula 1-C>

-continued

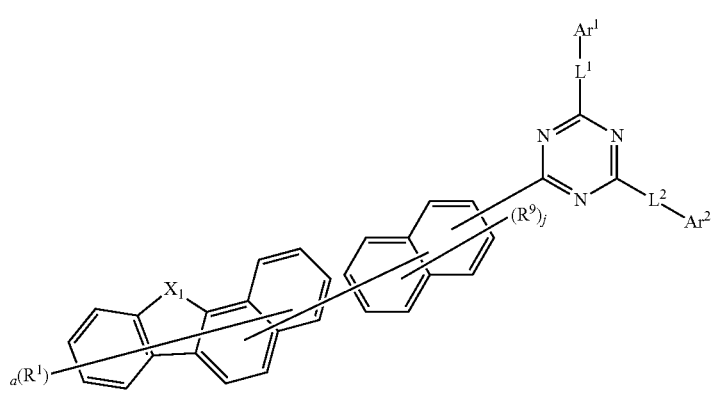

<Formula 1-D>

<Formula 1-E>

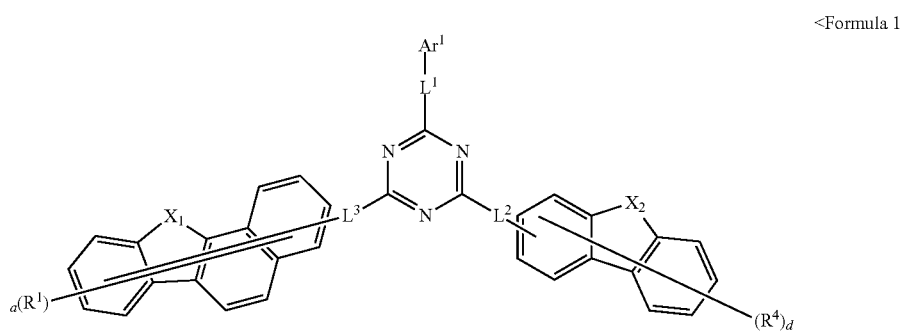

wherein Ar¹, Ar², L¹-L³, X₁, R¹ and a are the same as defined in claim 1,

X₂ and X₃ are each independently O or S,

R⁴, R⁸ and R⁹ are each independently selected from the group consisting of hydrogen, deuterium, halogen, a cyano group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_1$-$C_{20}$ alkyl group, a $C_2$-$C_{20}$ alkenyl group, and a $C_2$-$C_{20}$ alkynyl group, and adjacent groups may be linked to each other to form a ring, d is an integer of 0-7, i and j are each an integer of 0-6, and where each of these is an integer of 2 or more, each of a plurality of R⁴s, each of a plurality of R⁸s and each of a plurality of R⁹s are the same as or different from each other.

4. The organic electric element of claim 3, wherein Formula 1-A is represented by one of Formula 1-A-1 to Formula 1-A-6:

<Formula 1-A-1>

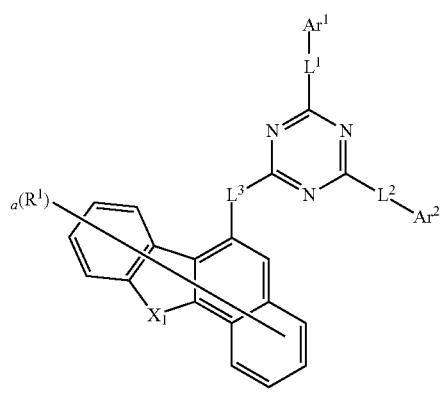

<Formula 1-A-2>
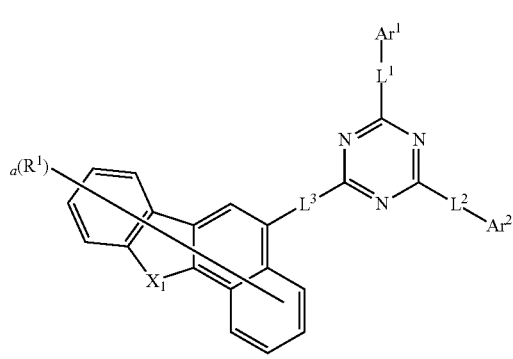
<Formula 1-A-6>
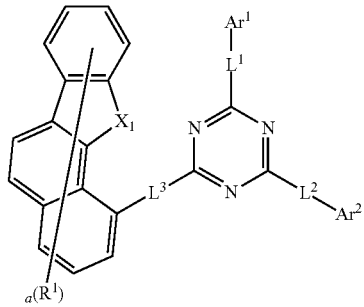
wherein Ar¹, Ar², L¹-L³, X₁, R¹ and a are the same as defined in claim 3.
5. The organic electric element of claim 3, wherein Formula 1-D is represented by Formula 1-D-1 or Formula 1-D-2:
<Formula 1-A-3>
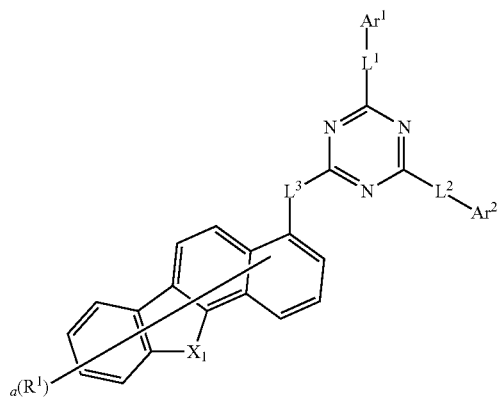
<Formula 1-D-1>
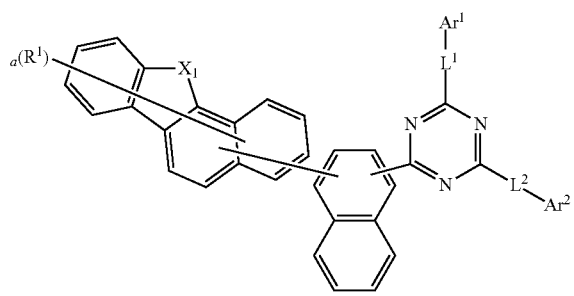
<Formula 1-A-4>
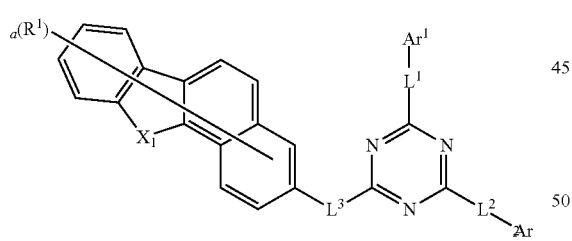
<Formula 1-D-2>
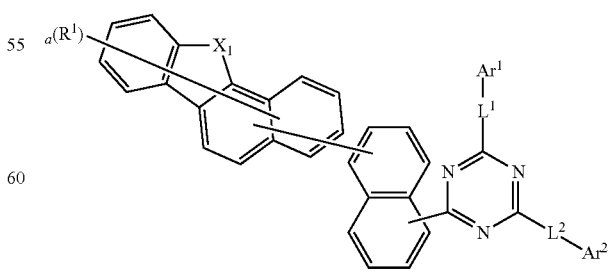
<Formula 1-A-5>
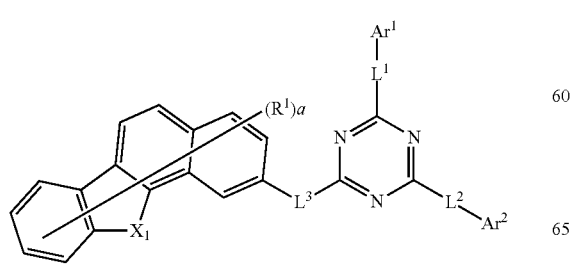
wherein Ar¹, Ar², L¹, L², X₁, R¹ and a are the same as defined in claim 4.

6. The organic electric element of claim 3, wherein Formula 1-E is represented by one of Formula 1-E-1 to Formula 1-E-7:
<Formula 1-E-1>
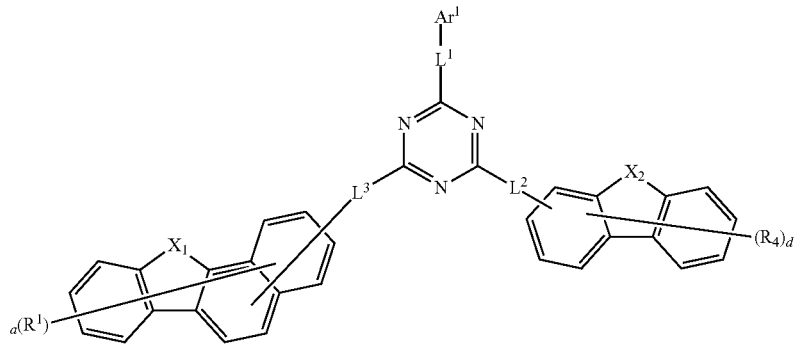
<Formula 1-E-2>
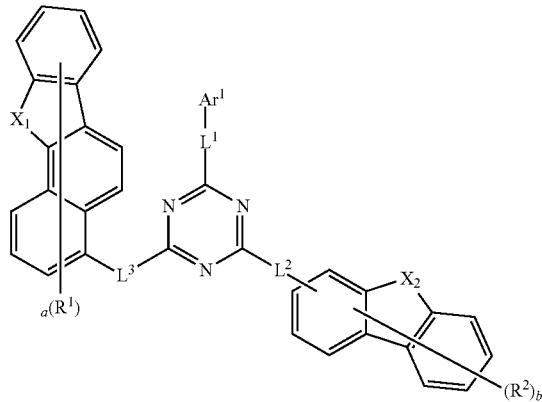
<Formula 1-E-3>
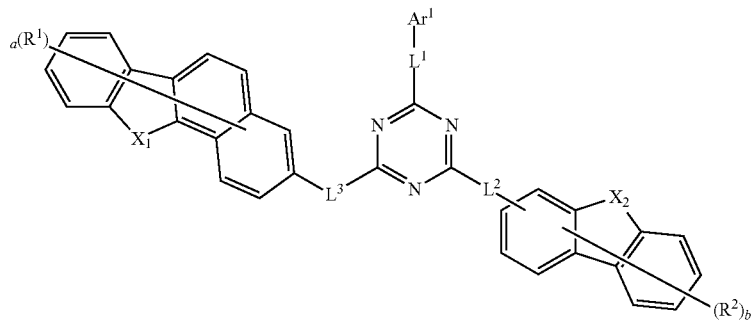
<Formula 1-E-4>
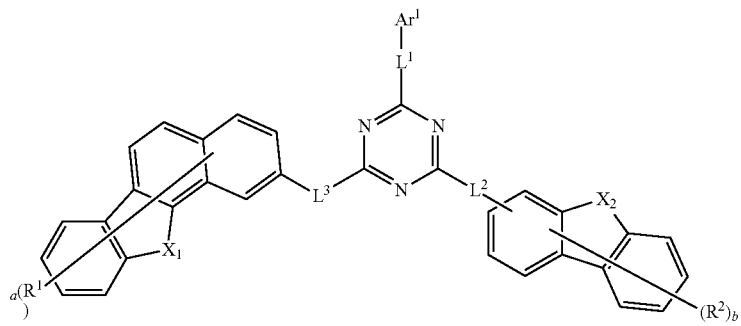

<Formula 1-E-5>

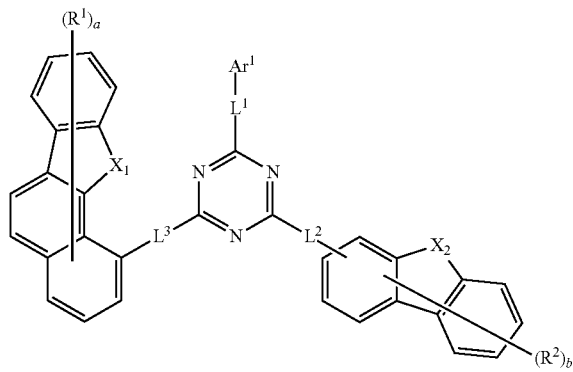

<Formula 1-E-6>

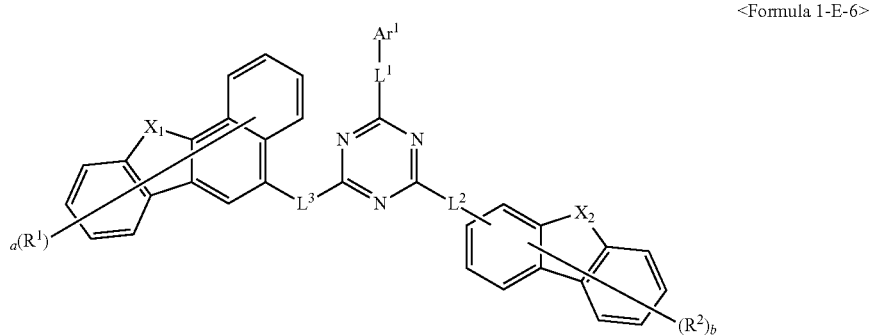

<Formula 1-E-7>

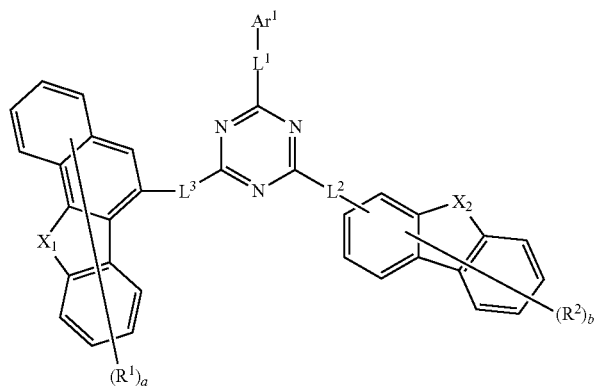

wherein $Ar^1$, $L^1$-$L^3$, $X_1$, $X_2$, $R^1$, a and d, and $R_4$ and $R^2$ are the same as defined in claim 4, b is an integer of 0 to 7, wherein b is an integer of 2 or more, each of a plurality of $R^2$s are the same as or different from each other, and wherein d is an integer of 2 or more, each of a plurality of $R_4$s are the same as or different from each other.

7. The organic electric element of claim 1, wherein Formula 2 is represented by Formula 2-A or Formula 2-B:

<Formula 2-A>

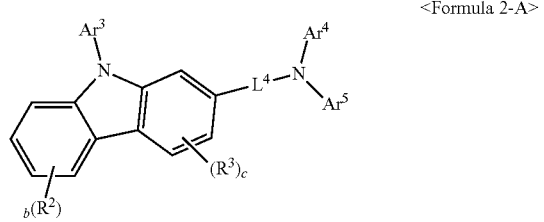

<Formula 2-B>

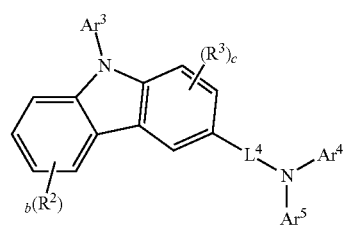

wherein $L^4$, $Ar^3$ to $Ar^5$, $R^2$, $R^3$, b and c are the same as defined in claim 1.

8. The organic electric element of claim 1, wherein Formula 2 is represented by one of Formula 2-C to Formula 2-F:

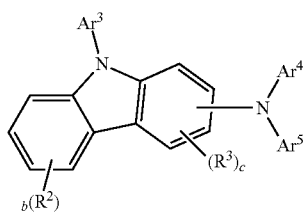

<Formula 2-C>

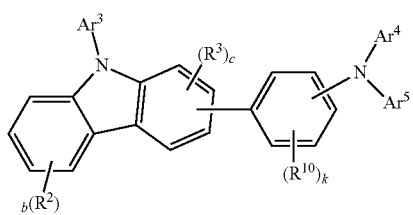

<Formula 2-D>

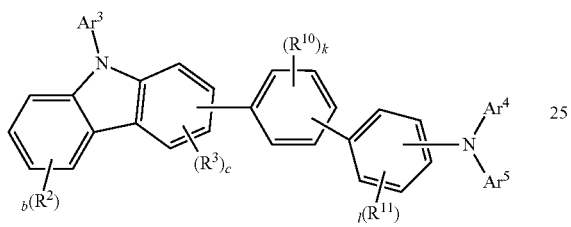

<Formula 2-E>

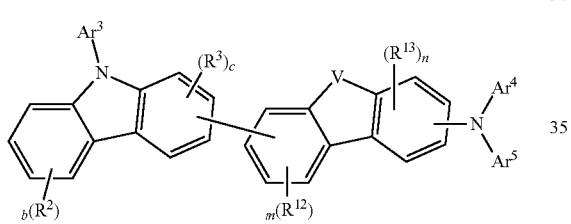

<Formula 2-F> wherein Ar³ to Ar⁵, R², R³, b and c are the same as defined in claim 1,

R¹⁰ to R¹³ are each independently selected from the group consisting of hydrogen, deuterium, halogen, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_1$-$C_{20}$ alkyl group, a $C_2$-$C_{20}$ alkenyl group, and a $C_2$-$C_{20}$ alkynyl group, and adjacent groups may be linked to each other to form a ring, k and l are each an integer of 0-4, n and m are each an integer of 0-3, and where each of these is an integer of 2 or more, each of a plurality of R¹⁰s, each of a plurality of R¹¹s, each of a plurality of R¹²s, and each of a plurality of R¹³s are the same as or different from each other, V is N-($L^a$-$Ar^a$), O, S or C(R')(R"), R' and R" are each independently selected from the group consisting of hydrogen, deuterium, halogen, a cyano group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_1$-$C_{20}$ alkyl group, a $C_2$-$C_{20}$ alkenyl group, and a $C_2$-$C_{20}$ alkynyl group, and R' and R" may be linked to each other to form a ring, $Ar^a$ is selected from the group consisting of a $C_6$-$C_{20}$ aryl group, a fluorenyl group, a $C_2$-$C_{20}$ heterocyclic group comprising at least one heteroatom selected from the group consisting of O, N, S, Si and P, and a $C_3$-$C_{20}$ aliphatic ring, $L^a$ is selected from the group consisting of a single bond, a $C_6$-$C_{20}$ arylene group, a fluorenylene group, a $C_2$-$C_{20}$ heterocyclic group comprising at least one heteroatom selected from the group consisting of O, N, S, Si and P, and a $C_3$-$C_{20}$ aliphatic ring.

9. The organic electric element of claim 1, wherein Formula 2 is represented by one of Formula 2-G to Formula 2-R:

<Formula 2-G>

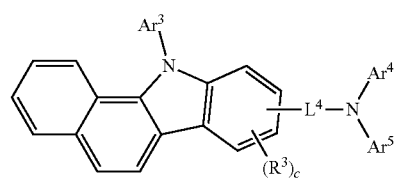

<Formula 2-H>

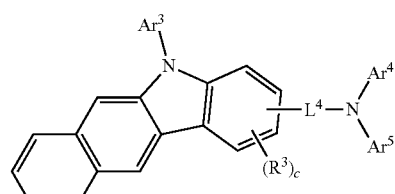

<Formula 2-I>

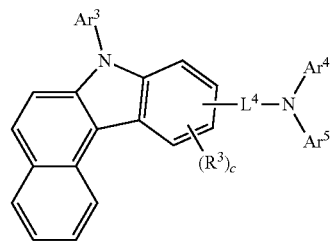

<Formula 2-J>

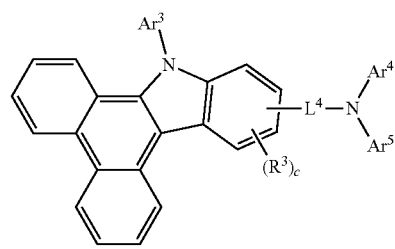

<Formula 2-K>

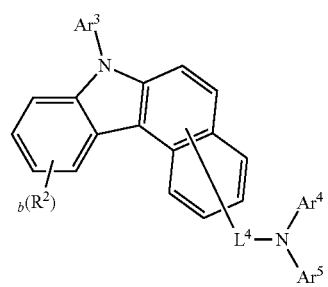

<Formula 2-L>

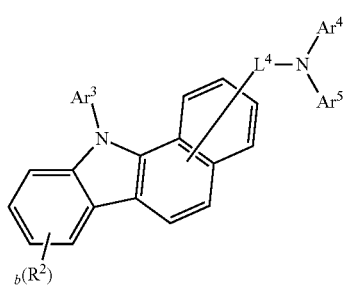

<Formula 2-M>

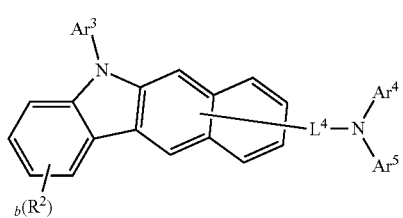

<Formula 2-N>

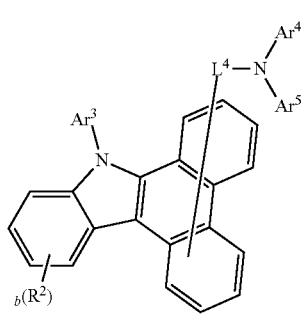

<Formula 2-O>

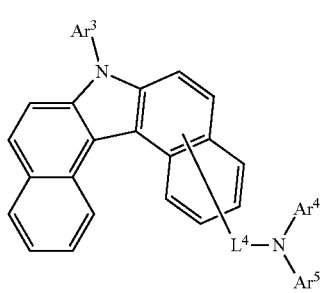

<Formula 2-P>

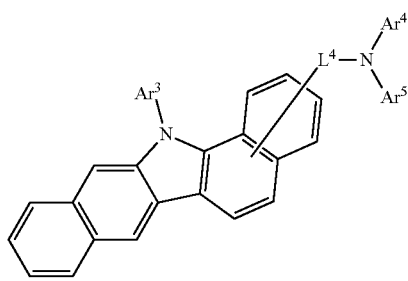

<Formula 2-Q>

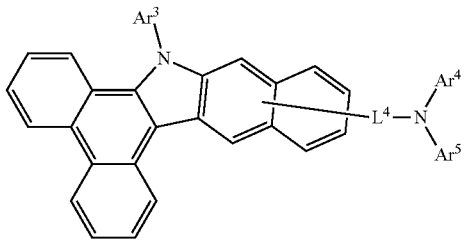

<Formula 2-R>

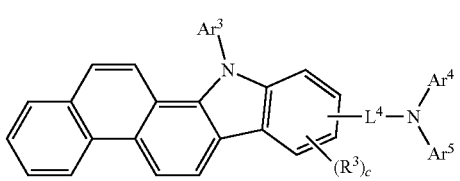

wherein Ar³ to Ar⁵, L⁴, R², R³, b and c are the same as defined in claim 1.

10. The organic electric element of claim 1, wherein Formula 2 is represented by Formula 2-S or Formula 2-T:

<Formula 2-S>

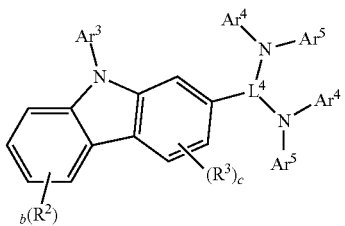

<Formula 2-T>

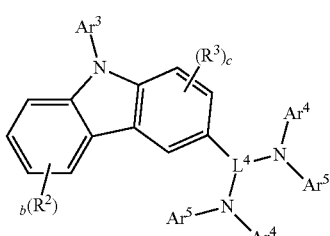

wherein Ar³ to Ar⁵, L⁴, R², R³, b and c are the same as defined in claim 1.

11. The organic electric element of claim 1, wherein n in Formula 2 is 1.

12. The organic electric element of claim 1, wherein n in Formula 2 is 2.

13. The organic electric element of claim 1, wherein Formula 2 is represented by Formula 2-U:

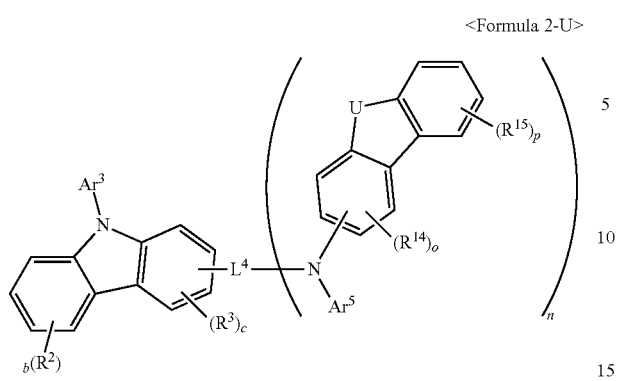

<Formula 2-U> wherein Ar³, Ar⁵, L⁴, R², R³, b, c and n are the same as defined in claim 1,

U is N-($L^a$-$Ar^a$), O, S or C(R')(R"), $R^{14}$ and $R^{15}$ are each independently selected from the group consisting of hydrogen, deuterium, halogen, a cyano group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_1$-$C_{20}$ alkyl group, a $C_2$-$C_{20}$ alkenyl group, and a $C_2$-$C_{20}$ alkynyl group, and adjacent groups may be linked to each other to form a ring, o is an integer of 0-3, p is an integer of 0-4, and where each of these is an integer of 2 or more, each of a plurality of $R^{14}$s, and each of a plurality of $R^{15}$s are the same as or different from each other, R' and R" are each independently selected from the group consisting of hydrogen, deuterium, halogen, a cyano group, a $C_6$-$C_{20}$ aryl group, a fluorenyl group, a $C_2$-$C_{20}$ heterocyclic group comprising at least one heteroatom selected from the group consisting of O, N, S, Si and P, a $C_3$-$C_{20}$ aliphatic ring, a $C_1$-$C_{20}$ alkyl group, a $C_2$-$C_{20}$ alkenyl group, and a $C_2$-$C_{20}$ alkynyl group, and R' and R" may be linked to each other to form a ring, $Ar^a$ is selected from the group consisting of a $C_6$-$C_{20}$ aryl group, a fluorenyl group, a $C_2$-$C_{20}$ heterocyclic group comprising at least one heteroatom selected from the group consisting of O, N, S, Si and P, and a $C_3$-$C_{20}$ aliphatic ring, and $L^a$ is selected from the group consisting of a single bond, a $C_6$-$C_{20}$ arylene group, a fluorenylene group, a $C_2$-$C_{20}$ heterocyclic group comprising at least one heteroatom selected from the group consisting of O, N, S, Si and P, a $C_3$-$C_{20}$ aliphatic ring.

14. The organic electric element of claim 1, wherein the compound of Formula 1 is one of the following compounds:

1-1

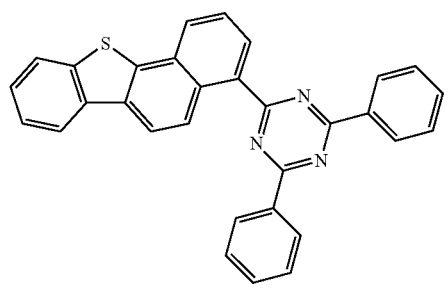

1-2

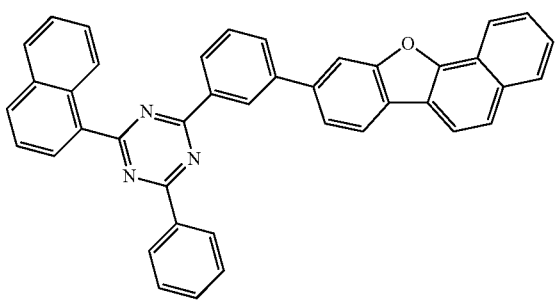

1-3

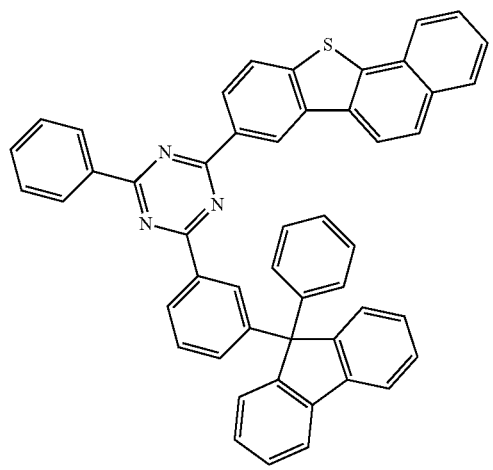

1-4

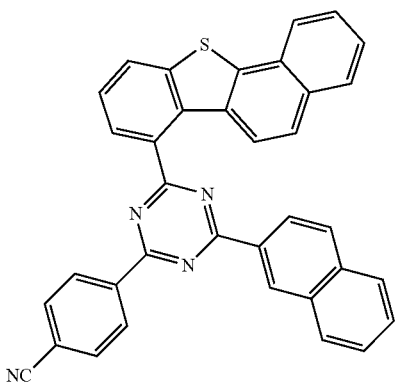

-continued
1-5
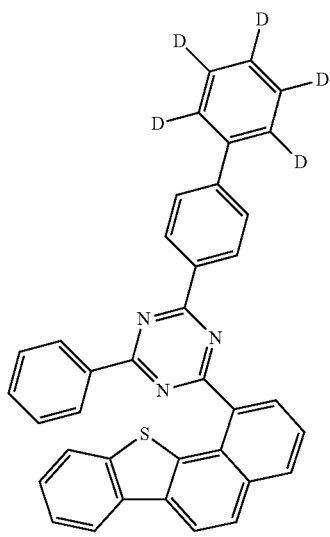
1-6
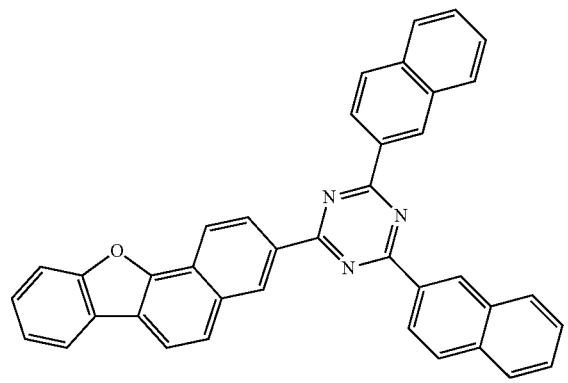
1-7
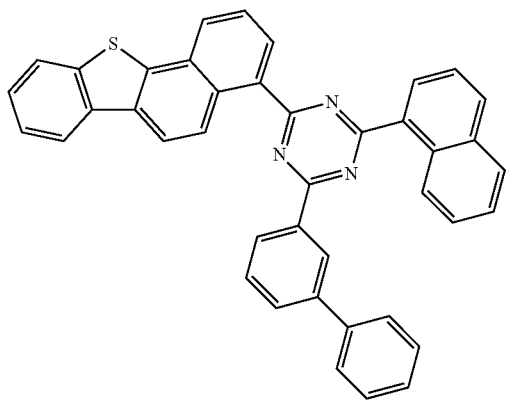
1-8
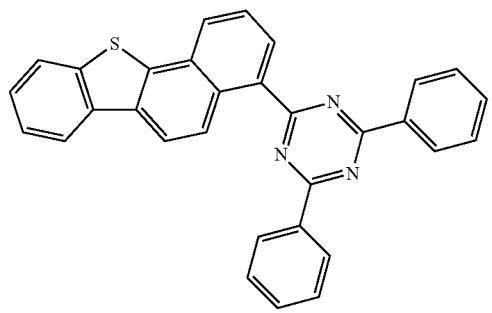
1-9
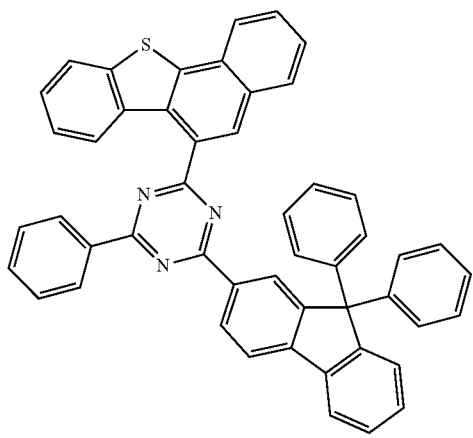
1-10
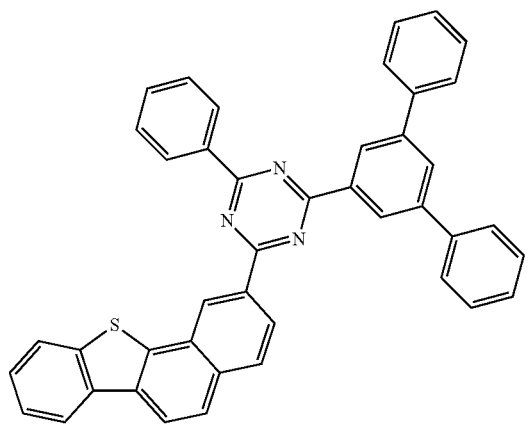

-continued
1-11
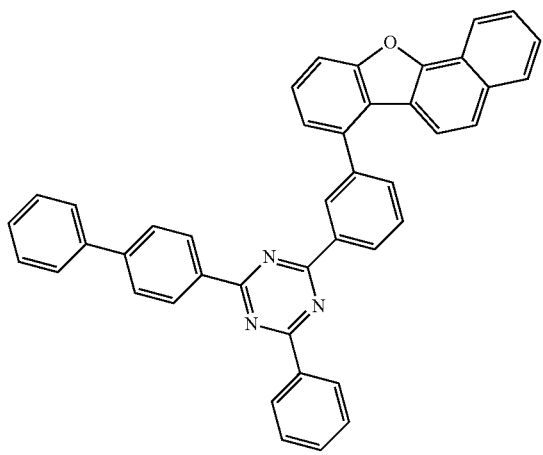
1-12
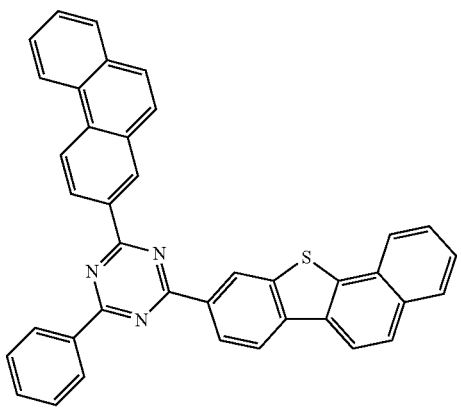
1-13
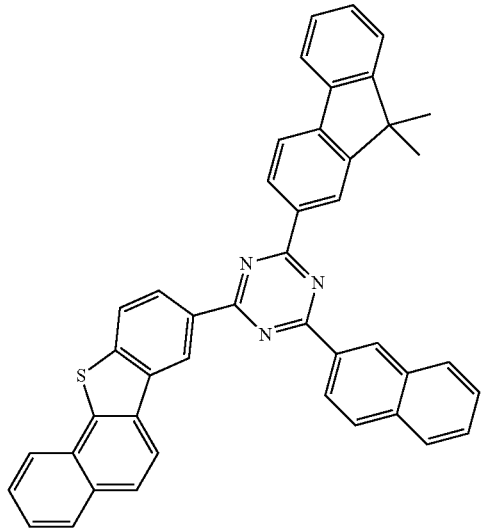
1-14
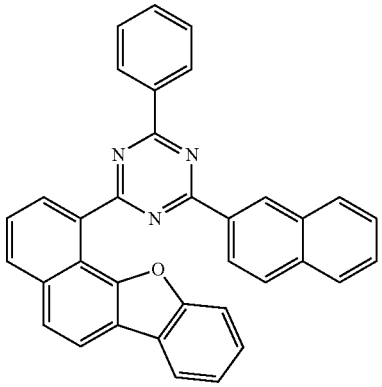
1-15
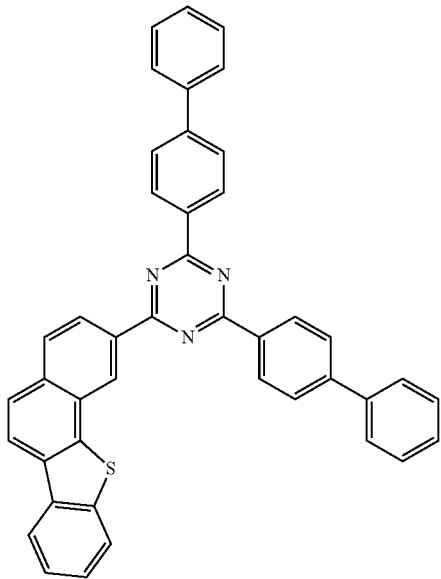
1-16
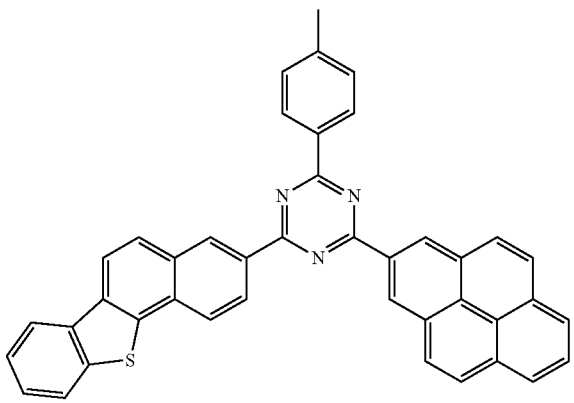

-continued
1-17
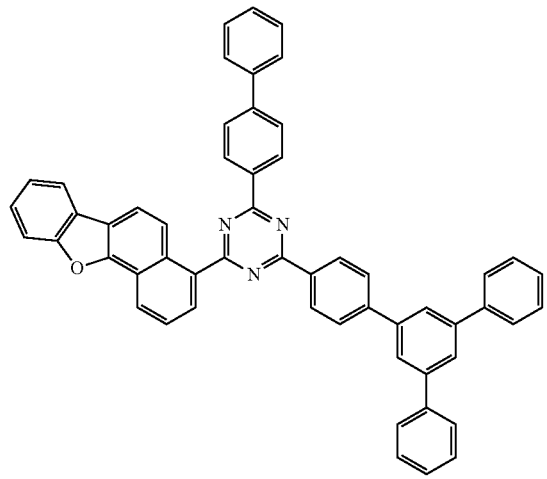
1-18
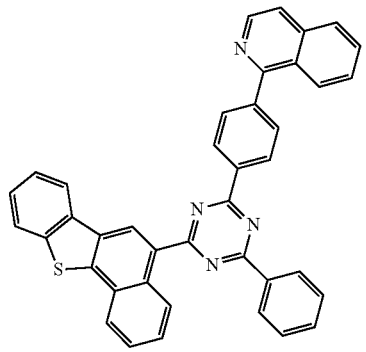
1-19
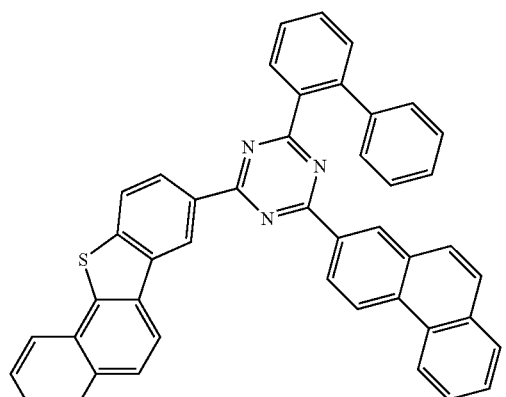
1-20
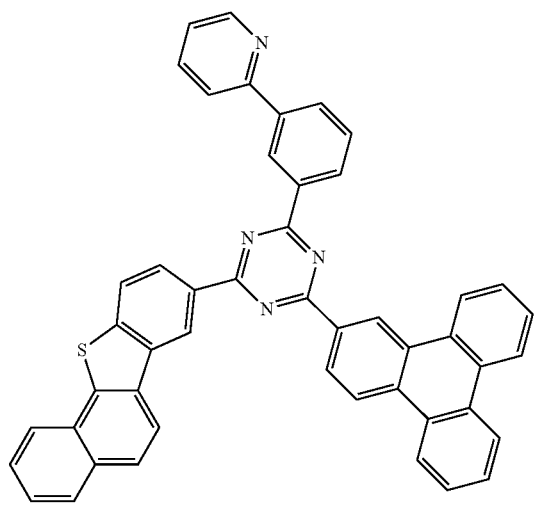
1-21
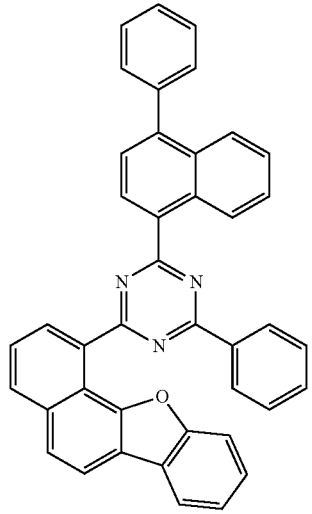
1-22
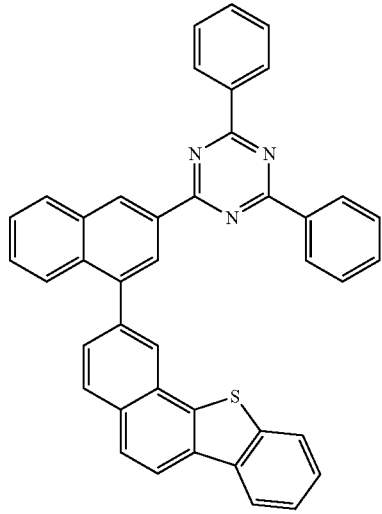

-continued
1-23
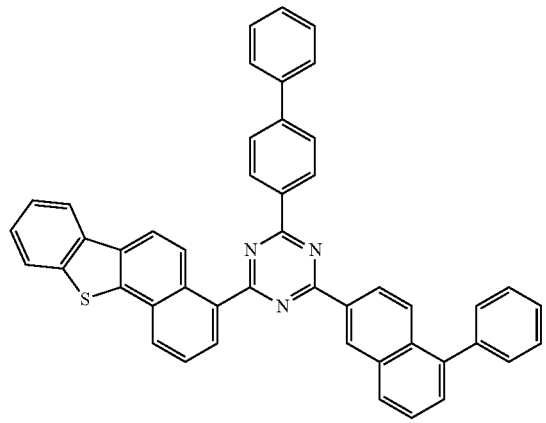
1-24
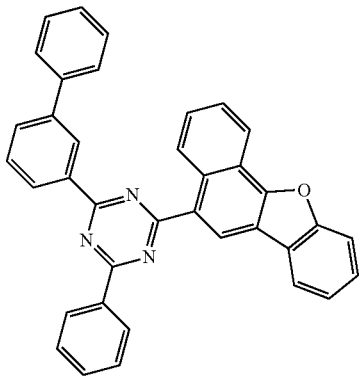
1-25
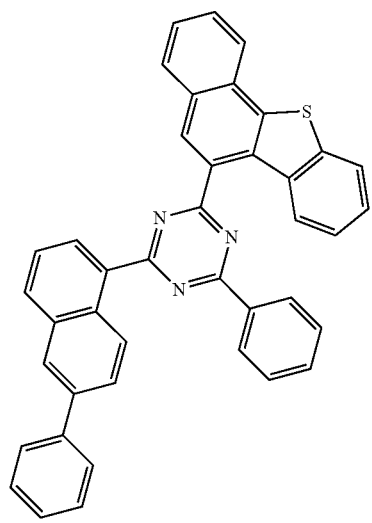
1-26
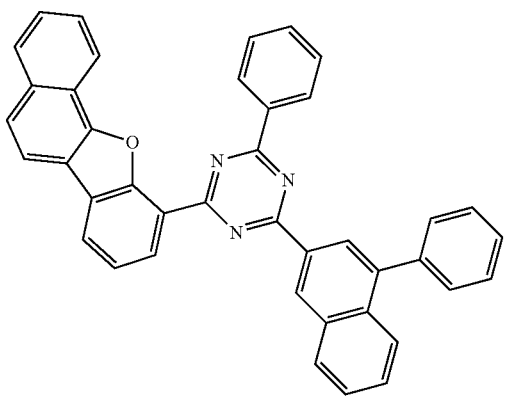
1-27
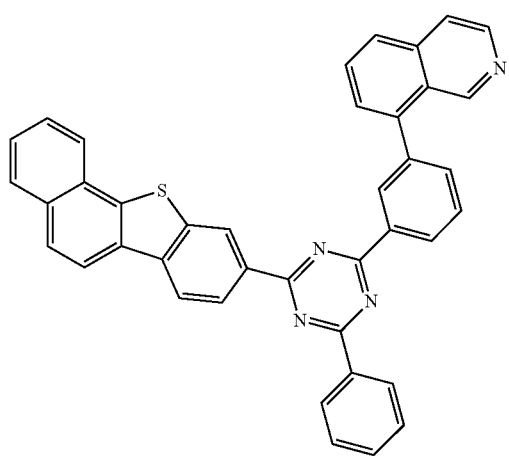
1-28
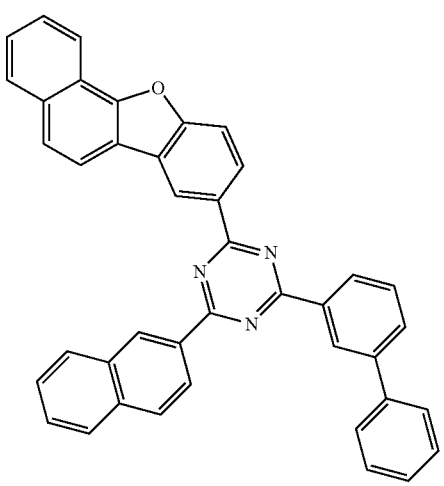

-continued
1-29
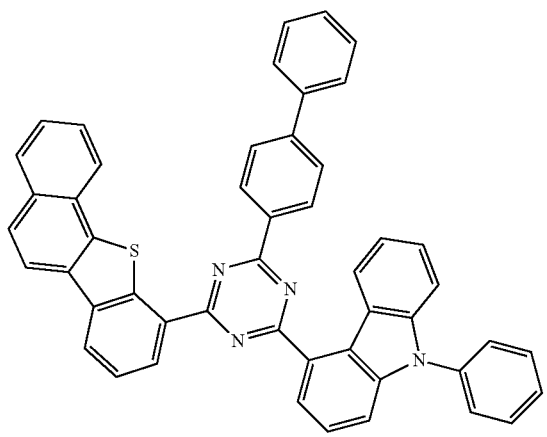
1-30
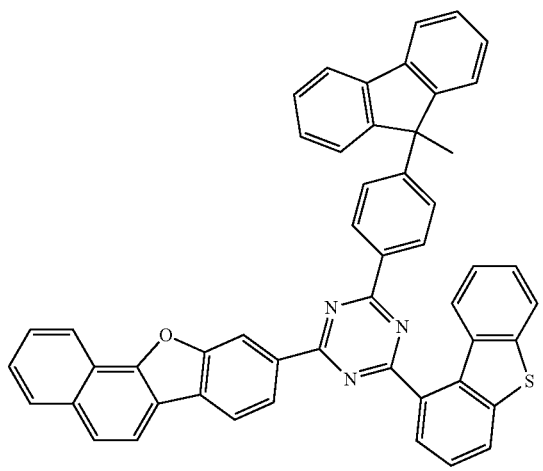
1-31
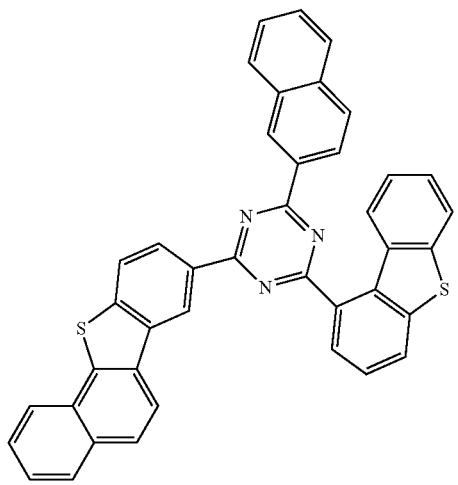
1-32
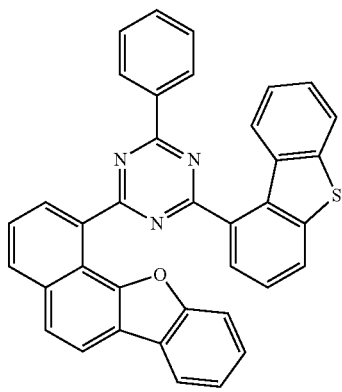
1-33
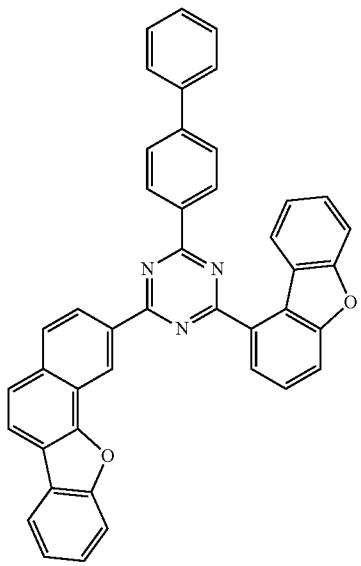
1-34
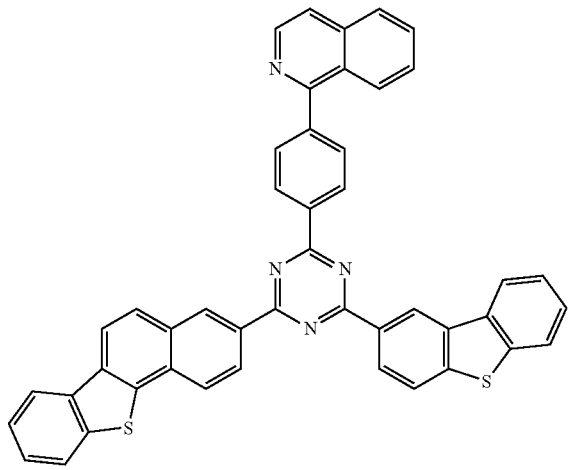

1-35
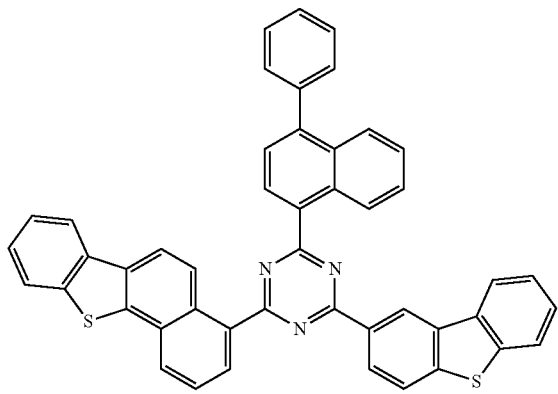
1-36
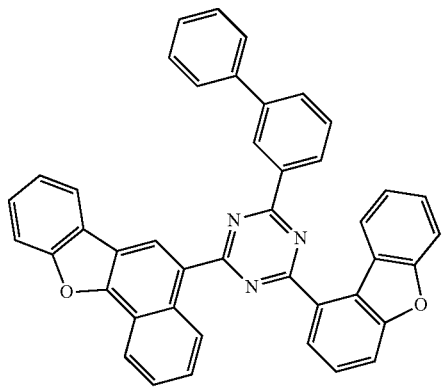
1-37
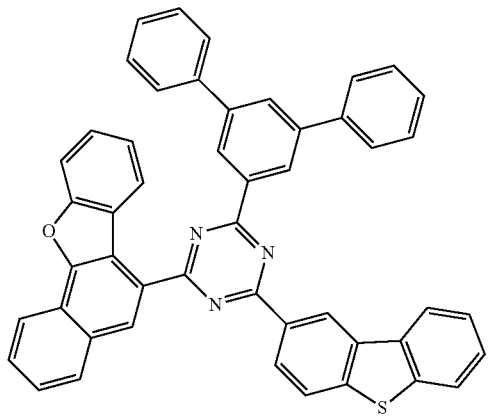
1-38
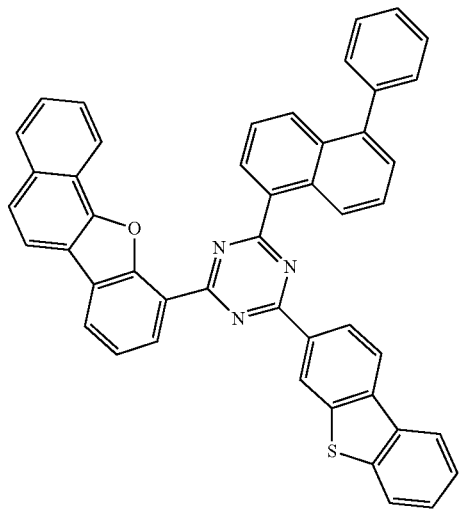
1-39
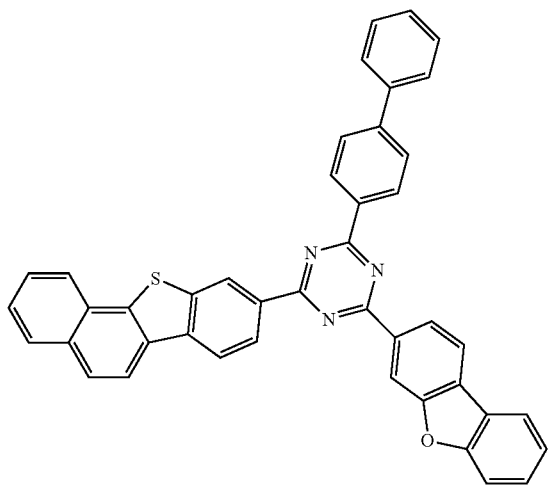
1-40
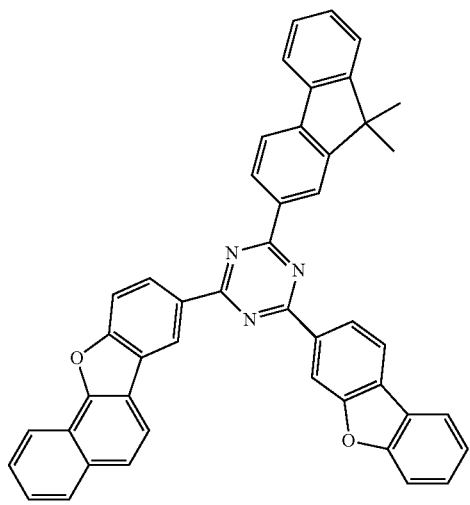

-continued
1-41
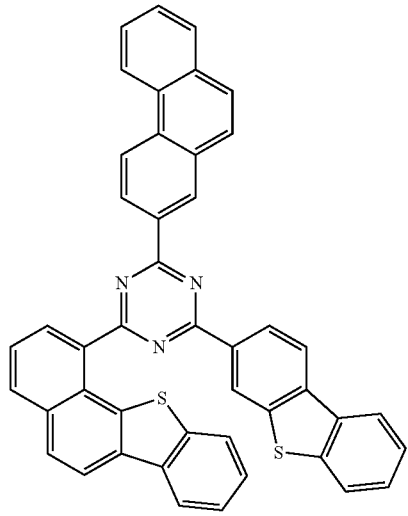
1-42
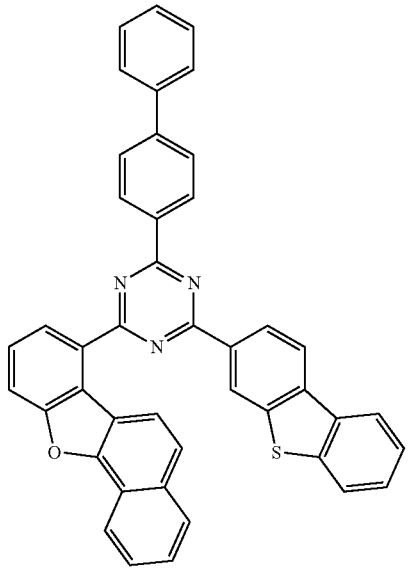
1-43
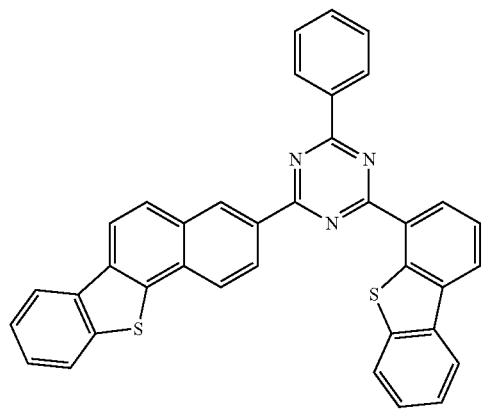
1-44
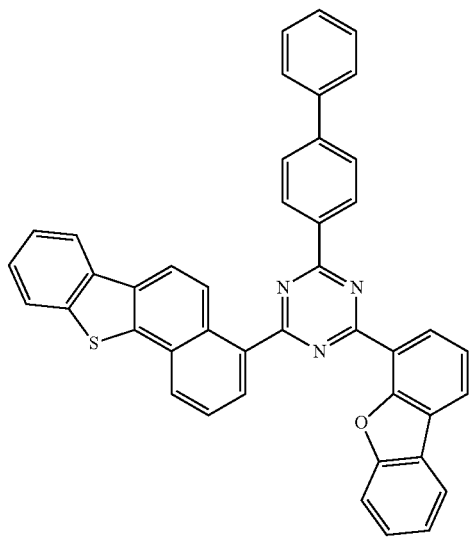
1-45
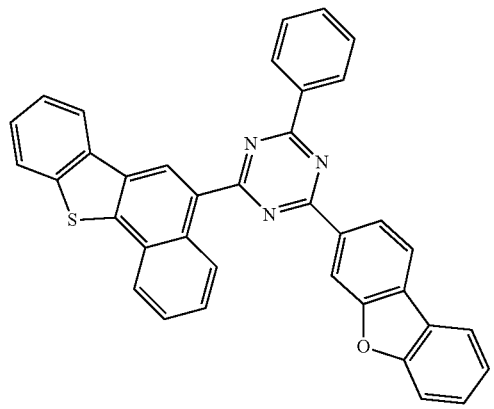
1-46
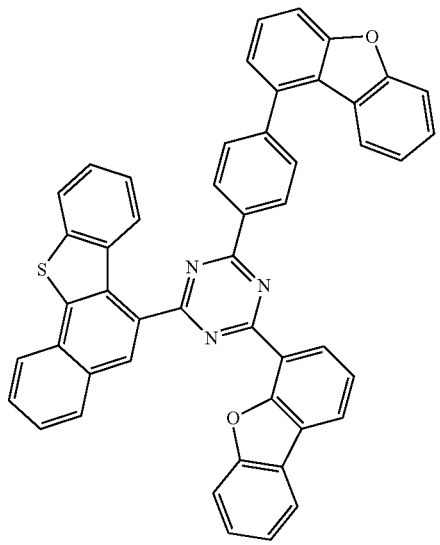

-continued
1-47
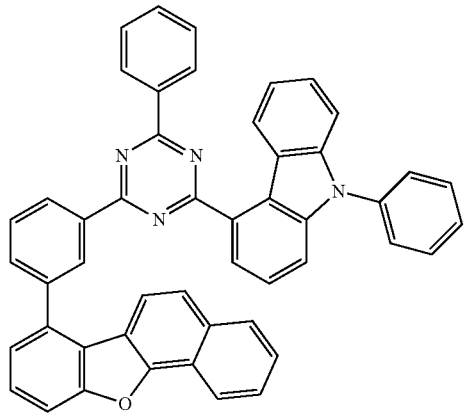
1-48
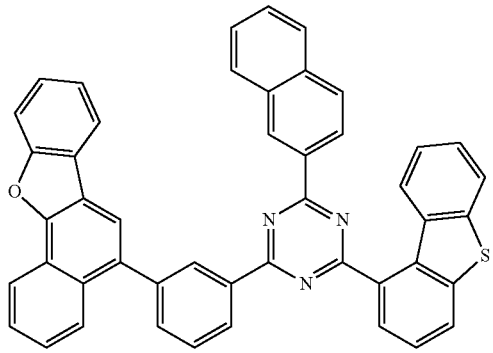
1-49
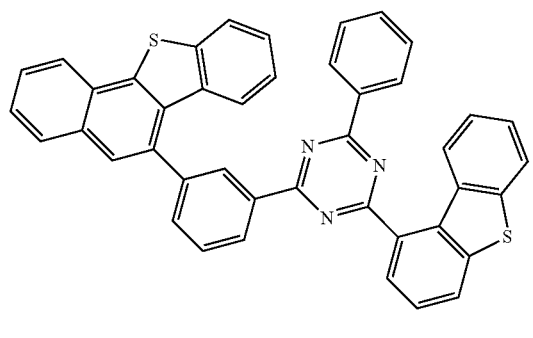
1-50
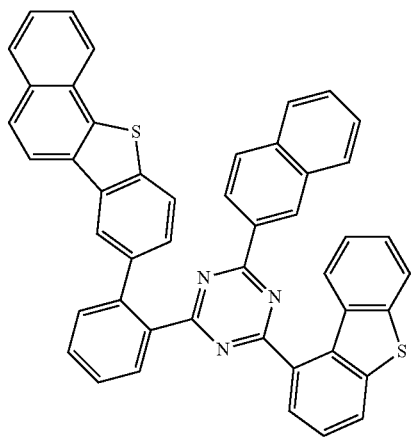
1-51
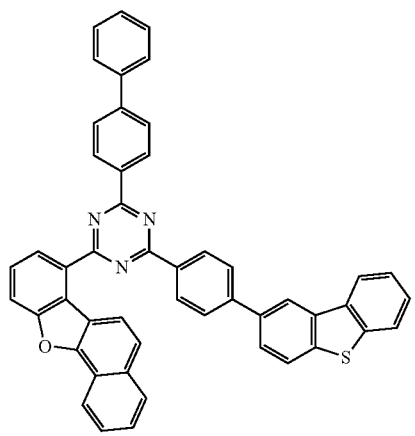
1-52
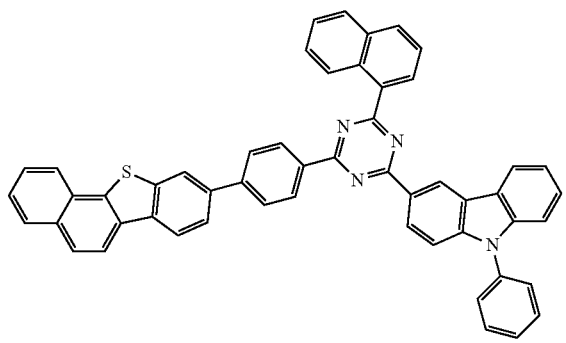

-continued
1-53
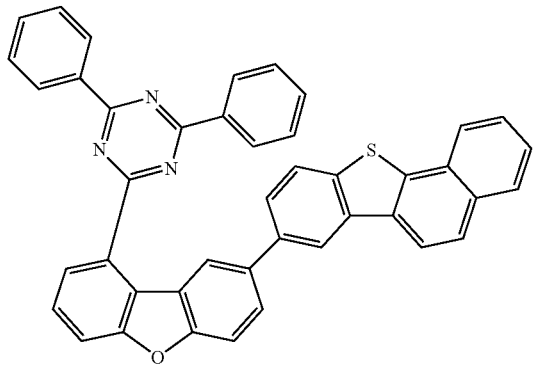
1-54
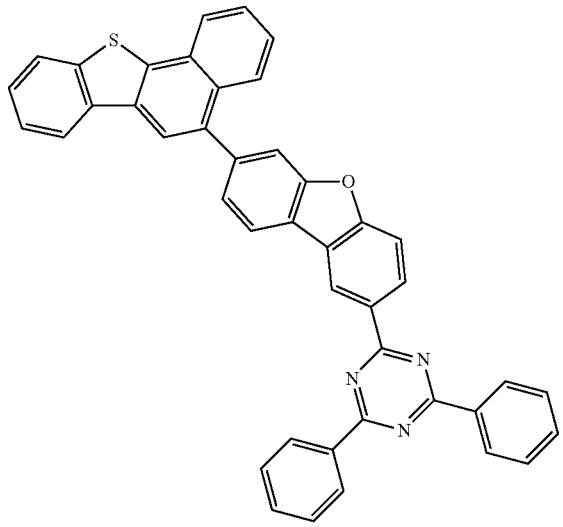
1-55
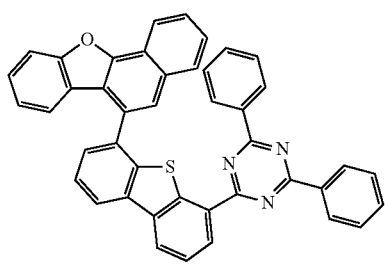
1-56
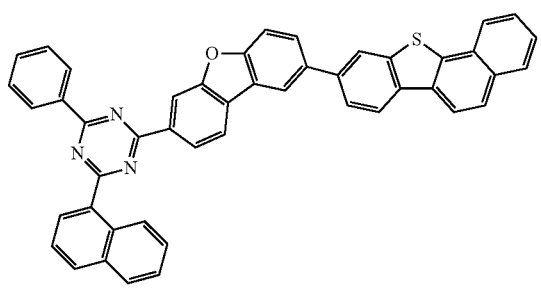
1-57
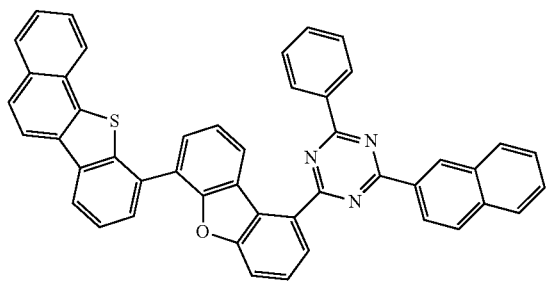
1-58
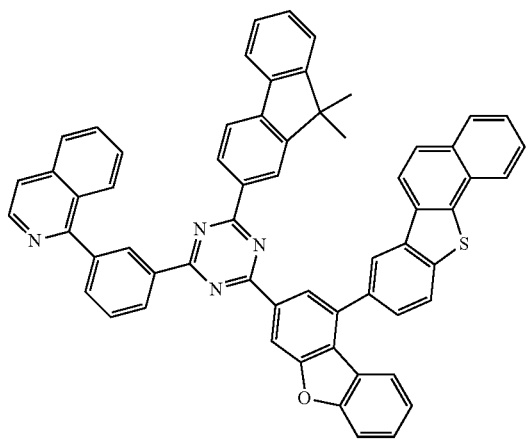

1-59
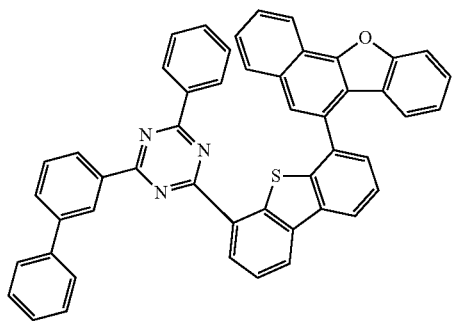
1-60
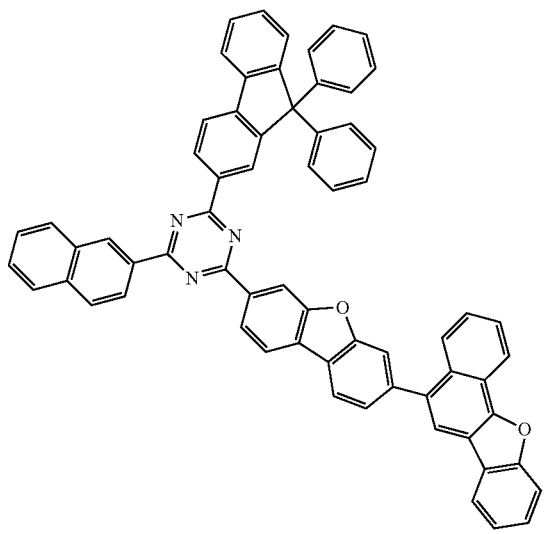
1-61
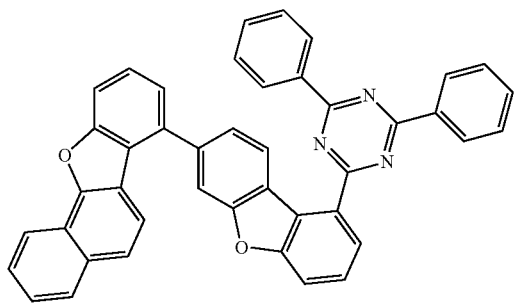
1-62
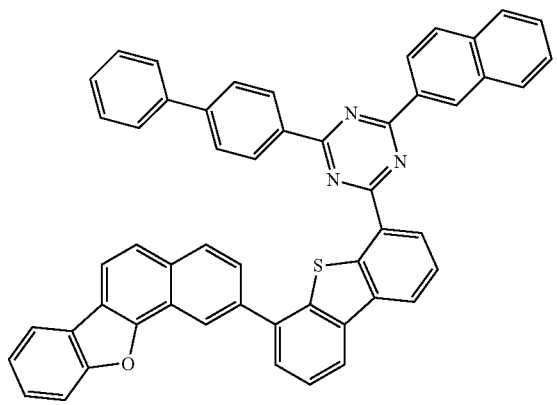
1-63
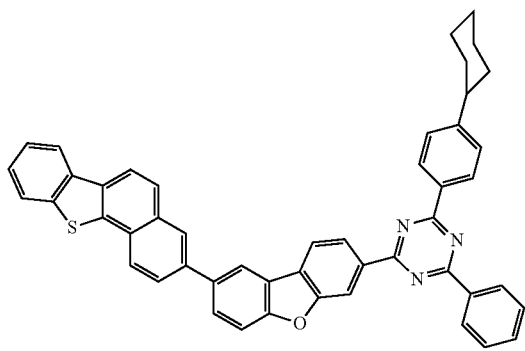
1-64
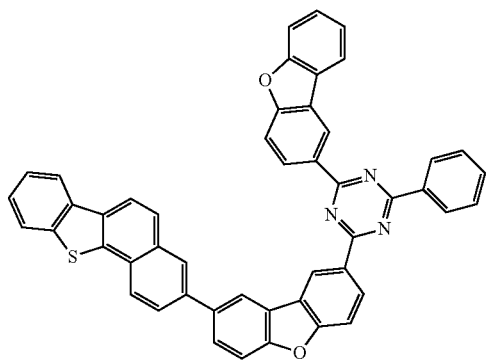

-continued
1-65
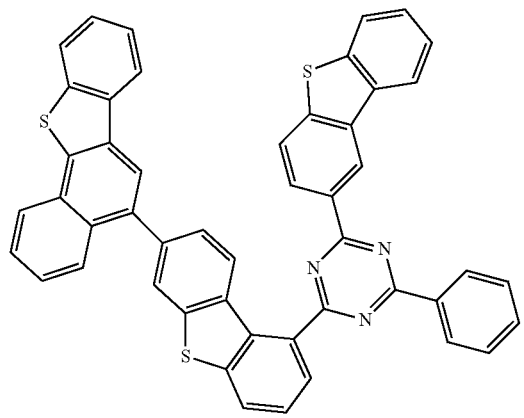
1-66
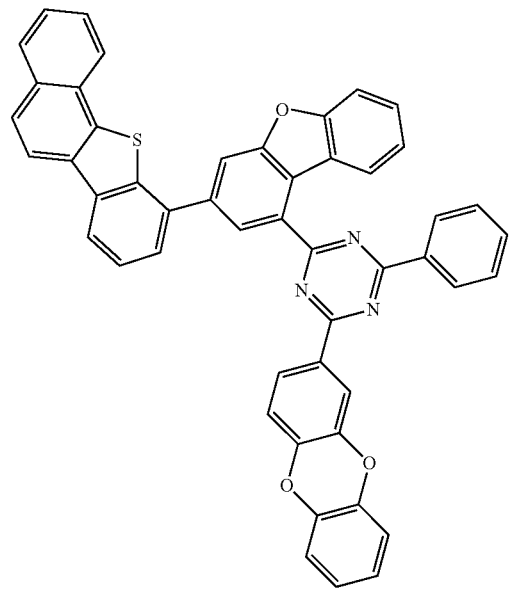
1-67
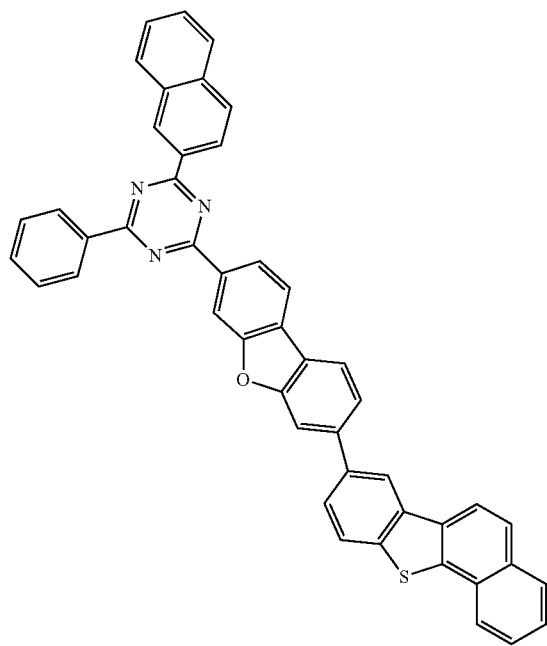
1-68
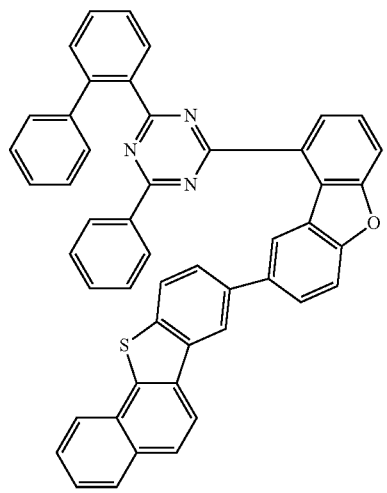

-continued
1-69
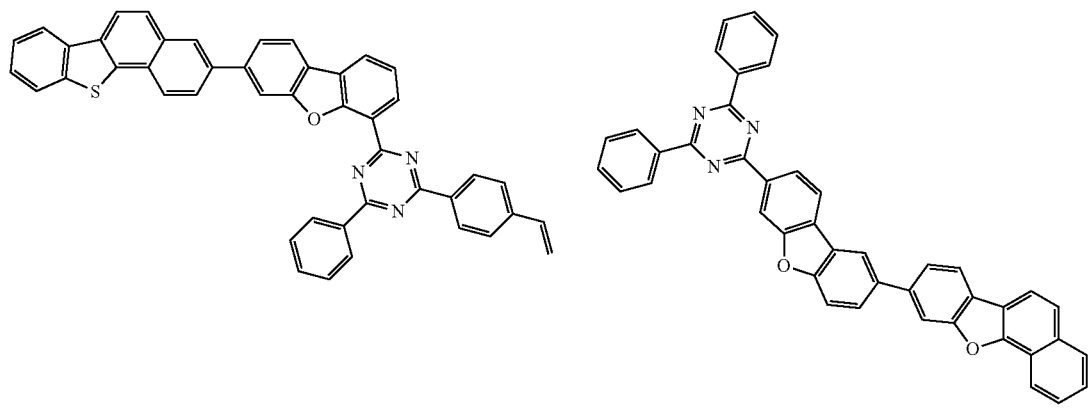
1-70
1-71
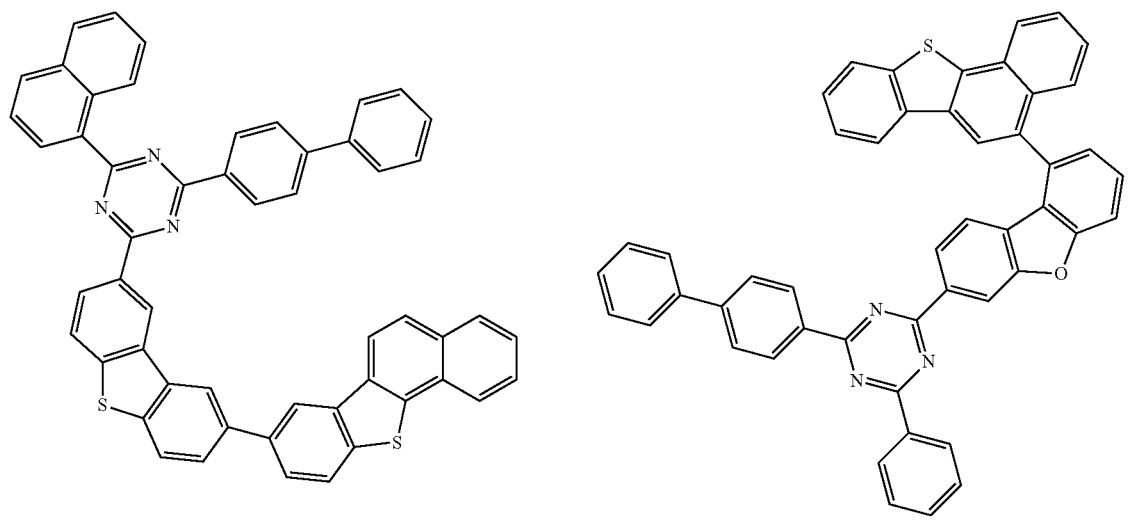
1-72
1-73
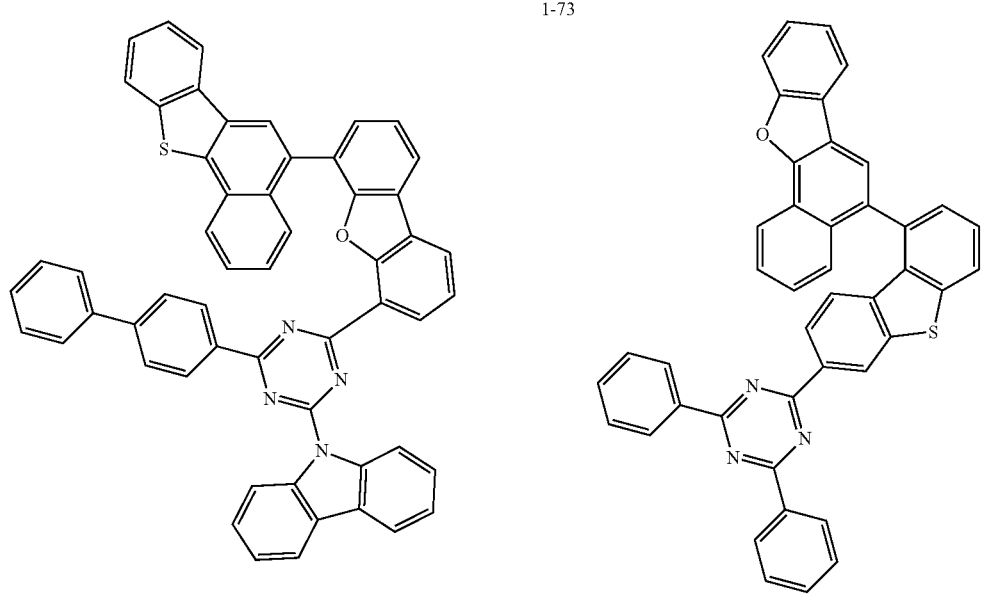
1-74

-continued
1-75
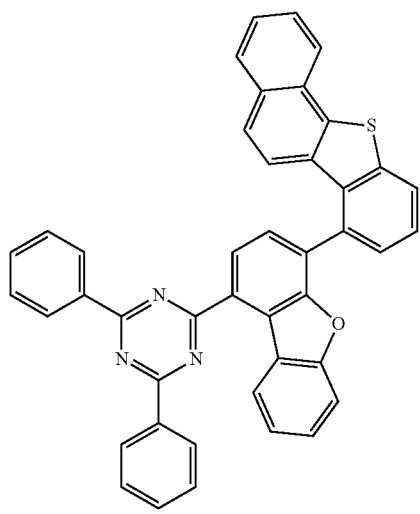
1-76
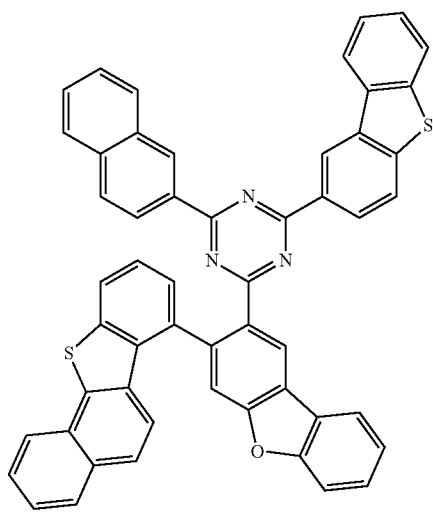
1-77
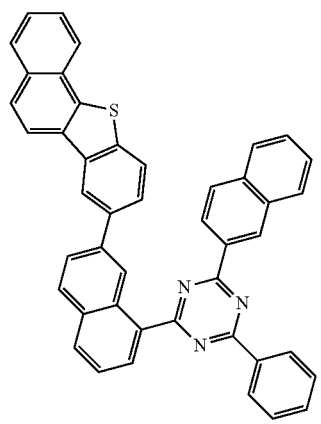
1-78
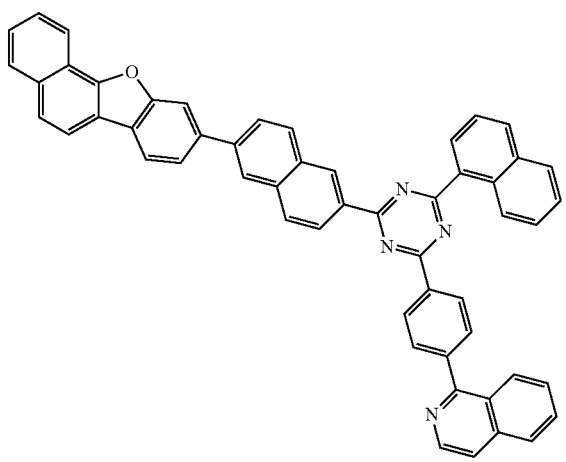
1-79
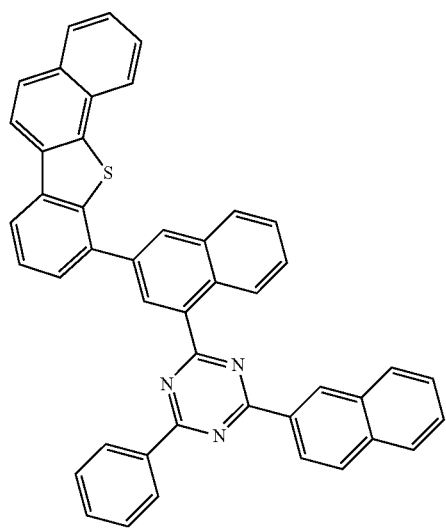
1-80
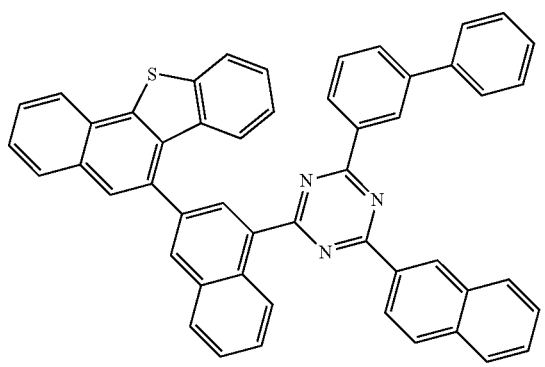

1-81
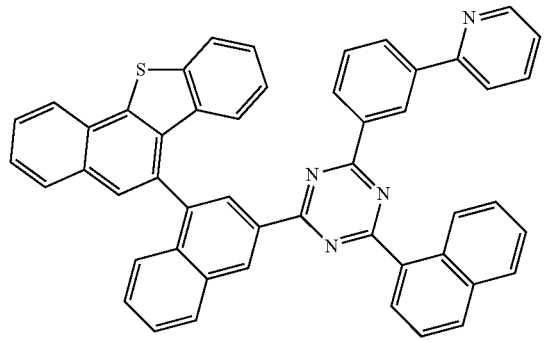
1-82
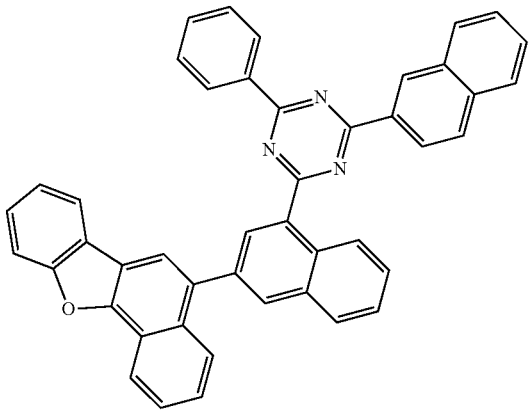
1-83
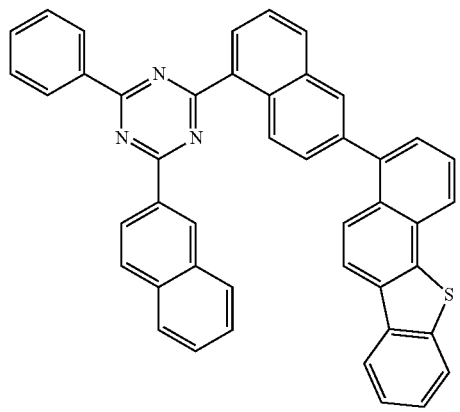
1-84
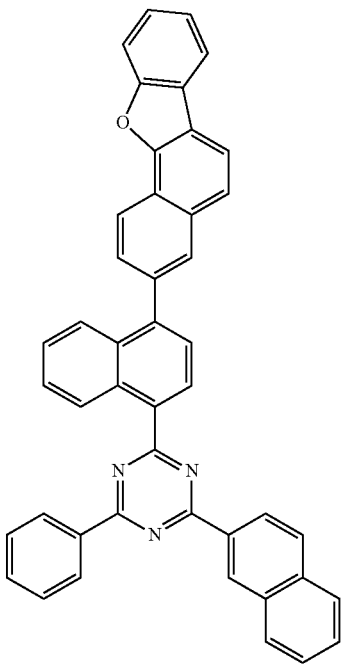
1-85
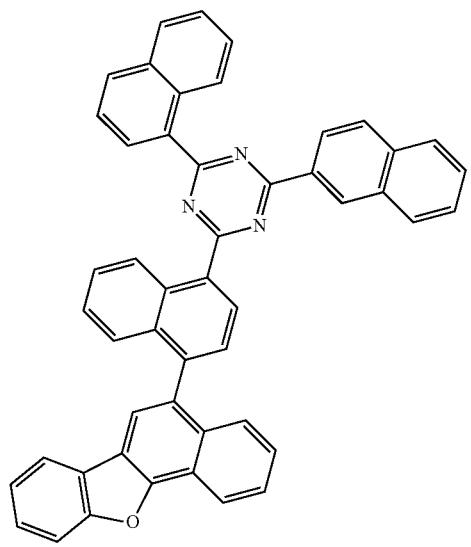
1-86
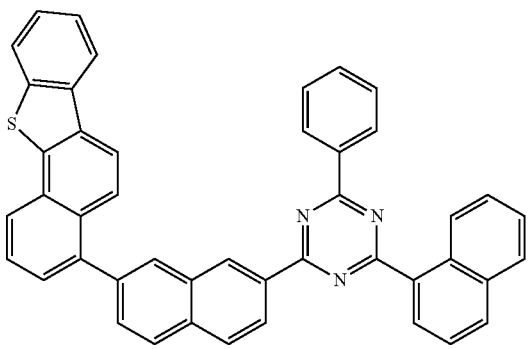

-continued
1-87
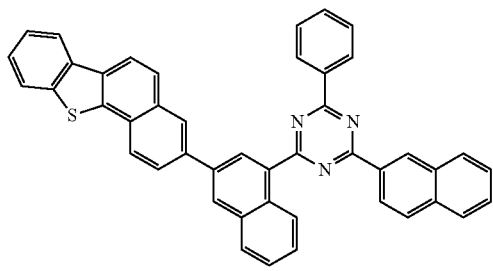
1-88
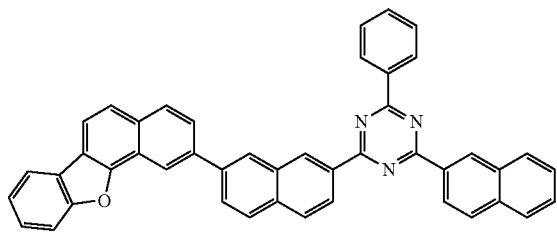
1-89
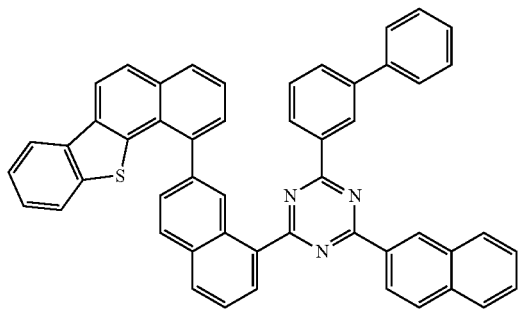
1-90
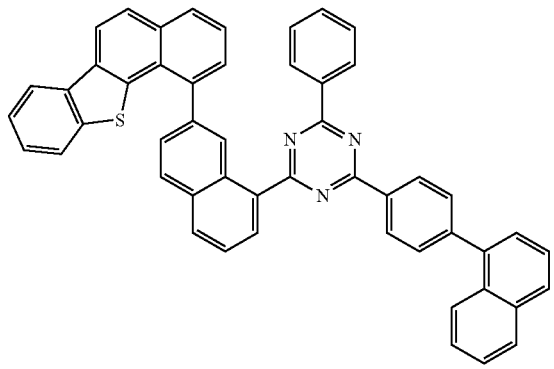
1-91
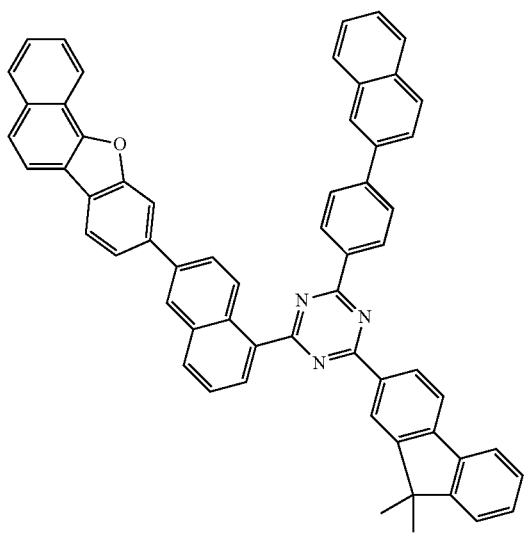
1-92
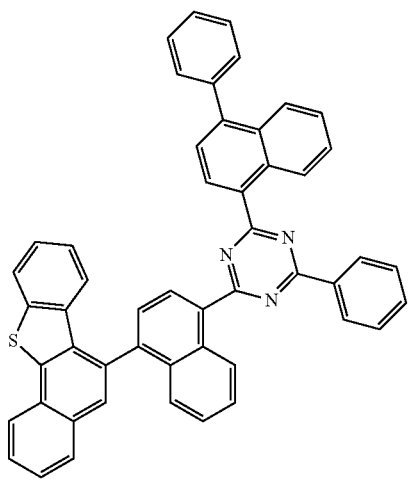

-continued
1-93
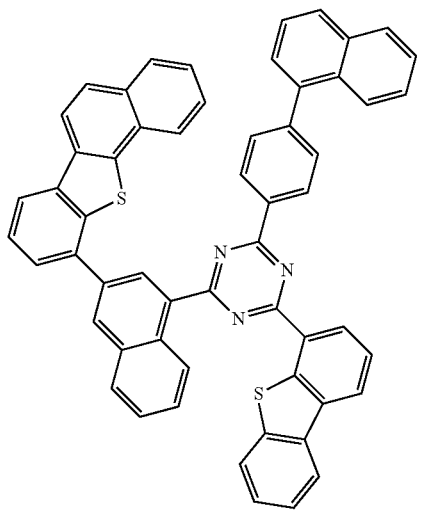
1-94
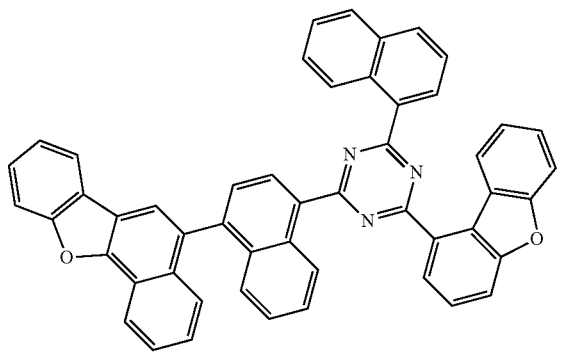
1-95
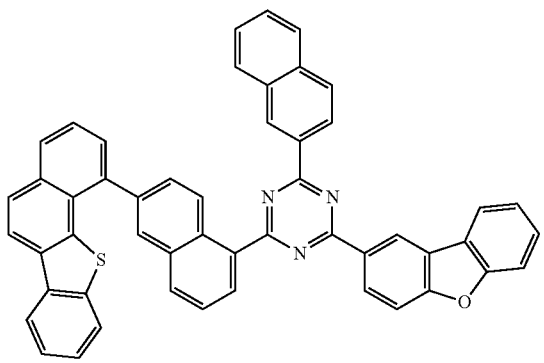
1-96
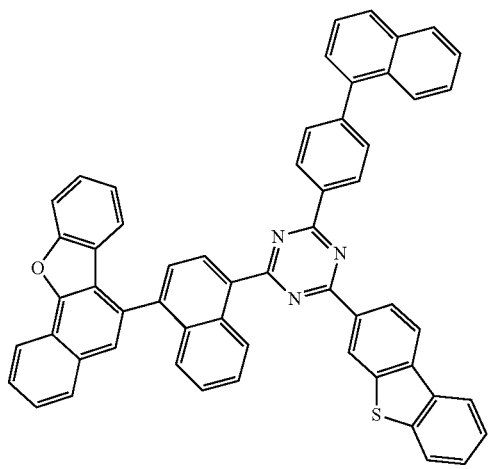
1-97
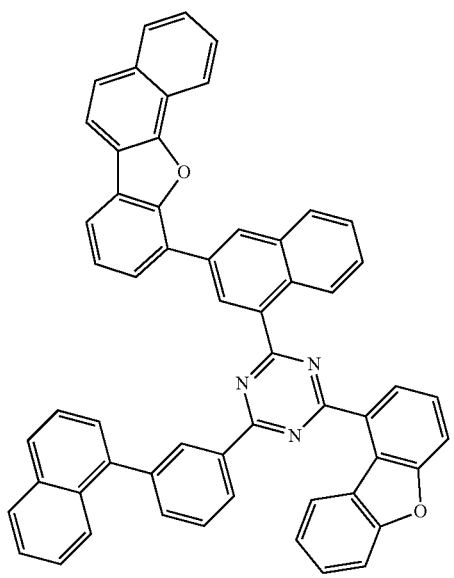
1-98
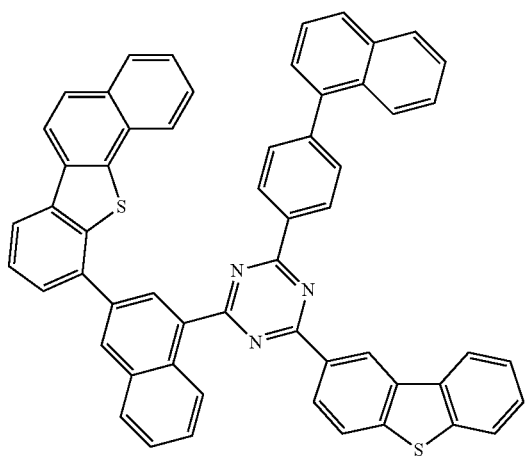

1-99
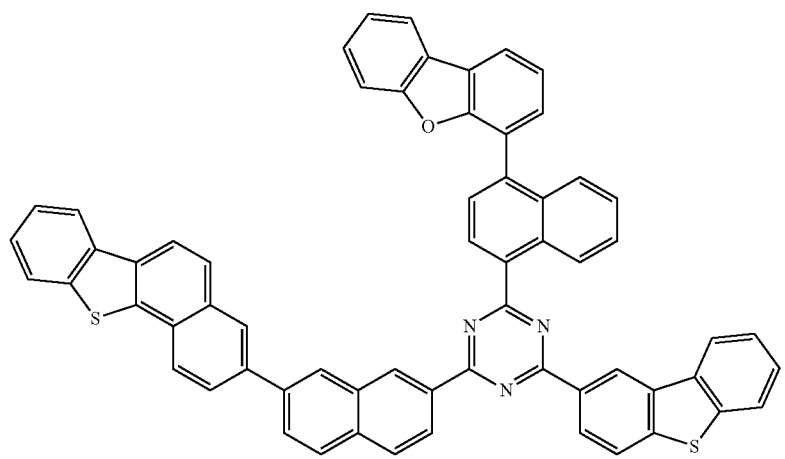
1-100
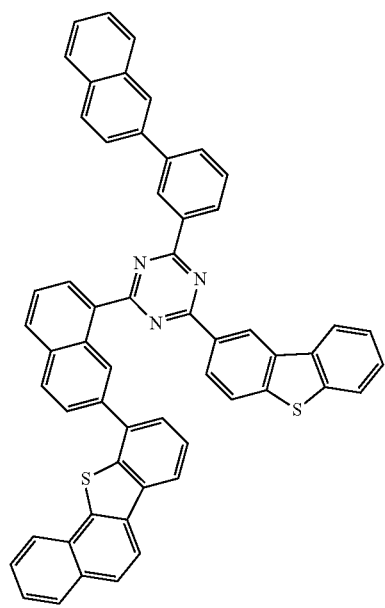
1-101
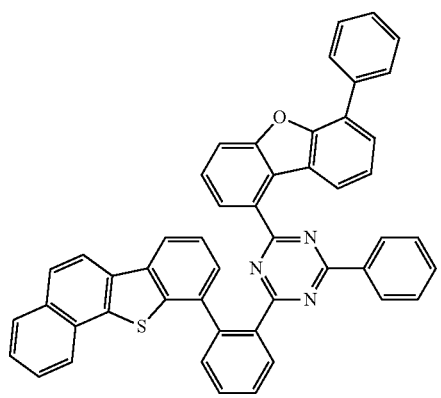

-continued
1-102
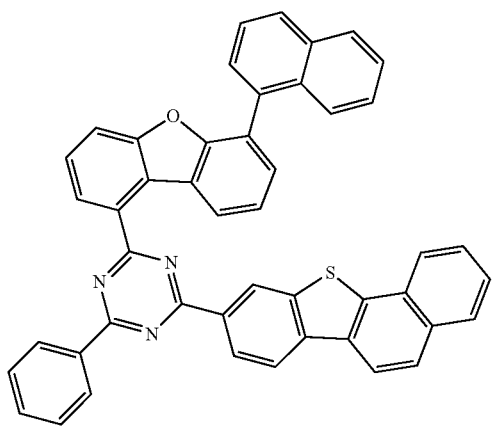
1-103
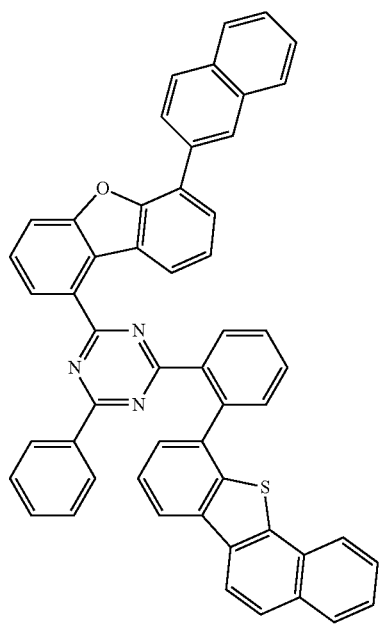
1-104
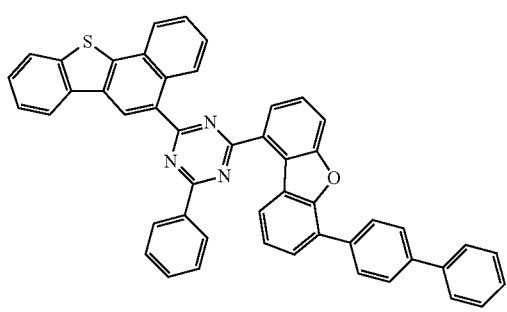
1-105
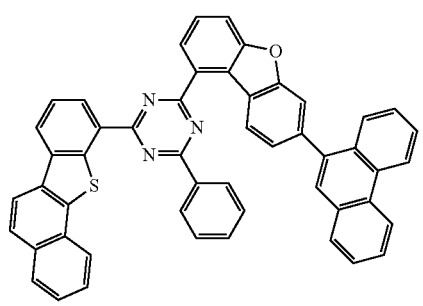
1-106
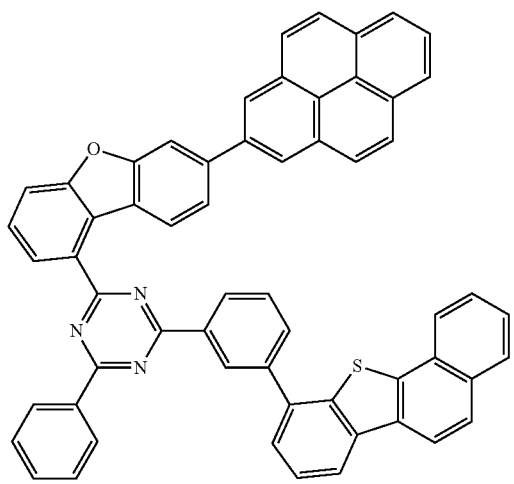
1-107
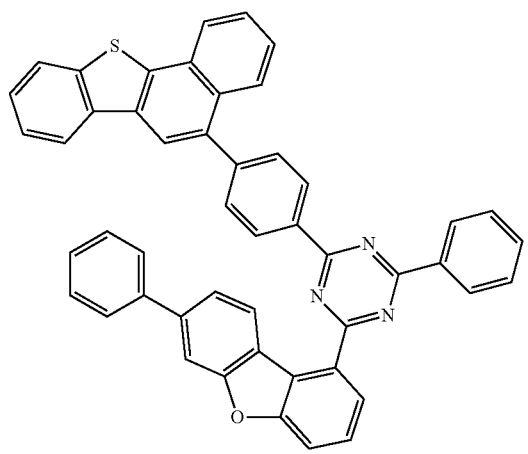

-continued
1-108
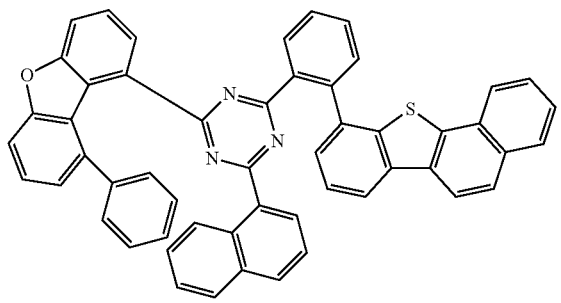
1-109
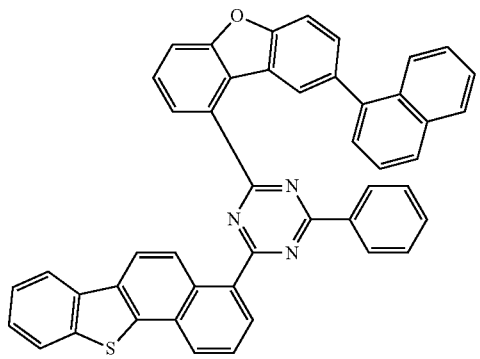
1-110
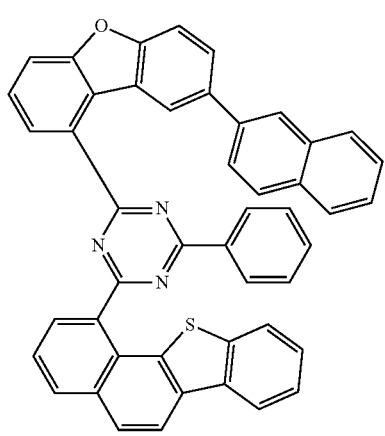
1-111
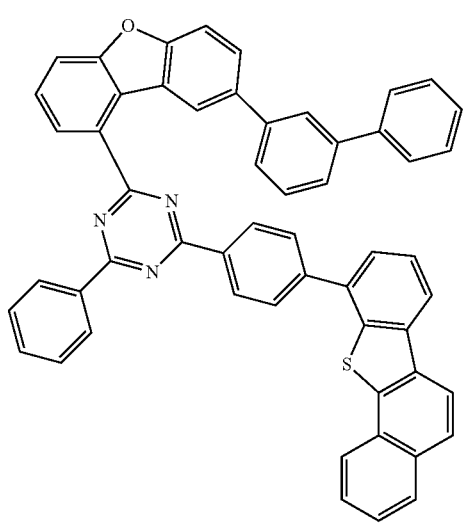
1-112
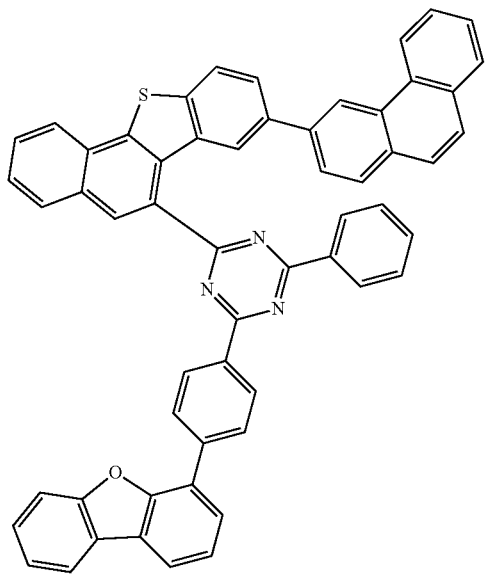
1-113
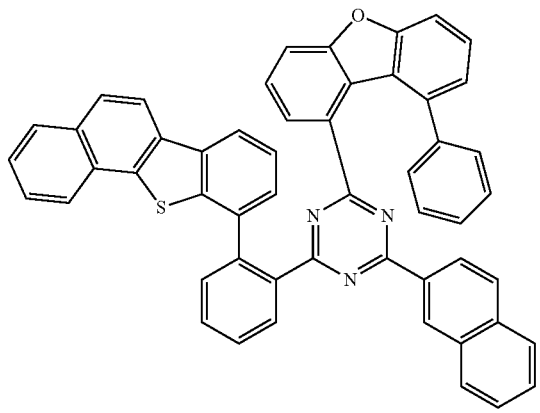

-continued
1-114
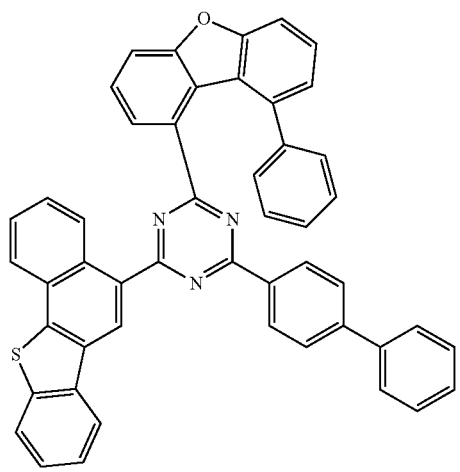
1-115
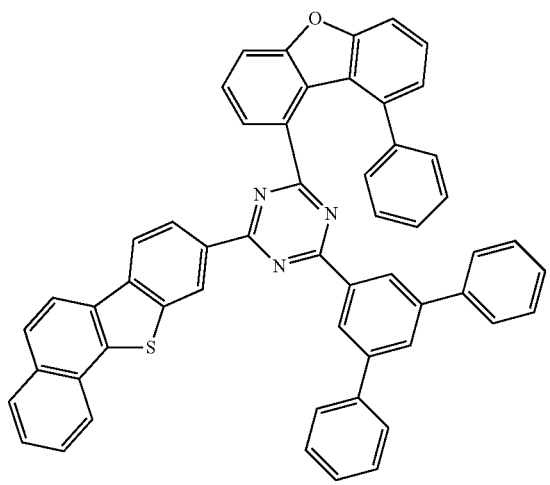
1-116
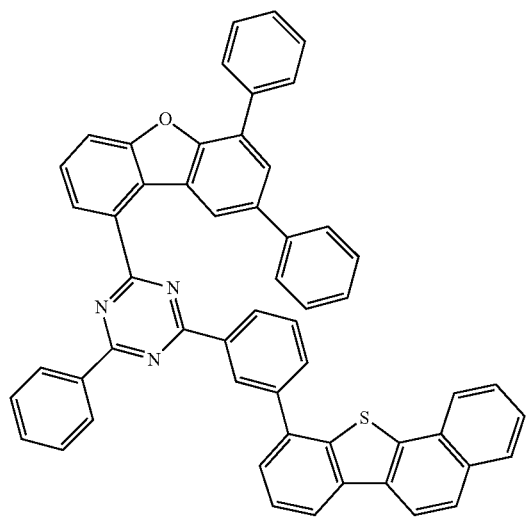
1-117
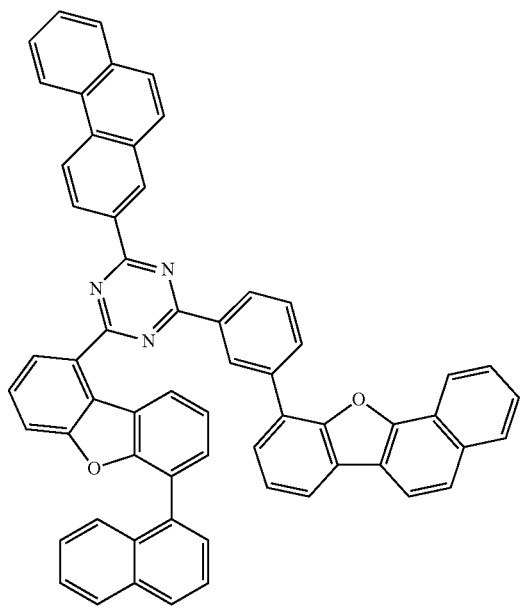
1-118
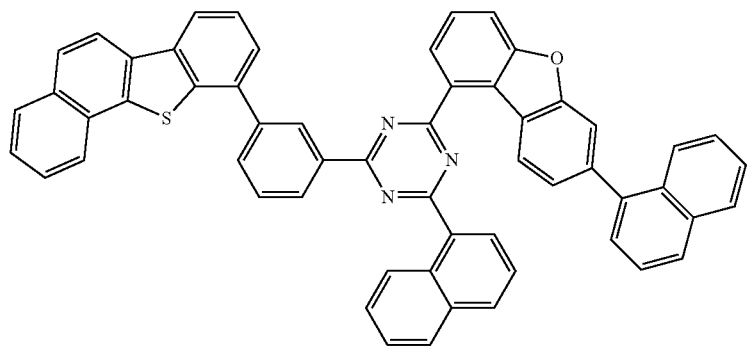

-continued
1-119
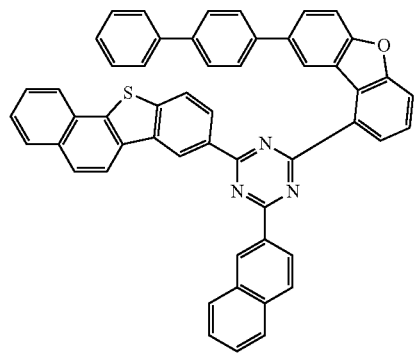
1-120
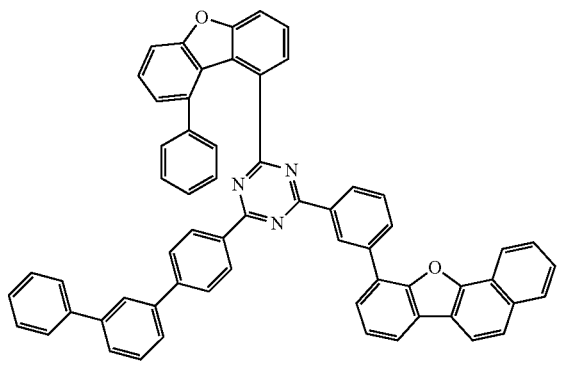
1-121
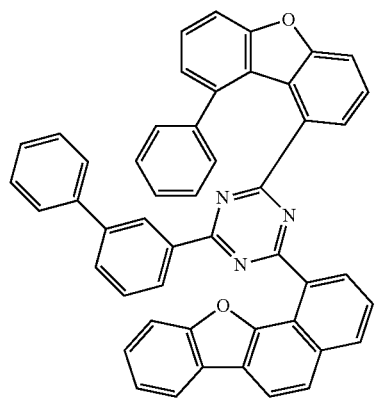
1-122
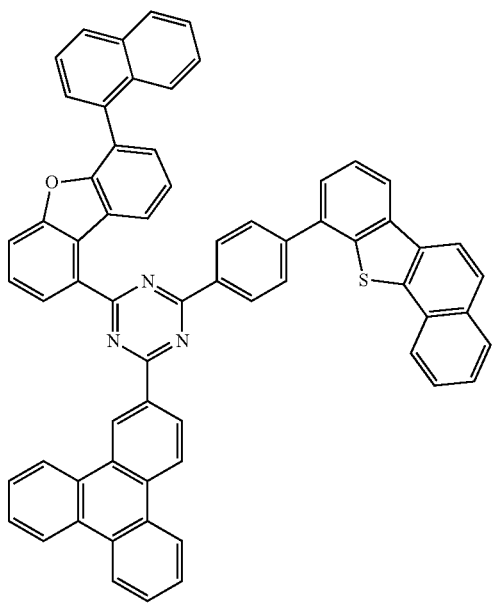
1-123
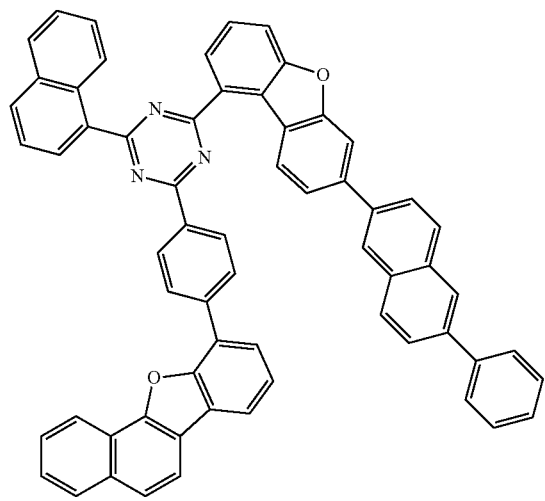
1-124
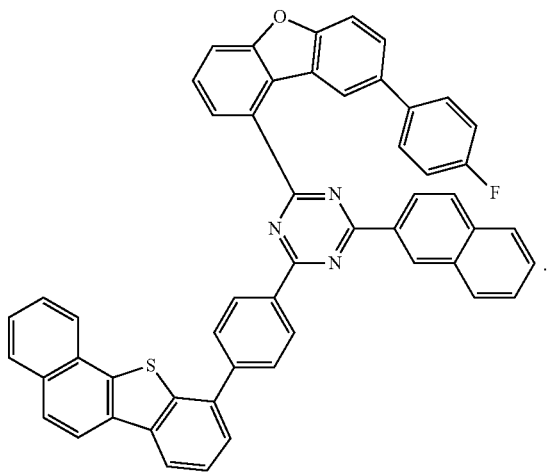

15. The organic electric element of claim 1, wherein the compound of Formula 2 is one of the following compounds:
2-1
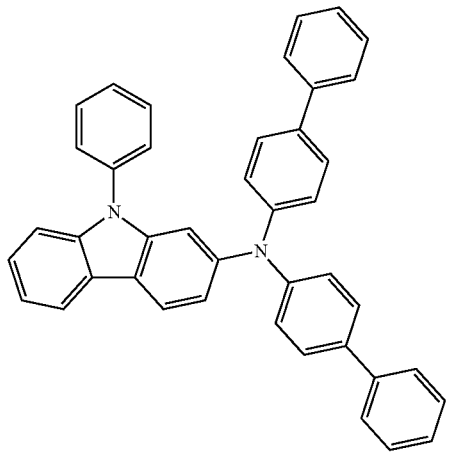
2-2
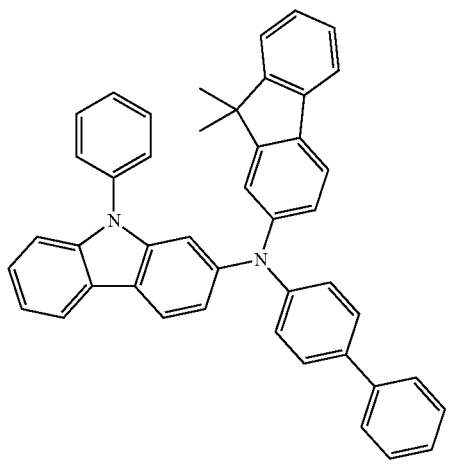
2-3
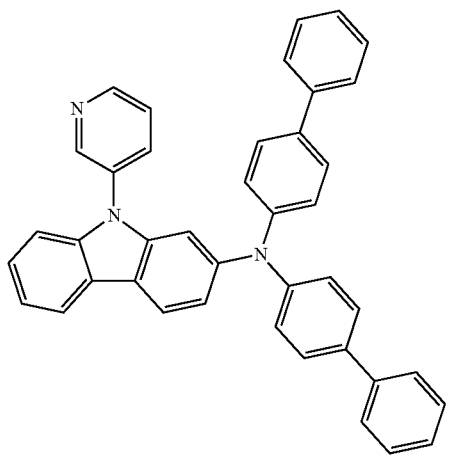
2-4
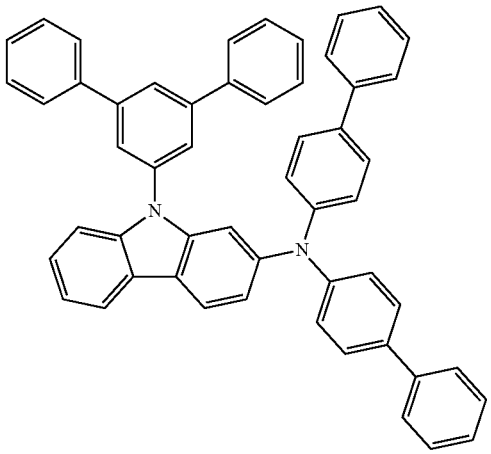
2-5
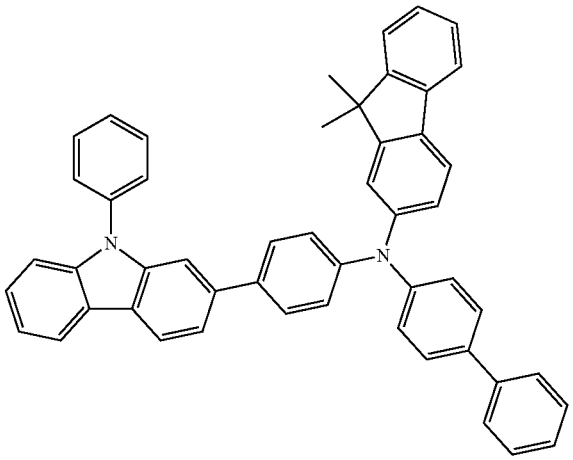
2-6
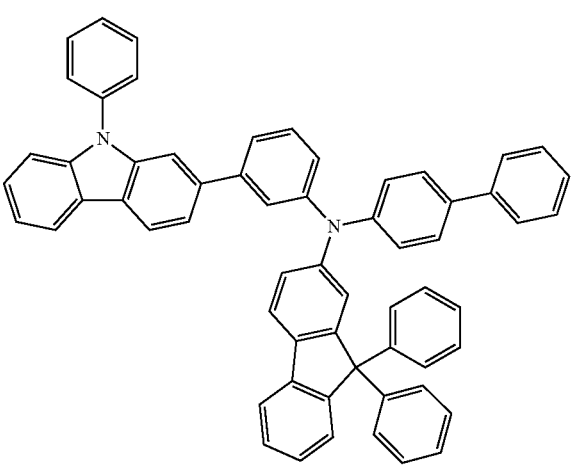

2-7
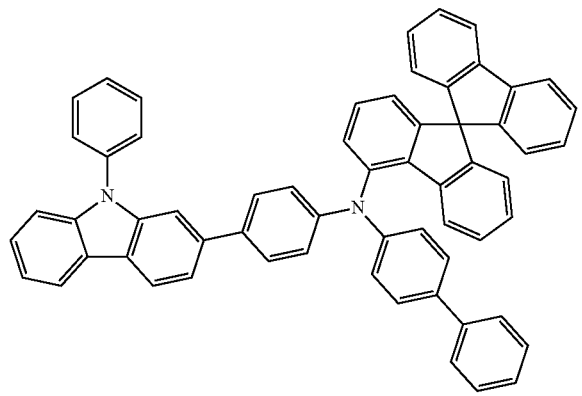
2-8
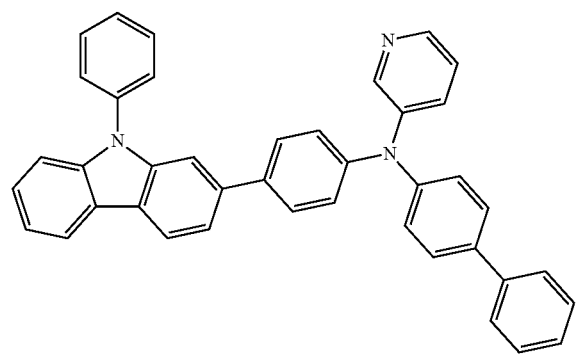
2-9
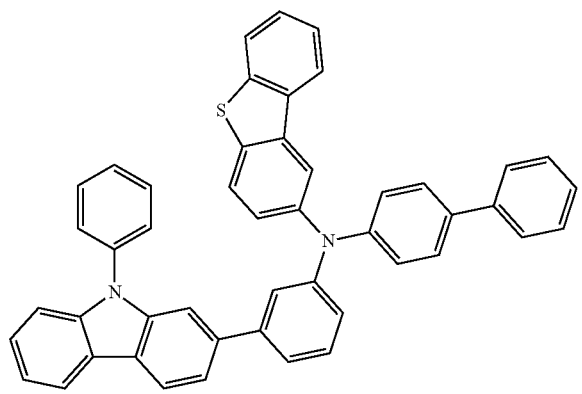
2-10
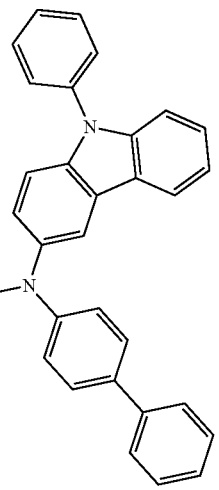
2-11
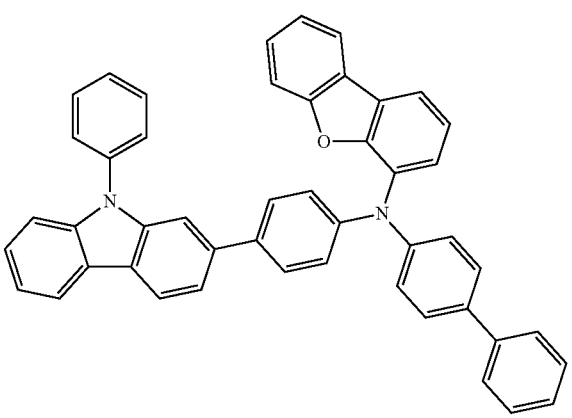
2-12
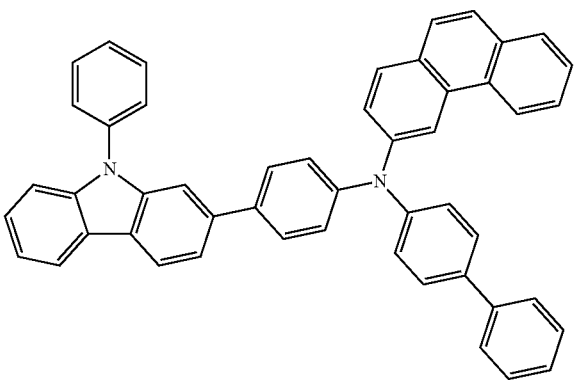
2-13
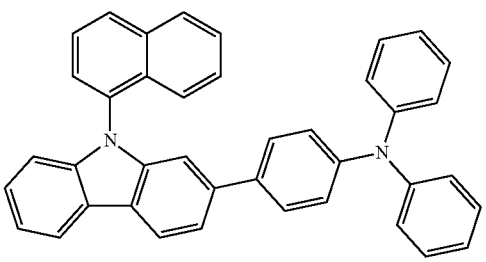

2-14
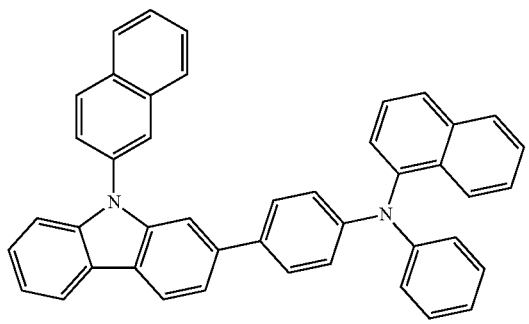
2-15
2-16
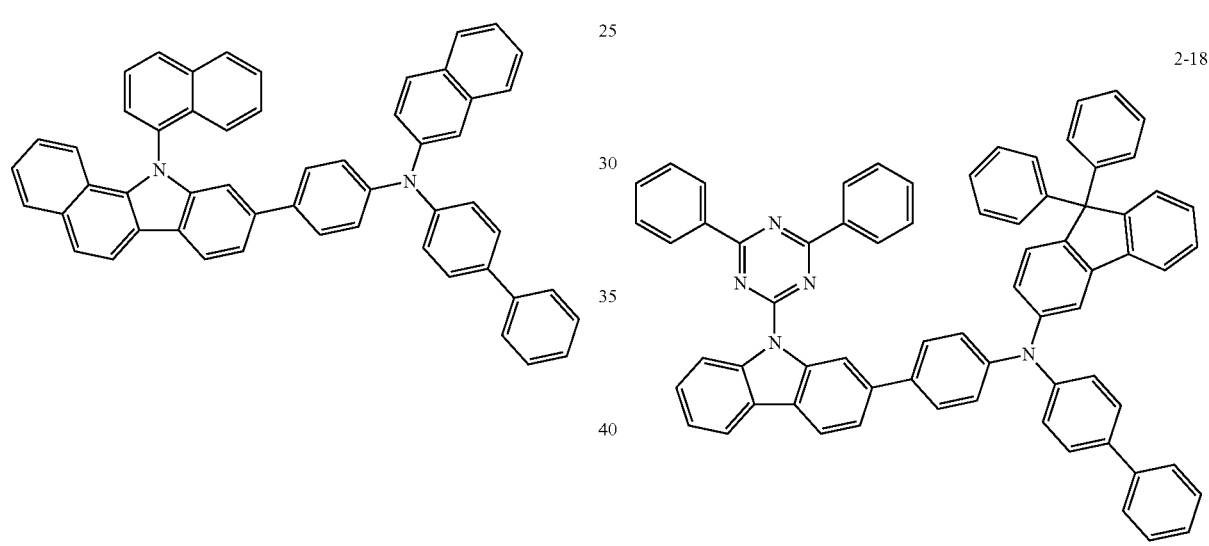
2-17
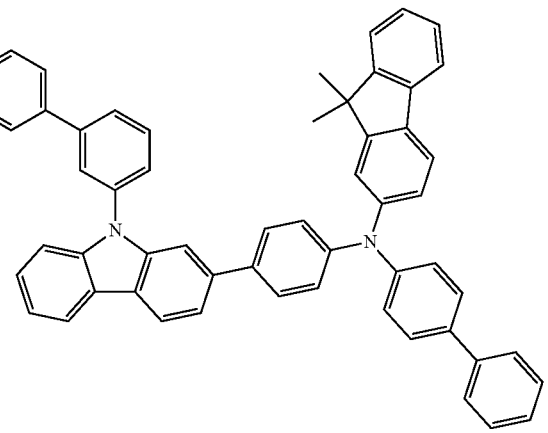
2-18
2-19
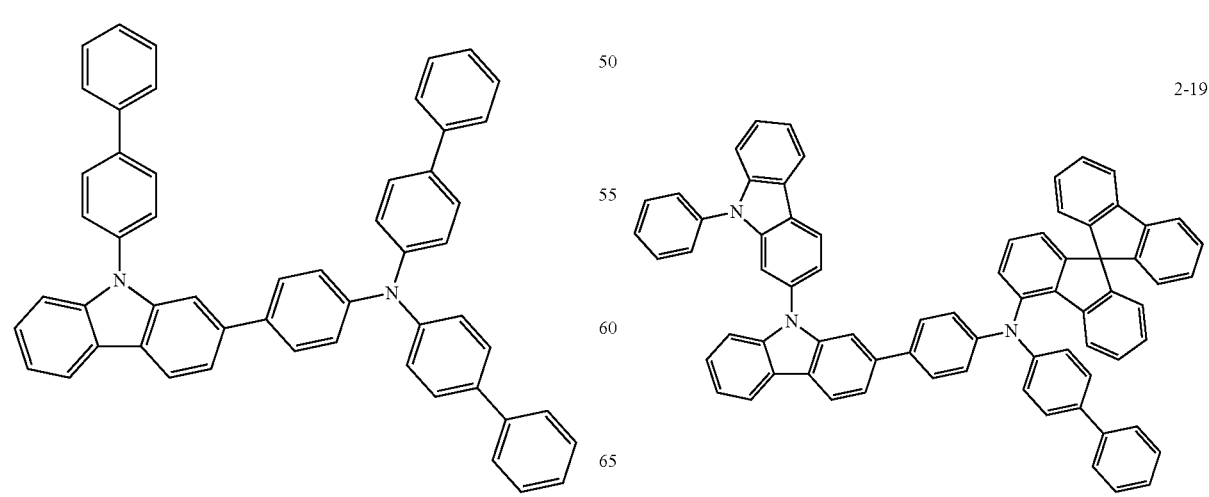

2-20
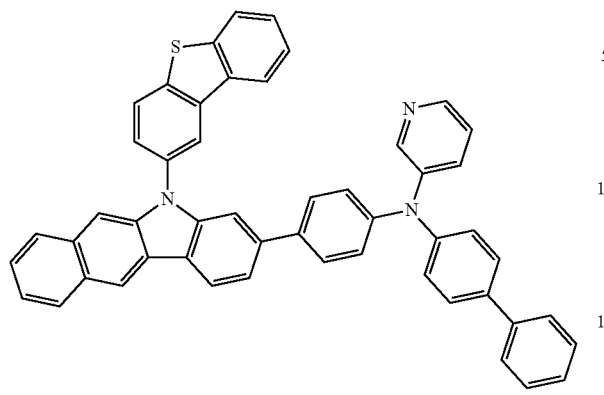
2-23
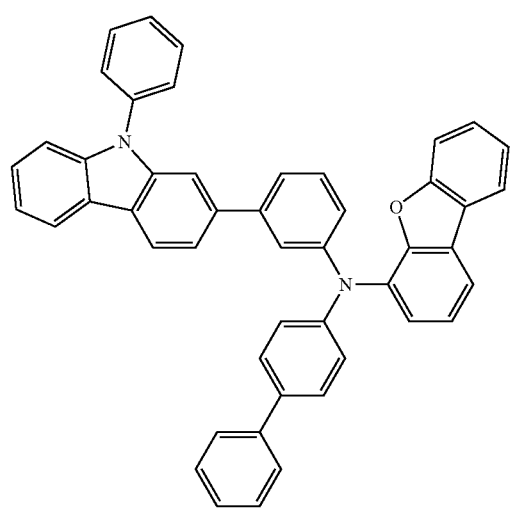
2-21
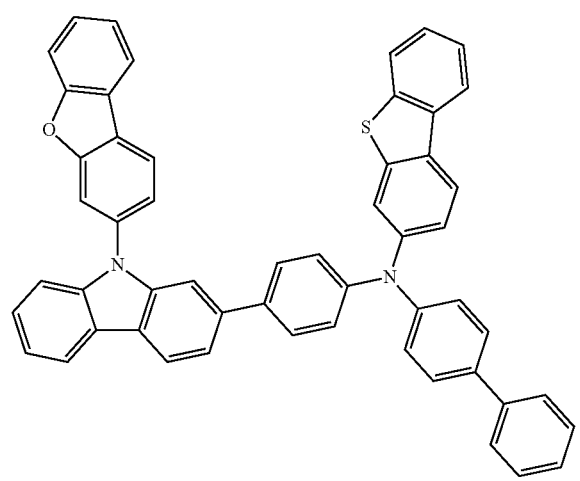
2-24
2-22
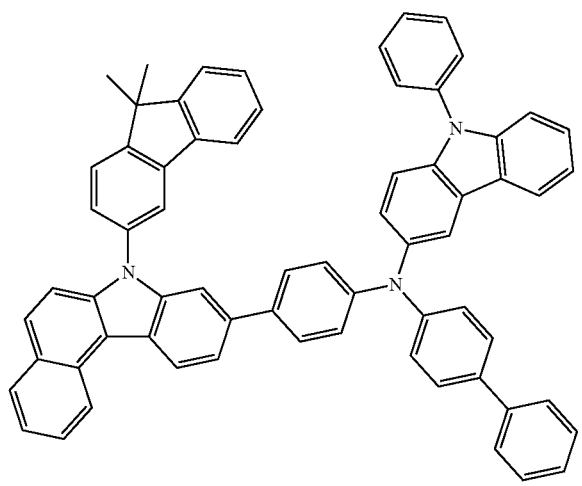
2-25
2-26
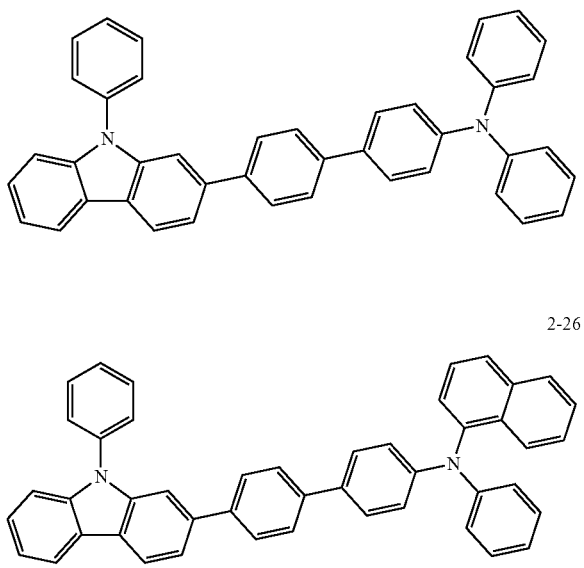

2-27
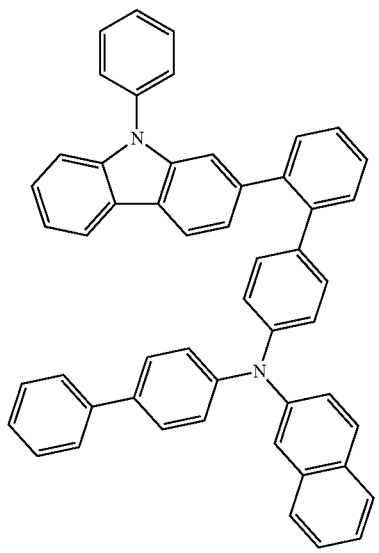
2-29
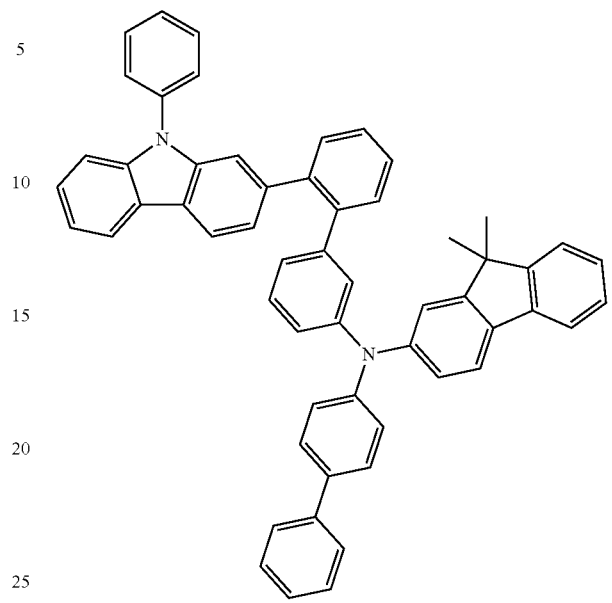
2-30
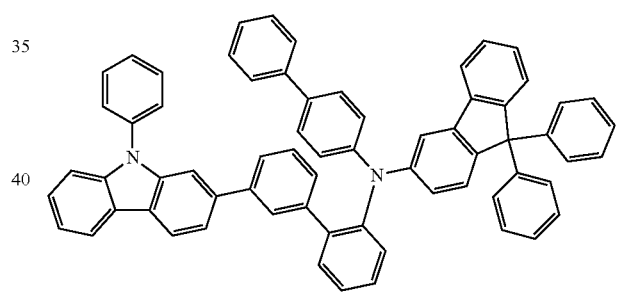
2-28
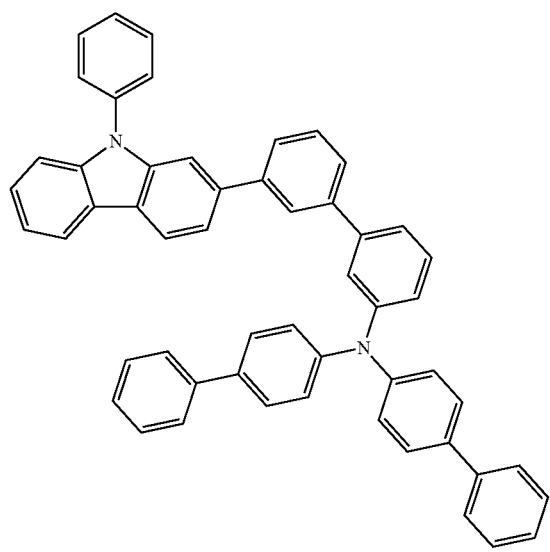
2-31
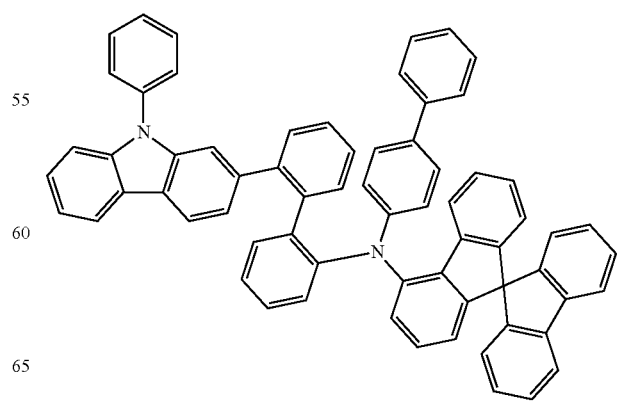

2-32
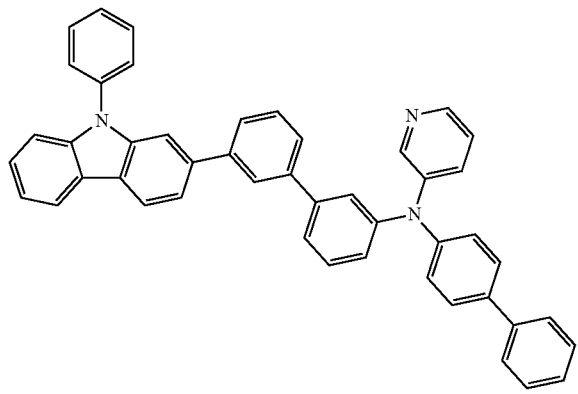
2-35
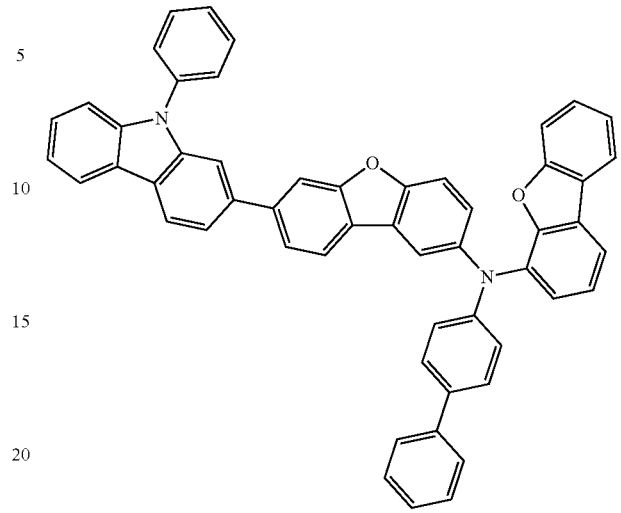
2-33
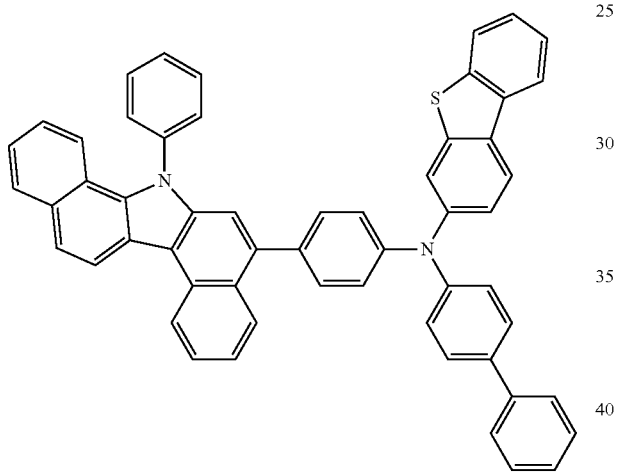
2-36
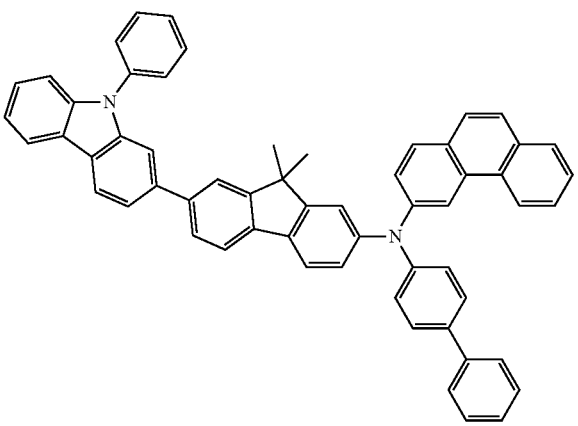
2-37
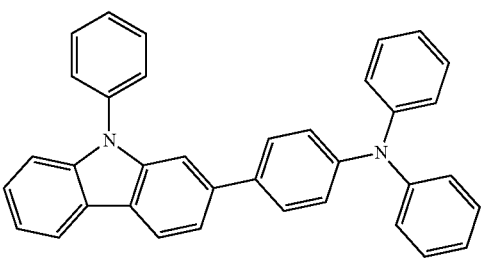
2-34
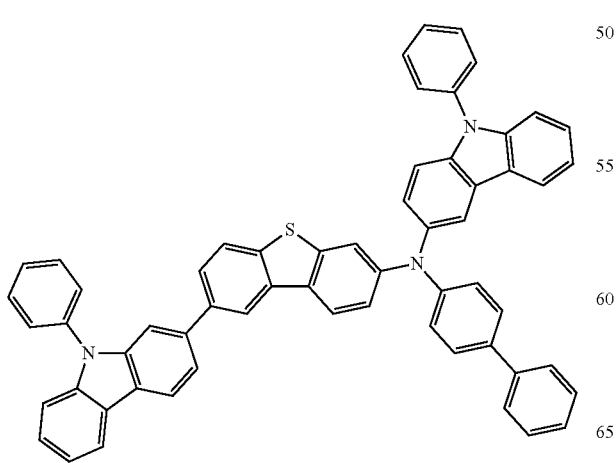
2-38
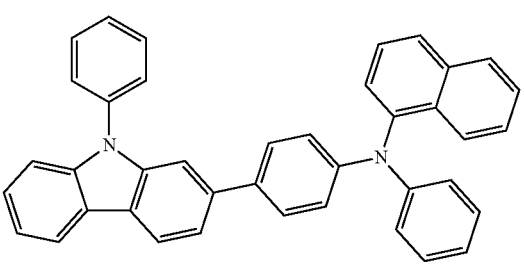

2-39
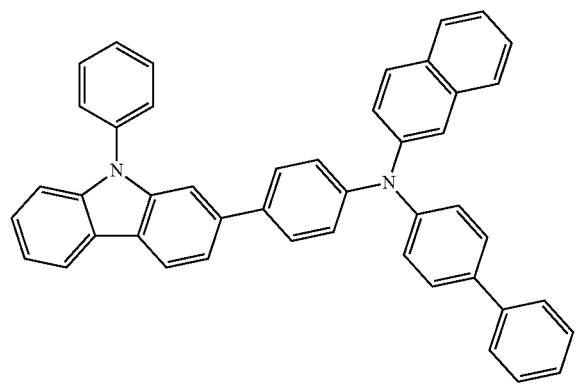
2-43
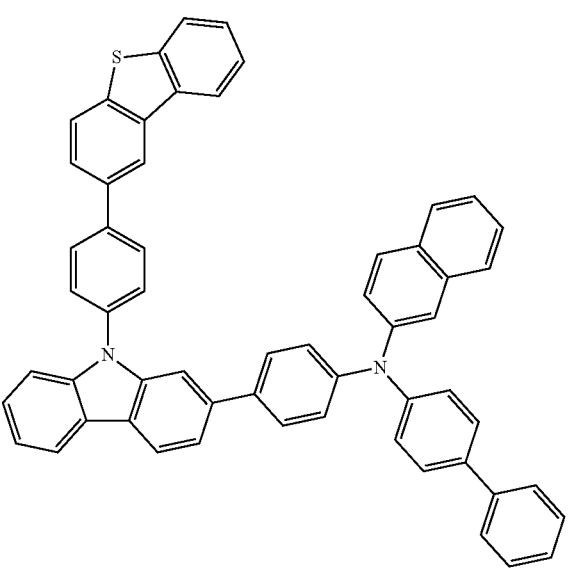
2-40
2-44
2-41
2-42
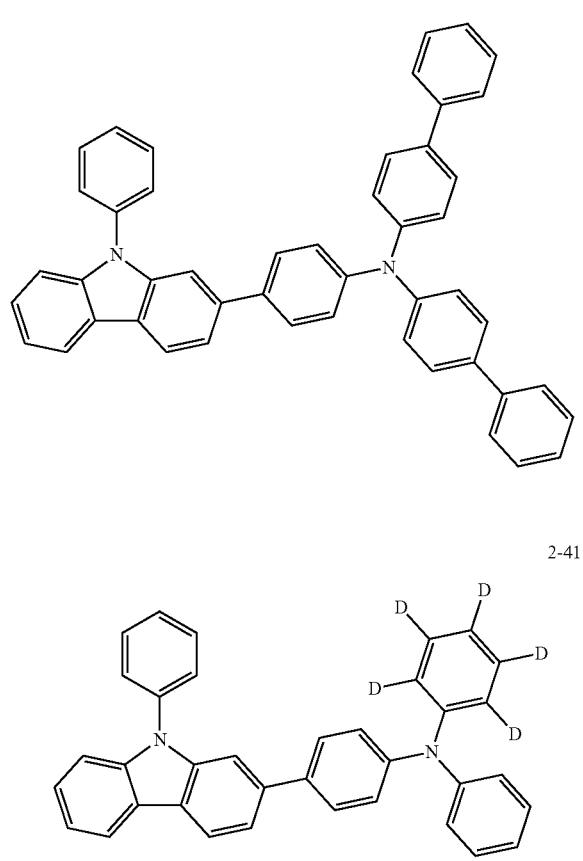
2-45
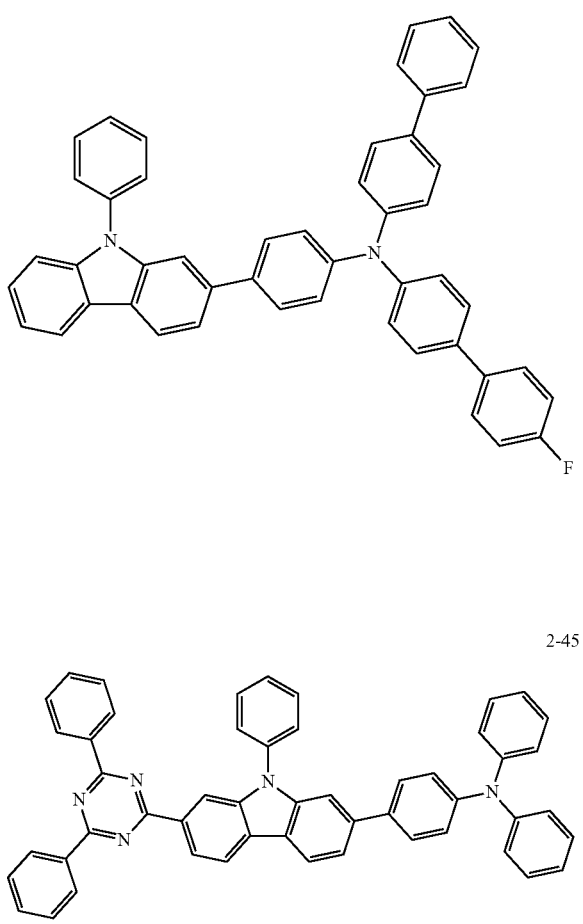

2-46
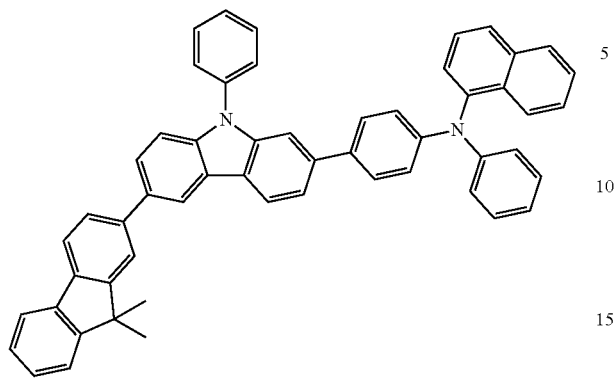
2-49
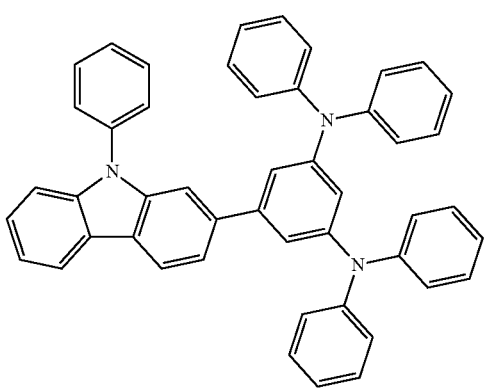
2-47
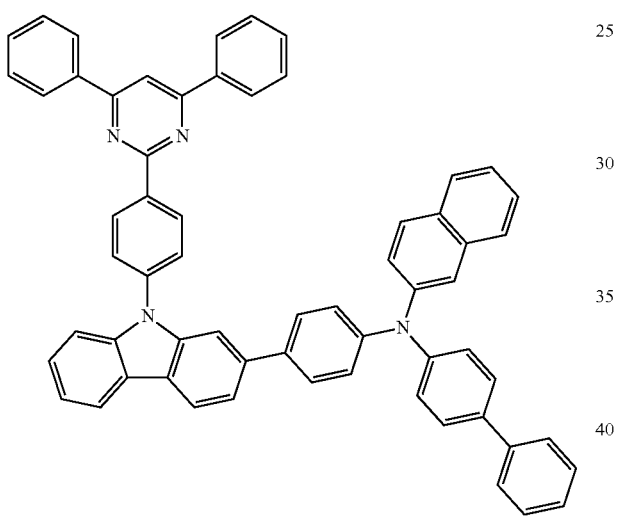
2-50
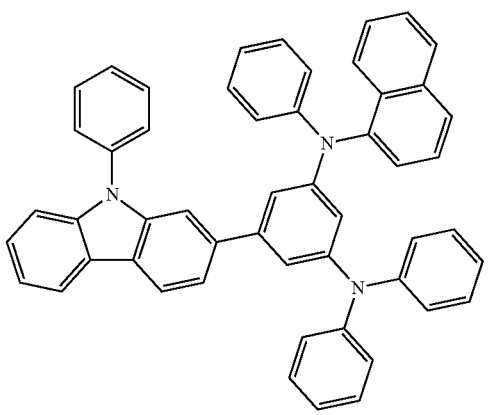
2-48
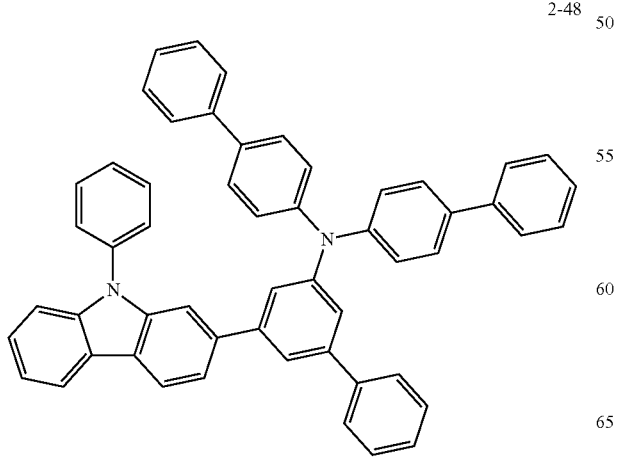
2-51
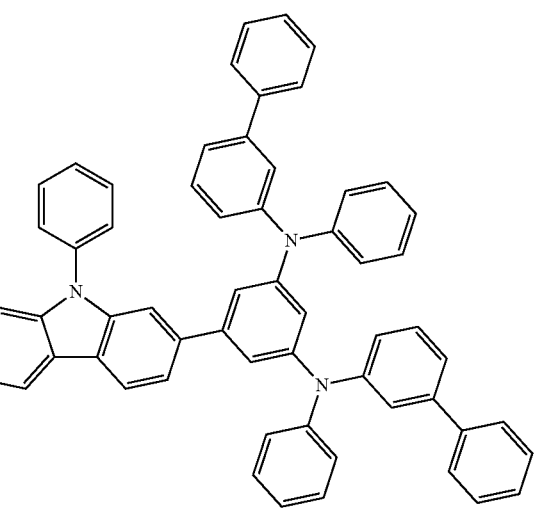

-continued
2-52
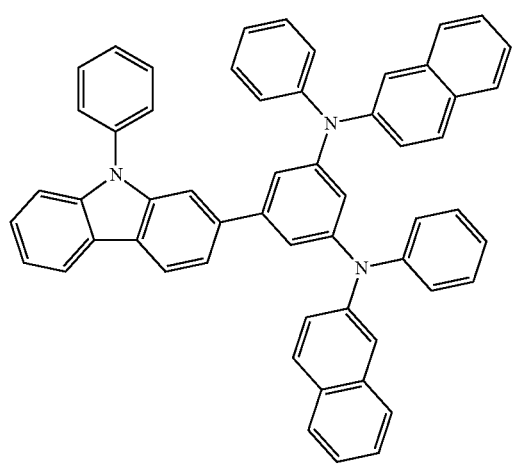
2-53
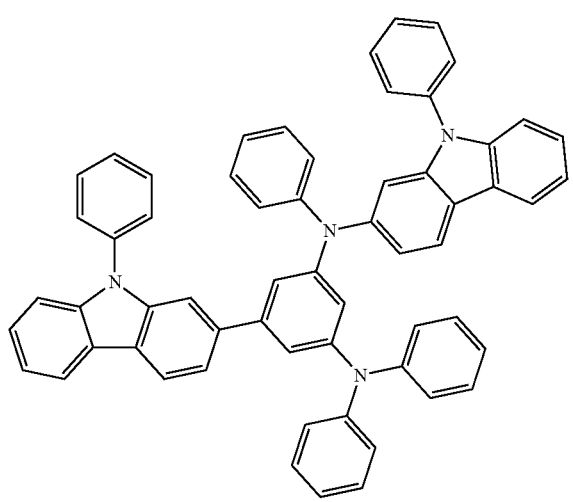
2-54
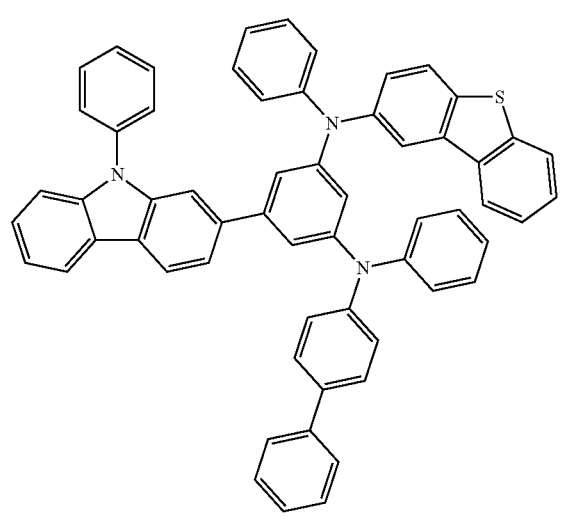
-continued
2-55
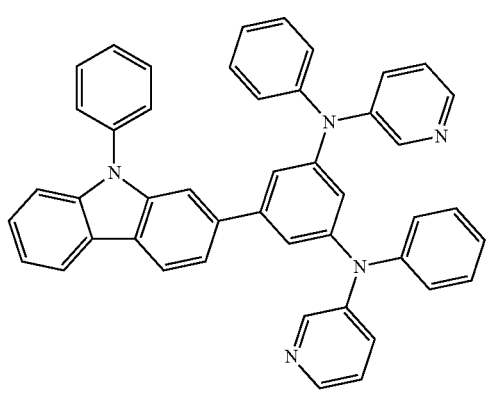
2-56
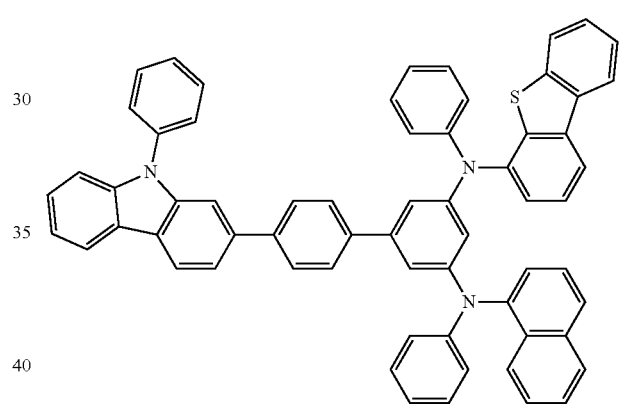
2-57
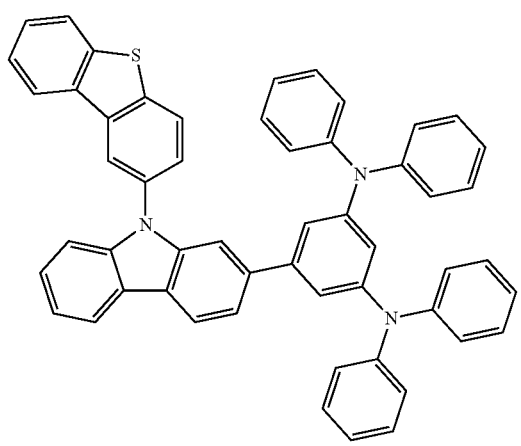

2-58
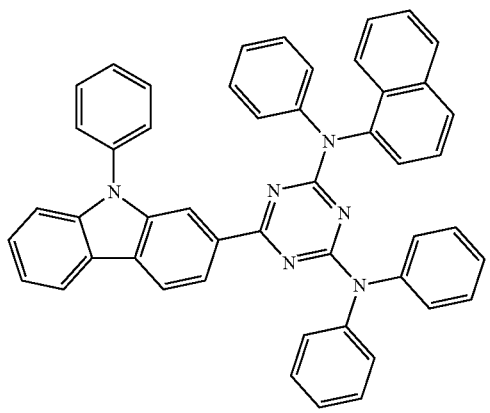
2-59
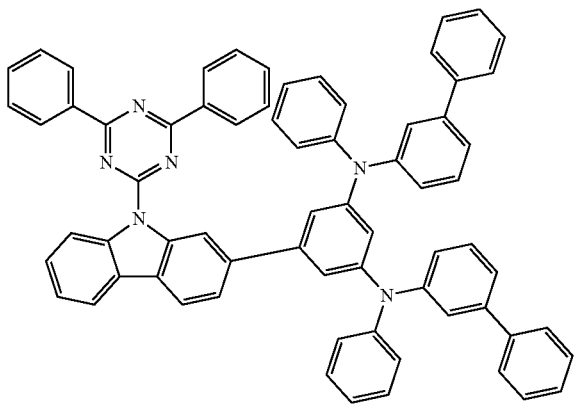
2-60
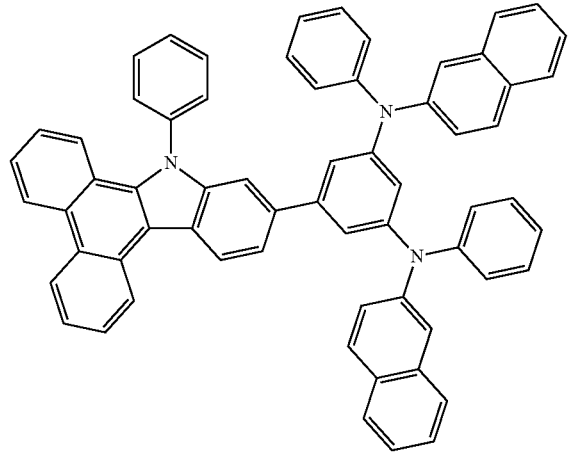
2-61
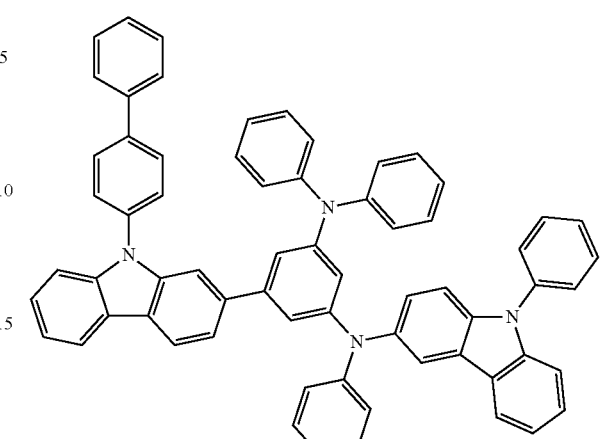
2-62
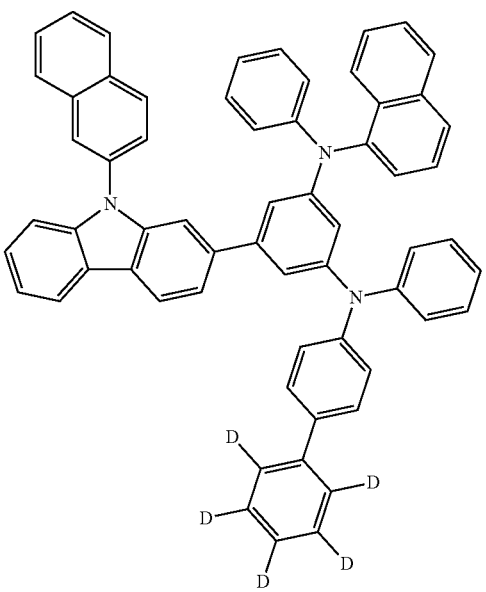
2-63
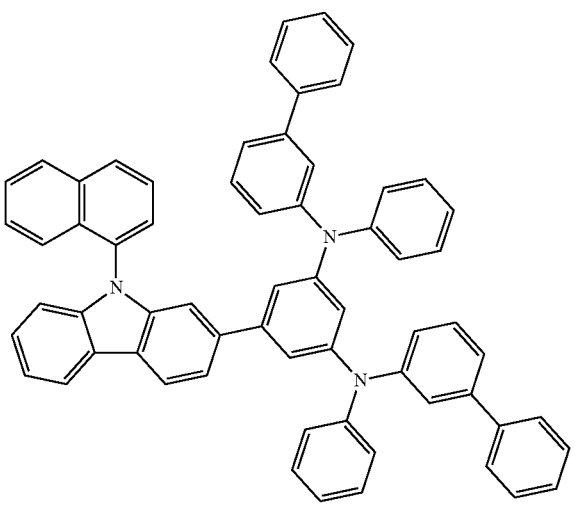

2-64
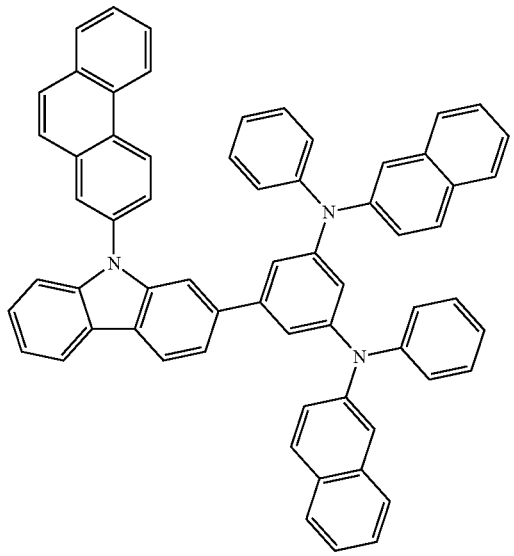
2-65
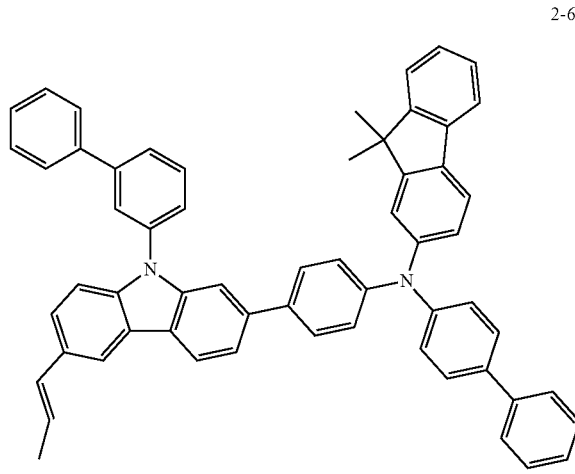
2-66
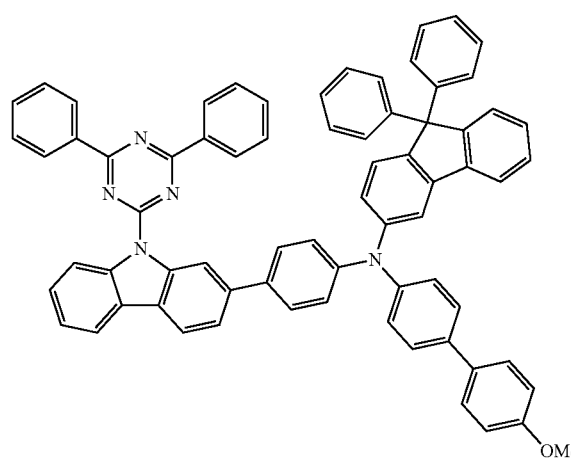
2-67
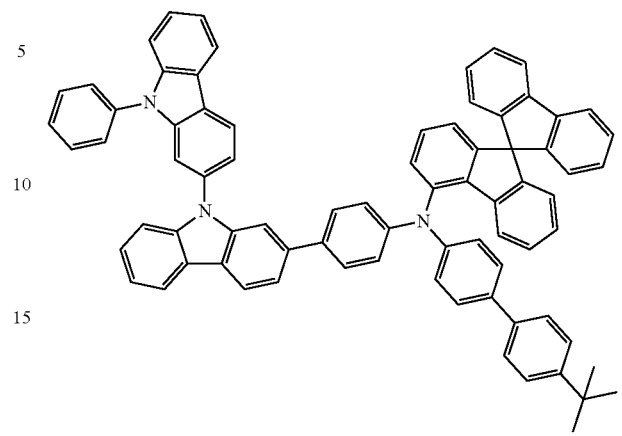
2-68
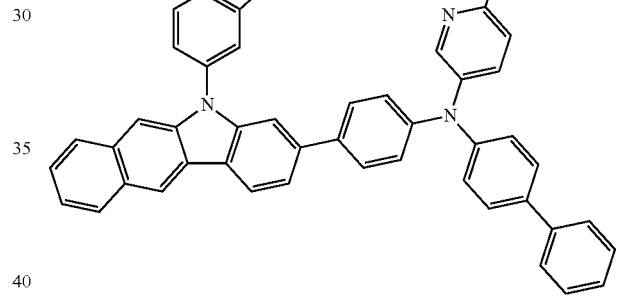
2-69
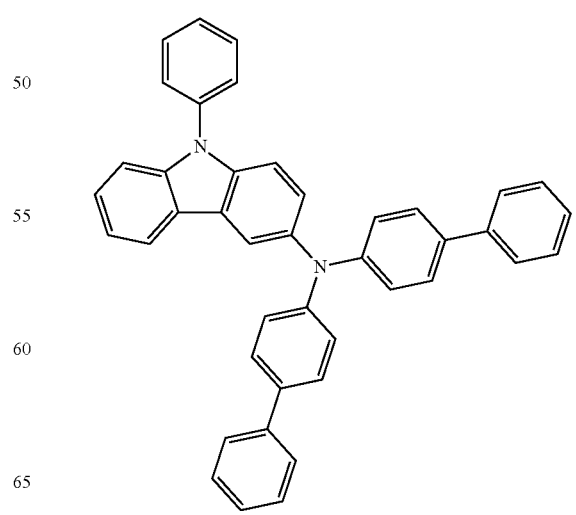

2-70
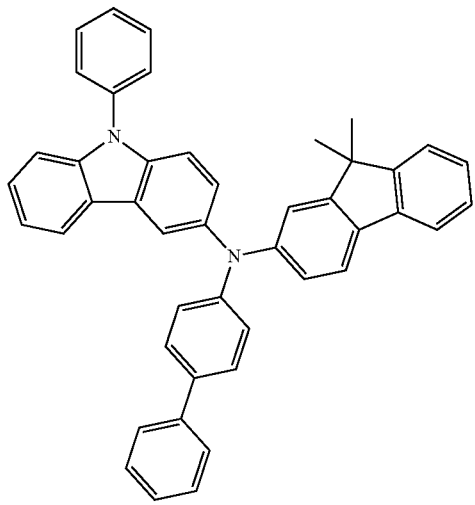
2-71
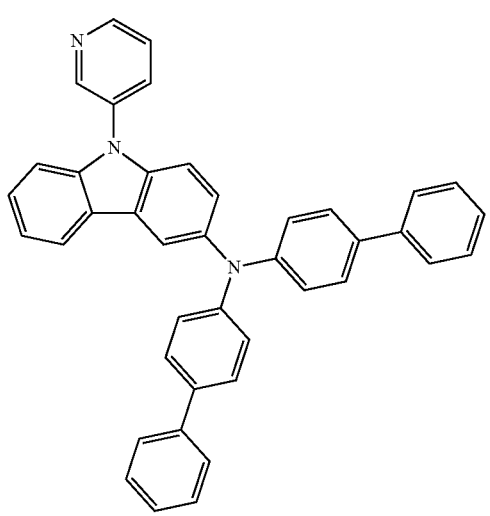
2-72
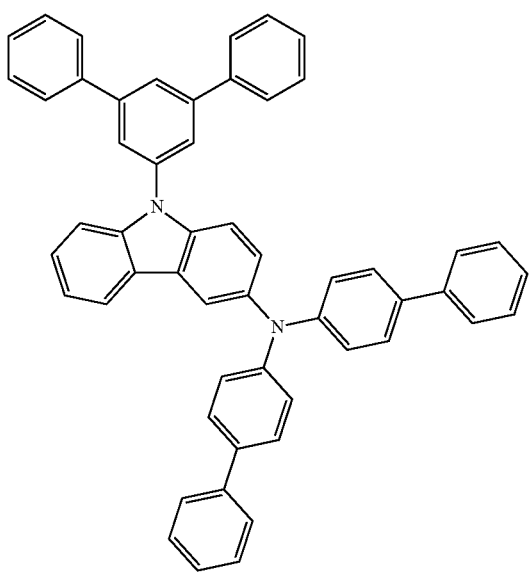
2-73
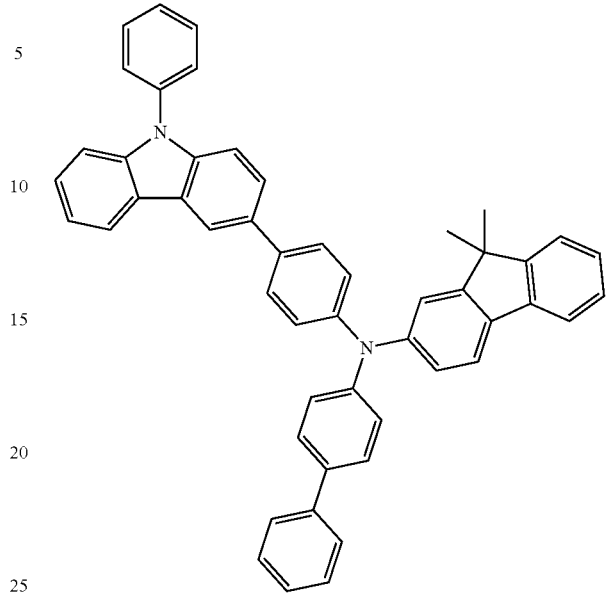
2-74
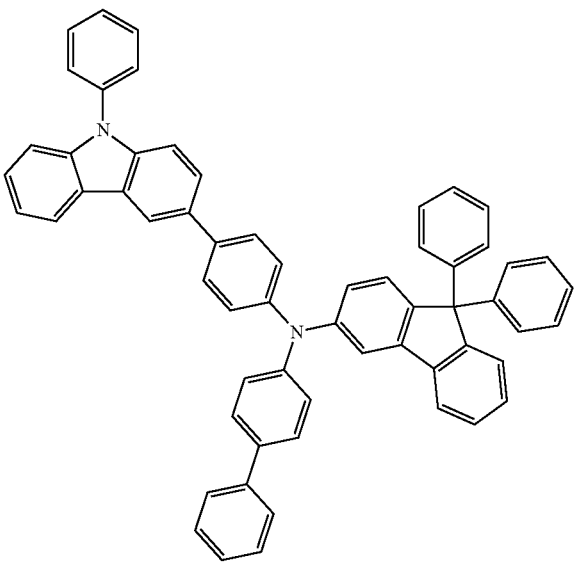

2-75
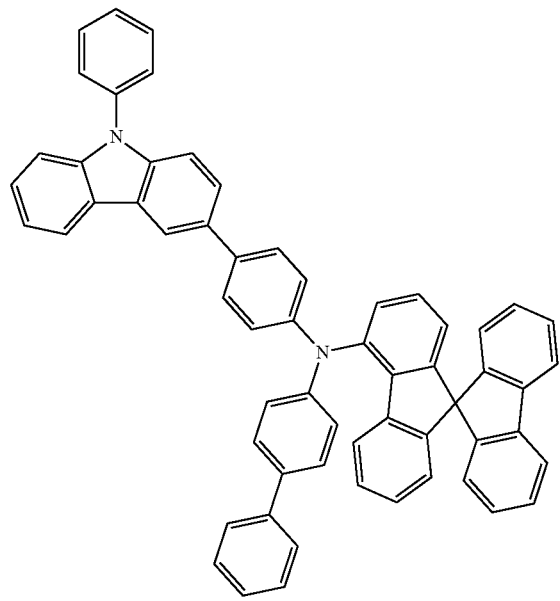
2-76
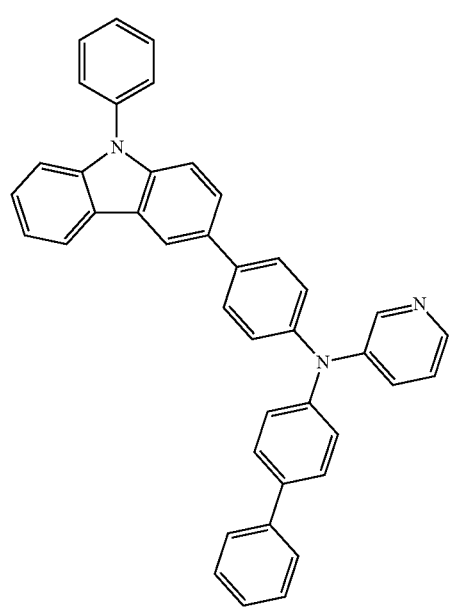
2-77
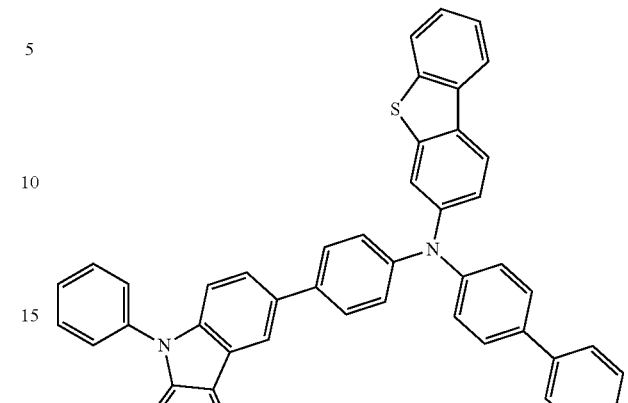
2-79
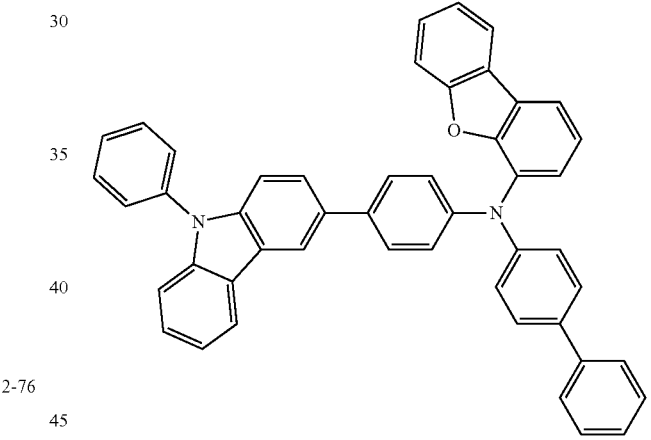
2-80
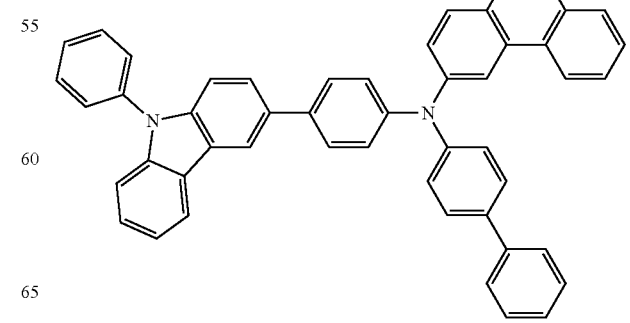

2-81
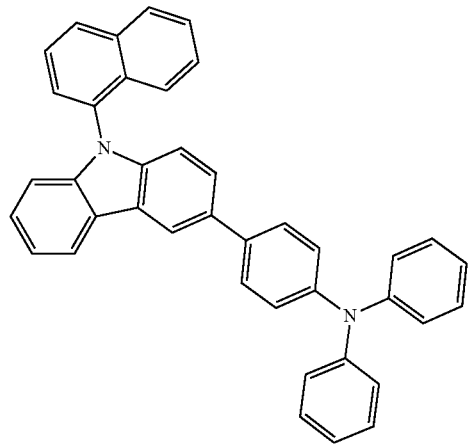
2-84
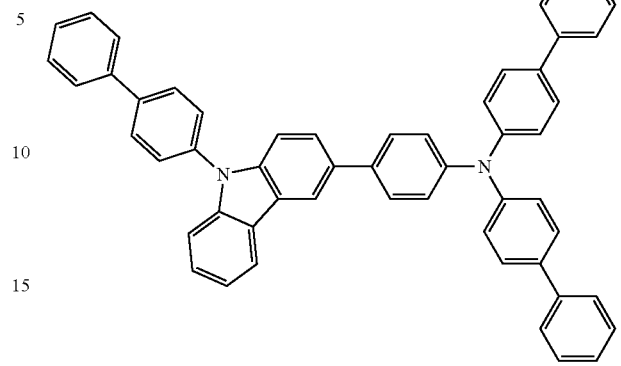
2-82
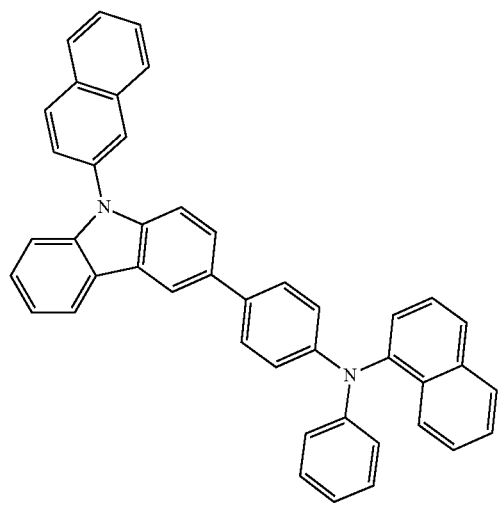
2-85
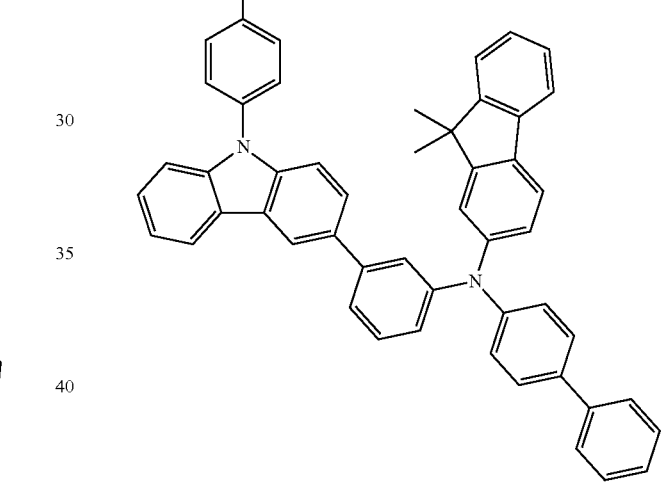
2-83
2-86
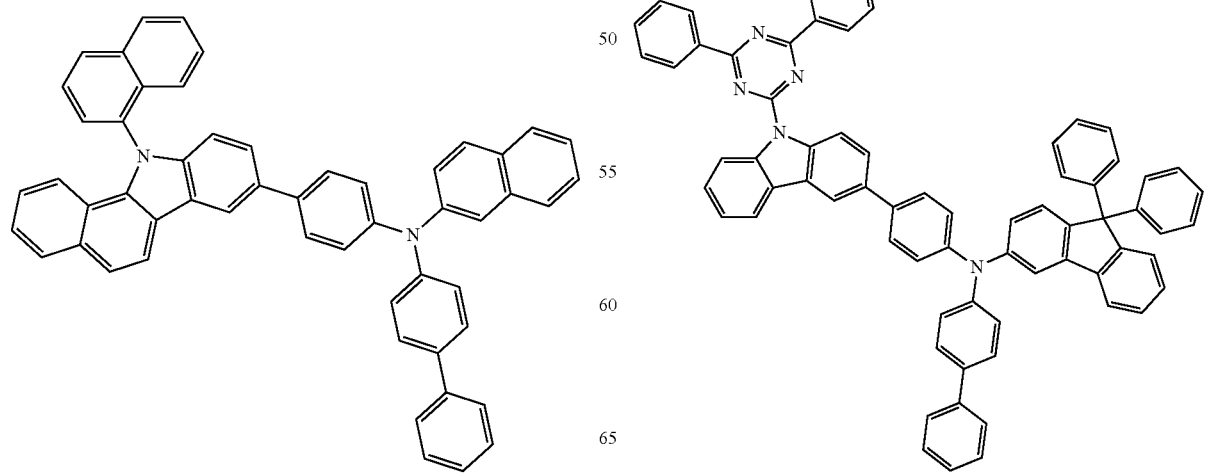

2-87
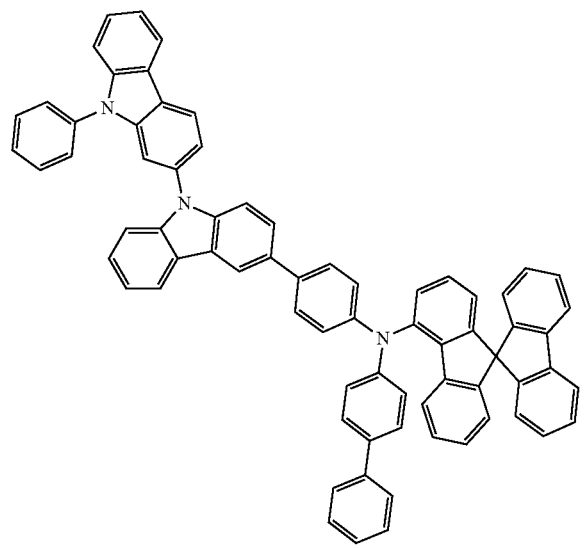
2-90
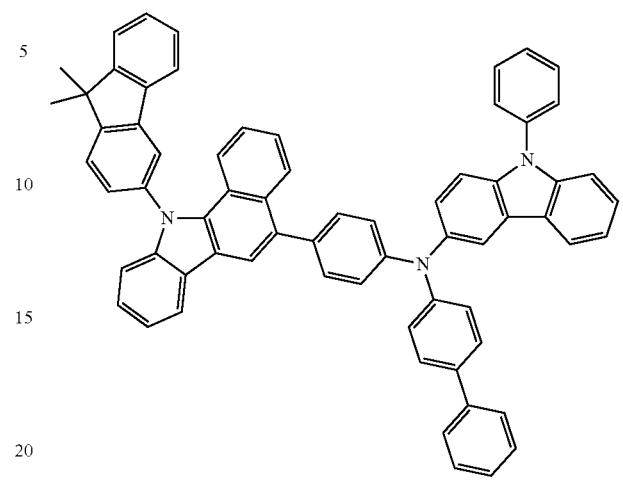
2-88
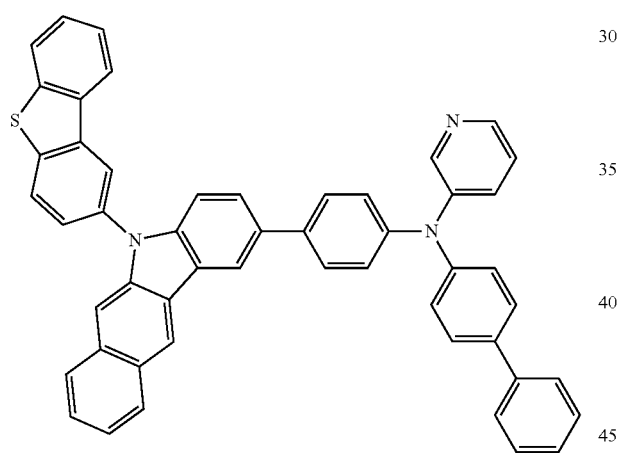
2-91
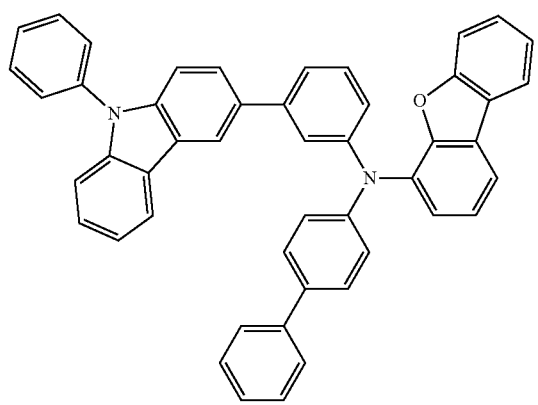
2-89
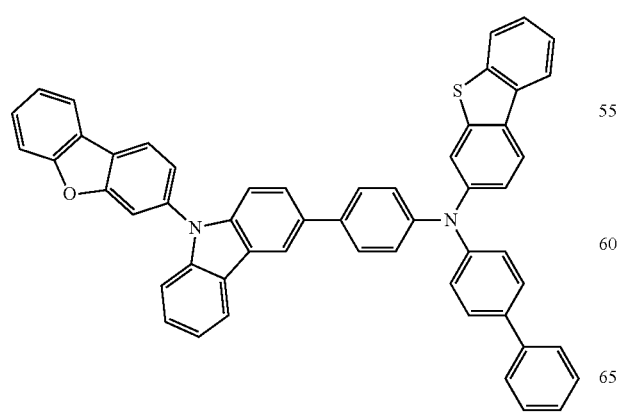
2-92
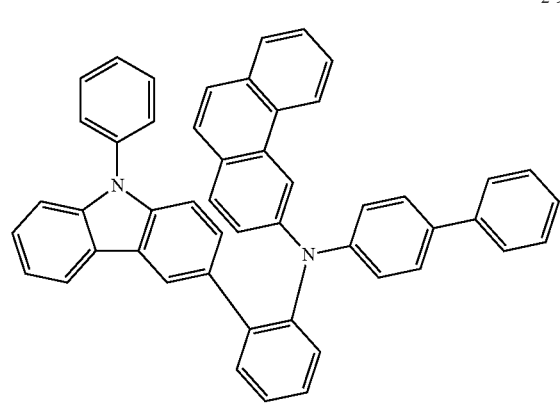

2-93
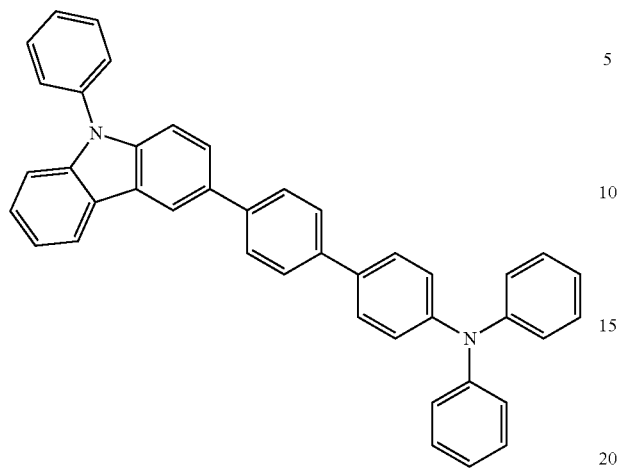
2-94
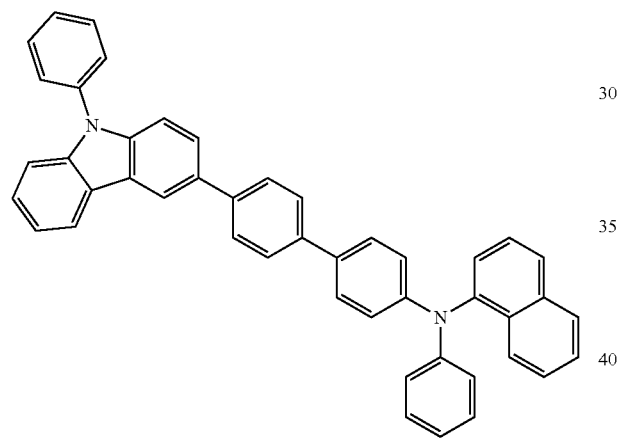
2-95
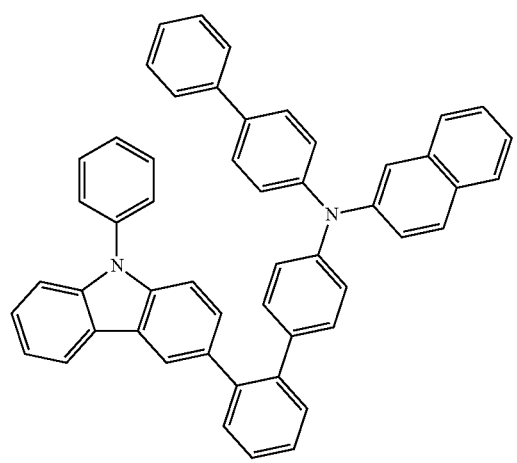
2-96
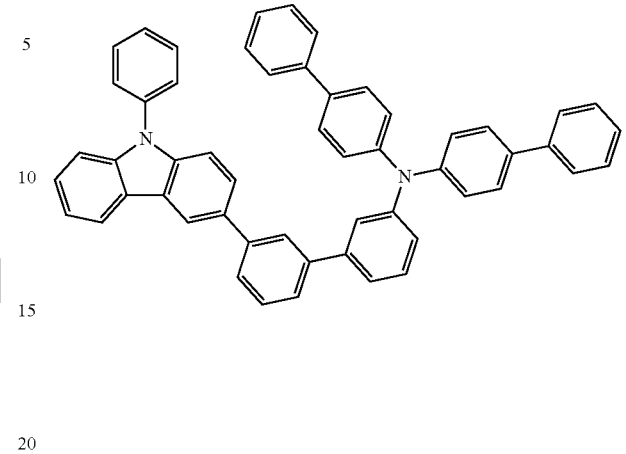
2-97
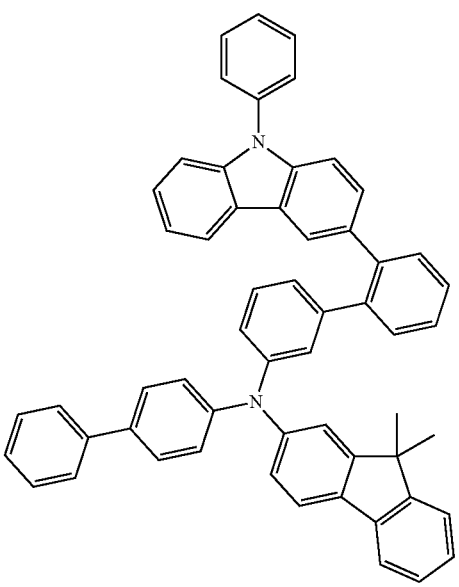
2-98
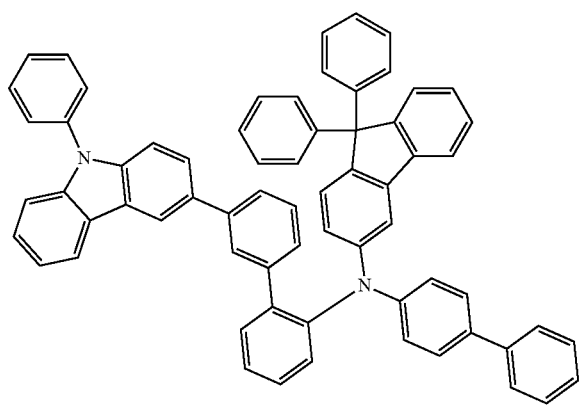

2-99
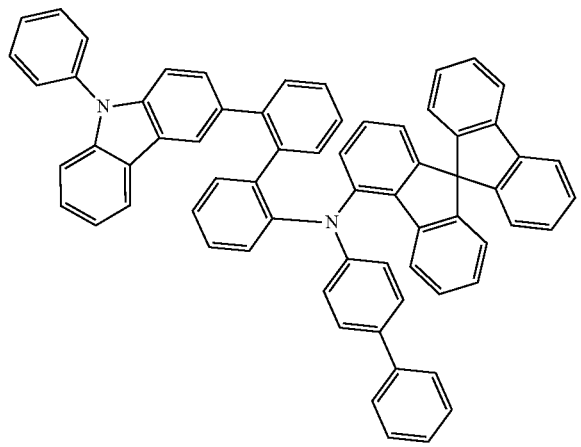
2-100
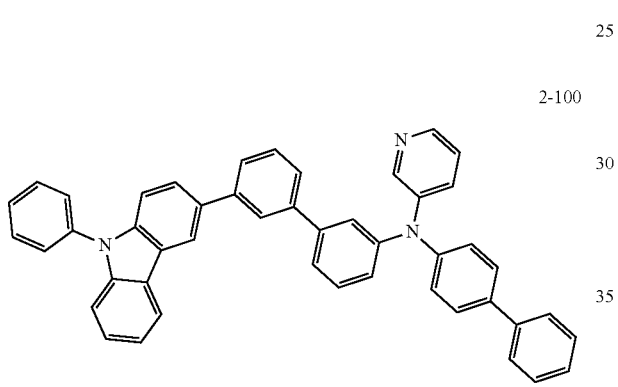
2-101
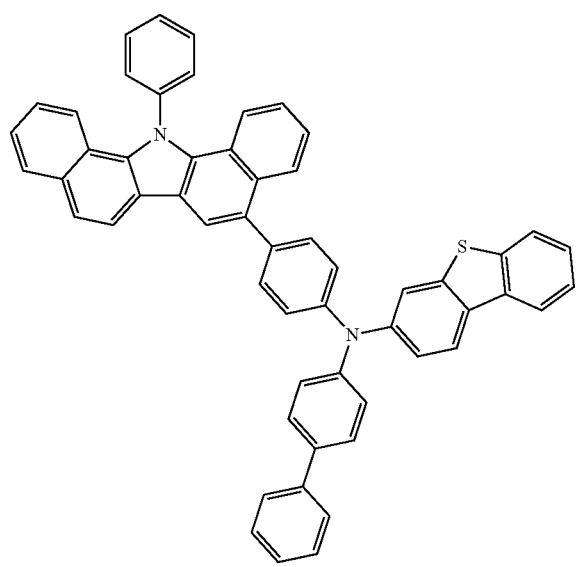
2-102
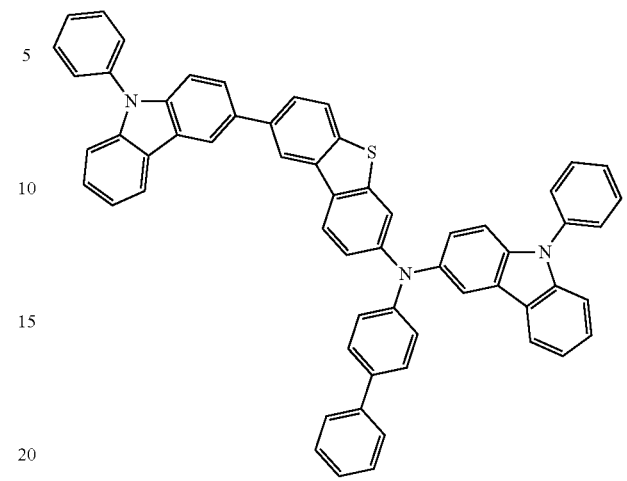
2-103
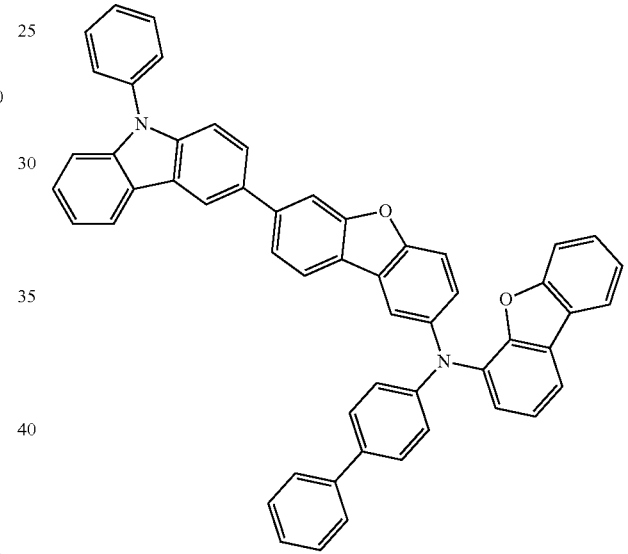
2-104
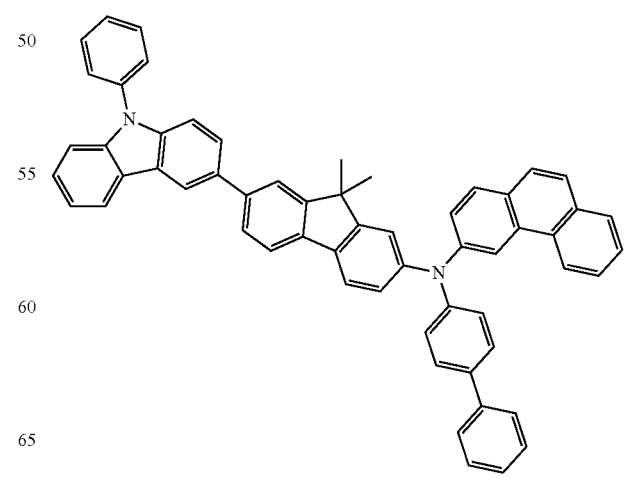

-continued
2-105
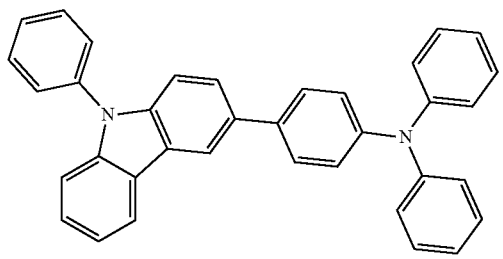
2-106
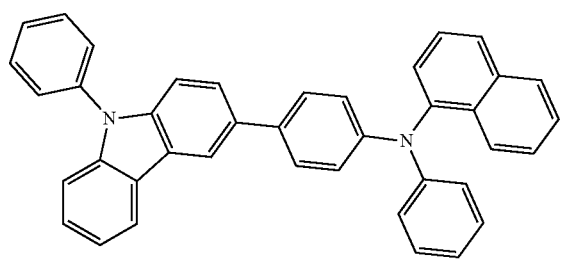
2-107
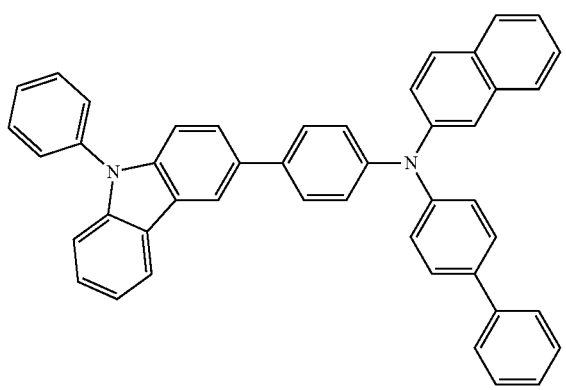
2-108
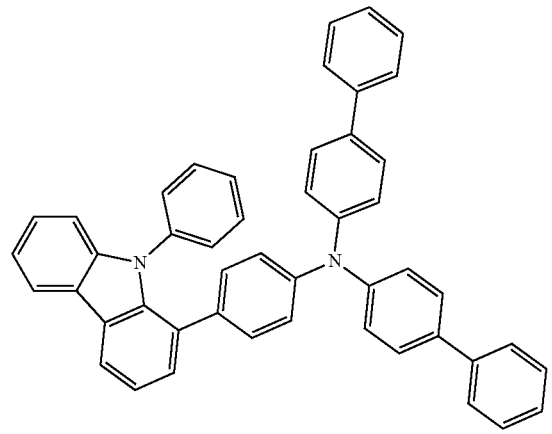
-continued
2-109
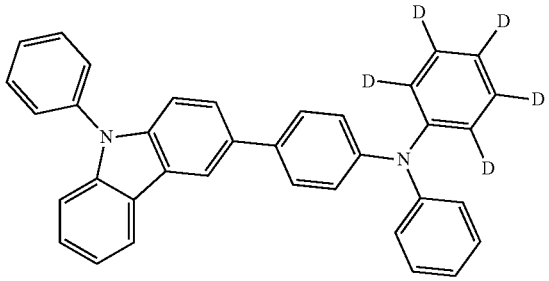
2-110
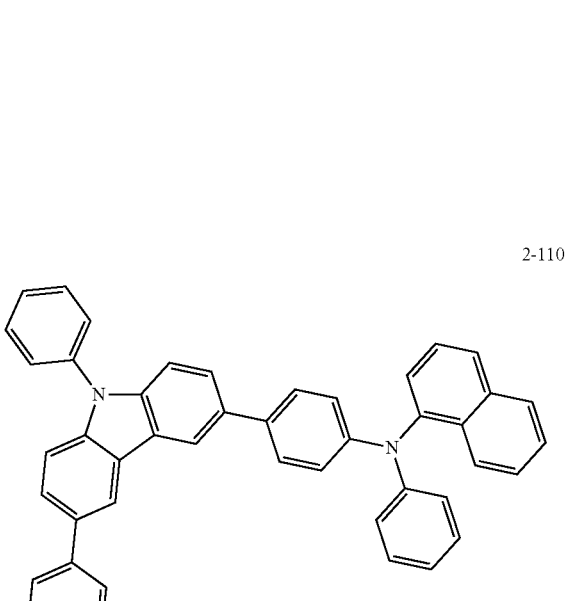
2-111
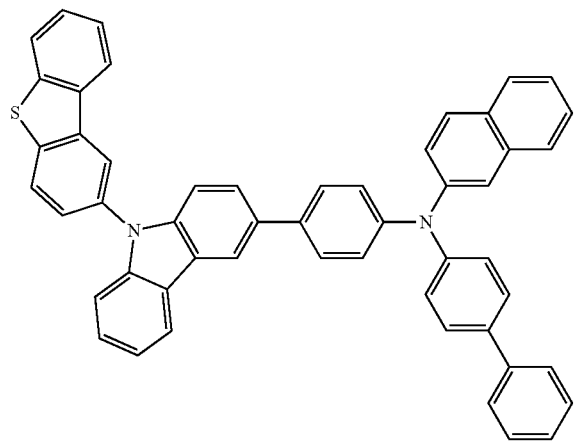

2-112
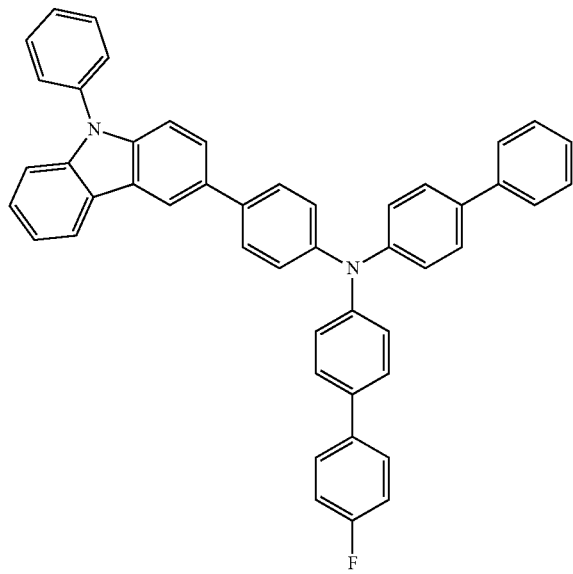
2-115
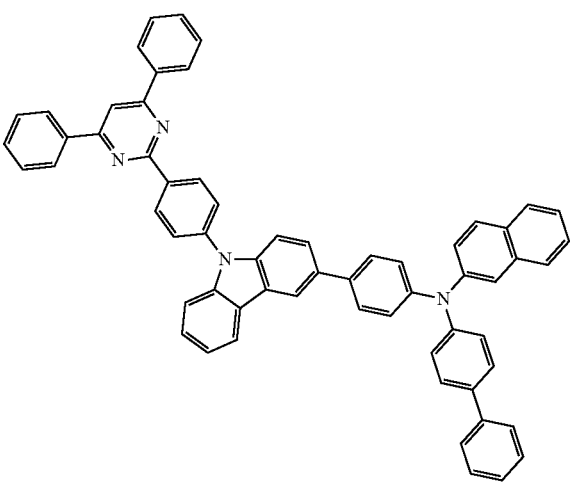
2-113
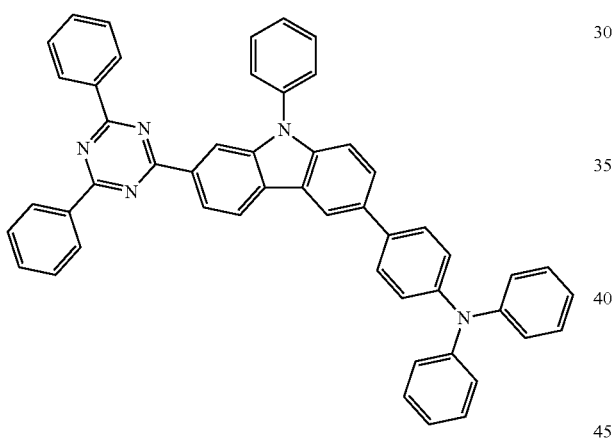
2-116
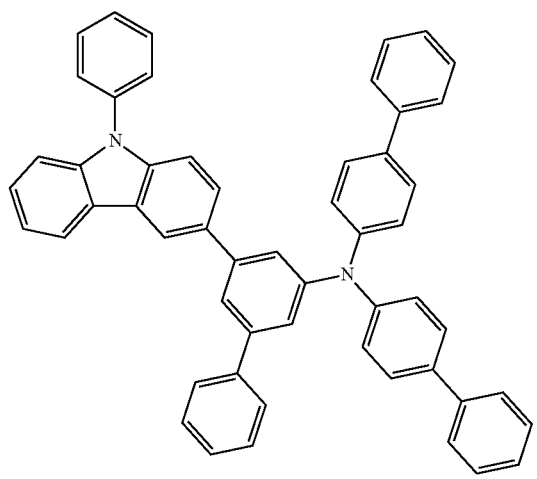
2-114
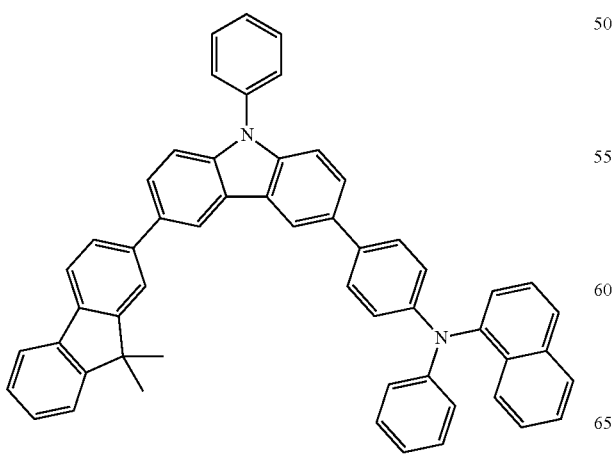
2-117
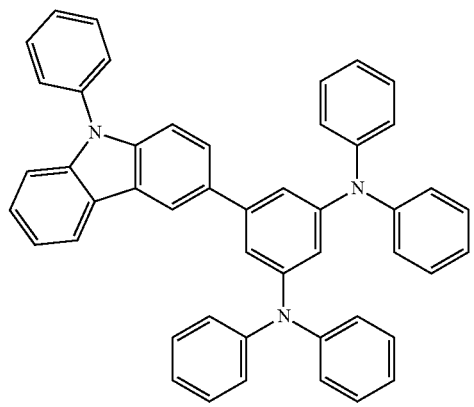

2-118
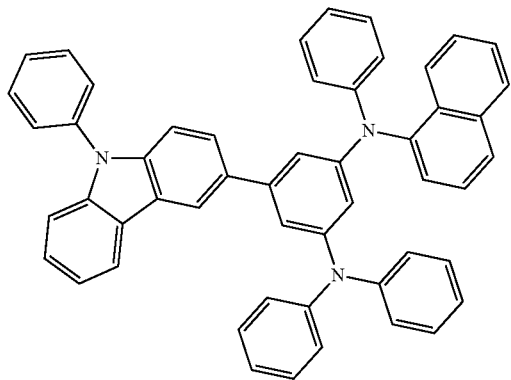
2-119
2-120
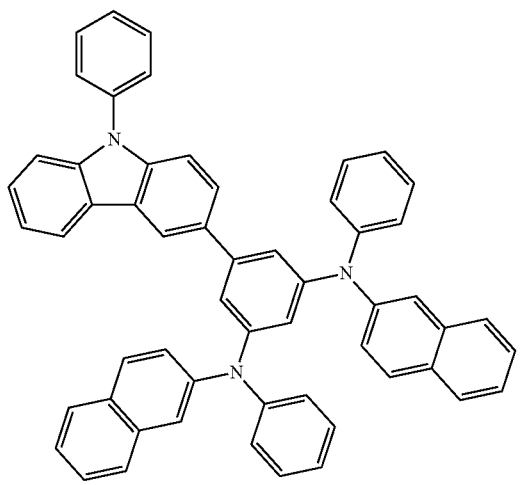
2-121
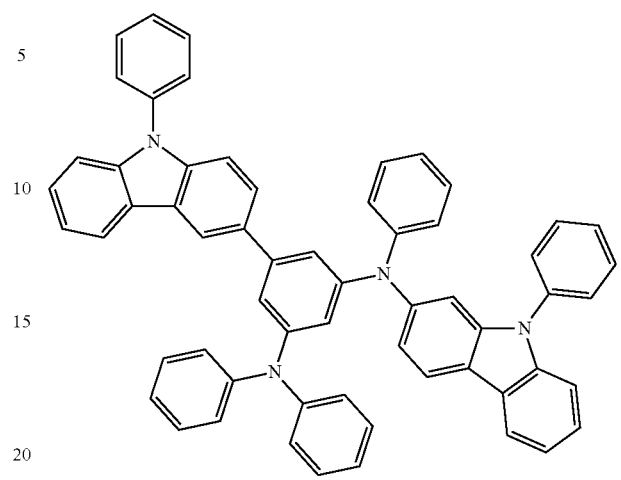
2-122
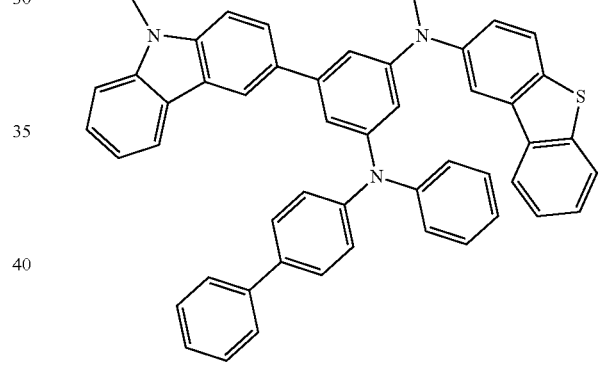
2-123
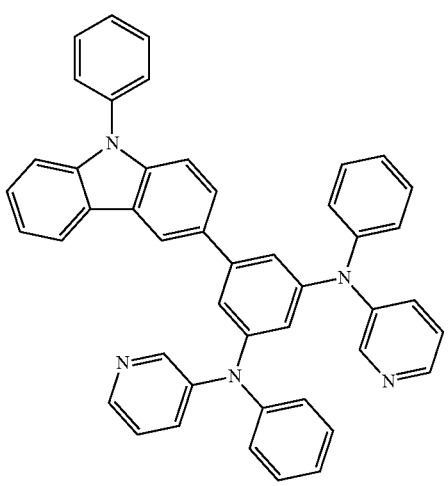

2-124
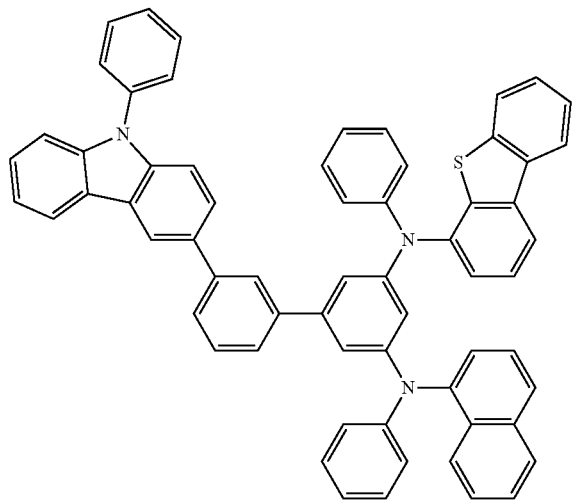
2-125
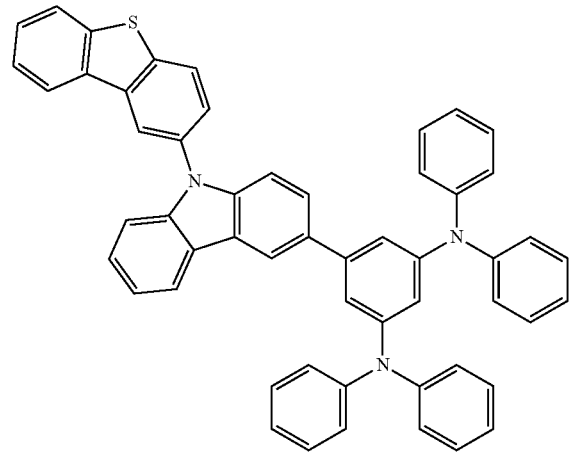
2-126
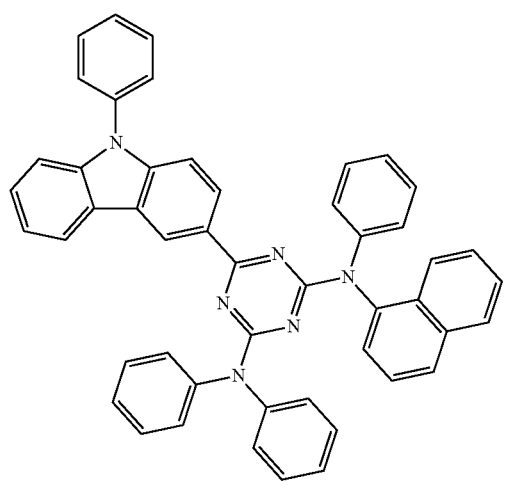
2-127
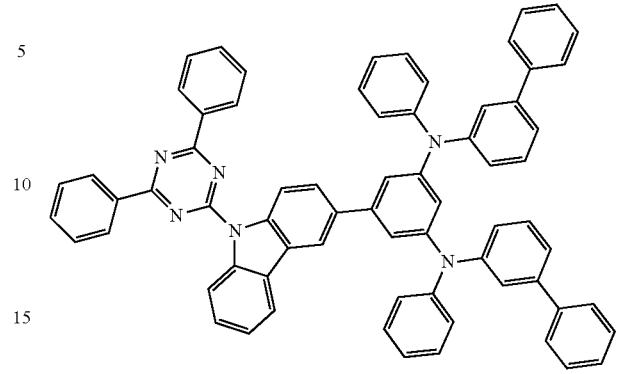
2-128
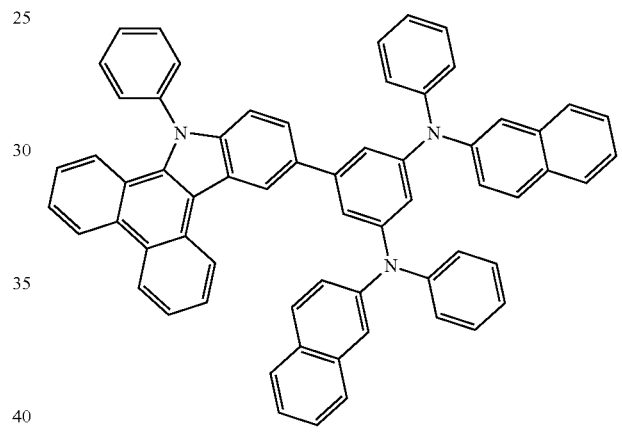
2-129
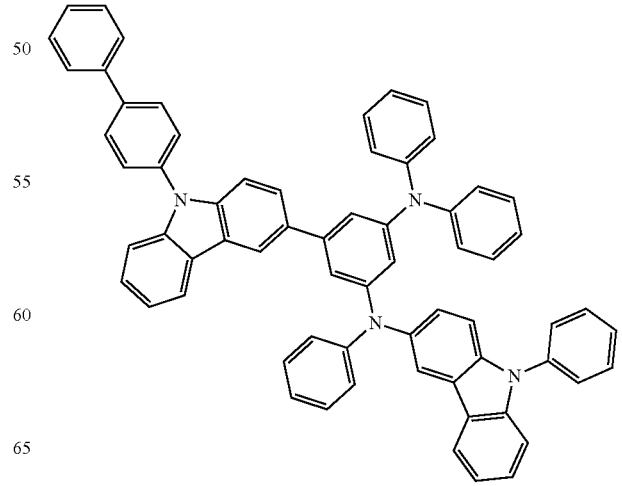

2-130
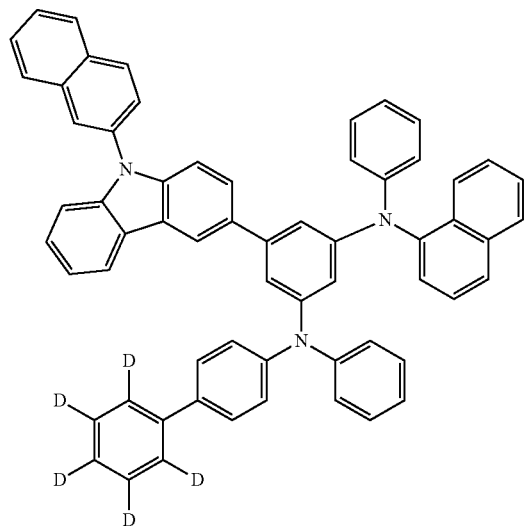
2-131
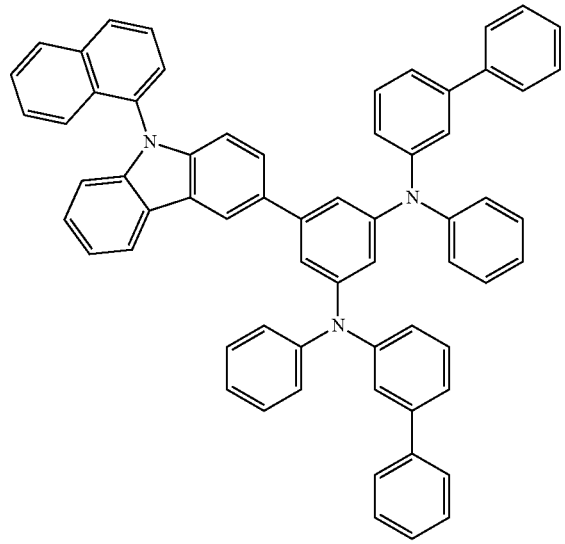
2-132
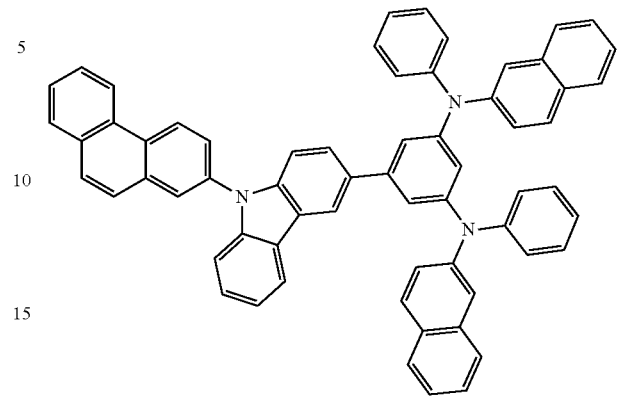
2-133

301
-continued 2-134

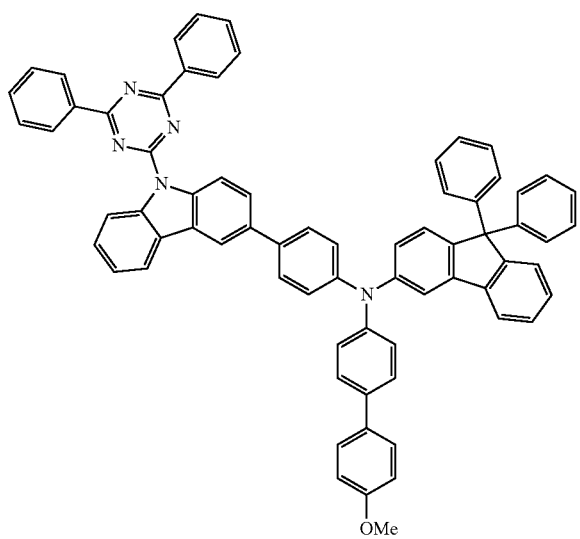

2-135

302
-continued 2-136

16. An electronic device comprising a display device and a control unit for driving the display device, wherein the display device comprises the organic electric element of claim 1.

17. The electronic device of claim 16, wherein the organic electric element is selected from the group consisting of an organic light emitting diode, an organic solar cell, an organic photo conductor, an organic transistor, an element for monochromatic illumination and a quantum dot display.

* * * * *

UNITED STATES PATENT AND TRADEMARK OFFICE
CERTIFICATE OF CORRECTION

PATENT NO. : 12,127,476 B2
APPLICATION NO. : 17/309586
DATED : October 22, 2024
INVENTOR(S) : Lee et al.

Page 1 of 2

It is certified that error appears in the above-identified patent and that said Letters Patent is hereby corrected as shown below:

In the Claims

Column 200, Claim 2, Line 8:
Please delete "Res" and replace with -- $R^6$s --

Column 204, Claim 5, Line 67:
Please delete "4" and replace with -- 3 --

Column 207, Claim 6, Line 48:
Please delete "4" and replace with -- 3 --

Column 222, Claim 14, Formula 1-24:

Please delete " 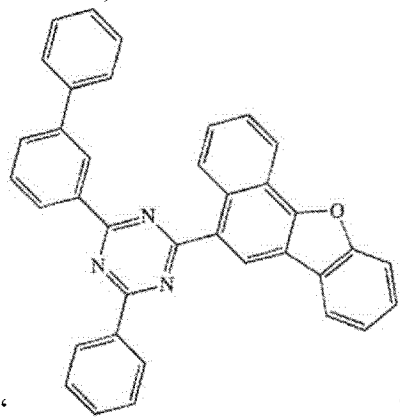 " and replace with -- 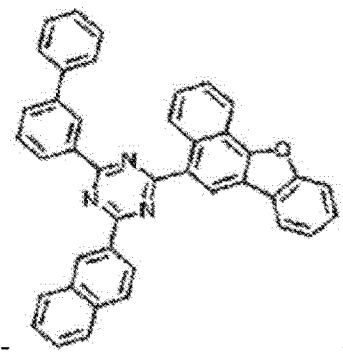 --

Signed and Sealed this
Thirty-first Day of December, 2024

Derrick Brent
*Acting Director of the United States Patent and Trademark Office*

CERTIFICATE OF CORRECTION (continued)
U.S. Pat. No. 12,127,476 B2

Column 282, Claim 15, Formula 2-78:
Formula 2-78 was missing

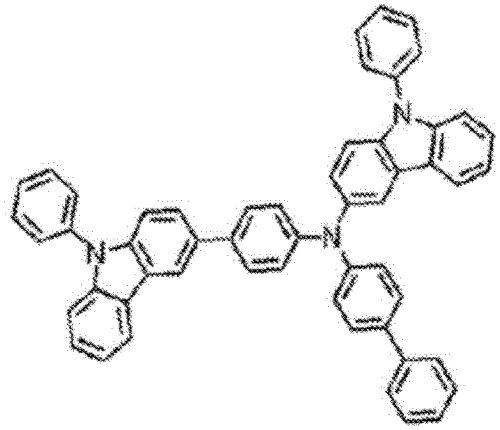

Please insert formula 2-78 --        2-78        --

Column 292, Claim 15, Formula 2-111:

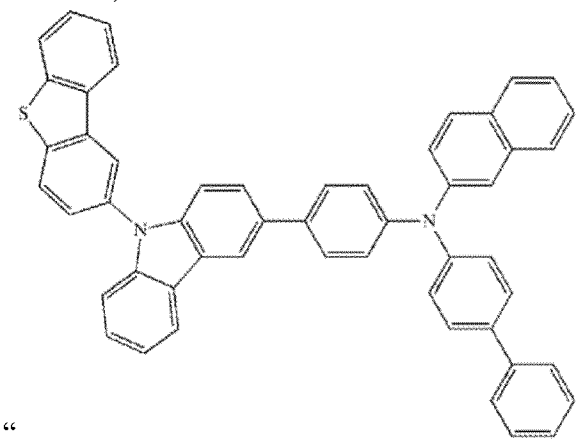

Please delete "                                                                    " and replace with

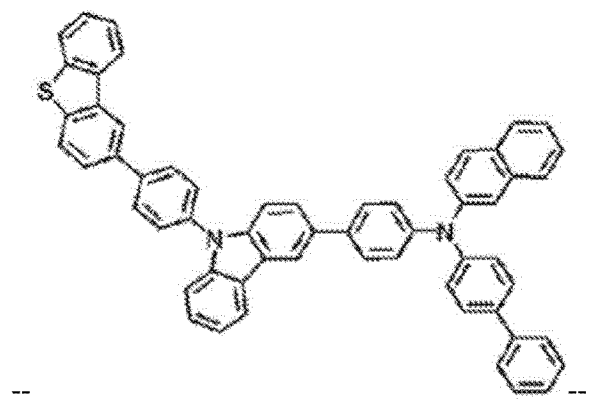

--                                                                    --